United States Patent [19]

Rea et al.

[11] Patent Number: 6,166,290
[45] Date of Patent: Dec. 26, 2000

[54] GLUTATHIONE-S-CONJUGATE TRANSPORT IN PLANTS

[75] Inventors: Philip A. Rea, Ardmore; Yu-Ping Lu, Havertown; Ze-Sheng Li, Prospect Park, all of Pa.

[73] Assignee: The Trustees of the University of Pennsylvania

[21] Appl. No.: 08/972,927

[22] Filed: Nov. 18, 1997

Related U.S. Application Data

[60] Provisional application No. 60/031,040, Nov. 18, 1996, and provisional application No. 60/061,328, Oct. 8, 1997, abandoned.

[51] Int. Cl.$^7$ ............................. C12N 15/82; C12N 5/04; C12N 15/29; A01H 5/00
[52] U.S. Cl. .................. 800/278; 536/23.1; 536/23.6; 536/23.2; 435/419; 435/320.1; 435/252.3; 435/410; 800/295; 800/298
[58] Field of Search ................................. 536/23.6, 23.1, 536/23.2; 800/205, DIG. 17, 295, 298, 278; 435/69.1, 468, 410, 419, 320.1, 252.3

[56] References Cited

PUBLICATIONS

Napoli et al. The Plant Cell. 1989. vol. 2: 278–289, 1989.
Bonnard and Grienenberger. Molecular and General Genetics. 1995. Jan. issue. vol. 246: 91–99, 1995.
Mayer et al. Journal of Cell Biology. 1995. Oct. issue. vol. 131: 137–150, 1995.
Ausubel et al. Short Protocols in Molecular Biology. Published by Greene Publishing Associates and Wiley–Interscience. 1989.
Valvekens et al. Proc. Natl. Acad. Sci. 1988. vol. 85: 5536–5540, 1988.
Theodoulou et al. 11th Int. Workshop Plant Membrane Biol., Cambridge, Urk. Aug. 1998.
Rea, P. J. Exper. Bot.50:895–913, Jun. 1999.
Altschul et al., 1990, *J. Mol. Biol.*, 215: 403–410.
Ausubel et al., 1992, *Current Protocols in Molecular Biology*, pp 27–28.
Balzi et al., 1994, *J. Bioenerg. Biomemb.* 27:71–76.
Berhane et al., 1994, Proc. Natl. Acad. Sci. USA 91:1480–1484.
Bevan, 1984, *Nucl. Acids Res.* 12:8711–8721.
Choi et al., 1995, *Weeds World*, 2: 17–20.
Cole et al., 1992, *Science* 258:1650–1654.
Cunningham et al., 1996. Plant Physiol. 110:715–719.
Cunningham et al., 1995, *Trends Biotechnol.* 13:393–397.
Daniel, 1993, CRC Crit. Rev. Biochem 25:173–207.
DeRisi et al., 1997, Science 278:680–686.
Dixon et al., 1995, *Physiol. Plant* 93:385.
Esterbauer et al., 1991, Biochem. J. 208:129–140.
Fahey and Sundquist 1991, Adv. Enzymol. Relat. Mol. Biol. 64:1–53.
Friling et al., 1992, Proc. Natl. Acad. Sci. USA 89:668–672.
Gietz et al., 1991, Yeast 7:252–263.
Harlow et al. 1988, Antibodies, A Laboratory Manual, Cold Spring Harbor, NY—(too voluminous to submit).
Higgins, 1995, *Cell* 82:693–696.
Hinder et al. 1966, *J. Biol. Chem.* 271:27233–27236.
Hirata et al., 1994, Mol. Gen. Genet. 242:250–257.
Hofte et al., 1993, *Plant J.*, 4:1051–1061.
Horsch et al. 1988, *Leaf Disc Transformation, Plant Molecular Biology Manual A5*:1.
Howden et al., 1995, *Plant Physiol.* 107:1067–1073.
Howden et al., 1995,*Plant Physiol.*107:1059–1066.
Howden et al., 1992, *Plant Physiol.* 99:100–107.
Huang et al, 1992, *Plant Mol. Biol.* 10:372–384.
Hyde et al., 1990, *Nature* 346:362–365.
Inze and Montagu 1995, Current Opinion in Biotech. 6:153–158.
Ishikawa et al., 1997, *Bioscience Reports*. 17:189–208.
Ishikawa et al., 1996, J. Biol. Chem. 271:14981–14988.
Ishikawa et al., 1994, *J. Biol. Chem.* 269:29085–29093.
Ishikawa 1989, J.Biol. Chem. 264:17343–17348.
Jansen et al., 1987, Hepatol. 7:71–76.
Jedlitschky et al., 1996, Cancer Res. 56:988–994.
Jefferson et al., 1987, EMBO J., 6:3901–3907.
Kang, 1992, *Drug Metabolism and Disposition* 20:714–718.
Kapoor et al., 1965, *Biochem. Biophys. Acta* 100:376–383.
Kieber et al., 1993, *Cell*, 72: 427–441.
Kim et al., 1995, *J. Biol. Chem.* 270:2630–2635.
Kim et al., 1994, *Proc. Natl. Acad. Sci. USA* 91:6128–6132.
Kohrer et al., 1991, *Methods in Enzymol.* 194:390–398.
Kowsower et al., *J. Am. Chem. Soc.* 102:4983–4993.
Krautler et al., 1992, *Plant Physiol. Biochem.* 30:333–346.
Kunst et al., 1989, *Biochim. Biophys. Acta* 983:123.
Kyte and Doolittle 1982, *J. Mol. Biol* 46:105–132.
Lagrimini et al., 1990, Plant Cell 2:7–18.
Lamoureux et al., 1986, *Pestic. Biochem. Physiol.* 26:323–342.
Leier et al., 1994, *J. Biol. Chem.* 269:27807–27810.
Li et al., 1955, *Metal Comp. of Sulfur–Containing Amino Acids, Duquesne Univ.*, 5225–5228.
Li et al., 1996, *J. Biol. Chem.* 271–6509–6517.
Li et al., 1995, *Plant Physiol.* 109:117–185.
Li et al., 1995, *Plant Physiol.* 107:1257–1268.
Li et al., 1954, *J. Am. Chem. Soc.* 76:225–229.
Maliga et al. 1994, *Methods in Plant Molecular Biology: A Laboratory Manual*, Cold Spring Harbor, New York—(too voluminous to submit).

(List continued on next page.)

*Primary Examiner*—David T. Fox
*Assistant Examiner*—Ousama M-Saiz Zaghmout
*Attorney, Agent, or Firm*—Evelyn H. McConathy; Dilworth Paxson LLP

[57] ABSTRACT

The invention includes an isolated DNA encoding a plant GS-X pump polypeptide and an isolated preparation of a plant GS-X pump polypeptide. Also included is an isolated preparation of a nucleic acid which is antisense in orientation to a portion or all of a plant GS-X pump gene. The invention also includes a cells, vectors and transgenic plants having an isolated DNA encoding a plant GS-X pump and methods of use thereof. In addition, the invention relates to plant GS-X pump promoter sequences and the uses thereof.

29 Claims, 40 Drawing Sheets

OTHER PUBLICATIONS

Mannervick et al., 1981, *Methods Enzymol.*, 77:231–235.
Marrs et al., 1995, *Nature*, 375:397–400.
Martinoia et al., 1993, *Nature* 364:247–249.
Muller et al., 1994, *Proc. Natl. Acad. Sci.* USA 91:13033–13037.
Nriagu et al., 1988, *Nature* 333:134–138.
Opheim 1978, *Biochem. Biophys. Acta* 524:121–125.
Oude Elferink et al., 1993 *Hepatology* 17:343–444.
Parry et al., 1980, *J. Biol. Chem.* 264:20025–20032.
Paulusma et al., 1996, Science 271:1126–1128.
Perrin et al., 1971, *Biochem. Biophys. Acta* 230:96–104.
Peterson 1977, *Anal. Biochem.* 83:346–356.
Raskin, 1996, *Proc. Natl. Acad. Sci. USA* 93:3164–3166.
Rea et al., 1992, *Plant Physiol.* 100:727–740.
Rea and Turner, 1990, *Methods Plant Biochem.* 3:385–405.
Roberts et al., 1991, *Methods. Enzymol.* 194:644–661.
Ruetz et al., 1994, Cell 77: 1071–1081.
Sambrook et al., 1989, *Molecular Cloning: A Laboratory Manual*, Cold Springs Harbor, NY (too voluminous sumbit).
Sathirakul et al., 1993, *J. Pharmacol. Exp. Therap.* 268:65–73.
Sherman et al., 1983, *Methods in Yeast Genetics*, Cold Springs Harbor Laboratory, New York—(too voluminous to submit).
Shrieve et al., 1988, *J. Biol. Chem.* 263:14107–12114.
Singhal et al., 1987, FASEB J. 1:220–223.
Srivstava and Beutler 1969, *J. Biol. Chem.* 244:9–16.
Szczypka et al., 1994, *J. Biol. Chem.* 269:22853–22857.
Takahashi et al., 1992, *Proc. Natl. Acad. Sci.* USA 89:56–59.
Teeter et al., 1990, *Mol. Cell. Biol.* 10:5728–5735.
Timmerman, 1989, *Physiol. Plant* 77:465.
Valvekens et al., 1988, *Proc. Natl. Acad. Sci. USA* 85:5536–5540.
van der Krol et al., 1988, Gene 72:45–50.
Walker et al., 1992, EMBO J. 1:945–951.
Wemmie et al., 1994, *J. Biol. Chem.* 269:32592–32597.
Wu et al., 1994, *Mol. Cell. Biol.* 14:5832–5839.
Ynagisawa et al., 1990, *J. Biol. Chem.* 265:19351–19355.
Zamam et al., 1995, *Proc. Natl. Acad. Sci. USA* 92:7690–7694.

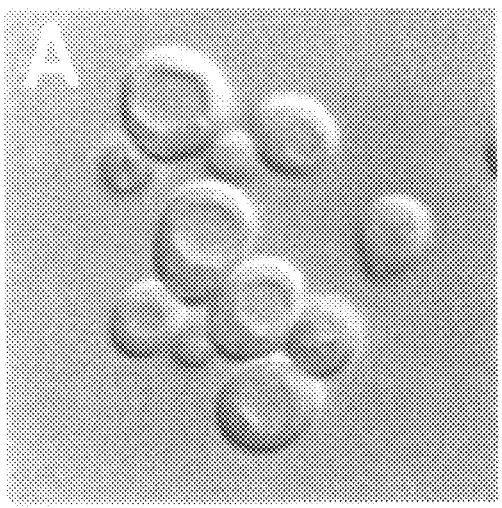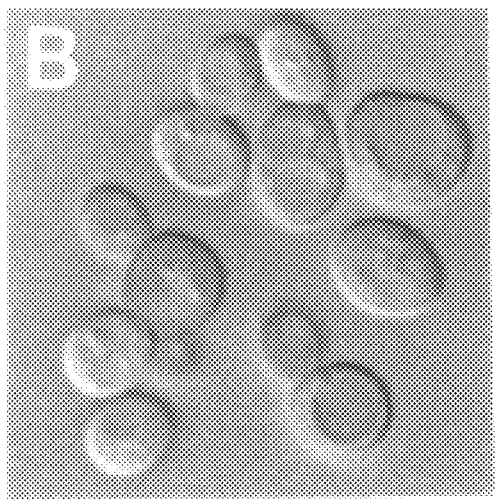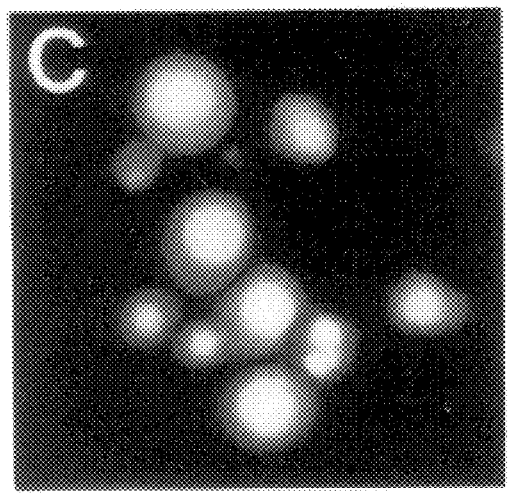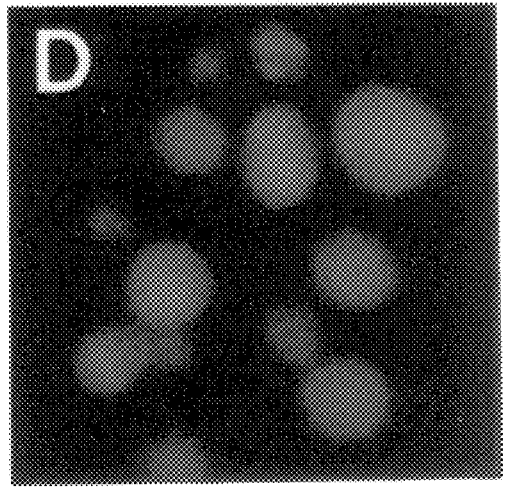
FIG. 7

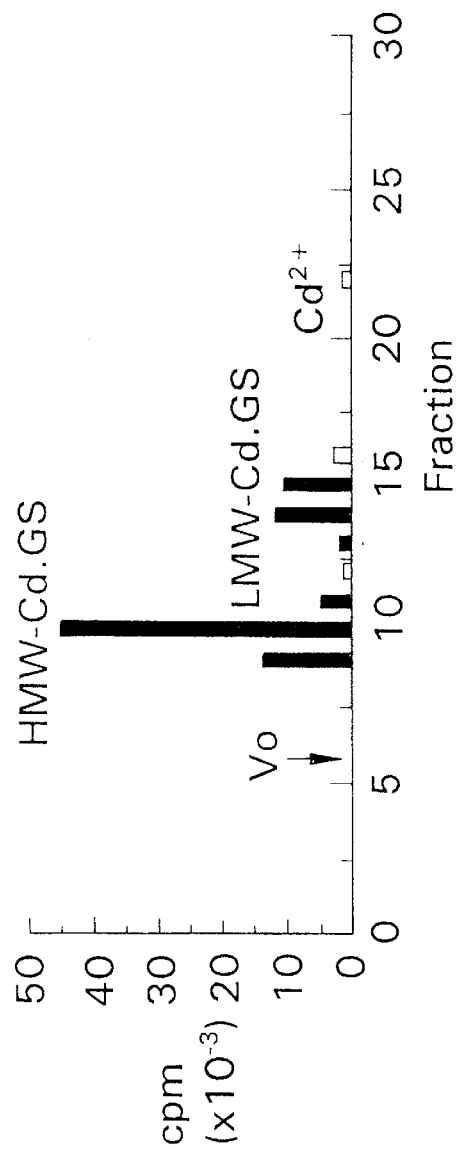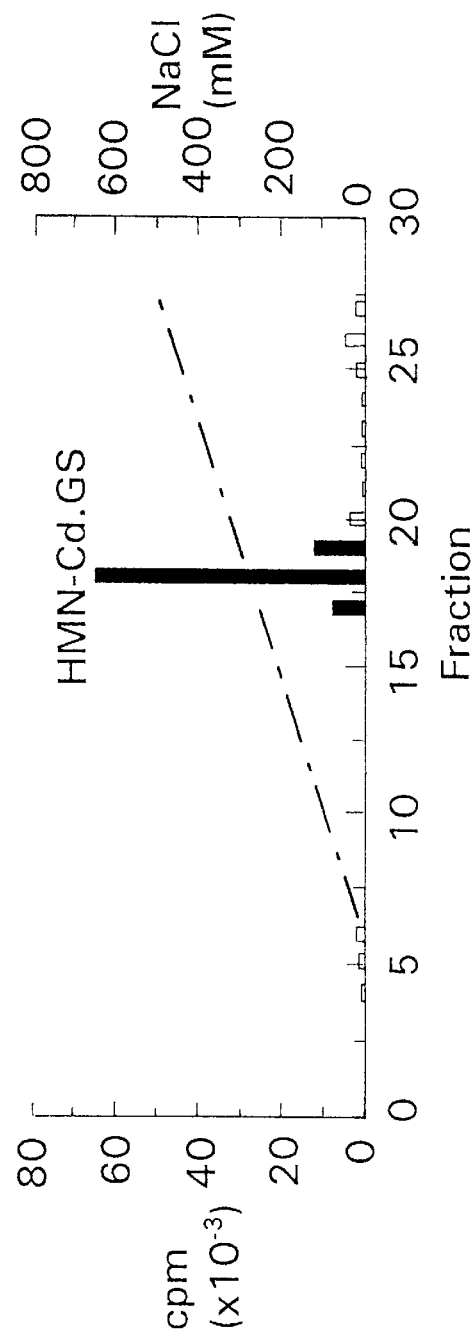

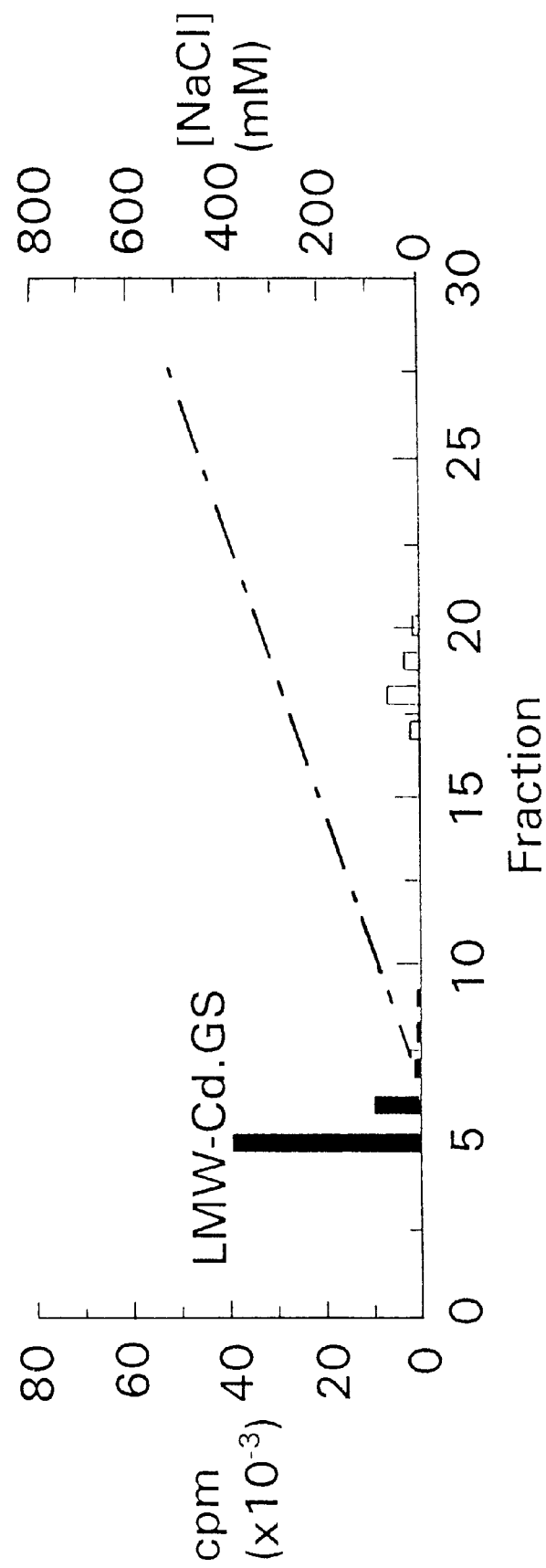

ttatgaaaatttattattttttgttgctatggttttttggaattagaagctcatttcaaagt
tgttgattttctttgcagggtagggaattggtgtggtagcttgtgatgcactgtgtttgag
ggaaaggaaaggataacgATGGGGTTTGAGTTTATTGAATGGTATTGTAAGCCGGTGCCTA
ATGGTGTGTGGACTAAAACAGTGGCTAATGCATTTGGTGCATACACGCCTTGTGCTACTGA
CTCTTTTGTGCTTGGTATCTCTCAACTGGTTCTGTTGGTTCTGTGCCTGTATCGTATATGG
CTCGCCTTAAAGGATCACAAGGTGGAGAGGTTCGTTTGAGGTCGAGATTGTATAACTATT
TCCTGGCTTTGTTGGCTGGTATGCTACTGCTGAGCCTTTGTTTAGATTGATCATGGGGATT
TCAGTTTTAGATTTTGATGGACCTGGACTTCCTCCTTTTGAGGCATTCGGATTGGGTGTCA
AAGCTTTTGCTTGGGGCGCTGTAATGGTCATGATTTTAATGGAAACTAAAATTTACATCCG
TGAACTCCGTTGGTATGTCAGGTTTGCTGTCATATATGCTCTTGTGGGGATATGGTCTTG
TTAAATCTTGTTCTCTCAGTCAAGGAGTACTATAGCAGTTATGTTCTGTATCTCTACACAA
GCGAAGTGGGAGCTCAGGTTCTGTTTGGAATTCTCTTGTTTATGCATCTTCCCAATTTGGA
TACTTACCCTGGCTACATGCCAGTGCGGAGTGAAACTGTGGATGATTATGAGTATGAAGAG
ATTTCTGATGGACAACAAATATGCCCTGAGAAGCATCCAAATATATTTGACAAAATCTTCT
CTCATGGATGAATCCCTTGATGACTTTGGGATCTAAAAGGCCTCTAACAGAGAAGGATGT
GTGGTATCTAGACACTTGGGATCAGACTGAAACTCTGTTCACGAGTTTCCAGCATTCCTGG
GATAAGGAACTACAAAAGCCGCAACCGTGGCTGTTGAGAGCATTGAACAATAGCCTGGGAG
GAAGGTTTTGGTGGGAGGATTTTGGAAGATCGGGAATGATTGCTCACAGTTTGTGGGACC
TCTTTTACTGAATCAACTCTTAAAGTCAATGCAAGAGGATGCGCCAGCTTGGATGGGTTAC
ATCTATGCGTTCTCAATCTTTGGTGGAGTGGTGTTCGGGGTGCTATGTGAAGCTCAATATT
TCCAGAATGTCATGCGTGTTGGTTACCGACTGAGATCTGCTCTGATTGCTGCTGTGTTCCG
CAAATCGTTGAGGTTAACTAATGAAGGTCGTAGAAAGTTTCAAACAGGAAAGATAACCAAC
TTAATGACGACTGATGCCGAATCTCTTCAGCAAATATGCCAATCACTTCATACCATGTGGT
CGGCTCCATTTCGTATAATTATAGCACTGATTCTCCTCTATCAGCAATTGGGTGTTGCCTC
GCTCATTGGTGCATTGTTGTTGGTCCTTATGTTCCCTTTACAGACTGTTATTATAAGCAAA
ATGCAGAAGCTGACAAAGGAAGGTCTGCAGCGTACTGACAAGAGAATTGGCCTTATGAATG
AAGTTTTAGCTGCAATGGATACAGTAAAGTGTTATGCTTGGGAAAACAGTTTCCAGTCCAA
GGTCCAAACTGTACGTGATGATGAATTATCTTGGTTCCGGAAATCACAGCTCCTGGGAGCG
TTGAATATGTTCATACTGAATAGCATTCCTGTTCTTGTGACTATTGTTTCATTTGGTGTGT
TCACATTACTTGGAGGAGACCTGACCCCTGCAAGAGCATTTACGTCACTCTCTCTCTTTGC
TGTGCTTCGTTTCCCTCTCTTCATGCTTCCAAACATTATAACTCAGGTGGTAAATGCTAAT
GTATCCTTAAAACGTCTTGAGGAGGTATTGGCGACAGAAGAAAGAATTCTCTTACCAAATC
CTCCCATTGAACCTGGAGAGCCAGCCATCTCAATAAGAAATGGATATTTCTCTTGGGATTC
TAAGGGGATAGGCCGACGTTGTCAAATATCAACTTGGATGTACCTCTTGGCAGCCTAGTT
GCTGTGGTTGGTAGTACAGGCGAAGGAAAAACCTCTCTAATATCTGCTATCCTTGGTGAAC
TTCCTGCAACATCTGATGCAATAGTTACTCTCAGAGGATCAGTTGCTTATGTTCCACAAGT
TTCATGGATCTTTAATGCAACAGTACGCGACAATATACTGTTTGGTTCTCCTTTCGACCGT
GAAAAGTATGAAAGGGCCATTGATGTGACTTCACTGAAGCATGACCTAGAGTTACTGCCTG
GTGGTGATCTCACGGAGATTGGAGAAAGAGGTGTTAATATCAGTGGAGGACAGAAGCAGAG
GGTTTCCATGGCTAGGGCCGTTTACTCAAATTCAGATGTGTACATCTTTGATGACCCGTTA
AGTGCCCTTGATGCTCATGTTGGTCAACAGGTTTTTGAAAAATGCATAAAAAGAGAACTGG
GGCAGAAAACGAGAGTTCTTGTTACAAACCAGCTCCACTTCCTATCACAAGTGGACAGAAT
TGTACTTGTGCATGAAGGCACAGTGAAAGAGGAAGGAACATATGAAGAGCTATCCAGTAAT
GGCCCTTTGTTCCAGAGGCTAATGGAAATGCAGGGAAGGTGGAAGAATATTCAGAAGAAA
ATGGAGAAGCTGAGGCAGATCAAACAGCGGAACAACCAGTTGCGAATGGGAACACAAATGG
TCTTCAAATGGATGGAAGTGACGATAAAAAATCCAAAGAAGGAAATAAAAAGGAGGGAAA
TCTGTCCTCATCAAGCAAGAAGAACGTGAAACCGGAGTTGTAAGTTGGAGAGTCCTGAAGA
GGTACCAGGATGCACTTGGAGGGCATGGGTAGTGATGATGCTCCTTTTATGTTACGTCTT
AACAGAAGTATTTCGGGTTACTAGCAGCACGTGGTTGAGTGAGTGGACTGATGCAGGAACT
CCAAAGAGTCATGGACCCCTTTTCTACAATCTCATATATGCACTTCTCTCGTTTGGACAGG
TTTTGGTGACATTGACCAATTCATATTGGTTGATTATGTCCAGTCTTTATGCAGCTAAGAA
GTTACACGACAATATGCTTCATTCCATACTGAGGGCCCCGATGTCCTTCTTCCATACCAAT
CCGCTAGGACGGATAATCAATCGATTCGCAAAAGATCTGGGTGATATTGATCGAACTGTGG
CCGTCTTTGTAAACATGTTTATGGGTCAAGTCTCACAGCTTCTTTCAACTGTAGTGTTGAT
```

FIG. 13A

```
TGGCATTGTAAGCACTTTGTCCTTGTGGGCCATCATGCCCCTCCTGGTCTTGTTTTATGGA
GCTTATCTTTATTATCAGAACACAGCCCGTGAGGTTAAGCGTATGGATTCAATTTCAAGAT
CGCCTGTTTATGCACAGTTTGGAGAGGCATTGAATGGCTTATCAACTATCCGTGCTTACAA
AGCATATGATCGTATGGCTGATATCAACGGAAGATCAATGGATAATAACATCAGATTCACT
CTTGTCAACATGGGTGCCAATCGGTGGCTTGGAATCCGTTTAGAAACTCTGGGTGGTCTTA
TGATATGGCTGACAGCATCGTTTGCTGTCATGCAGAATGGAAGAGCGGAGAACCAACAGGC
ATTTGCATCTACAATGGGTTTGCTTCTCAGTTATGCCTTAAATATTACTAGCTTGTTAACA
GGTGTTCTGAGACTTGCGAGTTTGGCTGAGAATAGTCTAAACGCGGTCGAGCGTGTTGGCA
ATTATATAGAGATTCCGCCAGAGGCTCCGCCTGTCATTGAGAACAACCGTCCACCTCCTGG
ATGGCCATCATCTGGATCCATAAAGTTTGAGGATGTTGTTCTCCGTTACCGCCCTCAGTTA
CCGCCTGTGCTTCATGGGGTTTCTTTCTTCATTCATCCAACAGATAAGGTGGGGATTGTTG
GAAGGACTGGTGCTGGAAAGTCAAGCCTGTTAATGCATTGTTTAGAATTGTGGAGGTGGA
AGAAGGAAGGATCTTAATCGATGATTGTGACGTTGGAAAGTTTGGACTGATGGACCTACGT
AAAGTGCTCGGAATCATTCCACAGTCACCGGTTCTTTTCTCAGGAACTGTGAGGTTCAATC
TTGATCCATTTGGTGAACACAATGATGCTGATCTTTGGGAATCTCTAGAGAGGGCACACTT
GAAGGATACCATCCGCAGAAATCCTCTTGGTCTTGATGCTGAGGTCTCTGAGGCAGGAGAG
AATTTCAGCGTGGGACAGAGGCAATTGTTGAGTCTTTCACGTGCGCTGTTACGGAGATCTA
AGATACTCGTCCTTGATGAAGCAACTGCTGCTGTAGATGTTAGAACCGATGCCCTCATTCA
GAAGACTATCCGAGAAGAATTCAAGTCATGCACGATGCTCATTATCGCTCACCGTCTCAAT
ACCATCATTGACTGTGACAAAATTCTCGTGCTTGATTCTGGAAGAGTTCAAGAATTCAGTT
CACCGGAGAACCTTCTTTCAAATGAAGGAAGCTCTTTCTCCAAGATGGTTCAAAGCACTGG
AGCTGCAAATGCTGAGTACTTGCGTAGTTTAGTACTCGACAACAAGCGTGCCAAAGATGAC
TCACACCACTTACAAGGCCAAAGGAAATGGCTGGCTTCTTCTCGCTGGGCTGCAGCCGCTC
AGTTTGCTCTGGCTGCGAGTCTTACTTCGTCGCACAACGATCTTCAAAGCCTTGAAATTGA
AGATGACAGCAGCATTTTGAAGAGAACAAACGATGCAGTTGTGACTCTGCGCAGTGTTCTC
GAGGGGAAACACGACAAAGAGATTGCAGAGTCGCTTGAGGAACATAATATCTCTAGAGAGG
GATGGTTGTCATCACTCTATAGAATGGTAGAAGGGCTTGCAGTGATGAGCAGATTGGCAAG
GAACCGAATGCAACAACCGGATTACAATTTCGAAGGAAATACATTTGACTGGGACAACGTC
GAGATGTAGataagttcatgttaaactaggaatcattgtctcttccgtaagaaacatatat
ttatcttaaccaaaattattagtttggtttccatttcataaacttaattttcacctgcaaa
gaaaatcaaaccctgttgtgttcttcgtgataagtagagaaattacttgagtatccttcta
actcaaaaaaaaaaaaaaaaaaaaaaaaaaaaaaaaaaaaaaaaa
```

FIG. 13B

```
gactcgataccatcttaaatgcagagtcttttcgtgataataaaattatggattcgtttca
aagttttttttttttcgtatggaaaacacttgagctctctcaatcttgtagtcttgactct
tgatgattcttctatgttctcgttgtgattgcttgtcactgttctatctttatatatgatt
aaatgcaattttgccccttttttacgcgcgaatgtatttattatctttcgcactctgggtcc
atttcttgtcacttgagcacataatgattgatttatgacttttaaagttatgaaaattta
ttattttgttgctatggttttttggaattagaagctcatttcaaagttgttgattttctt
tgcagggtagggaattggtgtggtagcttgtgatgcactgtgtttgagggaaaggaaagga
taacgATGGGGTTTGAGTTTATTGAATGGTATTGTAAGCCGGTGCCTAATGGTGTGTGGAC
TAAAACAAGTGGCTAATGCATTTGGTGCATACACGCCTTGTGCTACTGACTCTTTTGTGCT
TGGTATCTCTCAACTGGTTCTGTTGGTTCTGTGCCTGTATCGTATATGGCTCGCCTTAAAG
GATCACAAGGTGGAGAGGTTCTGTTTGAGGTCGAGATTGTATAACTATTTCCTGGCTTTGT
TGGCTGCGTATGCTACTGCTGAGCCTTTGTTTAGATTGATCATGGGGATTTCAGTTTTAGA
TTTTGATGGACCTGGACTTCCTCCTTTTGAGgtgctttatttctgttccttattctttat
cttttagtttgttgtgtatgttttacctgaaacatgctattgtttgtgtgatttctttggc
agGCATTCGGATTGGGTGTCAAAGCTTTTGCTTGGGGCGCTGTAATGGTCATGATTTTAAT
GGAAACTAAAATTTACATCCGTGAACTCCGTTGGTATGTCAGGTTTGCTGTCATATATGCT
CTTGTGGGGATATGGTCTTGTTAAATCTTGTTCTCTCAGTCAAGGAGTACTATAGCAGgt
tggtacaattttggagttactttggtttattgaagtcattgttcttcttctacagggtgaa
ttcatgttttgttttcattgcagTTATGTTCTGTATCTCTACACAAGCGAAGTGGGAGCTC
AGgttagctcacttggactccttagagagtccagaatcctagcatgtgctatgattataa
atcagaatccgatacagtttgttttctaacatcttaagagggtgaattttggttttacttc
agGTTCTGTTTGGAATTCTCTTGTTTATGCATCTTCCCAATTTGGATACTTACCCTGGCTA
CATGCCAGTGCGGAGTGAAACTGTGGATGATTATGAGTATGAAGAGATTTCTGATGGACAA
CAAATATGCCCTGAGAAGCATCCAAATATATTTGACAgtaagtcactctacatgattttca
tttggtcgcctggctgaaacttataattagtaatcataatttgcaaacatcgtctctgact
tttgttcagattgatcatggggatttaggttttgaaatttcacctgatttccttcttccaa
tttccttgtttggtcacagAAATCTTCTTCATGGATGAATCCCTTGATGACTTTGGGAT
CTAAAAGGCCTCTAACAGAGAAGGATGTGTGGTATCTAGACACTTGGGATCAGACTGAAAC
TCTGTTCACGAGtacttctaacaataattatatctcttaaaatgtatattactgaattgg
ctatttgatatttctgtatccttttttagTTTCCAGCATTCCTGGGATAAGGAACTACAAA
AGCCGCAACCGTGGCTGTTGAGAGCATTGAACAATAGCCTGGGAGGAAGgtagatagattt
tctcaccttatcgtgctgtgttctcatctcttttgagttttgagtatgattagatagtgct
ggatttcactgtgatgtgcagatgtttaagtgatctcttgaaagaaccatcaggttttag
aatgtgtaggaagcaagatcagaatatttctacttatttaatgttagttgtttgctatagc
agcttaacacatttccatcttatcataggcaatcatgcttgctttcgtactcttataaatt
taagacatagggatacaacttttactgtagattggttaaatatgtttttttttcttggtt
catattgcttaagcattatttcgtttgttaactacatgtcgtatggggatctaatttttg
aattttgtagGTTTTGGTGGGGAGGATTTTGGAAGtattttcgtctacctcttctctttt
tattcgtgcttccagagtcttttcctctcttttattcatatgatcacaggttctgcgtcatg
ttggataaccttctgtcacgtggaagtcatttataatttacatggtgttacagattattag
aaggaactagtgggttcttagttttctttatcaattcattgtacttgaacatatttattt
acatttgtatgcacagATCGGGAATGATTGCTCACAGTTTGTGGGACCTCTTTTACTGAAT
CAACTCTTAAAGtttgttcttttcttggcagattcggaaacctattattggttcaatatt
cttatctgacaatatctctcattttggatgtcaaactatatacagTCAATGCAAGAGGATG
CGCCAGCTTGGATGGGTTACATCTATGCGTTCTCAATCTTTGGTGGAGTGgtatgaaatga
agtcctctttctctctctctctgtctatttggactctcttctatcaacttgtgaaactg
acacttgttatacttctgtatgtttggtctaaggttcttctaaactgattataatagcaac
actagatgtcccctaatgccacttttgatttgttgctcttggatttttgcgtctgtta
gataggttctgactttatctagtgtagggtgatacttaaagctacaaactcatcgagtgac
tgatgttgatgacaacgtttctagGTGTTCGGGGTGCTATGTGAAGCTCAATATTTCCAGA
ATGTCATGCGTGTTGGTTACCGACTGAGATCTGCTCTGtaaattttaaatttgctaccct
gacgttcttcctttgccatatgttttggtgcagatatgtttgctgatagcatgattccca
gtatcttgtataggaataagtatatcaacatggtttctttatcctctatatatgatgcata
aataagccttgtgccaaaagtttaggaataagtttgtgttgcttcagatgattgagtatgc
```

FIG. 14A

```
tgttttattctggaaatttccaccattttcagatcctttcactagagaaatacaaattt
agctgtatttcctgattcagttcatcgttttctgcgtttgtagtggagtgaaattagcttg
tacgaaatggaagatattttgaacacagatgatttttaaaattggtcttcctgttgatgac
tgttttttttttagATTGCTGCTGTGTTCCGCAAATCGTTGAGGTTAACTAATGAAGGTCG
TAGAAAGTTTCAAACAGGAAAGATAACCAACTTAATGACGACTGATGCCGAATCTCTTCAG
gtgagtatccctttcatattttcgaattcaagtttgcatgtttctctatatcatagttgca
gggctgttaacatccggatcttgaatatttattttgtccgcagctggtattgagtgggtt
acagttacttttatgttcggtaatagaagttggatttacttagaaatgatttccagcata
ctgatctactgaatctgtttgttaggtctaagattggctatgaatagtgattgcattttca
tttctagctagcactttgttatcattgaattttctttcttcttttttattttgtttctta
tgccaacttaaactgtgtcttgtttaatgttttcgtcttaactgtgtctggtatcaatatt
gttatctaatcaaccagatgtactttgtactaattttccattttctgtggcagCAAATAT
GCCAATCACTTCATACCATGTGGTCGGCTCCATTTCGTATAATTATAGCACTGATTCTCCT
CTATCAGCAATTGGGTGTTGCCTCGCTCATTGGTGCATTGTTGTTGGTCCTTATGTTCCCT
TTACAGgtacatgacttctaaatttcctcattttttttcctttgtagcttattttctcta
tactgttcgcttgttcattcgtactcctaaaggctacttcttcttcgtctcctgaacttgt
tctctgttttcttaaaacagACTGTTATTATAAGCAAAATGCAGAAGCTGACAAAGGAAGG
TCTGCAGCGTACTGACAAGAGAATTGGCCTTATGAATGAAGTTTTAGCTGCAATGGATACA
GTAAAgtaagaaattctagaaccaattttgttaacatagttattaatttgcaggaaacttg
tactaaaccaaaatgctacagGTGTTATGCTTGGGAAAACAGTTTCCAGTCCAAGGTCCAA
ACTGTCGTGATGATGAATTATCTTGGTTCCGGAAATCACAGCTCCTGGGAGCGgtatgact
acagcgtagttacttttgttttcctctaattattgtatatttctaactcttgcttggtct
tgtcttgttttgcagTTGAATATGTTCATACTGAATAGCATTCCTGTTCTTGTGACTATTG
TTTCATTTGGTGTGTTCACATTACTTGGAGGAGACCTGACCCCTGCAAGAGCATTTACGTC
ACTCTCTCTTTGCTGTGCTTCGTTTCCCTCTCTTCATGCTTCCAAACATTATAACTCAG
gtgatttcttaaatatgttgttgcaatgcatgtgtattaagtagaactgttagtgcttgta
gtaactgtcgtttggttatcaaatccatgacttatatttcgaatttacatgctggagggta
tccttgctggtgccagaaacagatgccgatgctgactagttttcacttgtagGTGGTAAAT
GCTAATGTATCCTTAAAACGTCTTGAGGAGGTATTGGCGACAGAAGAAAGAATTCTCTTAC
CAAATCCTCCCATTGAACCTGGAGAGCCAGCCATCTCAATAAGAAATGGATATTTCTCTTG
GGATTCTAAGgtgtcgcttggctattctataccatgttccttctttcgcttctctcattac
ctttatccatagaaagtacaaaaatcgagctaaccctatgtatctacagGGGGATAGGCCG
ACGTTGTCAAATATCAACTTGGATGTACCTCTTGGCAGCCTAGTTGCTGTGGTTGGTAGTA
CAGGCGAAGGAAAAACCTCTCTAATATCTGCTATCCTTGGTGAACTTCCTGCAACATCTGA
TGCAATAGTTACTCTCAGAGGATCAGTTGCTTATGTTCCACAAGTTTCATGGATCTTTAAT
GCAACAgtatgttcttcttttctttgacttttaagttgggctgacgttgcaaattttctg
ttgtacataatgttaaatgtattttctgtcttttatagtagaacaatatgtgttctcaaat
gcgtcagttacttcaccaacttagtggaaaccttcttcaatatttgattctctaagctatt
ttgaacagaagactgatatgcattttcttataaaaatttgtagGTACGCGACAATATACTG
TTTGGTTCTCCTTTCGACCGTGAAAAGTATGAAAGGGCCATTGATGTGACTTCACTGAAGC
ATGACCTAGAGTTACTGCCTgtaagttttgaggagagcttcgtggagttgataacaaggat
ttgtcttgcctgttctcgtgttgctaagtttgtttcaacctcttttctcttgcttaatagGG
TGGTGATCTCACGGAGATTGGAGAAAGAGGTGTTAATATCAGTGGAGGACAGAAGCAGAGG
GTTTCCATGGCTAGGGCCGTTTACTCAAATTCAGATGTGTACATCTTTGATGACCCGTTAA
GTGCCCTTGATGCTCATGTTGGTCAACAGgtactaactcattgattctctttgataaggct
agtctatttcattttgaatttatctaacattttgtgtctggtcattatgggaatactgt
cagtctgatttctaggaatattgtttcagGTTTTTGAAAAATGCATAAAAAGAGAACTGGG
GCAGAAAACGAGAGTTCTTGTTACAAACCAGCTCCACTTCCTATCACAAGTGGACAGAATT
GTACTTGTGCATGAAGGCACAGTGAAAGAGGAAGGAACATATGAAGAGCTATCCAGTAATG
GGCCTTTGTTCCAGAGGGTAATGGAAAATGCAGGGAAGGTGGAAGAATATTCAGAAGAAAA
TGGAGAAGCTGAGGCAGACCAAACAGCGGAACAACCAGTTGCGAATGGGAACACAAATGGT
CTTCAAATGGATGGAAGTGACGATAAAAAATCCAAAGAAGGAAATAAAAAGGAGGGAAAT
CTGTCCTCATCAAGCAAGAAGAACGTGAAACCGGAGTTGTAAGTTGGAGAGTCCTGAAGAG
gtaacttgaacatttggcttttgcaatcttactatttgtttgcaactttccccatactcga
```

FIG. 14B tccaagaggtccattcatttgtggtgtttcacaacaaactagcatgttccttatgttttta
ggctgaactataccttttgcgggatatcagaatgacttttccaggcttttcaatgttttcagG
TACCAGGATGCACTTGGAGGGGCATGGGTAGTGATGATGCTCCTTTTATGTTACGTCTTAA
CAGAAGTATTTCGGGTTACTAGCAGCACGTGGTTGAGTGAGTGGACTGATGCAGGAACTCC
AAAGAGTCATGGACCCCTTTTCTACAATCTCATATATGCACTTCTCTCGTTTGGACAGgta
tgagttatgtttgcttgatggatgagtgaagatttgatataatcttgacctcatgatataa
catatatagctgaaacctgaccagcttagaaagatcttatataattctacttttgtgattt
tactttgagaatccaaaggtggaggtagaaaaggttagtaaagaattgattttttttgctga
gactcttcttcttgcttacagGTTTTGGTGACATTGACCAATTCATATTGGTTGATTATG
TCCAGTCTTTATGCAGCTAAGAAGTTACACGACAATATGCTTCATTCCATACTGAGGGCCC
CGATGTCCTTCTTCCATACCAATCCGCTAGGACGGATAATCAATCGATTCGCAAAGATCT
GGGTGATATTGATCGAACTGTGGCCGTCTTTGTAAACATGTTTATGGGTCAAGTCTCACAG
CTTCTTTCAACTGTAGTGTTGATTGGCATTGTAAGCACTTTGTCCTTGTGGGCCATCATGC
CCCTCCTGGTCTTGTTTTATGGAGCTTATCTTTATTATCAGgtaatgtaccttctgaccgc
agcatttaaataactgagattaagtgacagaaagagaaaaggacacagatgatggatgtta
cacatacttttttagcctcatttgtcatgtctgagttcgtttggtgcttaagctatctaca
ctcatctgtcaccaaaaatcatgctgtatatgttgtgtgttaaatatttttcttattgcag
AACACAGCCCGTGAGGTTAAGCGTATGGATTCAATTTCAAGATCGCCTGTTTATGCACAGT
TTGGAGAGGCATTGAATGGCTTATCAACTATCCGTGCTTACAAAGCATATGATCGTATGGC
TGATATCAACGGAAGATCAATGGATAATAACATCAGATTCACTCTTGTCAACATGGGTGCC
AATCGGTGGCTTGGAATCCGTTTAGAAACTCTGGGTGGTCTTATGATATGGCTGACAGCAT
CGTTTGCTGTCATGCAGAATGGAAGAGCGGAGAACCAACAGGCATTTGCATCTACAATGGG
TTTGCTTCTCAGTTATGCCTTAAATATTACTAGCTTGTTAACAGGTGTTCTGAGACTTGCG
AGTTTGGCTGAGAATAGTCTAAACGCGGTCGAGTGTTGGCAATTATATAGAGATTCCGCCA
GAGGTCCGCCTGTCATTGAGAACAACCGTCCACCTCCTGGATGGCCATCATCTGGATCCAT
AAAGTTTGAGGATGTTGTTCTCCGTTACCGCCCTCAGTTACCGCCTGTGCTTCATGGGGTT
TCTTTCTTCATTCATCCAACAGATAAGGTGGGGATTGTTGGAAGGACTGGTGCTGGAAAGT
CAAGCCTGTTAATGCATTGTTTAGAATTGTGGAGGTGGAAAAAGGAAGGATCTTAATCGA
TGATTGTGACGTTGGAAAGTTTGGACTGATGGACCTACGTAAAGTGCTCGGAATCATTCCA
CAGTCACCGGTTCTTTTCTCAGGAACTGTGAGGTTCAATCTTGATCCATTTGGTGAACACA
ATGATGCTGATCTTTGGGAATCTCTAGAGAGGGCACACTTGAAGGATACCATCCGCAGAAA
TCCTCTTGGTCTTGATGCTGAGgtattcagttgctgcctatattgatatgaagtctcattt
tttaagtggtaataactgattttcaatctttgttcagGTCTCTGAGGCAGGAGAGAATTTC
AGCGTGGGACAGAGGCAATTGTTGAGTCTTTCACGTGCGCTGTTACGGAGATCTAAGATAC
TCGTCCTTGATGAAGCAACTGCTGCTGTAGATGTTAGAACCGATGCCCTCATTCAGAAGAC
TATCCGAGAAGAATTCAAGTCATGCACGATGCTCATTATCGCTCACCGTCTCAATACCATC
ATTGACTGTGACAAAATTCTCGTGCTTGATTCTGGAAGAtatgatttaaacactctctc
tctttcaatctcacactctccttgtttctcagctaacctgttctattccaatttgttaact
cagGTTCAAGAATTCAGTTCACCGGAGAACCTTCTTTCAAATGAAGGAAGCTCTTTCTCCA
AGATGGTTCAAAGCACTGGAGCTGCAAATGCTGAGTACTTGCGTAGTTTAGTACTCGACAA
CAAGCGTGCCAAAGATGACTCACACCACTTACAAGGCCAAAGGAAATGGCTGGCTTCTTCT
CGCTGGGCTGCAGCCGCTCAGTTTGCTCTGGCTGCGAGTCTTACTTCGTCGCACAACGATC
TTCAAAGCCTTGAAATTGAAGATGACAGCAGCATTTTGAAGAGAACAAACGATGCAGTTGT
GACTCTGCGCAGTGTTCTCGAGGGGAAACACGACAAAGAGATTGCAGAGTCGCTTGAGGAA
CATAATATCTCTAGAGAGGGATGGTTGTCATCACTCTATAGAATGGTAGAAGgtaaaccaa
atatgcatctctacaaatgcttatgcaaaatcttaatcaccacactgaaacattaaagtca
aatcgtgctcttatattgcaagcctgctttccgctgtctacgtttcagGCTTGCAGTGAT
GAGCAGATTGGCAAGGAACCGAATGCAACAACCGGATTACAATTTCGAAGGAAATACATTT
GACTGGGACAACGTCGAGATGTAGATAAGTTCATGTTAAACTAGGAATCATTGTCTCTTCC
GTAAGAAACATATATTTATCTTAACCAAAATTATTAGTTTGGTTTCCATTTCATAAACTTA
ATTTTCACCTGCAAAGAAAATCAAACCCTGTTGTGTTCTTCGTGATAAGTAGAGAAATTAC
TTGAGTATCCTTCTAACTCataaatgggatctcatgattcatgaacaagcagcaacacaat
aatacccttttcagattttggagctggacaaagttgtt.aagttgagtttctcttacagtca

FIG. 14C ttcatatacaaaaacctcttcgactgaagcaccaagaaagaaacaaacatcaaaagggaat
gaggtcttttcttagggctgagatcatcggaatgtgggagtgcggaacacgacc

FIG. 14D

```
MGFEFIEWYCKPVPNGVWTKTVANAFGAYTPCATDSFVLGISQLVLLVLCLYRIWLALKD
HKVERFCLRSRLYNYFLALLAAYATAEPLFRLIMGISVLDFDGPGLPPFEAFGLGVKAFA
WGAVMVMILMETKIYIRELRWYVRFAVIYALVGDMVLLNLVLSVKEYYSSYVLYLYTSEV
GAQVLFGILLFMHLPNLDTYPGYMPVRSETVDDYEYEEISDGQQICPEKHPNIFDKIFFS
WMNPLMTLGSKRPLTEKDVWYLDTWDQTETLFTSFQHSWDKELQKPQPWLLRALNNSLGG
RFWWGGFWKIGNDCSQFVGPLLLNQLLKSMQEDAPAWMGYIYAFSIFGGVVFGVLCEAQY
FQNVMRVGYRLRSALIAAVFRKSLRLTNEGRRKFQTGKITNLMTTDAESLQQICQSLHTM
WSAPFRIIALILLYQQLGVASLIGALLLVLMFPLQTVIISKMQKLTKEGLQRTDKRIGL
MNEVLAAMDTVKCYAWENSFQSKVQTVRDDELSWFRKSQLLGALNMFILNSIPVLVTIVS
FGVFTLLGGDLTPARAFTSLSLFAVLRFPLFMLPNIITQVVNANVSLKRLEEVLATEERI
LLPNPPIEPGEPAISIRNGYFSWDSKGDRPTLSNINLDVPLGSLVAVVGSTGEGKTSLIS
AILGELPATSDAIVTLRGSVAYVPQVSWIFNATVRDNILFGSPFDREKYERAIDVTSLKH
DLELLPGGDLTEIGERGVNISGGQKQRVSMARAVYSNSDVYIFDDPLSALDAHVGQQVFE
KCIKRELGQKTRVLVTNQLHFLSQVDRIVLVHEGTVKEEGTYEELSSNGPLFQRLMENAG
KVEEYSEENGEAEADQTAEQPVANGNTNGLQMDGSDDKKSKEGNKKGGKSVLIKQEERET
GVVSWRVLKRYQDALGGAWVVMMLLLCYVLTEVFRVTSSTWLSEWTDAGTPKSHGPLFYN
LIYALLSFGQVLVTLTNSYWLIMSSLYAAKKLHDNMLHSILRAPMSFFHTNPLGRIINRF
AKDLGDIDRTVAVFVNMFMGQVSQLLSTVVLIGIVSTLSLWAIMPLLVLFYGAYLYYQNT
AREVKRMDSISRSPVYAQFGEALNGLSTIRAYKAYDRMADINGRSMDNNIRFTLVNMGAN
RWLGIRLETLGGLMIWLTASFAVMQNGRAENQQAFASTMGLLLSYALNITSLLTGVLRLA
SLAENSLNAVERVGNYIEIPPEAPPVIENNRPPPGWPSSGSIKFEDVVLRYRPQLPPVLH
GVSFFIHPTDKVGIVGRTGAGKSSLLNALFRIVEVEEGRILIDDCDVGKFGLMDLRKVLG
IIPQSPVLFSGTVRFNLDPFGEHNDADLWESLERAHLKDTIRRNPLGLDAEVSEAGENFS
VGQRQLLSLSRALLRRSKILVLDEATAAVDVRTDALIQKTIREEFKSCTMLIIAHRLNTI
IDCDKILVLDSGRVQEFSSPENLLSNEGSSFSKMVQSTGAANAEYLRSLVLDNKRAKDDS
HHLQGQRKWASSRWAAAAQFALAASLTSSHNDLQSLEIEDDSSILKRTNDAVVTLRSVLE
GKHDKEAESLEEHNISREGWLSSLYRMVEGLAVMSRLARNRMQQPDYNFEGNTFDWDNVE
M
```

FIG. 15

```
gaattcgcggccgccggcgaatttgcactctttacctctctttgactccgtgagattcgag
gattgttagtttcttgtgatgtgtagtctttgaagcaggggattttttattgtattgaggaa
gaagATGGGGTTTGAGCCGTTGGATTGGTATTGCAAGCCGGTGCCGAATGGTGTGTGGACT
AAAACTGTGGATTATGCGTTTGGTGCATACACGCCTTGTGCTATTGACTCTTTTGTGCTTG
GTATCTCTCATCTGGTTCTGTTGATTCTGTGTCTTTATCGCTTGTGGCTCATCACGAAGGA
TCACAAAGTGGATAAGTTCTGCTTGAGGTCTAAATGGTTTAGCTATTTTCTGGCTCTTTTG
GCTGCTTATGCTACTGCGGAGCCTTTGTTTAGATTGGTCATGAGGATCTCTGTTTTGGATT
TGGATGGAGCTGGGTTTCCTCCCTATGAGGCGTTTATGTTGGTCCTTGAGGCTTTTGCTTG
GGGTTCTGCTTTGGTCATGACTGTTGTGGAAACTAAAACGTATATCCATGAACTCCGTTGG
TATGTCAGATTCGCTGTCATTTATGCTCTTGTGGGAGACATGGTGTTGTTAAATCTTGTTC
TCTCTGTTAAGGAGTACTATGGCAGTTTTAAACTGTATCTTTACATAAGCGAGGTGGCAGT
TCAGGTTGCATTTGGAACCCTCTTGTTTGTGTATTTCCCTAATTTGGACCCTTACCCTGGT
TACACACCAGTTGGGACTGAAAATTCCGAGGATTACGAGTATGAAGAGCTTCCTGGAGGAG
AAAATATATGTCCTGAGAGGCATGCAAATTTATTTGACAGTATCTTCTTCTCATGGTTGAA
CCCATTGATGACTCTGGGATCAAAACGACCTCTCACCGAGAAGGATGTATGGCATCTGGAC
ACTTGGGATAAAACTGAAACTCTTATGAGGAGCTTCCAGAAGTCCTGGGATAAGGAACTAG
AAAAGCCCAAACCGTGGCTTTTGAGAGCACTGAACAACAGCCTTGGGGGAAGGTTTTGGTG
GGGTGGCTTTTGGAAGATTGGGAATGACTGTTCACAGTTCGTGGGGCCTCTTCTACTGAAT
GAGCTCTTAAAGTCAATGCAACTTAATGAACCAGCGTGGATAGGTTACATCTATGCAATCT
CAATCTTTGTTGGAGTGGTATTGGGGGTTTTATGTGAAGCTCAGTATTTCCAAAATGTGAT
GCGTGTTGGTTACCGGCTTAGGTCTGCACTGATTGCTGCTGTGTTCCGAAAATCTTTGAGG
CTAACTAATGAGGGGCGGAAGAAGTTTCAAACAGGAAAAATAACAAACTTAATGACTACTG
ATGCTGAGTCGCTGCAGCAAATCTGCCAATCACTTCATACCATGTGGTCGGCGCCATTTCG
TATAATTGTAGCACTGGTTCTCCTCTATCAACAATTGGGTGTTGCCTCGATCATTGGTGCA
TTGTTTCTTGTCCTTATGTTCCCCATACAGACTGTTATTATAAGCAAAACGCAGAAGTTAA
CAAAAGAAGGGTTGCAGCGTACTGACAAGAGAATTGGCCTAATGAATGAGGTTTTAGCGGC
AATGGATACAGTGAAGTGTTACGCTTGGGAAAACAGTTTTCAGTCCAAGGTTCAAACTGTA
CGTGATGATGAATTATCTTGGTTCCGGAAAGCACAACTCCTGTCAGCGTTCAATATGTTCA
TACTAAACAGCATCCCTGTCCTCGTGACTGTTGTTTCATTTGGTGTGTTCTCATTGCTTGG
AGGAGATCTGACACCTGCAAGAGCGTTTACGTCACTCTCTCTATTTTCTGTGCTTCGCTTC
CCTTTATTCATGCTTCCAAACATTATAACTCAGATGGTAAATGCTAATGTATCCTAAACCG
TTTGGAGGAGGTACTGTCAACCGAAGAGAGAGTTCTCTTACCGAATCCTCCCATTGAACCT
GGACAGCCAGCTATCTCAATAAGAAATGGATACTTCTCCTGGGATTCAAAGGCGGATAGGC
CAACATTGTCAAACATCAACCTGGACATACCTCTTGGCAGCCTAGTTGCGGTAGTTGGCAG
CACAGGAGAAGGAAAAACCTCCCTGATATCTGCTATGCTTGGGGAACTTCCTGCAAGATCT
GATGCGACTGTTACTCTTAGAGGATCAGTCGCTTATGTTCCACAAGTTTCATGGATCTTTA
ACGCAACAGTACGTGACAATATATTGTTTGGGGCTCCTTTTGACCAAGAAAAATATGAAAG
GGTGATTGATGTGACAGCACTCCAGCATGACCTTGAGTTACTGCCTGGAGGTGACCTCACG
GAGATCGGAGAAGGGGTGTTAACATCAGTGGGGACAAAAGCAGAGGGTTTCTATGGCTA
GGGCCGTTTACTCAAATTCAGACGTGTGCATCTTAGATGAACCATTGAGTGCCCTTGATGC
GCATGTTGGTCAGCAGGTTTTTGAAAAATGCATAAAAGGGAACTAGGGCAGACAACGAGA
GTACTTGTTACAAATCAGCTCCACTTCCTATCACAAGTGGATAAAATCCTACTTGTCCATG
AGGGAACAGTAAAAGAGGAAGGAACATATGAAGAATTATGCCATAGTGGCCCGTTGTTCCC
GAGGTTAATGGAAAATGCAGGGAAGGTTGAAGATTATTCCGAAGAAATGGAGAAGCTGAA
GTACATCAAACATCTGTAAAACCAGTTGAAATGGGAACGCTAATAATCTGCAGAAGGATG
GAATCGAGACAAAGAATTCCAAAGAAGGAAACTCTGTTCTTGTCAAACGAGAAGAACGTGA
AACTGGAGTTGTGAGTTGGAAAGTCCTGGAGAGGTACCAGAATGCACTTGGAGGTGCATGG
GTAGTGATGATGCTCGTTATATGCTACGTCTTGACTCAAGTATTTCGGGTTTCAAGCATCA
CTTGGTTGAGTGAGTGGACTGATTCAGGAACCCCAAAGACTCATGGACCCCTATTCTATAA
TATTGTCTATGCGCTTCTTTCGTTTGGACAGGTCTCTGTGACATTGATCAATTCATATTGG
TTGATTATGTCCAGTCTATATGCAGCTAAAAGATGCATGATGCTATGCTTGGTTCCATAC
TAAGGGCTCCAATGGTGTTCTTTCAAACCAATCCATTAGGACGGATAATCAATCGATTTGC
AAAAGATATGGGAGATATTGATCGAACTGTGGCAGTCTTTGTAAACATGTTTATGGGTTCA
ATCGCACAGCTTCTTTCAACTGTTATCTTGATTGGCATTGTCAGCACTCTGTCCCTGTGGG
```

FIG. 16A

```
CCATCATGCCCCTGTTGGTCGTGTTCTATGGAGCTTATCTGTATTACCAGAACACATCTCG
GGAAATTAAACGTATGGATTCCACTACAAGATCGCCAGTTTATGCTCAATTTGGTGAGGCA
TTGAATGGACTATCTAGTATCCGTGCTTATAAAGCATATGACAGGATGGCTGAAATTAATG
GAAGGTCAATGGACAATAACATCAGATTCACACTTGTAAACATGGCTGCAAATCGGTGGCT
GGGAATCCGTTTGGAAGTTTTGGGAGGTCTCATGGTTTGGTGGACTGCTTCATTAGCCGTC
ATGCAGAACGGAAAGGCAGCGAACCAACAAGCATATGCATCTACGATGGGTTTGCTTCTCA
GTTATGCGTTAAGCATTACCAGCTCTTTAACAGCTGTACTGAGACTCGCGAGTCTAGCTGA
GAATAGTTTAAACTCGGTTGAGCGTGTTGGAAATTATATCGAGATACCATCAGAGGCTCCA
TTGGTCATTGAAAACAACCGTCCACCTCCCGGATGGCCATCATCTGGATCCATAAAATTTG
AGGATGTTGTTCTTCGTTACCGCCCTGAGTTACCTCCTGTTCTTCATGGAGTTTCGTTCTT
GATTTCTCCAATGGATAAGGTGGGAATTGTTGGGAGGACAGGCGCTGGGAAATCAAGCCTC
TTAAATGCCTTATTCAGGATTGTGGAGCTGGAAAAGGAAGGATTTTAATTGATGAATGCG
ACATTGGAAGATTTGGACTGATGGACCTACGTAAAGTGGTCGGAATTATACCGCAAGCGCC
AGTTCTTTTCTCAGGTACCGTGAGATTCAATCTTGACCCATTTAGTGAACACAACGACGCC
GATCTCTGGGAATCTCTTGAGAGGGCACACTTGAAAGATACTATCCGCAGAAATCCTCTTG
GTCTTGATGCTGAGGTAACTGAGGCAGGAGAGAATTTCAGTGTTGGACAGAGACAGTTGTT
GAGTCTTGCACGTGCATTGTTACGAAGATCTAAGATACTTGTTCTTGATGAAGCAACTGCT
GCAGTTGACGTAAGAACTGATGTTCTCATCCAAAAGACCATCCGAGAAGAATTCAAGTCAT
GCACAATGCTAATCATCGCTCATCGTCTCAATACTATCATCGACTGTGACAAAGTTCTTGT
CCTTGATTCTGGAAAAGTTCAGGAATTCAGTTCACCGGAGAATCTTCTTTCAAATGGAGAA
AGTTCTTTCTCGAAGATGGTTCAAAGTACAGGAACTGCAAACGCGGAGTACTTACGTAGTA
TAACACTAGAGAACAAACGTACCAGAGAAGCTAACGGTGATGATTCACAACCTTTAGAAGG
TCAAAGGAAATGGCAAGCTTCTTCTCGTTGGGCTGCAGCTGCTCAATTTGCATTGGCTGTG
AGCCtCACTTCATCTCACAACGACCTCCAAAGCCTTGAAATCGAAGATGATAACAGTATTT
TGAAGAAAACAAAGGACGCCGTCGTCACTTTACGCAGTGTCCTTGAAGGGAAACATGATAA
AGAGATTGAAGACTCTCTAAACCAAAGTGACATCTCTAGAGAGCGTTGGTGGCCATCTCTT
TACAAAATGGTCGAAGGGCTTGCCGTGATGAGCAGATTGGCGAGGAACAGAATGCAACACC
CGGATTACAATTTAGAAGGGAATCGTTTGACTGGGACAATGTCGAGATGTAAacgatgaa
aggcttacactaatagacctaaaactcccatttttgatggaacttttatttgtattgcttgg
gatacacgtaacaaaatgcccattaatcgtggtgtaactatataggctatgcttcttttgg
gaaaagagagtttgattacagaggatgtgatgataacacaattggaattc
```

```
gggaggtttggttttttccctatcaatcgaattccatttcgtgctcgtaacgtggattttg
gtagattttttttaggggatggaaacttgtttattatctatagatgatgattttgttttc
tccatgagaatgtatgcttttaaactttttttttttgttttttgccttcggagctaactt
tgggggctggtctcggtctctgttttctctccactaaaaagataaaaagcttttgccatct
tttttttttctcaataatctatcacatcgttttttttctttgttttttctccatttgtc
ttcattgagttcatagccacataattattgatttcttttcttttagtgtttctgttactg
atgcgtttcattatttatacttctcacttgcagattcgaggattgttagtttcttgtgatg
tgtagtctttgaagcagggattttttattgtattgaggaagaagATGGGGTTTGAGCCGTT
GGATTGGTATTGCAAGCCGGTGCCGAATGGTGTGTGGACTAAAACTGTGGATTATGCGTTT
GGTGCATACACGCCTTGTGCTATTGACTCTTTTGTGCTTGGTATCTCTCATCTGGTTCTGT
TGATTCTGTGTCTTTATCGCTTGTGGCTCATCACGAAGGATCACAAAGTGGATAAGTTCTG
CTTGAGGTCTAAATGGTTTAGCTATTTTCTGGCTCTTTTGGCTGCTTATGCTACTGCGGAG
CCTTTGTTTAGATTGGTCATGAGGATCTCTGTTTTGGATTTGGATGGAGCTGGGTTTCCTC
CCTATGAGgtgtgttatcactttgctgttttgttgatgttgttctccttctgtatgttttt
tcctgagagatgctgttgttttgtgctttatttggcagGCGTTTATGTTGGTCCTTGAGGC
TTTTGCTTGGGGTTCTGCTTTGGTCATGACTGTTGTGGAAACTAAAACGTATATCCATGAA
CTCCGTTGGTATGTCAGATTCGCTGTCATTTATGCTCTTGTGGGAGACATGGTGTTGTTAA
ATCTTGTTCTCTCTGTTAAGGAGTACTATGGCAGgttggtaaatttgcagtctgtatggtt
tatgcaattttgtttccctggtctggcacgatgaacttatatgcgtcattttttttttgtt
tttggcagTTTTAAACTGTATCTTTACATAAGCGAGGTGGCAGTTCAGgtttgcacttaa
aactcctttttgcattctccaaactactctttaccatgtgctgtatctaagtcacactgta
aatgatacaactttgttttataatgacgttaaggatggttttggatccagGTTGCATTT
GGAACCCTCTTGTTTGTGTATTTCCCTAATTTGGACCCTTACCCTGGTTACACACCAGTTG
GGACTGAAAATTCCGAGGATTACGAGTATGAAGAGCTTCCTGGAGGAGAAAATATATGTCC
TGAGAGGCATGCAAATTTATTTGACAgtatgtcactctacacttctcattccctactttgt
ttttataggtgcatttctattttaattgtgagaattgccaccgcatcttttatcacttt
ctgcacttactacctatctaagttggttatttatgcagagcttaaatatttccctggaatt
gtaaattttcttatggagtgctaatacgtagtaggtcattaaaattgtttccgcagagagt
agtctatagtctcttcaaaattttttttgacttatcctcccgttctccctagaaatgaac
ttatgatttgtgactgtgccgaggttttgcttagtgatcatcacttcgactaagctgcaa
cattttatatagtatattcgtcaacatttgtcaaactttgactattatgttccttcttacc
cttgtctttcaacccacagGTATCTTCTTCTCATGGTTGAACCCATTGATGACTCTGGGAT
CAAAACGACCTCTCACCGAGAAGGATGTATGGCATCTGGACACTTGGGATAAAACTGAAAC
TCTTATGAGGAGtatattttaataaataacaactgttctcatactgtctatgactggcat
ggttgcgtgacatattttatctcatttttagCTTCCAGAAGTCCTGGGATAAGGAACTA
GAAAAGCCCAAACCGTGGCTTTTGAGAGCACTGAACAACAGCCTTGGGGAAGgtaaacaa
aaacttcttcacagtcatgtgttttcatcttttgggctttgacatgatgtgtgatttgta
aaaggaagcatttggttgtaataataaatgcattatgaataactagaagctgagaaatctg
ttatggctgtgacttcaagtatgttttgatgcgtgtcgagttgaataagaaatgtgttact
tttctggttataatctgccatagatacttccatccttatggactgtctgtttctgcattt
tgtagGTTTTGGTGGGGTGGCTTTTGGAAGgtacttttgtActctttattgtgttttattc
tttattctgaaacagtcttttccttgtctatttgataatattgatggcttctgaggtctta
gttttcctaaatggtgtgttttgtaactgtttaatcttgacatttcaatctaaattgtatc
atagATTGGGAATGACTGTTCACAGTTCGTGGGGCCTCTTCTACTGAATGAGCTCTTAAAG
gtttgttcctttacttcttttaccccgtgcacattgtgcttgaacctatttaacacaatg
ctttgtaattttccattcacatggatctttgagatggattcatattcctactggctcgaa
taagtgtttaaacgttcttgatagattcaaaatcctatcatcctttgaatattatgttctg
acgatatctcacaatgtctcctttaactttccgcagTCAATGCAACTTAATGAACCAGCGT
GGATAGGTTACATCTATGCAATCTCAATCTTTGTTGGAGTGgtatgcaacaaattctcttt
ttcttcgctgcctttattattctcttgcatggactgcaaaggatatgaaacaaaaactcta
ctttccttggattcttttctttcttgctaggacttcatggtattttggtctagagtagat
gctacgaattgtaggaccagtttaattttcttaagctgaaagtaatctctgtgcgattcga
ttgtattagaaaatagcctgattctactcttagagttagttttttttgtttgttaatacat
ttgcatgttgaaaaggttttgtttaatgtaggtcaaggtgacacttgaccaatggactcct
```

FIG. 17B

```
tgatcgcttgatgttgatgttgacattttcagGTATTGGGGGTTTTATGTGAAGCTCAGTA
TTTCCAAAATGTGATGCGTGTTGGTTACCGGCTTAGGTCTGCACTGgtaagaaaaagtttc
acatgaattatcttttgctacttagttttttctttttgctctgcttctcatgttttgatgca
atacctgtactgttatgtctgttgaaagctatagcagatgcttatagattgcttcattctg
ctgatgaattctcccttaatagATTGCTGCTGTGTTCCGAAAATCTTTGAGGCTAACTAAT
GAGGGGCGGAAGAAGTTTCAAACAGGAAAAATAACAAACTTAATGACTACTGATGCTGAGT
CGCTGCAGgtgtatctttgttacctttactctctttagccttgtctgtttcttgatataaa
tttacactgcatagttgtatatctacctcaaaatatgagtcttagatgcaatttaccaaga
tagtcttttcctgcaactgacgactgaatctgaagcttattctaagattctagaaatcct
aagagttgtgattacattttcaacacccttgttcttttgttgccgttgtaggatttgattt
tcctttattagccaataaacctttaattcgcttgatttgtagaaaaagttacctttgaac
agtgcttttatctaagctcttgcttgaaatcaaagtgtttatctagctgatagctgttctt
tttccctaacgtttctcttgtgtgtgacagCAAATCTGCCAATCACTTCATACCATGTGGT
CGGCGCCATTTCGTATAATTGTAGCACTGGTTCTCCTCTATCAACAATTGGGTGTTGCCTC
GATCATTGGTGCATTGTTTCTTGTCCTTATGTTCCCCATACAGgttcgtatatcttaataa
ttccccattctctttgcgctgtcggttttttttttccttttgattgcttatttctcatttgc
ttttcacaccaatgaaaatgattcatttcctccgtttatttggttgaaacagACTGTTATT
ATAAGCAAAACGCAGAAGTTAACAAAAGAAGGGTTGCAGCGTACTGACAAGAGAATTGGCC
TAATGAATGAGGTTTTAGCGGCAATGGATACAGTGAAgtacgatactttggaagcctgaaa
cctaatatttatttcttgcatagttggaagtttgtggcagtgtttaactatctcactaaa
ccaaaatactgtagGTGTTACGCTTGGGAAACAGTTTTCAGTCCAAGGTTCAAACTGTAC
GTGATGATGAATTATCTTGGTTCCGGAAAGCACAACTCCTGTCAGCGgtatggcttgagtg
cagtgactgttatattaattgattttatagaccgtatgcatgatgtgcatagttgtcttgg
tcatttacttgtcgctctcctaacggtatgattgtatacaaggacaaatccaagttgctcg
tcttttaaatgcctttgaccattttgagaatggtatccatcaatatgtgtttaggcatttt
tctgtactattttctagttcattgaacattgattcagttgtttcgggcatgtgtagcagca
ttcatgcatgatctttaacatatattgcattaatgtttctgactcattcttggtcttctat
ttgctctgcagTTCAATATGTTCATACTAAACAGCATCCCTGTCCTCGTGACTGTTGTTTC
ATTTGGTGTGTTCTCATTGCTTGGAGGAGATCTGACACCTGCAAGAGCGTTTACGTCACTC
TCTCTATTTTCTGTGCTTCGCTTCCCTTTATTCATGCTTCCAAACATTATAACTCAGgtga
tttccttaaaatgtttcttgaaccatgttttcatgtccagtactgaataatgtggcatcat
agtaatgattgcttctgattgctcttttaattttccatctctacctcttttctagaccag
tcgttgtcataatgttttgcagatgctgaccaggctttacttttgtagATGGTAAATGCT
AATGTATCCTTAAACCGTTTGGAGGAGGTACTGTCAACCGAAGAGAGAGTTCTCTTACCGA
ATCCTCCCATTGAACCTGGACAGCCAGCTATCTCAATAAGAAATGGATACTTCTCCTGGGA
TTCAAAGgtcttctttgtctattttatcacatgttcttacttctattagtttctatcatta
catattgtcaatgaagtacaaaaagtgagctagaagtatacatatgcagGCGGATAGGCCA
ACATTGTCAAACATCAACCTGGACATACCTCTTGGCAGCCTAGTTGCGGTAGTTGGCAGCA
CAGGAGAAGGAAAAACCTCCCTGATATCTGCTATGCTTGGGGAACTTCCTGCAAGATCTGA
TGCGACTGTTACTCTTAGAGGATCAGTCGCTTATGTTCCACAAGTTTCATGGATCTTTAAC
GCAACAgtaagtttatatatgctactcagtttatagtatggttctcaatgcgaaaatgtca
aattctcctcttggattgttacttattttgtatgtattttatgttttgtatatgatgatgt
gtgcttttagatacgtccacatgctgatggttgtaattaacatcgcgtagGTACGTGACAA
TATATTGTTTGGGGCTCCTTTTGACCAAGAAAAATATGAAAGGGTGATTGATGTGACAGCA
CTCCAGCATGACCTTGAGTTACTGCCgtaagttttgtggagagttacttagccatgtgca
ttgaaaatttcctgaggtgaaacgaaccttgaaatctgttggtgcgatgtaaatcgaaaaa
actgaattgcatcagttctgttgatagcatgtacttctattttctagtgctcaggtatcta
agcttgtttcctcttctttctcttgattgatagGGAGGTGACCTCACGGAGATCGGAGAAA
GGGGTGTTAACATCAGTGGGGGACAAAAGCAGAGGGTTTCTATGGCTAGGGCCGTTTACTC
AAATTCAGACGTGTGCATCTTAGATGAACCATTGAGTGCCCTTGATGCGCATGTTGGTCAG
CAGgtaaactagccataggctcttttggatagaacaatactttgttttctttcaattttg
caaatcgtgaactctataacgttttgttttcaatctgcatggatattctacttcttgttt
gccacggatctctgccatatactacttttaagcaaacattgttatctgatgttcgaaactg
gctgttatatatagGTTTTTGAAAATGCATAAAAGGGAACTAGGGCAGACAACGAGAGT
```

```
ACTTGTTACAAATCAGCTCCACTTCCTATCACAAGTGGATAAAATCCTACTTGTCCATGAG
GAACAGTAAAAGAGGAAGGAACATATGAAGAATTATGCCATAGTGGCCCGTTGTTCCCGA
GGTTAATGGAAAATGCAGGGAAGGTTGAAGATTATTCCGAAGAAAATGGAGAAGCTGAAGT
ACATCAAACATCTGTAAAACCAGTTGAAAATGGGAACGCTAATAATCTGCAGAAGGATGGA
ATCGAGACAAAGAATTCCAAAGAAGGAAACTCTGTTCTTGTCAAACGAGAAGAACGTGAAA
CTGGAGTTGTGAGTTGGAAAGTCCTGGAGAGgtaagttggcattcggattttttgctctttc
ttgttgtgttgttgcagtattcctttctatcgacagtggaaatatccgtaaataagacata
ttctttggtttagagcaatatgtcaatttatctgtggtgtttctttactacaaaatggata
tatattgtttgactcgctctattcatattcatacaaaatgtatatatattttccgtattaa
ggttcgtattgtaaagccattgtaataacttgtgaggtgtcaccatgttccagGTACCAGA
ATGCACTTGGAGGTGCATGGGTAGTGATGATGCTCGTTATATGCTACGTCTTGACTCAAGT
ATTTCGGGTTTCAAGCATCACTTGGTTGAGTGAGTGGACTGATTCAGGAACCCCAAAGACT
CATGGACCCCTATTCTATAATATTGTCTATGCGCTTCTTTCGTTTGGACAGtatgagttg
catttggcaaatgtttgagtcggtatcttcatgatcggataacaatatataactgaacatt
aaaggctgatcagttaagaatatacaccatgtttcttctgcgccaaagtatcgagcaaaca
aaatggaaaataaaaggatacagagagcaaaacgtttattgctaacacgtatttctgcggg
ggtttgtcagGTCTCTGTGACATTGATCAATTCATATTGGTTGATTATGTCCAGTCTATAT
GCAGCTAAAAAGATGCATGATGCTATGCTTGGTTCCATACTAAGGGCTCCAATGGTGTTCT
TTCAAACCAATCCATTAGGACGGATAATCAATCGATTTGCAAAAGATATGGGAGATATTGA
TCGAACTGTGGCAGTCTTTGTAAACATGTTTATGGGTTCAATCGCACAGCTTCTTTCAACT
GTTATCTTGATTGGCATTGTCAGCACTCTGTCCCTGTGGGCCATCATGCCCCTGTTGGTCG
TGTTCTATGGAGCTTATCTGTATTACCAGtgtaacctacatactttttaaacgcaatgcta
tctacattcatgactacagatcgagacatggaaaactgagaccaaaaggaacactgattgt
gtcatatctgttgtgtcataacctgattttccttattgtagAACACATCTCGGGAAATTA
AACGTATGGATTCCACTACAAGATCGCCAGTTTATGCTCAATTTGGTGAGGCATTGAATGG
ACTATCTAGTATCCGTGCTTATAAAGCATATGACAGGATGGCTGAAATTAATGGAAGGTCA
ATGGACAATAACATCAGATTCACACTTGTAAACATGGCTGCAAATCGGTGGCTGGGAATCC
GTTTGGAAGTTTTGGGAGGTCTCATGGTTTGGTGGACTGCTTCATTAGCCGTCATGCAGAA
CGGAAAGGCAGCGAACCAACAAGCATATGCATCTACGATGGGTTTGCTTCTCAGTTATGCG
TTAAGCATTACCAGCTCTTTAACAGCTGTACTGAGACTCGCGAGTCTAGCTGAGAATAGTT
TAAACTCGGTTGAGCGTGTTGGAAATTATATCGAGATACCATCAGAGGCTCCATTGGTCAT
TGAAAACAACCGTCCACCTCCCGGATGGCCATCATCTGGATCCATAAAATTTGAGGATGTT
GTTCTTCGTTACCGCCCTGAGTTACCTCCTGTTCTTCATGGAGTTTCGTTCTTGATTTCTC
CAATGGATAAGGTGGGAATTGTTGGGAGGACAGGCGCTGGGAAATCAAGCCTCTTAAATGC
CTTATTCAGGATTGTGGAGCTGGAAAAAGGAAGGATTTTAATTGATGAATGCGACATTGGA
AGATTTGGACTGATGGACCTACGTAAAGTGGTCGGAATTATACCGCAAGCGCCAGTTCTTT
TCTCAGGTACCGTGAGATTCAATCTTGACCCATTTAGTGAACACAACGACGCCGATCTCTG
GGAATCTCTTGAGAGGGCACACTTGAAAGATACTATCCGCAGAAATCCTCTTGGTCTTGAT
GCTGAGgtacttaattaaatatttccatttgggaaagtctcatgtattcagtaataataac
tcagtcttttggtcagGTAACTGAGGCAGGAGAGAATTTCAGTGTTGGACAGAGACAGTT
GTTGAGTCTTGCACGTGCATTGTTACGAAGATCTAAGATACTTGTTCTTGATGAAGCAACT
GCTGCAGTTGACGTAAGAACTGATGTTCTCATCCAAAAGACCATCCGAGAAGAATTCAAGT
CATGCACAATGCTAATCATCGCTCATCGTCTCAATACTATCATCGACTGTGACAAAGTTCT
TGTCCTTGATTCTGGAAAgtacgtatacaaaatattcgaccactacttgcatcaatttaa
tcactttgagctaacatatattgagattcccaacacctcagGTTCAGGAATTCAGTTCAC
CGGAGAATCTTCTTTCAAATGGAGAAAGTTCTTTCTCGAAGATGGTTCAAAGTACAGGAAC
TGCAAACGCGGAGTACTTACGTAGTATAACACTAGAGAACAAACGTACCAGAGAAGCTAAC
GGTGATGATTCACAACCTTTAGAAGGTCAAAGGAAATGGCAAGCTTCTTCTCGTTGGGCTG
CAGCTGCTCAATTTGCATTGGCTGTGAGCCtCACTTCATCTCACAACGACCTCCAAAGCCT
TGAAATCGAAGATGATAACAGTATTTTGAAGAAAACAAAGGACGCCGTCGTCACTTTACGC
AGTGTCCTTGAAGGGAAACATGATAAAGAGATTGAAGACTCTCTAAACCAAAGTGACATCT
CTAGAGAGCGTTGGTGGCCATCTCTTTACAAAATGGTCGAAGgtaacgttattcttaagat
ttctgatacgagtatacgacataagaattgttgaagtttcttgatctaataatttgtgta
tatactctcagGGCTTGCCGTGATGAGCAGATTGGCGAGGAACAGAATGCAACACCCGGAT
```

FIG. 17C

```
TACAATTTAGAAGGGAAATCGTTTGACTGGGACAATGTCGAGATGTAAacgatgaaaggct
tacactaatagacctaaaactcccatttttgatggaactttttatttgtattgcttgggatac
acgtaacaaaatgcccattaatcgtggtgtaactatataggctatgcttcttttgggaaaa
agagagtttgattacagaggatgtgatgataacacaattggaattcaaatttgcagcaaaa
tttgggagaaaaaaaaagtcaatgagtgcaacatgccaacatggtttcaacttctggaca
tggacaaccattggacataatttctctcacaggaccatgttttgtcattgacattttgcac
aaaaatgttctattaaacatatctataaagaatttgaacaattgttaaaaaaacactta
aaatataaattgcaatacaaatttccttttttt
```

FIG. 17D

```
MGFEPLDWYCKPVPNGVWTKTVDYAFGAYTPCAIDSFVLGISHLVLLILCLYRLWLITKDH
KVDKFCLRSKWFSYFLALLAAYATAEPLFRLVMRISVLDLDGAGFPPYEAFMLVLEAFAWG
SALVMTVVETKTYIHELRWYVRFAVIYALVGDMVLLNLVLSVKEYYGSFKLYLYISEVAVQ
VAFGTLLFVYFPNLDPYPGYTPVGTENSEDYEYEELPGGENICPERHANLFDSIFFSWLNP
LMTLGSKRPLTEKDVWHLDTWDKTETLMRSFQKSWDKELEKPKPWLLRALNNSLGGRFWWG
GFWKIGNDCSQFVGPLLLNELLKSMQLNEPAWIGYIYAISIFVGVVLGVLCEAQYFQNVMR
VGYRLRSALIAAVFRKSLRLTNEGRKKFQTGKITNLMTTDAESLQQICQSLHTMWSAPFRI
IVALVLLYQQLGVASIIGALFLVLMFPIQTVIISKTQKLTKEGLQRTDKRIGLMNEVLAAM
DTVKCYAWENSFQSKVQTVRDDELSWFRKAQLLSAFNMFILNSIPVLVTVVSFGVFSLLGG
DLTPARAFTSLSLFSVLRFPLFMLPNIITQMVNANVSLNRLEEVLSTEERVLLPNPPIEPG
QPAISIRNGYFSWDSKADRPTLSNINLDIPLGSLVAVVGSTGEGKTSLISAMLGELPARSD
ATVTLRGSVAYVPQVSWIFNATVRDNILFGAPFDQEKYERVIDVTALQHDLELLPGGDLTE
IGERGVNISGGQKQRVSMARAVYSNSDVCILDEPLSALDAHVGQQVFEKCIKRELGQTTRV
LVTNQLHFLSQVDKILLVHEGTVKEEGTYEELCHSGPLFPRLMENAGKVEDYSEENGEAEV
HQTSVKPVENGNANNLQKDGIETKNSKEGNSVLVKREERETGVVSWKVLERYQNALGGAWV
VMMLVICYVLTQVFRVSSITWLSEWTDSGTPKTHGPLFYNIVYALLSFGQVSVTLINSYWL
IMSSLYAAKKMHDAMLGSILRAPMVFFQTNPLGRIINRFAKDMGDIDRTVAVFVNMFMGSI
AQLLSTVILIGIVSTLSLWAIMPLLVVFYGAYLYYQNTSREIKRMDSTTRSPVYAQFGEAL
NGLSSIRAYKAYDRMAEINGRSMDNNIRFTLVNMAANRWLGIRLEVLGGLMVWWTASLAVM
QNGKAANQQAYASTMGLLLSYALSITSSLTAVLRLASLAENSLNSVERVGNYIEIPSEAPL
VIENNRPPPGWPSSGSIKFEDVVLRYRPELPPVLHGVSFLISPMDKVGIVGRTGAGKSSLL
NALFRIVELEKGRILIDECDIGRFGLMDLRKVVGIIPQAPVLFSGTVRFNLDPFSEHNDAD
LWESLERAHLKDTIRRNPLGLDAEVTEAGENFSVGQRQLLSLARALLRRSKILVLDEATAA
VDVRTDVLIQKTIREEFKSCTMLIIAHRLNTIIDCDKVLVLDSGKVQEFSSPENLLSNGES
SFSKMVQSTGTANAEYLRSITLENKRTREANGDDSQPLEGQRKWQASSRWAAAAQFALAVS
LTSSHNDLQSLEIEDDNSILKKTKDAVVTLRSVLEGKHDKEIEDSLNQSDISRERWWPSLY
KMVEGLAVMSRLARNRMQHPDYNLEGKSFDWDNVEM
```

FIG. 18

```
ttcacttttgtcctttttttcttaacatctacttttgtcatcagcaaattatctgtaaataa
gatagggtttatgcttattgctacaatgaacctaatcctatgatgtgtattgcaatttgcaa
ccatgcgagtttaattatttgtttactgctatagtgatcattttatgatgtgtttttattaa
ttacaaaacagagcatcaaaaatcaaaagaacatatcgcataatcgaactatgctaatacct
ctcctcaatctttgttgttgttatattcaagtagcttattcttttgttttattttacgatta
gatttctctagaATTTAATTTAtattATTTAatcatacttgatcaaggtttgtagcttaatc
aatatcgttatcgtgtcatcctgcagattcaaatgatcaagtctaataatctacttatatg
tattatatatattagataccaccaacgaaacaaaatcatatttctataacatttgtttggtt
aaatatATTTAaagatttgtaacagttgttcgggttcaaaactatcactttgtagttgtagg
atgaggaaaagtcgtgatatgatcatctactaaaatcatgtgttttttaaagaacatgattt
tcattggatagtttaataaatgttaaaaaaatactaagtgtcaaagaagagatttgaaccat
atgtagaatacttgattcgaattttcctgacgaataatctaatatccttttctcaaaagaa
aaaaatgtttgttaacttggacacgatattattatccaacttcctttctagatattcatttt
taaattacctatatattttattttctcaaaatatactaaaaattggatagagctattaaat
aaaaagatagaATTTAgagagaaatagcaacataatgaattataatataaatattttgtaa
agaaataacaaactttatagttagtttgcctaatatagaaaaaagatacagttATTTAccc
atttgtttgtgtgtaaaaaaggagtaaaataaacagagaaaagagcttcttgtttttactt
gtgaacgttattgacttttcggcctctctcttctctatacaaatatatggatcttcattt
cttcgtatagtgtaagcagtgacgcatccATTTAtcatcatctccttataaatctcgaatct
gccacagagagaGCGTGtgacaaaatgagttcataagattccgttatcgtcttcctgattc
ctccaaatctccgg
```

FIG. 23

```
aaacaattggtgtattttgaattttttcatgcaacgcacgtgaacagcttaattgcttgat
tggaaacaaaccttttttagaattcattaatcagttttaggtgttttggaaaattaacgaac
tatagtggagattaattaattttatattagtcttttttagtacacaaatcgaagtttccta
gattttttcaaagttgaaaataatattgataatATTTAtcaacaatgaatctacaaaaaca
taatttttttgccaaacaaataacaccgaaacaagattcattcactattttggtttaaaa
aaaaaaatcaaaattacactattatgaagccaattttttgtatgcaaaaaacctgtatgtat
caatttgtttgtattaaaaagtaagcATTTAtgtcttttttttataaataatagaaacact
tactagatgaatagattttttggttttagaacagaatactataattgtATTTAtatagctt
ttttatattattcgatatagaaaagtgttataataggaaaaatgtaccatatactgtcaat
aacatatttgattctaaatataaatagaattgttttaaagaaatatgatcgtttataatta
aatggttttttaatgtcttttcttggggcaaaaaacaaagcttgtctttcgtccatatattt
gcatcgtaaggggtgacgtatcactctctctttctctcaaatattattcttcaatctctttt
ttggggaatcttcgagcaaattagtgagagaacccacccactttctttctcatatgagtac
ataagatccctttttgagttttcgtgtttttgccaaaatctccaggtaaagcttctcccttt
tctctgttttctctgttttgttattctccttttctccattgtagcttttcctgtaaagt
gggattgatagttttgtttcatggatttcaaatttgtgttatttgactcgataccatctta
aatgcagagtcttttcgtgataataaaattatggattcgtttcaaagttttttttttttcg
tatggaaaacacttgagctctctcaatcttgtagtcttgactcttgatgattcttctatgt
tctcgttgtgattgcttgtcactgttctatctttatatatgattaaatgcaattttgcccc
tttttacgcgcgaatgtATTTAttatctttcgcactctgggtccatttcttgtcacttgag
cacataatgattgATTTAtgactttttaaagttatgaaaATTTAttattttttgttgctatg
gttttttggaattagaagctcatttcaaagttgttgatttctttgcagggtagggaattg
gtgtggtagcttgtgatgcactgtgtt
```

FIG. 24

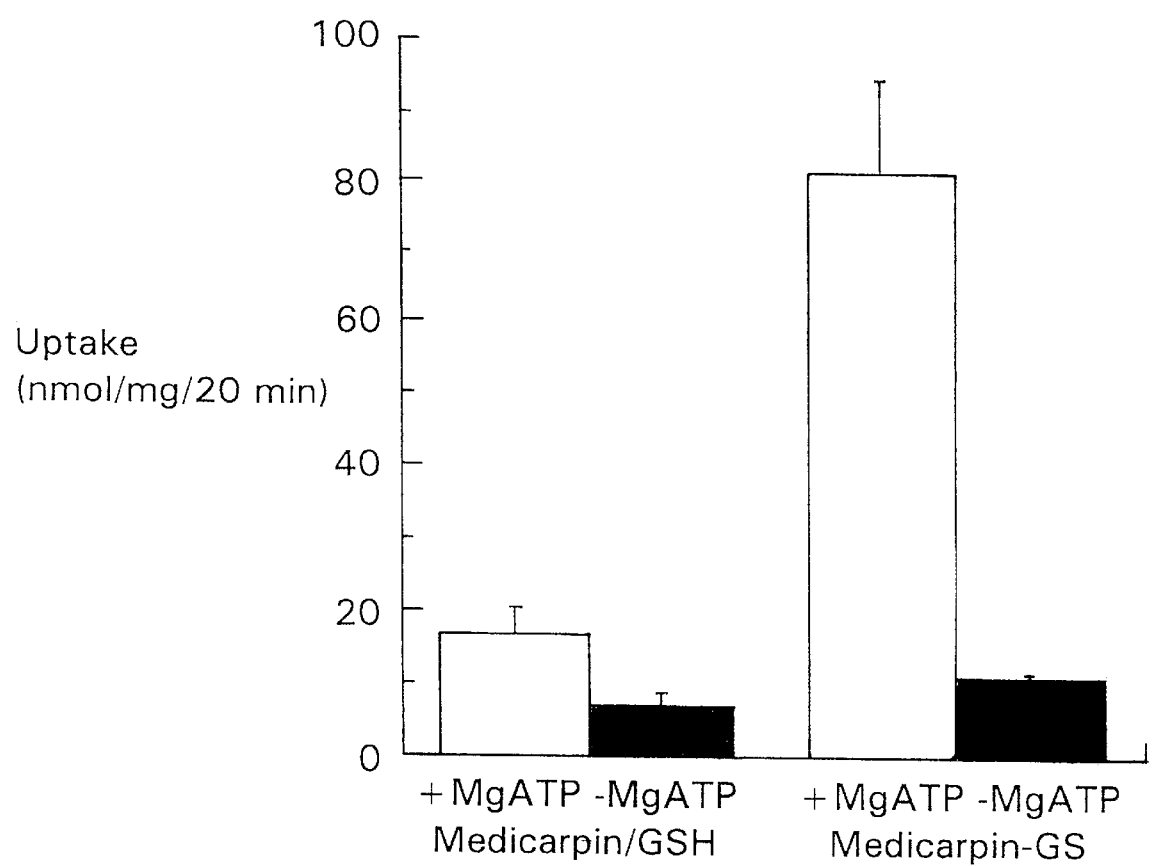

GLUTATHIONE-S-CONJUGATE TRANSPORT IN PLANTS

CROSS REFERENCE TO RELATED APPLICATIONS

This application claims priority under 35 U.S.C. § 119(e) to U.S. Provisional Application Ser. No. 60/031,040, filed on Nov. 18, 1996 and U.S. Provisional Application Ser. No. 60/061,328, filed on Oct. 8, 1997 abandoned.

GOVERNMENT SUPPORT

This invention was supported in part by funds from the U.S. Government (USDA NRICPG Grant Numbers 9303007 and 9503007 and Department of Energy Grant Number DE-FGO2-91ER20055) and the U.S. Government may therefore have certain rights in the invention.

BACKGROUND OF THE INVENTION

Animal and plant cells have the capacity to eliminate a diversity of lipophilic toxins from the cytosol following conjugation of the toxin with glutathione (GSH) (Ishikawa et al., 1997, *Bioscience Reports.* 17:189–208; Martinoia et al., 1993, *Nature* 364:247–249; Li et al., 1995, *Plant Physiol.* 107:1257–1268). This process is mediated by the glutathione S-conjugate (GS-X) pumps which are novel MgATP-dependent transporters that catalyze the efflux of GS-conjugates and glutathione disulfide (GSSG) from the cytosol via the plasma membrane and/or endomembranes. GS-X pumps are considered to constitute a terminal phase of xenobiotic detoxification in animals and plants.

The metabolism and detoxification of xenobiotics comprises three main phases (Ishikawa, 1992, supra). Phase I is a preparatory step in which toxins are oxidized, reduced or hydrolyzed to introduce or expose functional groups having an appropriate reactivity. Cytochrome P450 monooxygenases and mixed function oxidases are examples of phase I enzymes. In phase II, the activated derivative is conjugated with GSH, glucuronic acid or glucose. In the case of the GSH-dependent pathway, S-conjugates of GSH are formed by cytosolic glutathione-S-transferases (GSTs). In the final phase, phase III, of the GSH-dependent pathway, GS-conjugates are eliminated from the cytosol by the GS-X pump.

The GS-X pump is unique in its exclusive use of MgATP, rather than preformed transmembrane ion gradients, as a direct energy source for organic solute transport. Although an understanding of the constituents of GS-X pumps is relevant to an understanding of the mechanism by which cells combat, for example, chemotherapeutic agents and herbicides, there has until recently been a paucity of information on the molecular identity of GS-X pumps, particularly in plants.

A 190 kDa membrane glycoprotein encoded by the human multidrug resistance-associated protein gene (MRP1) has been implicated in the resistance of small cell lung cancer cell lines to a number of chemotherapeutic drugs (Cole et al., 1992, *Science* 258:1650–1654). This glycoprotein catalyzes the MgATP-dependent transport of leukotriene $C_4$ and related glutathione-S-conjugates (Leier et al., 1994, *J Biol. Chem.* 269:27807–27810; Muller et al., 1994, *Proc. Natl. Acad. Sci. USA* 91:13033–13037; Zamam et al., 1995, *Proc. Natl. Acad. Sci. USA* 92:7690–7694).

MRP1 is a member of the ATP binding cassette (ABC) superfamily of transporter proteins. Distributed throughout the major taxa, ABC transporters catalyze the MgATP-dependent transport of peptides, sugars, ions and lipophiles across membranes. ABC transporters comprise one or two copies each of two basic structural elements, a hydrophobic integral membrane sector containing approximately six transmembrane a helices and a cytoplasmically oriented ATP-binding domain known as a nucleotide binding fold (NBF) (Hyde et al., 1990, *Nature* 346:362–365; Higgins, 1995, *Cell* 82:693–696). The NBFs are a diagnostic feature of ABC transporters and are 30% identical between family members over a span of about 200 amino acid residues, having two regions known as a Walker A and a Walker B box (Walker et al., 1992, *EMBO J* 1:945–951), and also having an ABC signature motif (Higgins, 1995, supra).

ABC family members in eukaryotes include mammalian P-glycoproteins (P-gps or MDRS), some of which are implicated in drug resistance and others in lipid translocation (Ruetz et al., 1994, *Cell* 77:1071–1081), the pleiotropic drug resistance protein (PDR5) and STE6 peptide mating pheromone transporter of yeast, the cystic fibrosis transmembrane conductance regulator (CFTR) $Cl^-$ channel, the malarial *Plasmodium falciparum* chloroquine transporter (PFMDR1) and the major histocompatibility (MHC) transporters responsible for peptide translocation and antigen presentation (Balzi et al., 1994, *J Bioenerg. Biomemb.* 27:71–76; Higgins, 1995, supra).

Sequence comparisons between MRP1 and other ABC transporters reveal two major subgroups among these proteins (Cole et al., 1992, supra; Szczypka et al., 1994, *J Biol. Chem.* 269:22853–22857). One subgroup comprises MRP1, the Saccharomyces cerevisiae cadmium factor (YCF1) gene, the Leishmania P-glycoprotein-related molecule (Lei/PgpA) and the CFTRs. The other subgroup comprises the multiple drug resistance proteins (MDRs), MHC transporters and STE6.

The invention described herein relates to bioremediation (specifically phytoremediation), plant responses to herbicides, plant-pathogen interactions and plant pigmentation.

With respect to bioremediation, the massive global expansion in industrial and mining activities during the last two decades together with changes in agricultural practices, has markedly increased contamination of groundwaters and soils with heavy metals. Indeed, it is estimated that the annual toxicity of metal emissions exceeds that of organics and radionuclides combined (Nriagu et al., 1988, *Nature* 333:1340138). Since soil and water contamination results in the uptake of heavy metals and toxins by crop plants, and eventually humans, there remains a need for a means of manipulating the ability of a plant to sequester compounds from the soil in order to better manage soil detoxification through bioremediation using native species or genetically engineered organisms.

Regarding herbicides, these compounds are generally low molecular weight, lipophilic compounds that readily penetrate cells in a passive manner. Having entered cells, herbicides inhibit plant-specific processes such as photosynthetic electron transport (e.g., atrazine, chlortoluron) or the biosynthesis of essential amino acids (e.g., glyphosate, chlorsulfuron or phosphotricine), porphyrins (e.g., acidofluorfen), carotenoids (e.g., norflurazon), fatty acids (e.g., diclofop) or cellulose (e.g., dichlobenil) (Boger et al., 1989, *Target Sites of Herbicide Action*, CRC Press, Boca Raton, Fla.; Devine et al., 1993, *Physiology of Herbicide Action*, Prentice Hall, Englewood Cliffs, N.J.). Plants that are naturally tolerant of certain herbicides either contain a cellular target that does not interact with the herbicide, have efficient systems for inactivation of the herbicide, or have a high capacity for excluding or eliminating the herbicide from the target.

Herbicide metabolism comprises the three phases described above for general xenobiotic metabolism. The first two phases (the first being oxidation and hydrolysis and the second being conjugation with GSH or glucose) contribute to detoxification by decreasing the intrinsic biochemical activity of the herbicide and/or by increasing its hydrophilicity. These two phases render the herbicide less mobile in the plant. The third phase (compartmentation) is often critical for sustained detoxification since the conjugates themselves may interfere with metabolism. For example, the herbicide synergist tridiphane, is converted to its corresponding GS-conjugate in plants to generate a potent inhibitor of atrazine metabolism. (Lamoureux et al., 1986, *Pestic. Biochem. Physiol.* 26:323–342).

Likewise, and more generally, GS-conjugates of any given herbicide would be expected to act as end-product inhibitors of GSTs and thereby impair long-term detoxification unless they are removed from the intracellular compartment, usually the cytosol, in which they are formed. Since the vacuolar GS-X pump of plants is known to transport several GS-herbicide conjugates, for example, those of the chloroacetanilide herbicides (metolachlor) and triazines (simetryn) (Martinoia et al., 1993, supra; Li et al., 1995, supra), there is a long felt need for a knowledge of thy molecular identity of this transporter or family of transporters. Such knowledge will enable the development of new strategies for increasing or decreasing the resistance of plants to herbicides.

With regard to plant-pathogen interactions, a key event in the disease resistance response of legumes is the rapid and localized accumulation of isoflavonoid phytoalexins. The majority of the research on plant-pathogen interactions has centered on the enzymology and molecular biology of the isoflavonoid biosynthetic pathway (Dixon et al., 1995, *Physiol. Plant* 93:385). However, the mechanism and sites of intracellular accumulation of these compounds is not understood. Since many isoflavonoid phytoalexins are as toxic to the host plant as they are to its pathogens, the discovery of the molecular mechanism by which these compounds are sequestered within a plant is crucial to the development of plants with increased pathogen resistance.

With regard to plant pigmentation, functional analyses of the maize gene, Bronze-2, which participates in anthocyanin pigment biosynthesis, suggest that one of the endogenous substrates for the plant vacuolar GS-X pump are anthocyanin-GS conjugates (Marrs et al., 1995, *Nature*, 375:397–400). Anthocyanins share a common biosynthetic origin and core structure based on cyanidin-3-glucoside. It is through the species-specific decoration of cyanidin-3-glucoside by hydroxylation, methylation, glucosylation and acylation that the wide spectrum of red, blue and purple colors in the vacuoles of flowers, fruits and leaves is produced. The molecular nature of the plant GS-X pump which mediates transport of anthocyanin-GS conjugates was not known in the art until the present invention. There remains a need to determine the molecular nature of the GS-X pump responsible for transport of anthocyanin-GS conjugates in order that plant coloration may be manipulated at the molecular level.

The present invention satisfies the aforementioned needs.

BRIEF SUMMARY OF THE INVENTION

The invention includes an isolated DNA encoding a plant GS-X pump polypeptide. In one aspect, the isolated DNA is selected from the group consisting of DNA comprising AtMRP1 and AtMRP2, and any mutants, derivatives, homologs and fragments thereof encoding GS-X pump activity.

The invention also includes an isolated preparation of a polypeptide comprising a plant GS-X pump. In one aspect of this aspect of the invention, the polypeptide is selected from the group consisting of AtMRP1, AtMRP2, and any mutants, derivatives, homologs and fragments thereof having GS-X pump activity.

Also included in the invention is a recombinant cell comprising an isolated DNA encoding a plant GS-X pump polypeptide. In one aspect, the cell is selected from the group consisting of a prokaryotic cell and a eukaryotic cell.

Further included in the invention is a vector comprising an isolated DNA encoding a plant GS-X pump polypeptide.

The invention also includes an antibody specific for a plant GS-X pump polypeptide.

In addition, an isolated preparation of a nucleic acid which is in an antisense orientation to all or a portion of a plant GS-X pump gene is included in the invention and a cell and a vector comprising this isolated preparation of a nucleic acid are further included.

The invention also relates to a transgenic plant, the cells, seeds and progeny of which comprise an isolated DNA encoding a plant GS-X pump.

In addition, the invention relates to a transgenic plant, the cells, seeds and progeny of which comprise an isolated preparation of a nucleic acid which is in an antisense orientation to all or a portion of a plant GS-X pump gene.

Further, there is included a transgenic plant, the cells, seeds and progeny of which comprise an isolated DNA encoding YCF1, or any mutants, derivatives, homologs and fragments thereof having YCF1 activity.

The invention further relates to an isolated DNA comprising a plant GS-X pump promoter sequence. In one aspect, the promoter sequence is selected from the group consisting of an AtMRP1 and an AtMRP2 promoter sequence.

Also included in this aspect of the invention is a cell and a vector comprising an isolated DNA comprising a plant GS-X plant promoter sequence.

The invention additionally relates to a transgenic plant, the cells, seeds and progeny of which comprise a transgene comprising an isolated DNA comprising a GS-X pump promoter sequence, wherein the GS-X pump promoter sequence is selected from the group consisting of an AtMRP1, an AtMRP2 and a YCF1 promoter sequence. The promoter sequence may also have operably fused thereto a reporter gene.

There is also included in the invention a method of identifying a compound capable of affecting the expression of a plant GS-X gene. The method comprises providing a cell comprising an isolated DNA comprising a plant GS-X pump promoter sequence having a reporter sequence operably linked thereto, adding to the cell a test compound, and measuring the level of reporter gene activity in the cell, wherein a higher or a lower level of reporter gene activity in the cell compared with the level of reporter gene activity in a cell to which the test compound was not added, is an indication that the test compound is capable of affecting the expression of a plant GS-X pump gene.

In addition, the invention relates to a method of removing xenobiotic toxins from soil. The method comprises growing in the soil a transgenic plant of comprising an isolated DNA encoding a GS-X pump.

Also included is a method of removing heavy metals from soil comprising growing in the soil a transgenic plant of comprising an isolated DNA encoding a GS-X pump.

The invention further relates to a method of generating a transgenic pathogen resistant plant comprising introducing to the cells of the plant an isolated DNA encoding a GS-X pump, wherein the pump is capable of transporting glutathionated isoflavonoid alexins into the cells of the plant.

Additionally, there is included a method of manipulating plant pigmentation comprising modulating the expression of a GS-X pump protein in the plant, wherein the GS-X pump protein is selected from the group consisting of AtMRP1, AtMRP2 and YCF1.

The invention also relates to a method of alleviating oxidative stress in a plant comprising introducing into the cells of the plant DNA encoding a GS-X pump, wherein the DNA is selected from the group consisting of DNA encoding AtMRP1, AtMRP2 and YCF1.

Further included is a method of manipulating the expression of a gene in a plant cell. The method comprises operably fusing a GS-X pump promoter sequence to the DNA sequence encoding the gene to form a chimeric DNA, and generating a transgenic plant, the cells of which comprise the chimeric DNA, wherein upon activation of the GS-X pump promoter sequence, the expression of the gene is manipulated.

BRIEF DESCRIPTION OF THE DRAWINGS

FIG. 3A: MgATP concentration-dependence of uncoupler-insensitive uptake. FIG. 3B: DNP-GS concentration-dependence of MgATP-dependent uncoupler-insensitive uptake. The MgATP concentration-dependence of uptake was measured with 66.2 IM [ 3H] DNP-GS. The DNP-GS concentration-dependence of uptake was measured with 3 mM MgATP. Uptake was allowed to proceed for 10 minutes in standard uptake medium containing 5 $\mu$M gramicidin D. The kinetic parameters for vacuolar membrane vesicles purified from DTY165 cells were $K_{m(MgATP)}$ 86.5±29.5 $\mu$M, $K_{m(DNP-GS)}$ 14.1±7.4 $\mu$M, $V_{max(MgATP)}$ 38.4±5.6 nmol/mg/10 minutes, $V_{max(DNP-GS)}$ 51.0±6.3 nmol/mg/10 minutes. The lines of best fit and kinetic parameters were computed by nonlinear least squares analysis (Marquardt, 1963, J. Soc. Ind. Appl. Math. 11:431–441). Values shown are means ±S.E. (n=3).

FIGS. 7A–7D are a series of photomicrographs of DTY165 (FIGS. 7A and 7C) and DTY167 cells (FIGS. 7B and 7D) after incubation with monochlorobimane. Cells were grown in YPD medium for 24 hours at 30° C. and 100 $\mu$l aliquots of cell suspensions were transferred into 15 ml volumes of fresh YPD medium containing 100 $\mu$M monochlorobimane. After incubation for 6 hours, the cells were washed and examined in fluorescence (FIGS. 7C and 7D) or Nomarski mode (FIGS. 7A and 7B) as described herein.

FIG. 8C: Rate of $^{109}Cd^{2+}$ uptake by DTY165 membranes plotted as a function of the total concentration of $Cd^{2+}$ ($[Cd^{2+}]_{total}$) added to uptake medium containing 1 mM GSH, 3 mM MgATP and 5 $\mu$M gramidicin-D. Values shown are means ±SE (n=3–6).

FIGS. 9A–9C are a series of graphs depicting purification of cadmium glutathione complexes by gel-filtration (FIG. 9A) and anion-exchange chromatography (FIGS. 9B and 9C). Twenty mM $^{109}Cd_2SO_4$ was incubated with 40 mM GSH at 45° C. for 24 hours and the mixture was chromatographed on Sephadex G-15 to resolve a high molecular weight $^{109}$Cd-labeled component (HMW-$^{109}$Cd.GS) from a low molecular weight component (LMW-$^{109}$Cd.GS) (FIG.

9A). The peaks corresponding to HMW-$^{109}$Cd.GS and LMW-$^{109}$Cd.GS were then chromatographed on Mono-Q and eluted with a linear NaCl gradient (—) (FIGS. 9B and 9C). $^{109}$Cd (cpm ×10$_{-3}$) was determined on 5 μl aliquots of the column fractions by liquid scintillation counting.

Figure 10A:
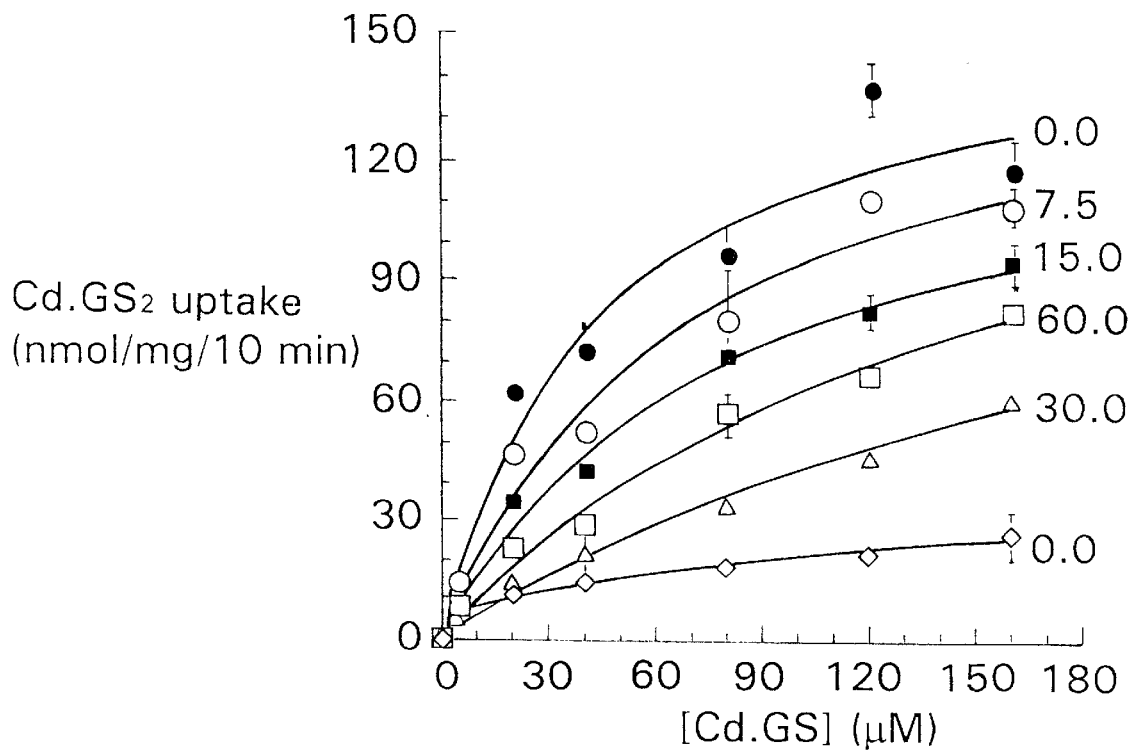
Figure 10B:
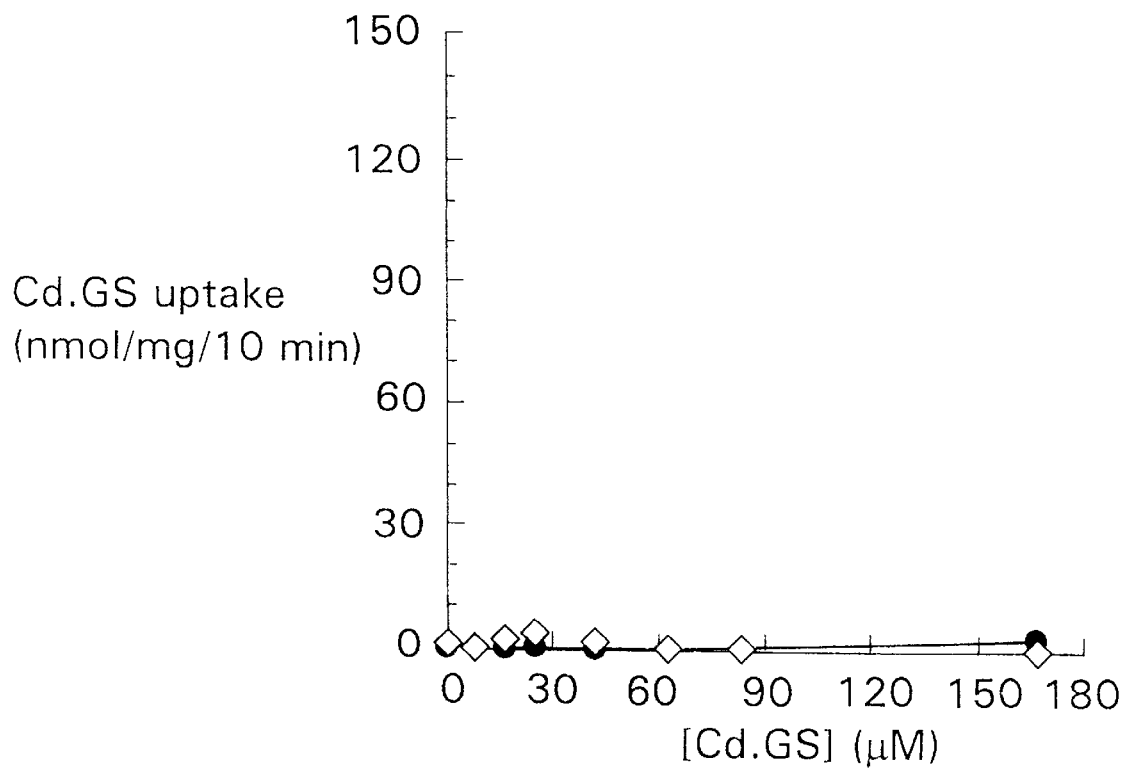
Figure 10C:
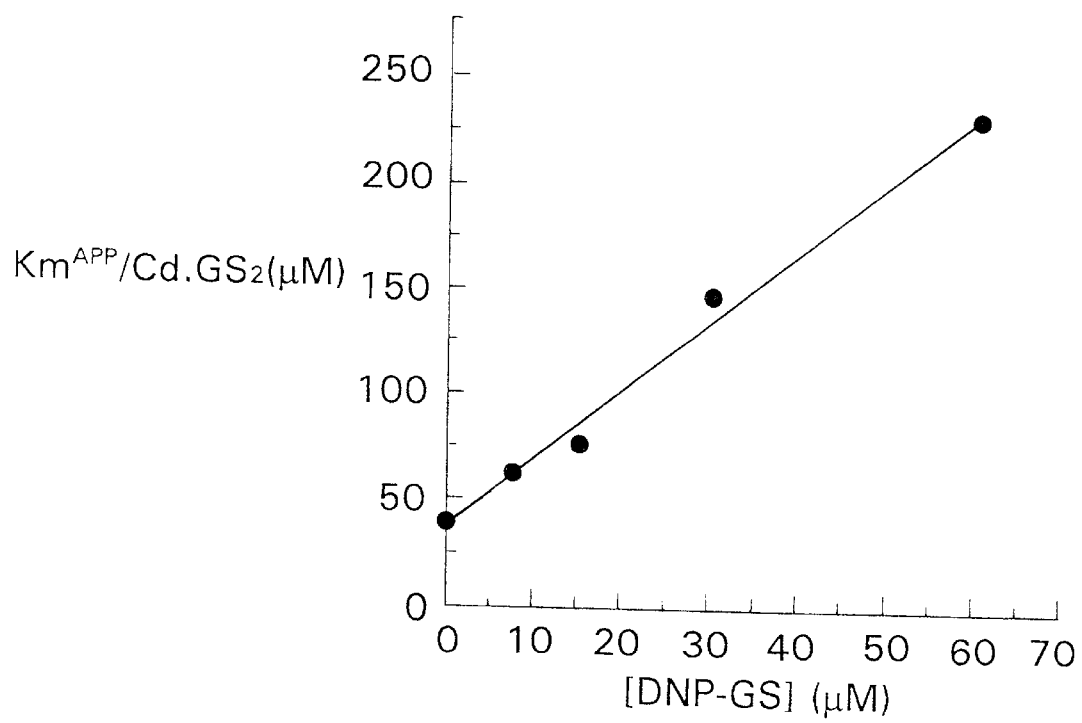

FIGS. 10A–10C are a series of graphs depicting the kinetics of MgATP-dependent, uncoupler-insensitive $^{109}$Cd.GS$_2$ (HMW-$^{109}$Cd.GS, FIG. 10A) and $^{109}$Cd.GS (LMW-$^{109}$Cd.GS, FIG. 10B) uptake. DNP-GS was added at the concentrations (EM) indicated to DTY165 membranes (●,○,■,□,∆) or DTY167 membranes (◇). A secondary plot of the apparent Michaelis constants for Cd.GS$_2$ uptake ($K_m^{aPP}$/Cd.GS$_2$) as a function of DNP-GS concentration is shown (FIG. 10C). The kinetic parameters for Cd.GS$_2$ transport by DTY165 membranes were $K_m$, 39.1±14.1 μM, $V_{max}$, 157.2±30.4 nmol/mg/10 minutes and $K_{i(DNP-GS)}$, 11.3±2.1 μM. Kinetic parameters were computed by nonlinear least squares analysis (Marquardt, 1963, supra). Values shown are means ±SE (n=6).

Figure 11:
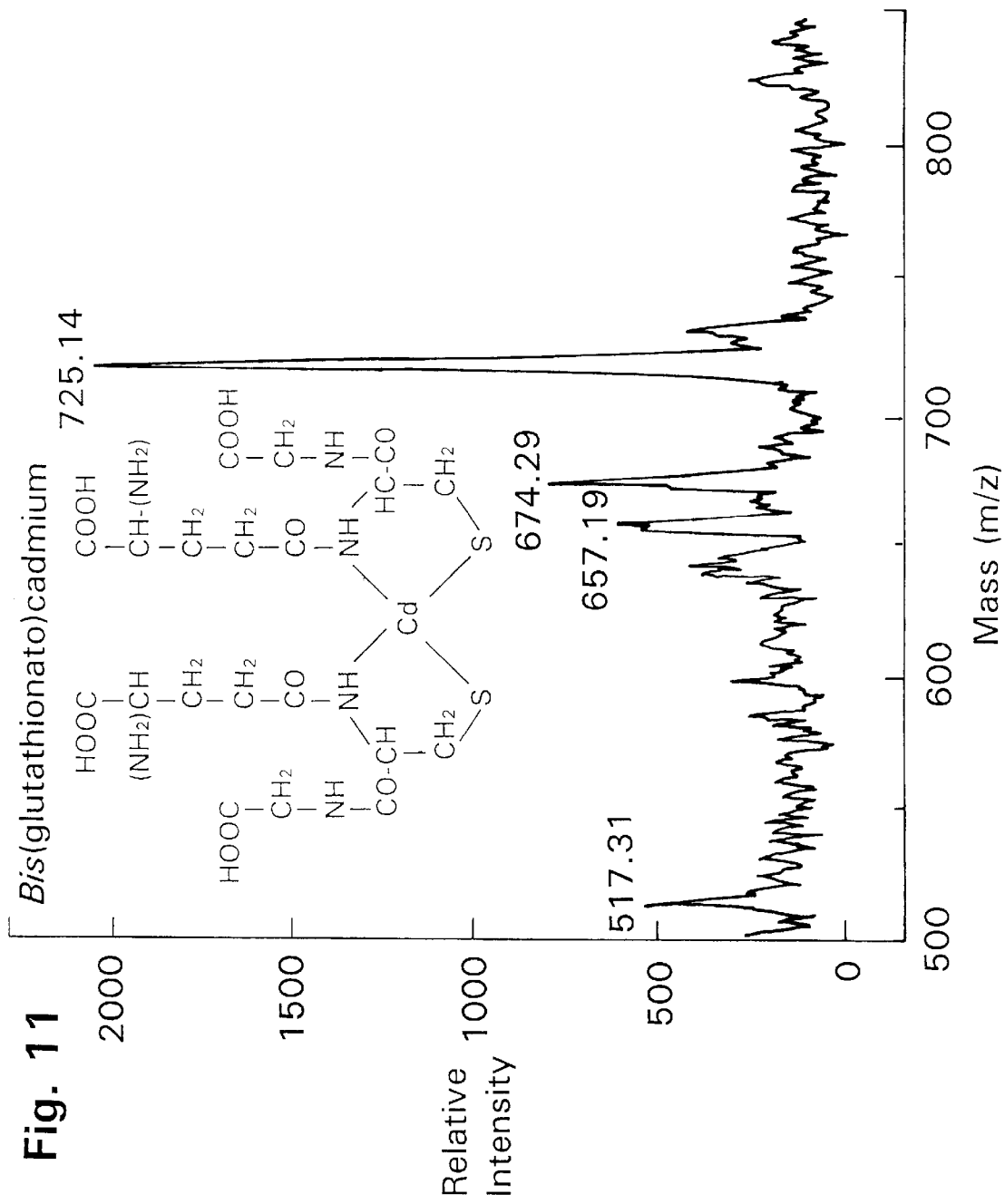

FIG. 11 is a graph depicting matrix-assisted laser desorption mass spectrometry (MALD-MS) of HMW-Cd.GS. MALD-MS was performed on Sephadex G-15-, Mono-Q-purified HMW-Cd.GS as described herein. The molecular structure inferred from a mean m/z ratio of 725.4±0.7 (n=9) and average Cd.GS stoichiometry of 0.5 [bis(glutathionato) cadmium, Cd.GS$_2$, molecular weight 724.6 Da] is shown.

Figure 12:
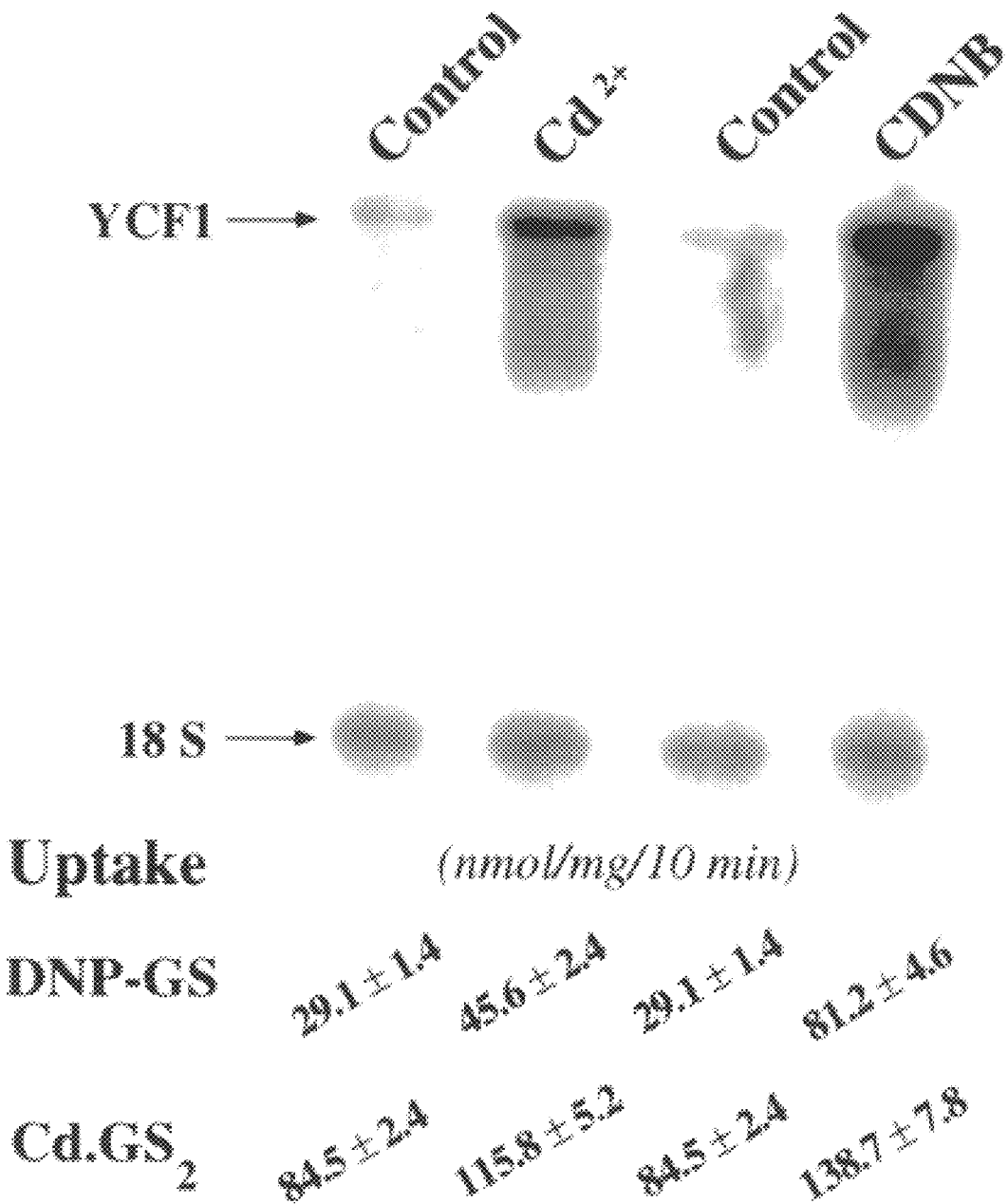

FIG. 12 is an image of a gel depicting induction of YCF1 expression and YCF1-dependent Cd.GS$_2$ and DNP-GS transport by pretreatment of DTY165 cells with CdSO$_4$ ($Cd^{2+}$, 200 μM) or CDNB (150 μM) for 24 hours. YCF1-specific mRNA and 18S rRNA were detected in the total RNA extracted from control or pretreated cells (10 μg/lane) by RNase protection. Uptake of $^{109}$Cd.GS$_2$ (50 μM) or [$^3$H]DNP-GS (66.2 μM) by vacuolar membrane vesicles was measured in standard uptake medium containing 5 μM gramicidin-D. Values shown are means ±SE (n=3).

FIGS. 13A and 13B is the sequence of AtMRP2 cDNA (SEQ ID NO: 1). Lower case letters correspond to 5'- and 3'-untranslated regions (UTRs).

FIGS. 14A–D is the genomic sequence of AtMPR2 (SEQ ID NO: 2). Lower case letters at the beginning and end of the sequence correspond to 5'- and 3'-UTRs, respectively; lower case letters nested within the sequence correspond to introns.

FIG. 15 is the deduced amino acid sequence of AtMRP2 (SEQ ID NO: 3).

FIGS. 16A and 16B is the sequence of AtMRP1 cDNA (SEQ ID NO: 4). Lower case letters correspond to 5'- and 3'-UTRs.

FIGS. 17A–D is the genomic sequence of AtMRP1 (SEQ ID NO: 5). Lower case letters at the beginning and end of the sequence correspond to 5'- and 3'-UTRs, respectively; lower case letters nested within the sequence correspond to introns.

FIG. 18 is the deduced amino acid sequence of AtMRP1 (SEQ ID NO: 6).

Figure 19A:
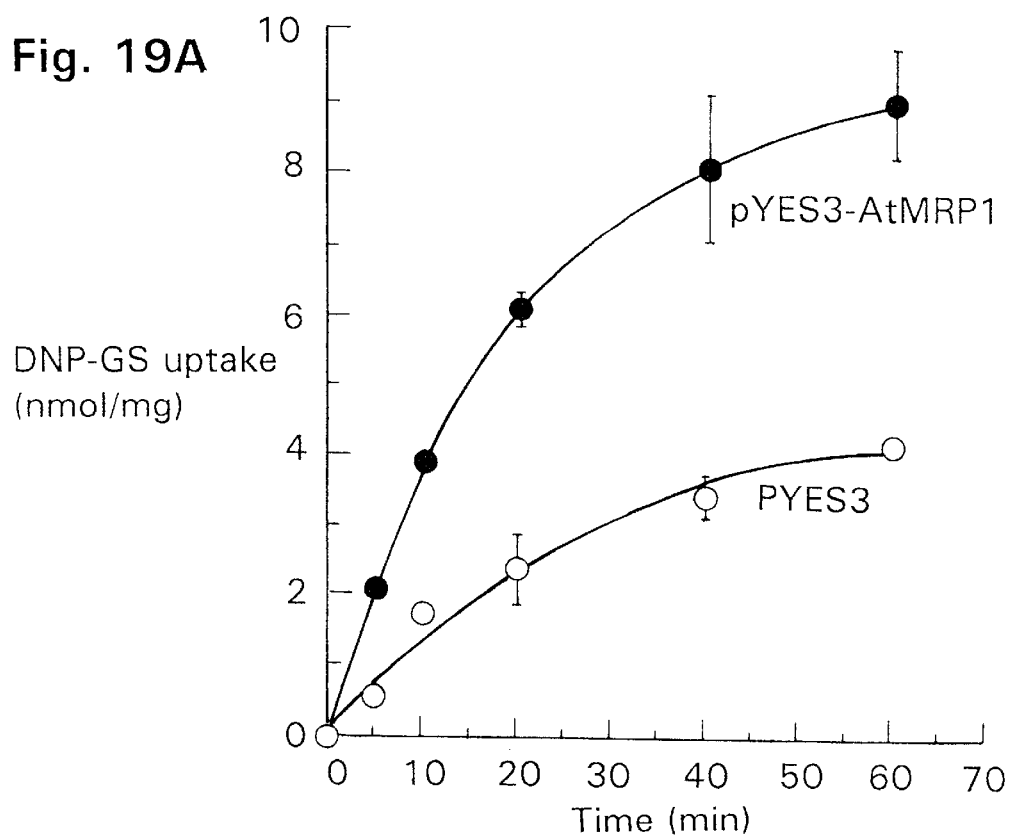
Figure 19B:
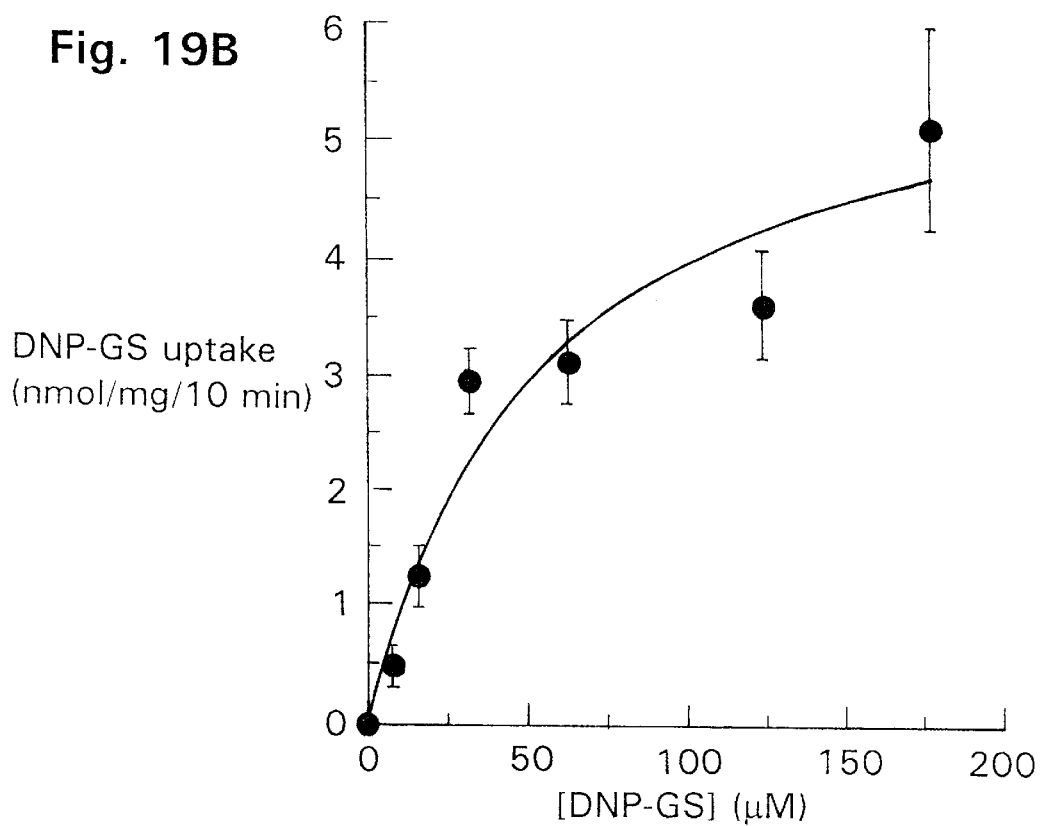

FIGS. 19A–19B are a series of graphs depicting the time course and concentration-dependence of DNP-GS uptake in AtMRP1-transformed yeast. FIG. 19A is a graph depicting the time course of [$^3$H]DNP-GS uptake by membrane vesicles purified from pYES3-AtMRP1-transformed or pYES3-transformed DTY168 cells. MgATP-dependent uptake was measured in reaction media containing 61.3 μM [$^3$H]DNP-GS, 5 μM gramicidin-D, 10 mM creatine phosphate, 16 units/ml creatine kinase, 50 mM KCl, 1 mg/ml bovine serum albumin, 400 mM sorbitol and 25 mM Tris-Mes (pH 8.0) at 25° C. Values shown are means ±SE (n=3). FIG. 19B is a graph depicting concentration dependence of MgATP-dependent, uncoupler-insensitive uptake of [$^3$H]DNP-GS by membrane vesicles purified from pYES3-AtMRP1-transformed DTY168 cells. Uptake was allowed to proceed for 10 minutes in standard uptake medium containing 5 μM gramicidin-D. The kinetic parameters for uptake were $K_{m(DNP-GS)}$ 49.7±15.4 μμM, $V_{max}$ 6.0±1.7 nmol/mg/10 minutes. The lines of best fit and kinetic parameters were computed by nonlinear least squares analysis (Marquardt, 1963, supra). Values shown are means±SE (n=3).

Figure 20A:
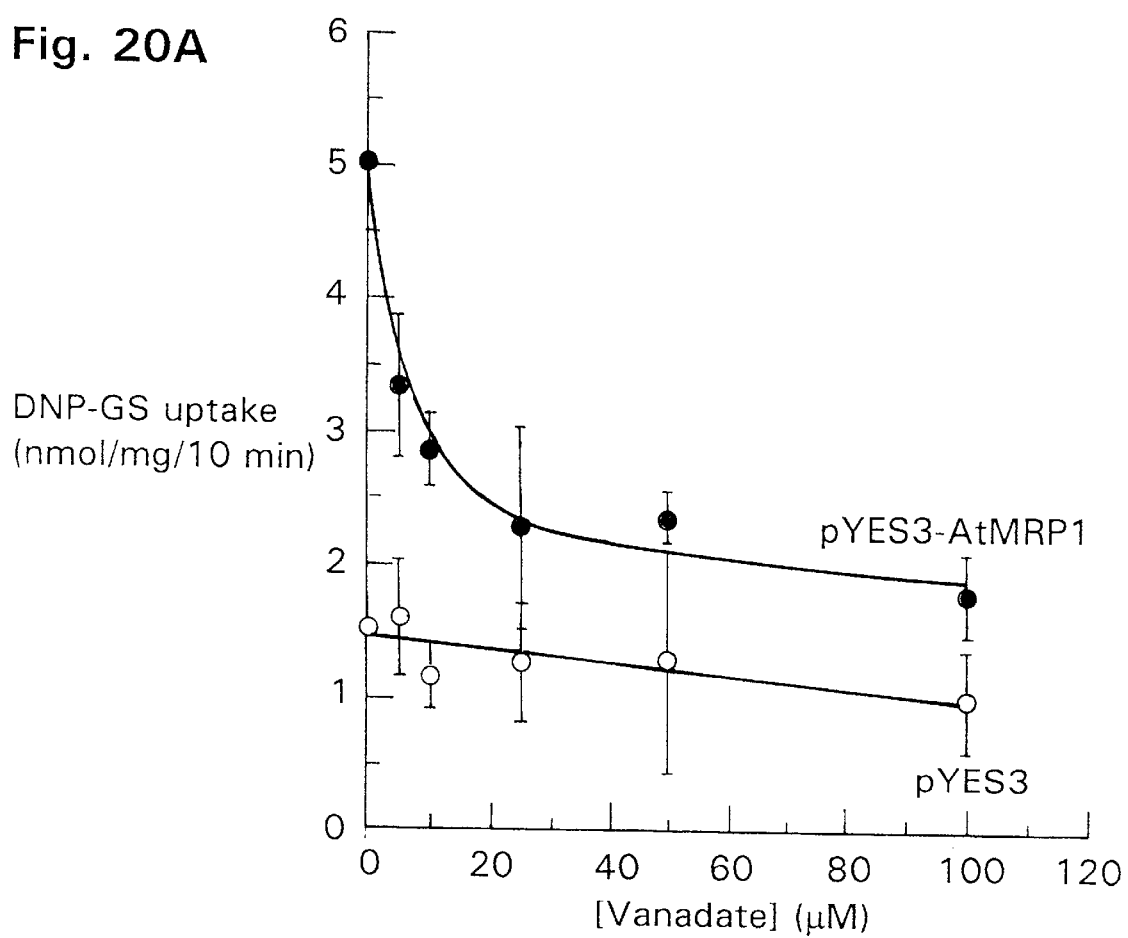
Figure 20B:
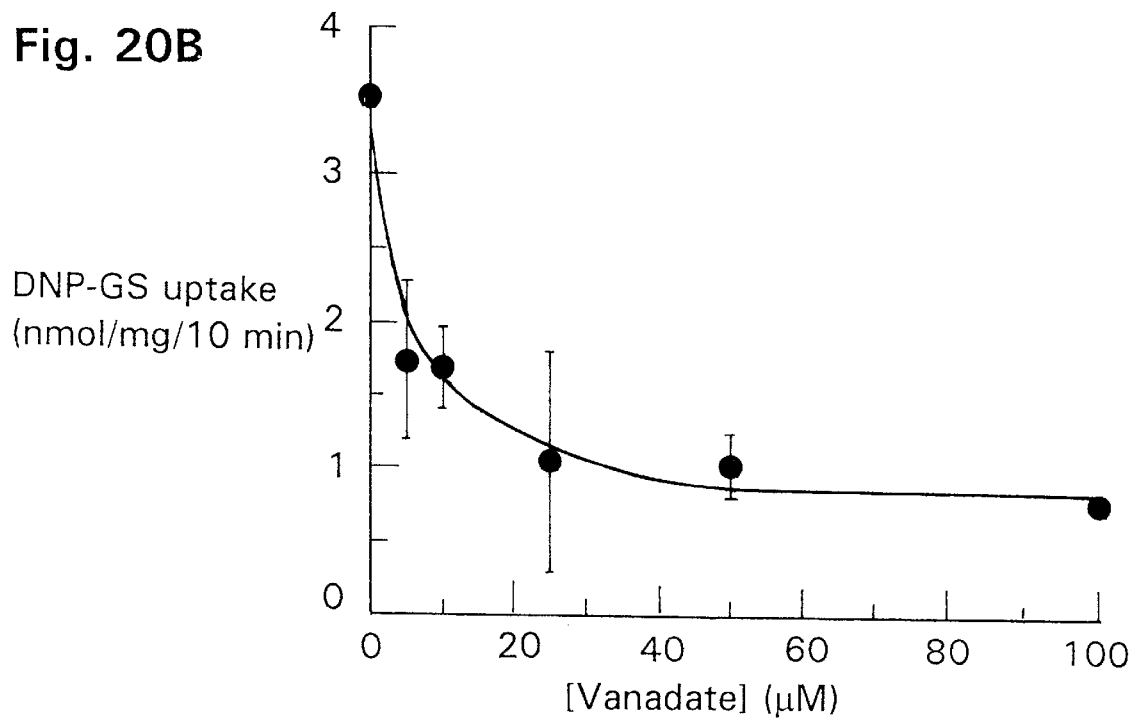

FIGS. 20A–20B are a series of graphs depicting sensitivity of MgATP-dependent, uncoupler-insensitive [$^3$H]DNP-GS uptake by membrane vesicles purified from pYES3-AtMRP1-transformed and pYES3-transformed DTY168 cells. Uptake was measured for 10 minutes in standard uptake medium containing the indicated concentrations of vanadate. In FIG. 20A, there is a graph depicting total MgATP-dependent, uncoupler-insensitive [$^3$H]DNP-GS uptake by membrane vesicles purified from pYES3-AtMRP1-transformed and pYES-transformed DTY168 cells. In FIG. 20B, there is a graph depicting AtMRP1-dependent uptake. $I_{50}$ (exclusive of uninhibitable AtMRP1-independent component)=8.3±3.2 μM. Values shown are means±SE(n=3).

Figure 21:
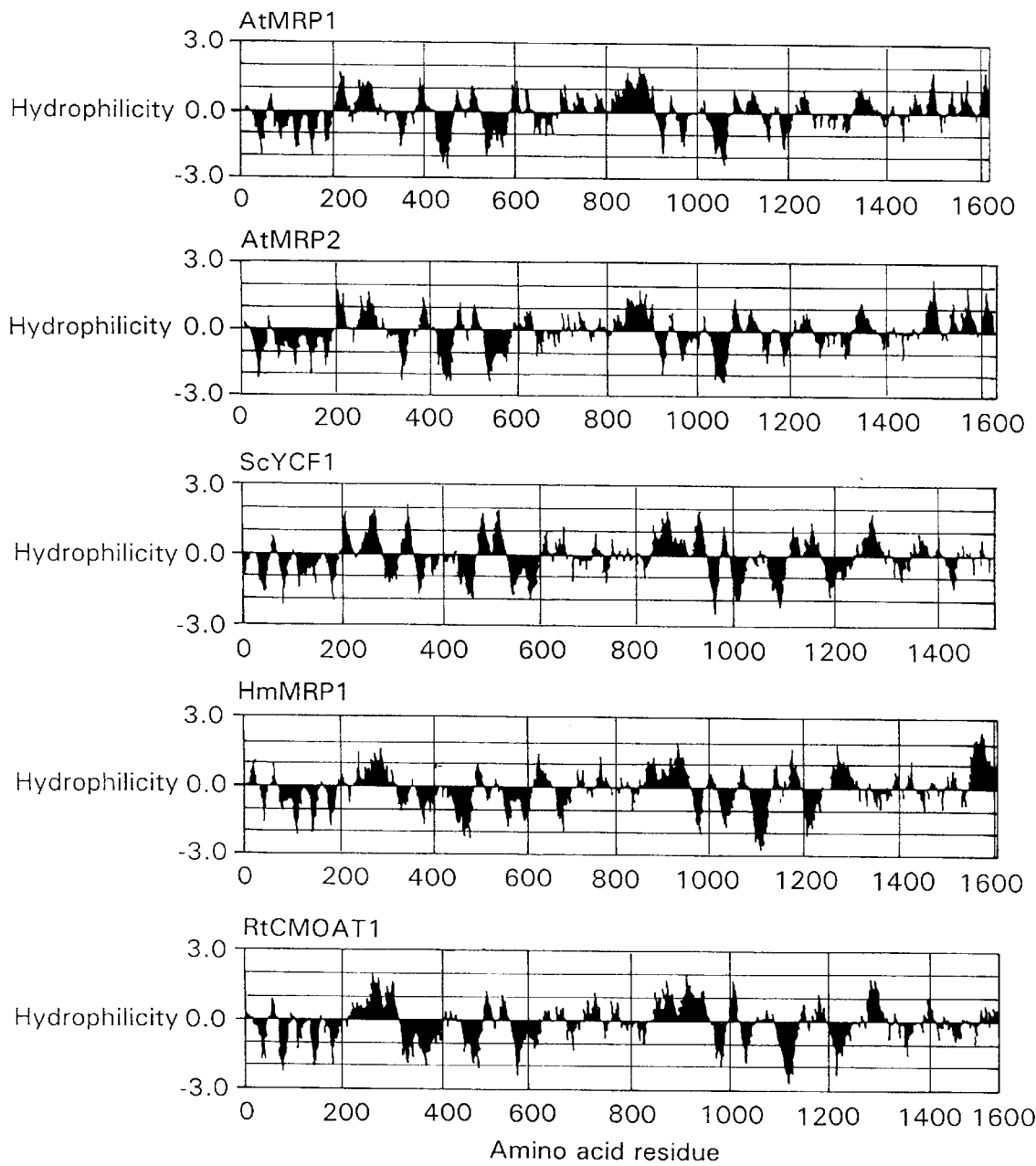

FIG. 21 is a series of graphs depicting the hydropathy alignment of AtMRP2, AtMRP1, S. cerevisiae YCF1 (ScYCF1), human MRP1 (HmMRP1) and rat cMOAT (RtCMOAT).

Figure 22:
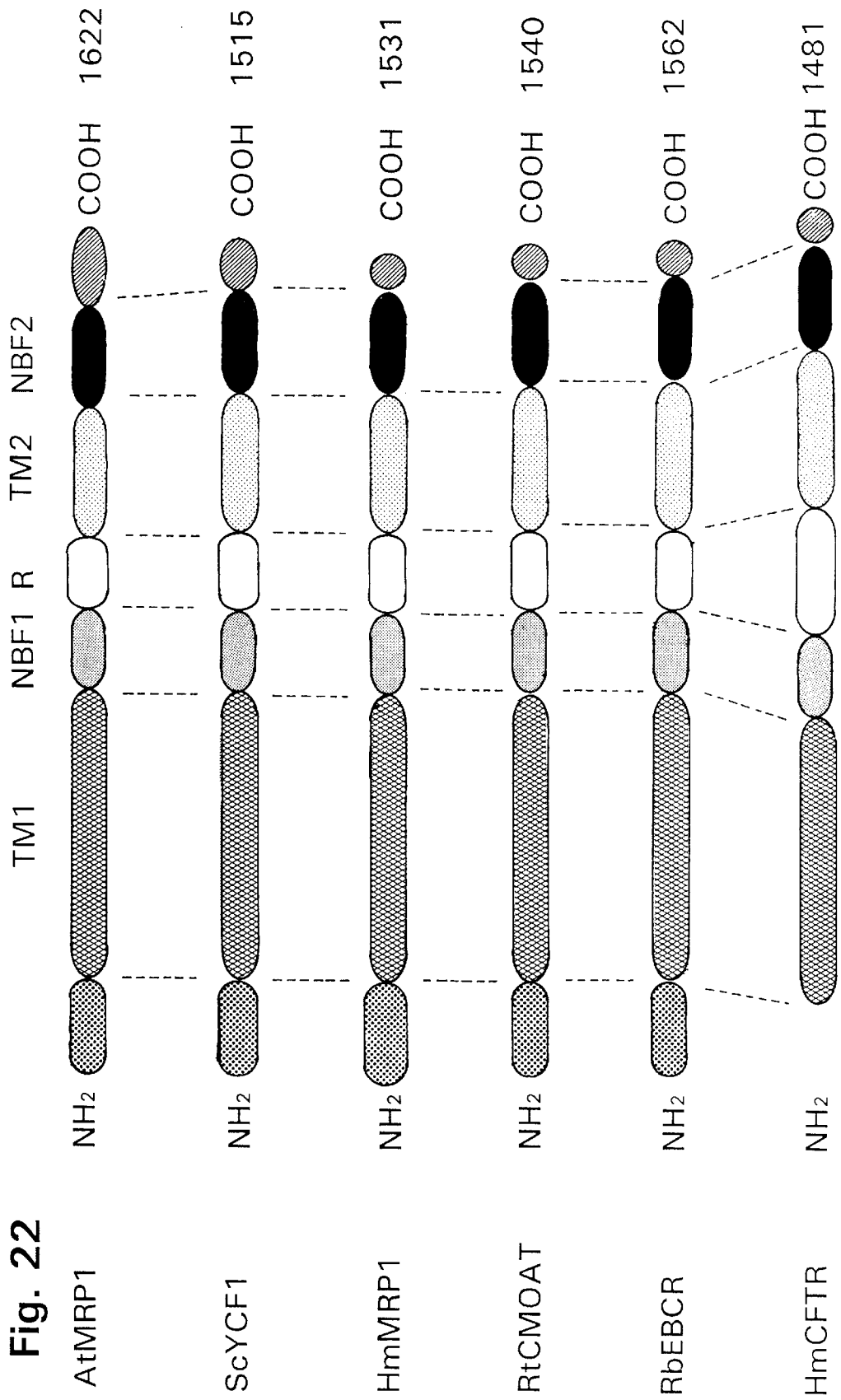

FIG. 22 is a diagram depicting domain comparisons between AtMRP1, ScYCF1, HmMRP1, RtCMOAT, rabbit EBCR (RbEBCR) and HmCFTR. The domains indicated are the N-terminal extension (NH$_2$), first and second sets of transmembrane spans (TM1 and TM2, respectively), first and second nucleotide binding folds (NBF1 and NBF2, respectively), putative CFTR-like regulatory domain (R), and the C-terminus (COOH).

FIG. 23 is the promoter sequence of the Arabidopsis AtMRP1 gene (SEQ ID NO: 7). Discrete elements which are present in the promoter sequence are indicated in boldface letters.

FIG. 24 is the promoter sequence of the Arabidopsis AtMRP2 gene (SEQ ID NO: 8). Discrete elements which are present in the promoter sequence are indicated in boldface letters.

FIG. 25 is a graph depicting MgATP-dependence of [$^3$H]medicarpin uptake by vacuolar membrane vesicles before (Medicarpin/GSH) and after maize GST-mediated conjugation with GSH (Medicarpin-GS). [3 H]medicarpin or [3 Hmedicarpin-GS was added at a concentration of 65 μM. MgATP was either omitted (-MgATP) or added at a concentration of 3 mM (+MgATP). Values shown are means ±SE (n=3).

Figure 26:
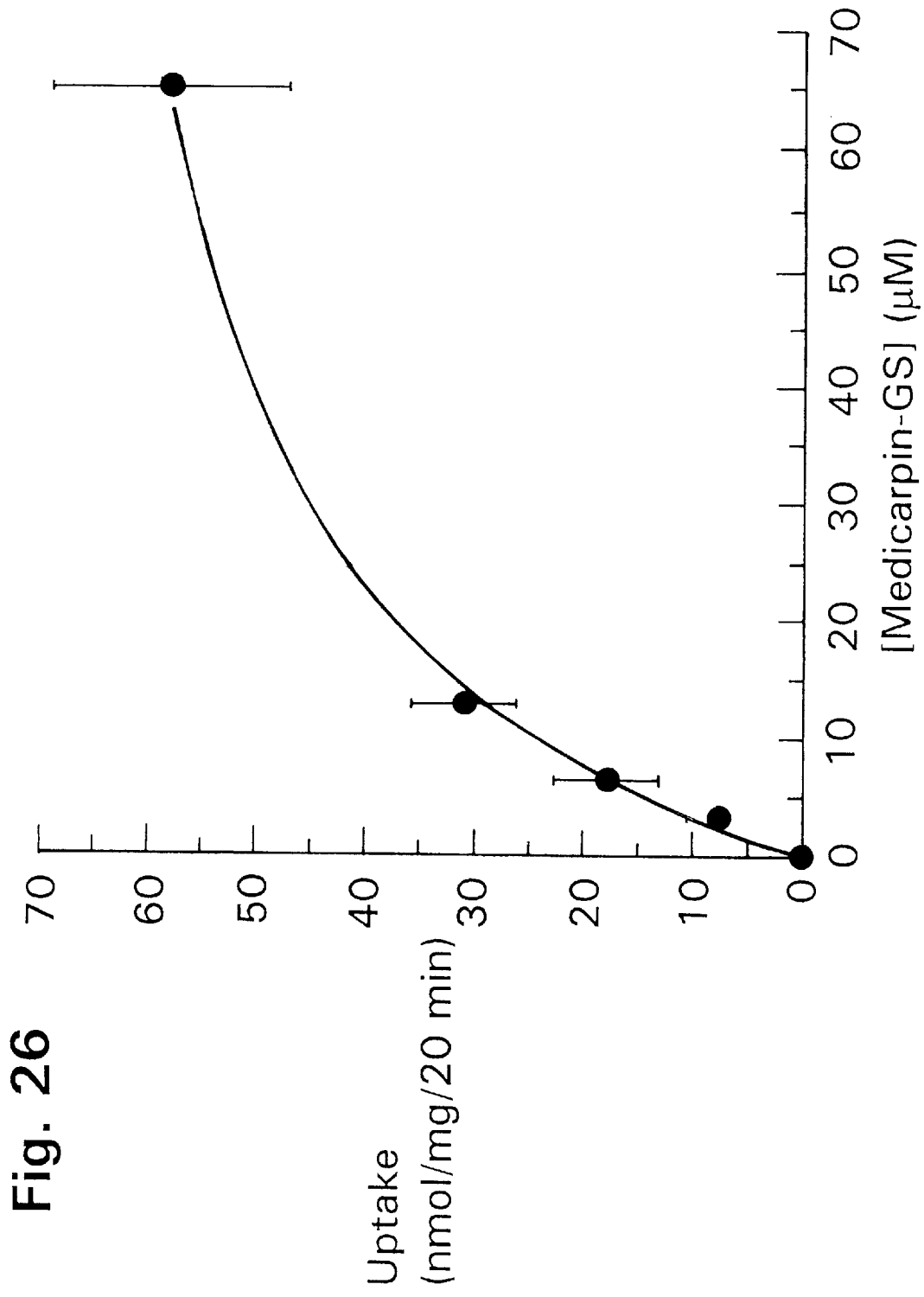

FIG. 26 is a graph depicting concentration dependence of MgATP-dependent, uncoupler-insensitive [3 H]medicarpin-GS uptake into vacuolar membrane vesicles. Uptake was allowed to proceed for 20 minutes in standard uptake medium containing 3 mM MgATP and 5 μM gramicidin D. The kinetic parameters were Km 21.5±15.5 μM and $V_{max}$ 77.8±23.3 nmol/mg/20 minutes. Values shown are means ±SE (n=3).

Figure 27A:
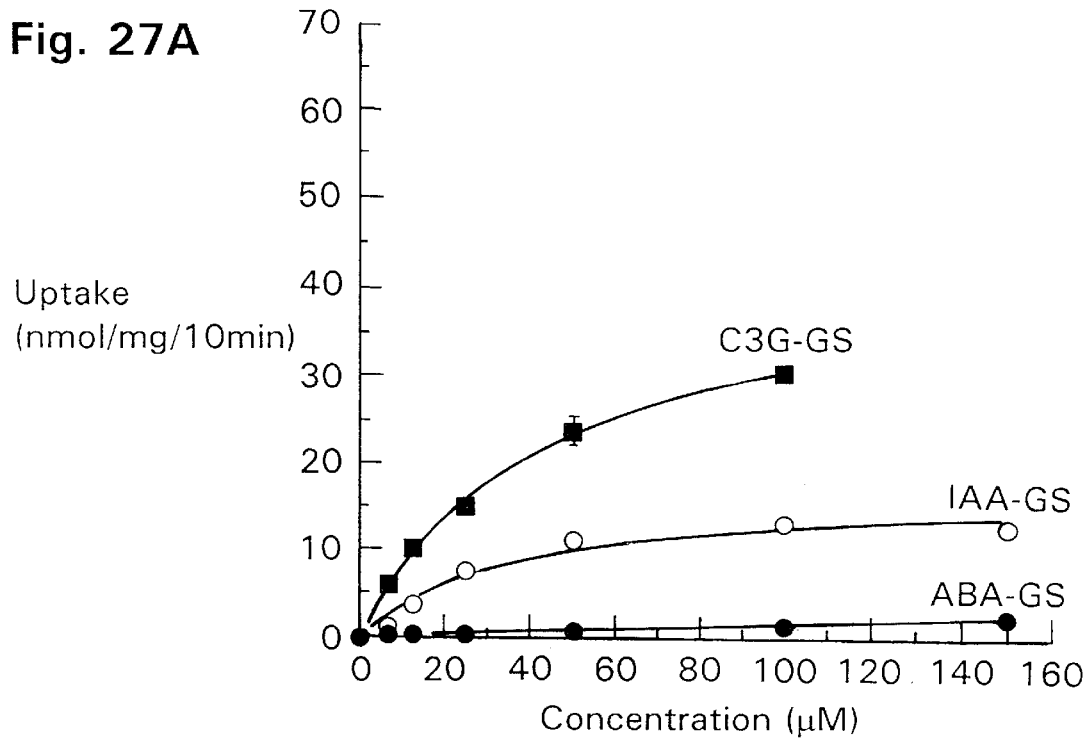
Figure 27B:
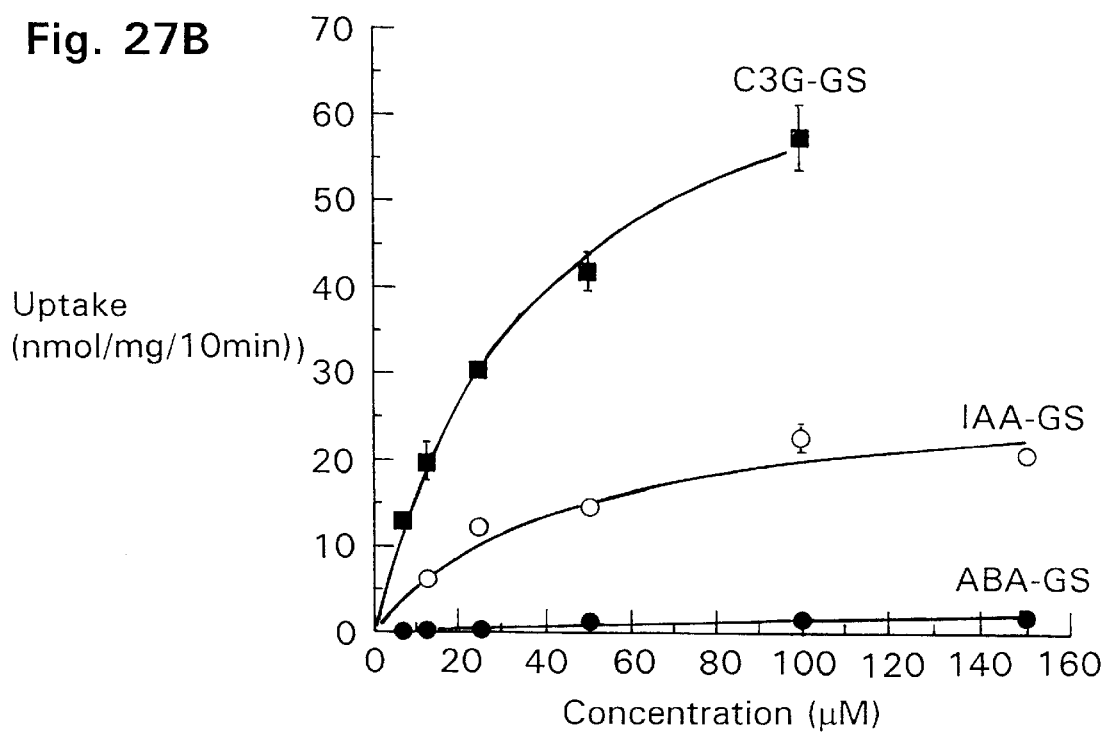

FIGS. 27A–27B are a series of graphs depicting concentration-dependence of MgATP-dependent, uncoupler-insensitive $C_3$G-GS, IAA-GS and ABA-GS uptake by vacuolar membrane vesicles purified from V radiata (FIG. 27A) and Z. mays (FIG. 27B). Uptake was allowed to proceed for 10 minutes in reaction medium containing 50 μM GS-conjugate, 400 mM sorbitol, 3 mM MgATP, 50 mM KCl, 0.1% (w/v) BSA, 5 μM gramicidin-D and 25 mM Tris-Mes (pH 8.0) at 25° C. Values shown are means ±SE (n=3).

Figure 28:
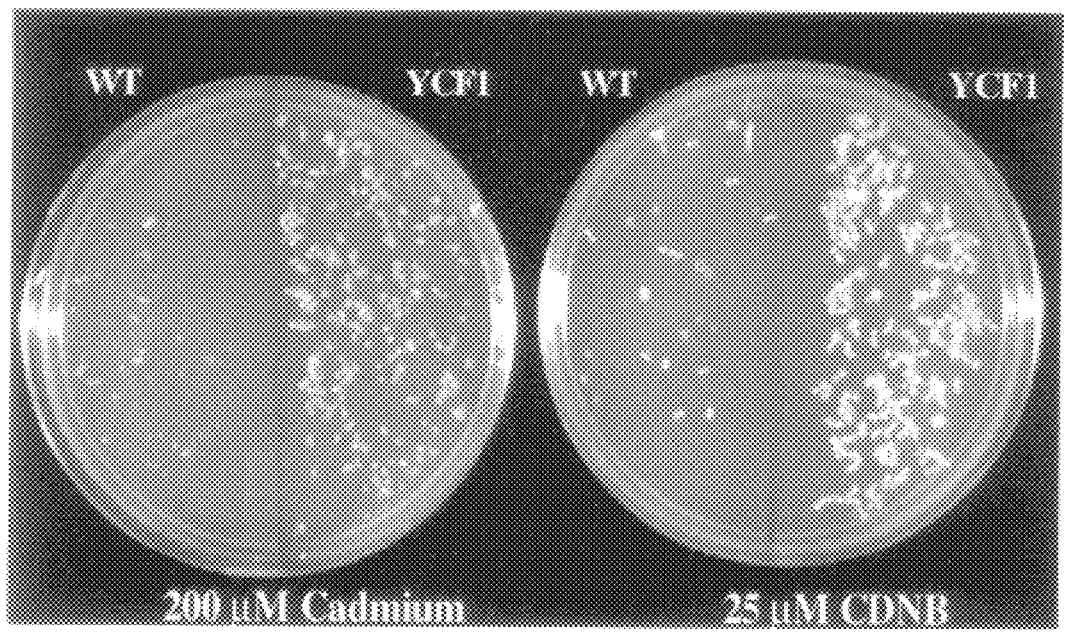

FIG. 28 is an image of a photograph depicting the growth of wild type (WT) and YCF1 transgenic Arabidopsis (YCF1) seeds on media containing $CdSO_4$ (200 μM) or 1-chloro-2, 4-dinitrobenzene (CDNB, 25 μM). Transgenic plants were generated as described herein.

DETAILED DESCRIPTION OF THE INVENTION

The invention is based upon the molecular identification of a new class of membrane transporter in yeast and plants, the GS-X pump. As a result of the present invention, new insights into the membrane transport phenomena associated with heavy metal tolerance, herbicide detoxification, plant-pathogen interactions, plant responses to (phyto)hormones, plant pigmentation and bioremediation are evident. These insights provide a means, as is evident from the description of the present invention, for the manipulation of plants and the cells thereof, to affect heavy metal tolerance, herbicide detoxification, plant-pathogen interactions, plant responses to (phyto)hormones, plant pigmentation and bioremediation.

The process of "storage excretion" is a necessity for plants. Whereas mammals have the option of excreting GS-conjugates to the extracellular medium for elimination by the kidneys, plants are nearly totally reliant on the sequestration of noxious compounds in the central vacuole, which frequently accounts for 40–90% of total intracellular volume. Due to the virtual absence of specialized excretory organs and the presence of massive vacuoles in plants, a process (intracellular compartmentation) that is probably only an intermediate step in the elimination of xenobiotics from the cytosol of mammalian cells, is believed to constitute a terminal phase of detoxification in plants.

The data which are described herein establish that the yeast gene YCF1 and two plant homologs of YCF1, AtMRP1 and AtMRP2, isolated from *Arabidopsis thaliana*, each encode a vacuolar GS-X pump. The data further establish that the GS-X pump participates in herbicide metabolism (exemplified by organic xenobiotic transport), heavy metal sequestration (exemplified by cadmium transport), plant-pathogen interactions (exemplified by vacuolar uptake of medicarpin), plant cell pigmentation (exemplified by transport of glutathionated anthocyanins) and plant hormone metabolism (exemplified by the transport of glutathionated auxins).

The plant AtMRP1 and AtMRP2 gene products use MgATP as an energy source for the transport of glutathionated derivatives of both endogenous and exogenous compounds in plants and thus, the discovery of these genes in the present invention is important at three levels. The identification of these genes and their encoded products represents the first identification of ABC transporters in plants for which a biochemical function is defined. The discovery establishes, contrary to the prevailing chemiosmotic model for solute transport in plants, that many energy-dependent solute transport processes in plants are not driven by a transmembrane H+ electrochemical potential difference. Further, the identification and isolation of these genes and their encoded products permits a plant element, critical for removal of compounds from the cytosol that can form glutathionine S-conjugates, to be manipulated.

It has been discovered in the present invention that two plant genes, AtMRP1 and AtMRP2, are the structural and functional homologs of the gene encoding yeast YCF1. Proteins encoded by plant AtMRP1 and AtMRP2 thus represent a new subclass of ATP binding cassette transporters.

It has been further discovered in the present invention that the yeast YCF1 protein, a GS-X pump, is capable of MgATP-energized transport of organic GS-conjugates and of MgATP-energized transport of cadmium upon complexation with GSH. In addition, when plants have introduced into the cells thereof the YCF1 gene (a transgenic plant comprising YCF1), expression of YCF1 therein confers upon the plants resistance to both inorganic and organic xenobiotics exemplified by cadmium and 1-chloro-2,4-dinitrobenzene, respectively.

Also discovered in the present invention is the fact that AtMRP1 and AtMRP2, when expressed in a strain of yeast which is deficient in YCF1, can substitute for YCF1 as a GS-X pump. In addition, transformation of plants by YCF1 confers upon the plant properties which are characteristic of YCF1 gene expression. Thus, it appears that YCF1 and the AtMRP genes are essentially functionally interchangeable.

In addition, there is provided as part of the invention the promoter/regulatory sequences which control expression of the plant AtMRP1 and AtMRP2 genes of the invention. These promoter sequences are useful for the identification of compounds which affect expression of these genes in plants and for conferring on other genes the ability to respond to factors that modulate AtMRP1 and/or AtMRP2 expression.

Further discovered in the present invention is the fact that the plant GS-X pump serves to facilitate the vacuolar storage of antimicrobial compounds induced following the hypersensitive response to fungal pathogens in the healthy cells surrounding fungally-induced lesions. Such a process is believed to limit the spread of tissue damage by limiting propagation of the pathogen and spatially delimiting the toxic action of the phytoalexin itself.

Ascription of specific enzymic and regulatory roles to most of the genes of the anthocyanin biosynthetic pathway has been achieved by genetic and biochemical studies of maize with one notable exception, the Bronze-2 gene. It is known that the characteristic coloration of Bronze-2 (bz2) mutants is a consequence of the accumulation of cyanidin-3-glucoside in the cytosol. However, in wild type (Bz2) plants, anthocyanins are transported into the vacuole and become purple or red. In the mutant (bz2) plants, anthocyanin is restricted to the cytoplasm where it is oxidized to a brown ("bronze") pigment. The biochemical basis for the accumulation of anthocyanins in the cytosol is not known. However, Marrs et al., (1995, supra) have discovered that Bz2 encodes a glutathione S-transferase which is responsible for conjugating anthocyanin with GSH. It has now been discovered in the present invention that the plant GS-X pump is the entity responsible for the delivery of glutathionated anthocyanins into the vacuole.

Identification of the GS-X pump at the molecular level has served to confirm its wide distribution and demonstrate that these transporters constitute a multigene family within the ABC transporter superfamily. The critical finding was that overexpression of the human multidrug resistance-associated protein (MRP1) gene (Cole et al., 1992, supra) confers increased MgATP-dependent GS-conjugate transport (Muller et al., 1994 supra; Leier et al.,, 1994, J. Biol. Chem. 269:27807–27810).

Several other closely related GS-X pump genes have been characterized. For example, a liver-specific GS-X pump (CMOAT), mutation of which is believed to cause hereditary hyperbilirubinemia, has been cloned (Paulusma et al., 1996, Science 271:1126–1128). The present invention establishes that YCF1 is a GS-X pump. In addition, as will become apparent from a reading of the present description, two plant genes, AtMRP1 and AtMRP2 have been discovered in the present invention to encode homologs of MRP1, YCF1 and cMOAT.

The identification of YCF1 as a vacuolar GS-X pump is described in detail in the experimental details section. Similarly, the identification of two plant homologs of YCF1, AtMRP1 and AtMRP2, is also described in detail in the experimental details section. Once armed with the present invention, the skilled artisan will know how to identify and isolate genes encoding other plant GS-X pumps involved in sequestration of a variety of compounds in plants by following the procedures described herein.

A plant gene encoding a GS-X pump is isolated using any one of several known molecular procedures. For example, primers comprising conserved regions of the sequences of any of YCF1, AtMRP1 or AtMRP2, or in fact primers comprising conserved regions of any MRP subclass (i.e., probes directed to human MRP1 cMOAT, and other MRP genes) may be used as probes to isolate, by polymerase chain reaction (PCR) or by direct hybridization, as yet unknown YCF1, AtMRP1 or AtMRP2 homologs in a DNA library comprising specific plant DNAs. Alternatively, antibodies directed against YCF1, AtMRP1 or AtMRP2 may be used to isolate clones encoding a GS-X pump from an expression library comprising specific plant DNAs. The isolation of primers, probes, molecular cloning and the generation of antibodies are procedures that are well known in the art and are described, for example, in Sambrook et al. (1989, *Molecular Cloning: A Laboratory Manual,* Cold Spring Harbor, New York) and in Harlow et al. (1988, Antibodies, A Laboratory Manual, Cold Spring Harbor, New York).

The invention includes an isolated DNA encoding a plant GS-X pump capable of transporting a glutathionated compound across a biological membrane. Preferably, the membrane is derived from a cell. Preferably, the DNA encoding a plant GS-X pump is at least about 40% homologous to at least one of YCF1, AtMRP1 or AtMRP2. More preferably, the isolated DNA encoding a plant GS-X pump is at least about 50%, even more preferably, at least about 60%, yet more preferably, at least about 70%, even more preferably, at least about 80%, yet more preferably, at least about 90% homologous, and more preferably, at least about 99% homologous to at least one of YCF1, AtMRP1 or AtMRP2. More preferably, the isolated DNA encoding a plant GS-X pump is Arabidopsis AtMRP1 or AtMRP2. Most preferably, the isolated DNA encoding a plant GS-X pump is SEQ ID NOS: 1, 2, 4 or 5.

Thus, the invention should be construed to include genes which encode Arabidopsis AtMRP1 and AtMRP2 and Arabidopsis AtMRP1 and AtMRP2-related genes.

By "GS-X pump" as used herein, is meant a protein which transports a glutathione-conjugated compound across a biological membrane.

By the term "DNA encoding a GS-X pump" as used herein is meant a gene encoding a polypeptide capable of transporting a glutathionated compound across a biological membrane.

By "AtMRP-related gene" as used herein, is meant a gene encoding a GS-X pump which is a member of the MRP/YCF1/cMOAT family of genes. An AtMRP1 or AtMRP2-related gene may be present in a cell which also encodes an AtMRP gene or it may be present in a different cell and in a different plant species.

As described in the Experimental Detail section, AtMRP genes encode proteins which have specific domains located therein, namely, the N-terminal extension, transmembrane spans, TM1 and TM2, nucleotide binding folds, NBF1 and NBF2, putative CFTR-like regulatory domain (R) and the C-terminus. An AtMRP-related gene is therefore also one in which selected domains in the related protein share significant homology (at least about 40% homology) with the same domains in either of YCF1, AtMRP1 or AtMRP2. For example, when the R-domain in the AtMRP-related protein shares at least about 40% homology with the R domain in YCF1, AtMRP1 or AtMRP2, and when the product of that is a GS-X pump, then that gene is an AtMRP-related gene. Similarily, when the N-terminal extension in the AtMRP-related protein shares at least about 40% homology with the N-terminal extension in YCF1, AtMRP1 or AtMRP2, and when the product of that is a GS-X pump, then that gene is an AtMRP-related gene. It will be appreciated that the definition of an AtMRP-related gene encompasses those genes having at least about 40% homology in any of the described domains contained therein with the same or a similar domain in either of YCF1, AtMRP1 or AtMRP2. In addition, when the term homology is used herein to refer to the domains of these proteins, it should be construed to be applied to homology at both the nucleic acid and the amino acid levels.

While a significant homology between similar domains in AtMRP-related genes or their protein products is considered to be at least about 40%, preferably, the homology between domains is at least about 50%, more preferably, at least about 60%, even more preferably, at least about 70%, even more preferably, at least about 80%, yet more preferably, at least about 90% and most preferably, the homology between similar domains is about 99% between a domain in an AtMRP-related gene or protein product thereof, and at least one of YCF1, AtMRP1 or AtMRP2 or the protein products thereof.

Plants from which AtMRP1, AtMRP2 or YCF1 related genes may be isolated include any plant in which the GS-X pump is found, including, but not limited to, soybean, castor bean, maize, petunia, potato, tomato, sugar beet, tobacco, oats, wheat, barley, pea, faba bean and alfalfa.

By the term "glutathionated-conjugated compound" as used herein is meant a compound, e.g., a metal, a xenobiotic, a isoflavonoid phytoalexin, anthocyanin or auxin, which is chemically conjugated to glutathionine. Conjugation of compounds to glutathione occurs naturally within cells and organisms and may also be accomplished enzymatically or non-enzymatically in vitro as described herein in the experimental details section.

Also included in the invention is an isolated DNA encoding a biologically active polypeptide fragment of a plant GS-X pump. Preferably, the isolated DNA encoding a biologically active polypeptide fragment of a plant GS-X pump is at least about 40% homologous to a biologically active polypeptide fragment of at least one of YCF1, AtMRP1 or AtMRP2. More preferably, the isolated DNA encoding a biologically active polypeptide fragment of a plant GS-X pump is at least about 50%, even more preferably, at least about 60%, yet more preferably, at least about 70%, even more preferably, at least about 80%, yet more preferably, at least about 90%, and even more preferably, at least about 99% homologous to a biologically active polypeptide fragment of at least one of YCF1, AtMRP1 or AtMRP2. Most preferably, the isolated DNA encoding a biologically active polypeptide fragment of a plant GS-X pump is a biologically active polypeptide fragment of Arabidopsis AtMRP1 or AtMRP2.

Preferably, the isolated DNA encoding a biologically active polypeptide fragment of a plant GS-X pump is about 200 nucleotides in length. More preferably, the isolated DNA encoding a biologically active polypeptide fragment of a plant GS-X pump is about 400 nucleotides, even more preferably, at least about 600, yet more preferably, at least about 800, even more preferably, at least about 1000, and more preferably, at least about 1200 nucleotides in length.

The invention further includes a vector comprising a gene encoding a plant GS-X pump and a vector comprising nucleic acid sequence encoding a biologically active fragment thereof. The procedures for the generation of a vector encoding a plant GS-X pump, or fragment thereof, are well known in the art once the sequence of the gene is known, and are described, for example, in Sambrook et al. (supra). Suitable vectors include, but are not limited to, disarmed Agrobacterium tumor-inducing (Ti) plasmids (e.g., pBIN19) containing the target gene under the control of the cauliflower mosaic virus (CaMV) 35S promoter (Lagrimini et al., 1990, Plant Cell 2:7–18) or its endogenous promoter (Bevan, 1984, Nucl. Acids Res. 12:8711–8721).

Also included in the invention is a cell comprising an isolated DNA encoding a plant GS-X pump and a cell comprising an isolated DNA encoding a biologically active fragment thereof. Such a cell is referred to herein as a "recombinant cell."

The procedures for the generation of a cell encoding a plant GS-X pump or fragment thereof, are well know in the art once the sequence of the gene is known, and are described, for example, in Sambrook et al. (supra). Suitable cells include, but are not limited to, yeast cells, bacterial cells, mammalian cells, and baculovirus-infected insect cells transformed with the gene for the express purpose of generating GS-X polypeptide. In addition, plant cells transformed with the gene for the purpose of producing cells and regenerated plants having increased resistance to and increased capacity for heavy metal accumulation, increased resistance to organic xenobiotics and increased capacity for organic xenobiotic accumulation or altered coloration.

The invention also includes an isolated preparation of a polypeptide comprising a plant GS-X pump capable of transporting a glutathionated compound across a biological membrane. Preferably, the isolated preparation of a polypeptide comprising a plant GS-X pump is at least about 30% homologous to at least one of YCF1, AtMRP1 or AtMRP2. More preferably, the isolated preparation of a polypeptide comprising a plant GS-X pump is at least about 40%, even more preferably, at least about 50%, yet more preferably, at least about 60%, even more preferably, at least about 70%, more preferably, at least about 80%, even more preferably, at least about 90% and more preferably, at least about 99% homologous to at least one of YCF1, AtMRP1 or AtMRP2. More preferably, the isolated preparation of a polypeptide comprising a plant GS-X pump is Arabidopsis AtMRP1 or AtMRP2. Most preferably, the isolated preparation of a polypeptide comprising a plant GS-X pump is SEQ ID NOS: 3 or 6.

Also included in the invention is an isolated preparation of a biologically active polypeptide fragment of a plant GS-X pump. Preferably, the isolated preparation of a biologically active polypeptide fragment of a plant GS-X pump is at least about 30% homologous to a biologically active polypeptide fragment of at least one of YCF1, AtMRP1 or AtMRP2. More preferably, the isolated preparation of a biologically active polypeptide fragment of a plant GS-X pump is at least about 40%, even more preferably, at least about 50%, yet more preferably, at least bout 60%, even more preferably, at least about 70% and yet more preferably, at least bout 80%, even more preferably, at least about 90% and more preferably, at least about 99% homologous to a biologically active polypeptide fragment of at least one of YCF1, AtMRP1 or AtMRP2. Most preferably, the isolated preparation of a biologically active polypeptide fragment of a plant GS-X pump is a biologically active polypeptide fragment of Arabidopsis AtMRP1 or AtMRP2.

Preferably, the polypeptide in the isolated preparation of a biologically active polypeptide fragment of a plant GS-X pump is about 60 amino acids in length. More preferably, the polypeptide in the isolated preparation of a biologically active polypeptide fragment of a plant GS-X pump is about 130 amino acids, even more preferably, at least about 200, yet more preferably, at least about 300, even more preferably, at least about 350, and more preferably, at least about 400 amino acids in length.

As used herein, the term "homologous" refers to the subunit sequence similarity between two polymeric molecules e.g., between two nucleic acid molecules, e.g., between two DNA molecules, or two polypeptide molecules. When a subunit position in both of the two molecules is occupied by the same monomeric subunit, e.g., if a position in each of two polypeptide molecules is occupied by phenylalanine, then they are homologous at that position. The homology between two sequences is a direct function of the number of matching or homologous positions, e.g., if half (e.g., 5 positions in a polymer 10 subunits in length) of the positions in two polypeptide sequences are homologous then the two sequences are 50% homologous; if 70% of the positions, e.g., 7 out of 10, are matched or homologous, the two sequences share 70% homology. By way of example, the polypeptide sequences ACDEFG and ACDHIK (SEQ ID NOS: 9 and 10, respectively) share 50% homology and the nucleotide sequences CAATCG and CAAGAC share 50% homology.

An "isolated DNA," as used herein, refers to a DNA sequence which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid (e.g., RNA, DNA or protein) in its natural state. The term therefore includes, for example, a recombinant DNA which is incorporated into a vector; into an autonomously replicating plasmid or virus; or into the genomic DNA of a prokaryote or eukaryote; or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "isolated preparation of a polypeptide" describes a polypeptide which has been separated from components which naturally accompany it. Typically, a polypeptide is isolated when at least 10%, more preferably at least 20%, more preferably at least 50%, more preferably at least 60%, even more preferably at least 75%, more preferably at least 90%, and most preferably at least 99% of the total material (by volume, by wet or dry weight, or by mole per cent or mole fraction) of a sample is the polypeptide of interest. The degree of isolation of the polypeptide can be measured by any appropriate method, e.g., by column chromatography, polyacrylamide gel electrophoresis, or by HPLC analysis. For example, a polypeptide is isolated when it is essentially free of naturally associated components or when it is separated from the native compounds which accompany it in its natural state.

As used herein, by the term "biologically active" as it refers to GS-X pump activity as used herein, is meant a polypeptide, or a fragment thereof, which is capable of transporting a glutathionated compound across a biological membrane.

In summary, the invention should be construed to include DNA comprising AtMRP1 and AtMRP2, and any mutants, derivatives, homologs and fragments thereof, which encode GS-X pump biological activity.

The invention further features an isolated preparation of a nucleic acid which is antisense in orientation to a portion or all of a plant GS-X pump gene, wherein the nucleic acid is capable of inhibiting expression of the GS-X pump gene when introduced into cells comprising the GS-X pump gene. The nucleic acid is antisense to either a portion or all of a plant GS-X pump gene, which gene is preferably Arabidopsis AtMRP1, Arabidopsis AtMRP2 or a homolog thereof. The "isolated preparation of a nucleic acid" and the "portion" of the gene to which the nucleic acid is antisense, should be of a sufficient length so as to inhibit expression of the desired target gene. The actual length of the isolated preparation of the nucleic acid may vary, and will depend on the particular target gene and the region of that gene which is targetted. Typically, the isolated preparation of the nucleic acid will be at least about 15 contiguous nucleotides; more typically, it will be between about 15 and about 50 contiguous nucleotides, or it may even be more than 50 contiguous nucleotides in length.

As used herein, a sequence of a nucleic acid is "antisense" to a portion or all of a GS-X pump gene when the sequence of nucleic acid does not encode a GS-X polypeptide. Rather, the sequence which is being expressed in the cells is identical to the non-coding strand of the GS-X pump gene and thus, does not encode a GS-X pump polypeptide. "Complementary," as used herein, refers to the subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

In yet another aspect of the invention, there is provided an antibody directed against a plant GS-X pump, preferably AtMRP1 or AtMRP2, which antibody is specific for the whole molecule or either the N-terminal or the C-terminal or internal portions of AtMRP1 or AtMRP2. Methods of generating such antibodies are well known in the art and are described, for example, in Harlow et al. (supra).

The present invention also provides for analogs of proteins or peptides encoded by AtMRP1 or AtMRP2. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The invention further includes a transgenic plant comprising an isolated DNA encoding a plant GS-X pump polypeptide or a fragment thereof, capable of transporting a glutathionated compound across a biological membrane. The transgenic plant of the invention may comprise a transgene encoding a plant GS-X pump polypeptide or a fragment thereof, or it may comprise a transgene encoding a yeast GS-X pump polypeptide or a fragment thereof, which yeast transgene is expressed in the plant to yield a biologically active GS-X pump protein product. By way of example, there is provided herein in the experimental examples section a transgenic Arabidopsis plant comprising a yeast YCF1 transgene, which when the transgene is expressed in the transgenic plant, confers upon the plant the ability to grow on media containing concentrations of heavy metal (cadmium) or organic xenobiotic (CDNB) that otherwise prevent of nontransgenic plants.

The invention also includes a transgenic plant comprising an isolated DNA comprising the sequence of a plant GS-X pump polypeptide or a fragment thereof, which plant GS-X pump is capable of transporting a glutathionated compound across a membrane derived from a cell, wherein the sequence of the isolated DNA is positioned in an antisense orientation with respect to the direction of transcription of the DNA.

Thus, included in the invention is a transgenic plant comprising an isolated DNA encoding a yeast YCF1 or a fragment thereof, capable of transporting a glutathionated compound across a membrane derived from a cell.

In addition, the invention includes a transgenic plant comprising an isolated DNA comprising the sequence of a yeast YCF1 gene or a fragment thereof, wherein the sequence of the isolated DNA is positioned in an antisense orientation with respect to the direction of transcription of the DNA.

By "transgenic plant" as used herein, is meant a plant, the cells, the seeds and the progeny of which comprise a gene inserted therein, which gene has been manipulated to be inserted into the cells of the plant by recombinant DNA technology. The manipulated gene is designated as a "transgene."

By the term "nontransgenic but otherwise substantially homozygous wild type plant" as used herein, is meant a nontransgenic plant from which the transgenic plant was generated.

"Positioned in an antisense orientation with respect to the direction of transcription of the DNA" as used herein, means that the transcription product of the DNA, the resulting mRNA, does not encode a GS-X pump. Rather, the mRNA comprises a sequence which is complementary to an mRNA which encodes a GS-X pump.

If vacuolar transport rate limits xenobiotic detoxification and if the amount of GS-X pump is rate limiting on the overall rate of vacuolar uptake, transgenic plants with increased YCF1, AtMRP1 or AtMRP2 expression are expected to be more resistant to the toxic effects of glutathione-conjugable xenobiotics and capable of accumulating higher vacuolar conjugate levels than non-transgenic plants. The former property permits the sustained growth of transgenic plants in the presence of xenobiotic concentrations that would retard the growth of plants exhibiting normal levels of transporter expression. The latter property confers on the plants the ability for hyperaccumulation of glutathionated xenobiotics.

Increased resistance to xenobiotics has application in herbicide technology and plant growth in habitats polluted with organics. Hyperaccumulation has application in the extraction of organic pollutants from contaminated ground soils.

The closest known similar technologies to those described herein (a) involve the isolation of mutants or the engineering of plants in which the target for xenobiotic action is no longer sensitive, (b) involve the generation of mutants with elevated cellular levels of glutathionine (GSH) or with increased glutathione-S-transferase activities, or (c) involve the application of chemical agents ("safeners") that elevate GSH and/or glutathione-S-transferase levies or activities. These known technologies differ from the strategy proposed herein in three respects: (i) The utility of mutated target gene products is limited in its application to those xenobiotics that directly interact with the target in question. In contrast, the vacuolar GS-X pump is of broad substrate specificity. (ii) Technologies based on elevated cellular GSH levels or increased glutathione-S-transferase catalytic efficiencies are limited by the capacity of cells to subsequently metabolize and/or sequester the conjugates generated. The success of these latter technologies eventually depends on delivery of GSH-conjugates into the vacuole and in turn, depends on the activity of the vacuolar GS-X pump. (iii) Since the plant vacuole frequently constitutes 40–90% of total intracellular volume and the GS-X pump mediates the uptake of xenobiotics into this compartment, the potential for hyperaccumulation on a tissue weight basis is great. Hyperaccumulators may therefore be used for the fixation/sequestration of toxins and their removal from soils. None of the other known technologies have this characteristic.

The generation of transgenic plants comprising sense or antisense DNA having the sequence of a GS-X pump or a fragment thereof, may be accomplished by transformation of the plant with a plasmid encoding the desired DNA sequence. Suitable vectors include, but are not limited to, disarmed Agrobacterium tumor-inducing (Ti) plasmids containing a sense or antisense strand placed under the control of the strong constitutive CaMV 35S promoter or under the control of an inducible promoter (Lagrimini et al., 1990, supra; van der Krol et al., 1988, Gene 72:45–50). Methods for the generation of such constructs, plant transformation and plant regeneration are well known in the art once the sequence of the desired gene is known and are described, for example, in Ausubel et al. (1993, *Current Protocols in Molecular Biology*, Greene and Wiley, New York).

Suitable vector and plant combinations will be readily apparent to those of skill in the art and can be found, for example, in Maliga et al. (1994, *Methods in Plant Molecular Biology: A Laboratory Manual*, Cold Spring Horbor, New York).

Transformation of plants may be accomplished using the Agrobacterium-mediated leaf disc transformation method described by Horsch et al. (1988, *Leaf Disc Transformation, Plant Molecular Biology Manual* A5:1).

A number of procedures may be used to assess whether the transgenic plant comprises the desired DNA. For example, genomic DNA obtained from the cells of the transgenic plant may be analyzed by Southern blot hybridization or by PCR to determine the length and orientation of any inserted, transgenic DNA present therein. Northern blot hybridization analysis or PCR may be used to characterize mRNA transcribed in cells of the transgenic plant. In situations where it is expected that the cells of the transgenic plant express GS-X polypeptide or a fragment thereof, Western blot analysis may be used to identify and characterize polypeptides so expressed using antibody raised against the GS-X pump or fragments thereof. The procedures for performing such analyses are well known in the art and are described, for example, in Sambrook et al. (supra).

The transgenic plants of the invention are useful for the manipulation of xenobiotic detoxification, heavy metal detoxification, control of plant pathogens, control of plant coloration, herbicide metabolism and phytohormone metabolism. For example, a transgenic plant encoding an AtMRP1 or an AtMRP2 gene or an AtMRP1- or AtMRP2-related gene, or a yeast YCF1 or YCF1-related gene, is useful for xenobiotic detoxification and heavy metal detoxification when grown on soil containing xenobiotics or heavy metals. Such plants are capable of removing xenobiotic toxins or heavy metals from the soil thereby generating soil which has reduced levels of compounds that are detrimental to the overall health of the environment.

Accordingly, the invention includes a method of removing xenobiotic toxins from soil comprising generating a transgenic plant having a transgene encoding a GS-X pump and planting the plant or the seeds of the plant in the soil wherein xenobiotic toxins in the soil are sequestered within the plant during growth of the plant in the soil.

Similarly, the invention includes a method of removing heavy metals from soil comprising generating a transgenic plant having a transgene encoding a GS-X pump and planting the plant or the seeds of the plant in the soil wherein heavy metals in the soil are sequestered within the plant during growth of the plant in the soil.

When the levels of xenobiotic toxins or heavy metals in the soil have been sufficiently reduced, the transgenic plant may be removed from the soil and destroyed or discarded in an environmentally safe manner. For example, the harvested plants can be reduced in volume and/or weight by thermal, microbial, physical or chemical means to decrease handling, processing and potential subsequent land filling costs (Cunningham et al., 1996, Plant Physiol. 110:715–719). In the case of valuable metals, subsequent smelting and recovery of the metal may be cost-effective (Raskin, 1996, *Proc. Natl. Acad. Sci. USA* 93:3164–3166).

This technique of remediating soil is more efficient, less expensive and easier than most chemical or physical methods. The estimated costs of remediation are as follows: U.S. $10–100 per cubic meter of soil for removal of volatile or water soluble pollutants by in situ remediation using plants; U.S. $60–300 per cubic meter of soil for landfill or low temperature thermal treatment remediation of soil contaminated with the same compounds; and, U.S. $200–700 per cubic meter of soil for remediation of soil contaminated with materials requiring special landfilling arrangements or high temperature thermal treatment (Cunningham et al., 1995, Trends Biotechnol. 13:393–397).

Preferably, the transgene in the transgenic plant of the invention is AtMRP1, AtMRP2, YCF1 or genes encoding fragments or analogs of AtMRP1, AtMRP2 or YCF1, or the transgene is a gene which is related to AtMRP1, AtMRP2, YCF1.

The types of plants which are suitable for use in this method of the invention include, but are not limited to, high yield crop species for which cultivation practices have already been perfected, or engineered endemic species that thrive in the area to be remediated.

In certain situations, it may be necessary to prevent the removal of substances such as xenobiotic toxins and heavy metals from the soil. In such situations, transgenic plants are generated comprising a transgene comprising a GS-X pump sequence which is in the antisense orientation with respect to transcription. Such transgenes therefore serve to inhibit the function of a GS-X pump expressed in the plants thereby preventing removal of xenobiotics or heavy metals from the soil.

The production of plants having GS-X pump antisense sequences has application in the manipulation of plant/food coloration and in the diminution of organic xenobiotic (e.g., herbicide) or heavy metal accumulation by crop species. For example, ingestion by animals or humans of low organic toxin/low heavy metal crops will likely contribute to an improvement in the overall health of animals and humans.

Accordingly, the invention includes a method of preventing the removal of xenobiotic toxins or heavy metals from soil comprising generating a transgenic plant having a transgene comprising a GS-X pump sequence which is in the antisense orientation with respect to transcription and planting the plant or the seeds of the plant in the soil, wherein removal of xenobiotics and heavy metals from the soil is prevented during growth of the plant in the soil.

The antisense sequences which are useful for the generation of transgenic plants having antisense GS-X pump sequences are those which will inhibit expression of a resident GS-X gene in the plant.

The types of plants which are suitable for use in this method of the invention using antisense sequences include, but are not limited to, plants for which anthocyanins contribute to flower, fruit or leaf coloration and food crops for which decreased organic xenobiotic and/or heavy metal accumulation is desirable.

In a similar manner to that described herein, a transgenic plant may be generated which exhibits increased accumulation and/or resistance to isoflavonoid alexins by introducing into the cells of the plant a transgene encoding a GS-X pump capable of transporting glutathionated isoflavonoid alexins into vacuoles in the plant, thereby isolating the isoflavonoid alexins from the cytoplasm of the cells of the plant. Preferably, the transgene is AtMRP1, AtMRP2, YCF1 or genes encoding fragments or analogs of AtMRP1, AtMRP2 or YCF1, or the transgene is a gene which is related to AtMRP1, AtMRP2 or YCF1.

The invention thus includes a method of generating a pathogen-resistant transgenic plant comprising introducing into the plant a transgene encoding a GS-X pump capable of transporting glutathionated isoflavonoid alexins into vacuoles in the plant.

The types of plants suitable for the introduction of the desired transgene include, but are not limited to, plants which are leguminous plants, for example, alfalfa, cashew nut, castor bean, faba bean, french bean, mung bean, pea, peanut, soybean and walnut.

As discussed herein, it has also been discovered in the present invention that the Bz2 gene which encodes a glutathione-S-transferase, glutathionates anthocyanins and possibly other compounds for transport by the GS-X pump. The anthocyanin-derivatives so generated are subsequently transported across biological membranes by the vacuolar GS-X pump. Vacuolar anthocyanins are responsible for the red and purple hues of many plant organs (petals, leaves, stems, seeds, fruits, etc.). Vacuolar anthocyanins are found in most flowering plants. However, they are not solely responsible for plant coloration. Rather, plant coloration is determined by the relative amounts and combinations in which these various pigments are accumulated. Thus, it is possible to manipulate plant coloration by generating transgenic plants with increased (sense DNA) or decreased (antisense DNA) expression of the GS-X pump. Transgenic plants having GS-X pump sense sequences are expected to contain more red/purple pigmentation that their nontransgenic but otherwise homozygous counterparts and transgenic plants having GS-X pump antisense sequences are expected to contain less red/purple pigmentation and possibly more brown pigmentation that their nontransgenic but otherwise homozygous counterparts. The generation of such types of transgenic plants may be accomplished following the procedures described herein.

With respect to the aforementioned information regarding anthocyanins, it is important to note that accumulating evidence from studies of the MRP-subclass members from non-plant sources reveals that the group of transporters formerly referred to an GS-X pumps because of their affinity toward GS-conjugates, GSSG and cysteinyl leukotrienes, do not transport GS-conjugates exclusively (Ishikawa et al., 1997, Bioscience Reports 17:189–208). Investigation of the human MRP1 protein, cMOAT and ScYCF1 establish that these proteins are capable of transporting a broad range of compounds in addition to GS-conjugates and GSSG Jedlitschky et al., 1996, Cancer Res. 56:988–994; Paulusma et al., 1996, Science 271:1126–1128; Jansen et al., 1987, Hepatol. 7:71–76; Sathirakul et al., 1993, J. Pharmacol. Exp. Therap. 268:65–73). Thus, these proteins transport non-glutathionated compounds.

It has been discovered in the present invention that the plant proteins, AtMRP1 and AtMRP2, differ in their substrate preferences. For example, no only does AtMRP2 exhibit a much higher transport capacity than does AtMRP1, but AtMRP2 has the capacity to transport chlorophyll breakdown products in leaf senescence, which breakdown products are not glutathionated. Thus, according to the present invention, it is possible to manipulate plant coloration by changing the relative levels of expression of various members of this class of transporters in a plant cell. It is possible, using the information provided herein, to affect the rate of breakdown of chlorophyll, for example, by manipulating the expression of AtMRP2 in a plant cell.

In addition to the above, there is provided as part of the invention, AtMRP1 and AtMRP2 promoter sequences. By operably coupling the AtMRP1 or AtMRP2 promoters to other genes, it may be possible to confer on these other genes expression characteristics similar to those of AtMRP1 or AtMRP2, namely, modulation by xenobiotics, plant pathogens, etc. The data which are presented herein include the promoter sequences of these genes, which promoter sequences are useful in a variety of applications in plants. For example, GS-X pump activity which is associated with herbicide metabolism (exemplified by organic xenobiotic transport), heavy metal sequestration (exemplified by cadmium transport), plant-pathogen interactions (exemplified by vacuolar uptake of medicarpin), plant cell pigmentation (exemplified by transport of glutathionated anthocyanins) and plant hormone metabolism (exemplified by the transport of glutathionated auxins) may be examined as a result of the present invention. The present invention facilitates the identification of plants and cells therein which are capable of GS-X pump activity, and further facilitates the exploitation of plant cell GS-X pump activity for the purpose of affecting plant function with respect to herbicide metabolism, heavy metal sequestration, plant-pathogen interactions, plant cell pigmentation and plant hormone metabolism.

The invention includes an isolated DNA comprising a plant GS-X pump promoter sequence capable of driving expression of a plant GS-X pump gene, which gene is capable of transporting a glutathionated compound across a biological membrane. Preferably, the membrane is derived from a cell.

Figure 1A:
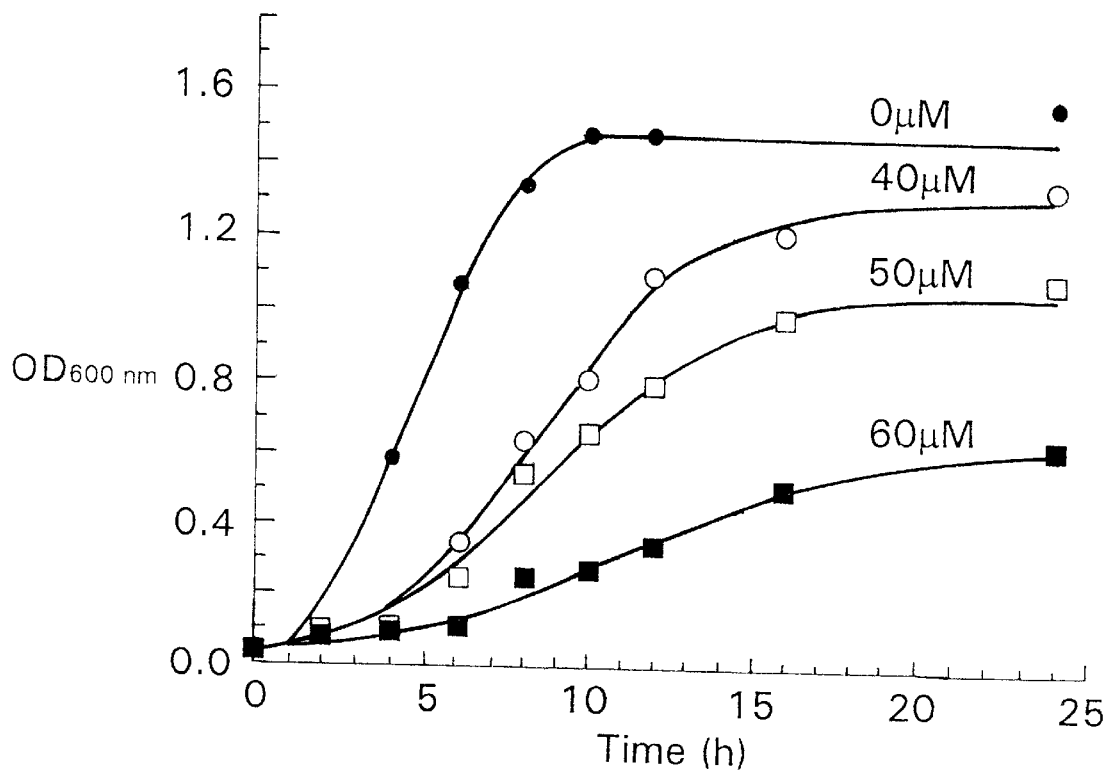
FIGS. 1A–1B are a series of graphs depicting differential sensitivities of DTY165 cells (wild type, FIG. 1A) and DTY167 cells (ycf1Δ mutant, FIG. 1B) to growth inhibition by 1-chloro-2,4-dinitrobenzene (CDNB). Cells were grown at 30° C. for 24 hours to an $OD_{600\ nm}$ of approximately 1.4 in YPD medium before inoculation of aliquots into 15 ml volumes of the same medium containing 0–60 $\mu$M CDNB. $OD_{600\ nm}$ was measured at the times indicated.
Figure 1B:
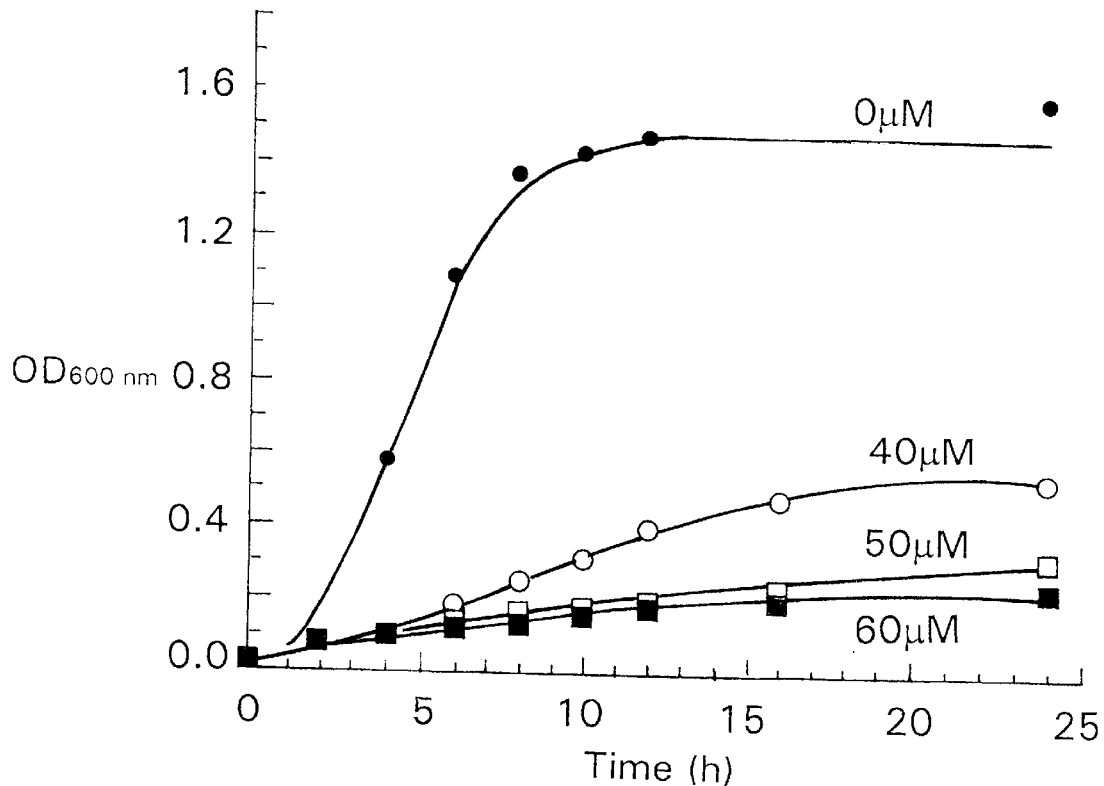
Figure 2:
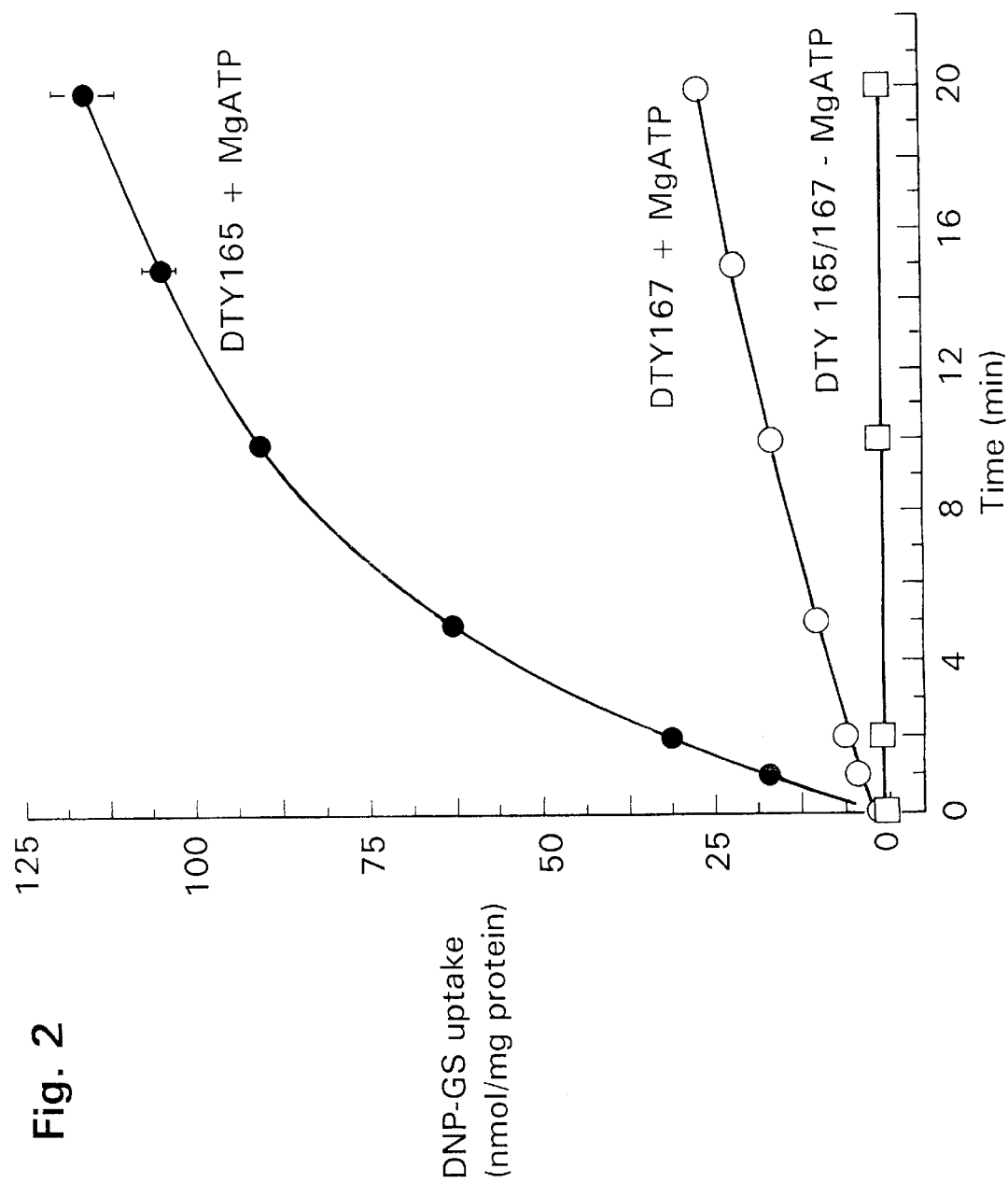
FIG. 2 is a graph depicting the time course of [$^3$H]DNP-GS uptake by vacuolar membrane vesicles purified from DTY165 and DTY167 cells. Uptake was measured in the absence (−MgATP) or presence of 3 mM MgATP (+MgATP) in reaction media containing 66.2 $\mu$M [$^3$H]DNP-GS, 10 mM creatine phosphate, 16 units/ml creatine kinase, 50 mM KCl, 0.1% (w/v) bovine serum albumin, 400 mM sorbitol, and 25 mM Tris-MES (pH 8.0) at 25° C. Values shown are means ±S.E. (n=3).

Preferably, the isolated DNA comprising a plant GS-X pump promoter sequence is at least about 40% homologous to at least one of the AtMRP1 or AtMRP2 promoter sequences presented herein in FIGS. 23 and 24, respectively. More preferably, the isolated DNA comprising a plant GS-X pump promoter sequence is at least about 50%, even more preferably, at least about 60%, yet more preferably, at least about 70%, even more preferably, at least about 80%, yet more preferably, at least about 90% homologous, and more preferably, at least about 99% homologous to at least one of AtMRP1 or AtMRP2 promoter sequences presented herein in FIGS. 23 and 24, respectively. Most preferably, the isolated DNA comprising a plant GS-X pump promoter sequence is Arabidopsis AtMRP] or AtMRP2 as shown in FIGS. 1 and 2, respectively.

Thus, the invention should be construed to include isolated DNA sequences comprising promoter sequences which in their natural form drive expression of genes which encode Arabidopsis AtMRP1 and AtMRP2 and Arabidopsis AtMRP1 and AtMRP2-related genes. Once armed with the present invention, it is a simple matter to isolate sequences which are related to those shown in FIGS. 1 and 2. For example, conventional hybridization technology and/or PCR technology may be employed, primers may be designed using the sequences provided herein, data bases may be searched and the like. Procedures for the isolation of promoter sequences which are related to those described herein are described in Sambrook et al. (1989, *Molecular Cloning: A Laboratory Manual,* Cold Spring Harbor, NY) and in Ausubel et al. (1993, *Current Protocols in Molecular Biology,* Greene and Wiley, New York).

By the term "promoter sequence" as used herein, is meant a DNA sequence which is required for expression of a gene which is operably linked thereto. In some instances, this sequence may be a core promoter sequence and in other instances, this sequence may also include an enhancer sequence and other regulatory elements which are required for expression of the gene in a tissue-specific manner. Thus, a promoter sequence must include an RNA polymerase binding site and may include appropriate transcription factor binding sites as are necessary for activation of transcription and expression of the gene to which the promoter sequence is attached at the 5' end of the gene.

Typically, the promoter sequence of the invention comprises at least about 150 bp in length. More typically, the promoter sequence comprises at least about 300 bp in length. More typically, the promoter sequence comprises at least about 400 bp, even more typically, at least about 500 bp, yet more typically, at least about 600 bp, even more typically, at least about 800 bp, yet more typically, at least about 1000 bp and even more typically, at least about 1200 or more bp in length.

The promoter sequence of the invention may also comprise discrete sequences (elements) which function to regulate the activity of the promoter. Frequently, such elements respond to the presence or absence of environmental factors, thereby controlling gene expression in direct response to factors which are associated with the environmental mileau of the plant. The response of the plant to these factors affects the overall well-being of the plant. Elements which may be present in the promoter sequence of the invention include, but are not limited to, a Myb recognition sequence, a xenobiotic regulatory element, an antioxidant response element, a bZIP recognition sequence, and the like.

Plants from which AtMRP1- or AtMRP2-related genes and therefore promoter sequences, may be isolated include any plant in which the GS-X pump is found, including, but not limited to, soybean, castor bean, maize, petunia, potato, tomato, sugar beet, tobacco, oats, wheat, barley, pea, faba bean and alfalfa.

The invention further includes a vector comprising a plant GS-X pump promoter sequence operably fused to a reporter gene and capable of driving expression of the reporter gene. The procedures for the generation of a vector comprising a plant GS-X pump promoter sequence are well know in the art once the sequence of the gene is known, and are described, for example, in Sambrook et al. (supra). Suitable vectors include, but are not limited to, disarmed Agrobacterium tumor-inducing (Ti) plasmids (e.g., pBIN1 9) (Lagrimini et al., 1990, *Plant Cell* 2:7–18; Bevan, 1984, *Nucl. Acids Res.* 12:8711–8721).

Also included in the invention is a cell comprising a plant GS-X pump promoter sequence operably fused to a reporter gene. The procedures for the generation of a cell encoding a plant GS-X pump or fragment thereof, are well know in the art once the sequence of the gene is known, and are described, for example, in Sambrook et al. (supra). Suitable cells include, but are not limited to, plant cells, yeast cells, bacterial cells, mammalian cells, and baculovirus-infected insect cells. In addition, plant cells transformed with the promoter/reporter gene construct, for the purpose of assessing the effect of various compounds on promoter activity are also contemplated in the invention. Normal plant cells and those plant cells having increased resistance to and increased capacity for heavy metal accumulation, increased resistance to organic xenobiotics and increased capacity for organic xenobiotic accumulation or altered coloration, which cells comprise the promoter sequence of the invention operably fused to a reporter gene, are all contemplated as part of the invention. When the promoter is fused to a reporter gene, the promoter is said to be operably linked to the reporter gene.

A "reporter gene" as used herein, is one which when expressed in a cell, results in the production of a detectable product in the cell. The level of expression the product in the cell is proportional to the activity of the promoter sequence which drives expression of the reporter gene.

By describing two nucleic acid sequences as "operably linked" as used herein, is meant that a single-stranded or double-stranded nucleic acid moiety comprises each of the two nucleic acid sequences and that the two sequences are arranged within the nucleic acid moiety in such a manner that at least one of the two nucleic acid sequences is able to exert a physiological effect by which it is characterized upon the other.

Suitable reporter genes include, but are not limited to, P-glucuronidase (GUS) and green fluorescent protein (GFP), although any reporter gene capable of expression and detection in plant cells which are either known or heretofore unknown, may be fused to the plant GS-X promoter sequences of the invention.

The invention further includes a transgenic plant comprising an isolated DNA comprising a plant GS-X pump promoter sequence as defined herein.

The generation of transgenic plants comprising a plant GS-X pump promoter sequence operably fused to a reporter gene, may be accomplished by transformation of the plant with a plasmid comprising the desired DNA sequence. Suitable vectors include, but are not limited to, disarmed Agrobacterium tumor-inducing (Ti) plasmids (Lagrimini et al., 1990, supra; van der Krol et al., 1988, Gene 72:45–50). Methods for the generation of such constructs, plant transformation and plant regeneration are well known in the art once the sequence of the desired nucleic acid is known and are described, for example, in Ausubel et al. (1993, *Current Protocols in Molecular Biology,* Greene and Wiley, New York).

Suitable vector and plant combinations will be readily apparent to those of skill in the art and can be found, for example, in Maliga et al. (1994, *Methods in Plant Molecular Biology: A Laboratory Manual,* Cold Spring Harbor, New York).

Transformation of plants may be accomplished using the Agrobacterium-mediated leaf disc transformation method described by Horsch et al. (1988, *Leaf Disc Transformation, Plant Molecular Biology Manual* A5:1).

A number of procedures may be used to assess whether the transgenic plant comprises the desired DNA. For example, genomic DNA obtained from the cells of the transgenic plant may be analyzed by Southern blot hybridization or by PCR to determine the length and orientation of any inserted, transgenic DNA present therein. Northern blot hybridization analysis or RT-PCR may be used to characterize mRNA transcribed in cells of the transgenic plant. In situations where it is expected that the cells of the transgenic plant express GS-X polypeptide or a fragment thereof, Western blot analysis may be used to identify and characterize polypeptides so expressed using antibody raised against the GS-X pump or fragments thereof. The procedures for performing such analyses are well know in the art and are described, for example, in Sambrook et al. (supra).

The transgenic plants of the invention are useful for the examination of xenobiotic detoxification, heavy metal detoxification, control of plant pathogens, control of plant coloration, herbicide metabolism and phytohormone metabolism. For example, a transgenic plant comprising an ATMRP1 or an AtMRP2 promoter sequence fused to a reporter gene is useful for the examination of xenobiotic detoxification and heavy metal detoxification when grown on soil having xenobiotic toxins or heavy metals. Such plants are useful to an understanding of the mechanisms by which GS-X pump gene expression is activated and are therefore useful for the eventual generation of plants which are capable of removing xenobiotic toxins or heavy metals from the soil thereby generating soil which has reduced levels of compounds that are detrimental to the overall health of the environment.

The types of plants which are suitable for use include, but are not limited to, high yield crop species for which cultivation practices have already been perfected, or engineered endemic species that thrive in the area to be remediated. In addition plants for which anthocyanins contribute to flower or leaf coloration and food crops for which decreased organic xenobiotic and/or heavy metal accumulation is desirable are also suitable for use in the invention. Further useful plants are those in which it is desirable that they are capable of increased accumulation and/or resistance to isoflavonoid alexins. Plants for which pathogen resistance is desired are also useful in the invention. Such plants include, but are not limited to, plants which are leguminous plants, for example, alfalfa, cashew nut, castor bean, faba bean, french bean, mung bean, pea, peanut, soybean and walnut. In addition, plants for which it is desirable to manipulate plant coloration are also useful in the invention.

The promoter sequences of Arabidopsis GS-X pump genes ATMRP1 and AtMRP2 are shown in FIGS. 23 and 24, respectively. The following should be noted. bZIP transcription factor recognition elements have the sequences CACGTG or TGACG(T/C). One of these is present in the AtMRP2 promoter sequence, but none are present in the AtMRP1 promoter sequence. Myb transcription factor recognition elements having the sequences A(a/D)(a/D)C(G/C) and AGTTAGTTA, wherein a/D=A, G or T with A being preferred, are present in the AtMRP1 promoter sequence, but are not present in the AtMRP2 promoter sequence. Xenobiotic regulatory elements (XREs) having the core sequence GCGTG are found in multiple copies in the promoters of cytochrome P450 monooxygenase genes and glutathione S-transferase genes (Rushmore et al., 1993, J. Biol. Chem. 268:11475–11478). One XRE is found in the promoter sequence of AtMRP1. Antioxidant response elements (AREs) consist typically of two core sequences GTGACA(A/T)(A/T)GC (SEQ ID NO: 11) that are binding sites for Activator Protein-1 (AP-1) transcription factor complex (Daniel, 1993, CRC Crit. Rev. Biochem 25:173–207; Friling et al., 1992, Proc. Natl. Acad. Sci. USA 89:668–672). There is only one ARE in the AtMRP1 promoter sequence shown in FIG. 23. It has been proposed that GST genes containing an ARE are induced by electrophiles and conditions that generate oxidative stress (Daniel, supra). RNA instability determinants having the sequence ATTTA have been found in several plant GSTs. These sequences, considered to target RNAs for degradation by RNases are usually found in the 3'-UTRs of genes (Takahashi et al., 1992, Proc. Natl. Acad. Sci. USA 89:56–59). Several of these sequences are found in both the AtMRP1 and AtMRP2 promoter sequences presented herein. However, it is not clear whether these sequences merely reflect the AT-richness of the sequences.

To assess GS-X pump gene expression in a plant cell whether the cell is contained within a plant or whether the cell is separated from the plant, a plasmid may be generated which comprises the β-glucuronidase (GUS) reporter gene fused to a plant GS-X promoter sequence. Preferably, the promoter sequence is either AtMRP1 or AtMRP2. The appropriate restriction fragment is subcloned into the GUS expression vector pBI101.3 (Jefferson et al., 1987, EMBO J., 6:3901–3907). After confirming the correct reading frame by sequencing, Agrobacterium or any other suitable vector, is transformed with the expression construct and is then used to used to transform the plant, or the cells thereof (Valvekens et al., 1988, Proc. Natl. Acad. Sci. USA 85:5536–5540).

Expression of GUS may be localized histochemically by staining with 5-bromo-4-chloro-3-indoyl β-D-glucuronide (X-Gluc) (Jefferson et al., supra). Sections are obtained from the plant, they are incubated in X-Gluc, cleared by boiling in ethanol and are examined under the microscope. To eliminate or enumerate complications arising from the transfer of GUS reaction product between cells, the distribution of GUS expression is then further examined both immunologically and biochemically. β-glucuronidase protein is assessed using standard dot-blotting and immunolocalization techniques (Harlow et al., 1988, *Antibodies: A Laboratory Manual*, Cold Spring Harbor Laboratory, NY) using rabbit anti-β-glucuronidase serum (Clontech). Direct estimates of GUS activity are be made fluorimetrically using 4-methyl-umbelliferyl glucuronide as substrate (Jefferson et al., supra) after dissection and extraction of explants.

GUS reporter gene analyses enable examination of plant responses to oxidative stress and pathogens as well as herbicides. In addition, GUS reporter gene analyses enable tests of whether certain pigment-rich cell types also exhibit high levels of AtMRP expression.

The AtMRP1 and AtMRP2 promoter sequences are also useful for manipulating the expression of other genes in plants in that, transgenic plants may be generated which contain a desired plant gene operably fused to a GS-X pump promoter sequence. The GS-X pump promoter sequence may be an AtMRP1 or an AtMRP2 promoter sequence or a YCF1 promoter sequence positioned in an orientation such that the promoter sequence drives expression of the desired gene. The desired gene may be a plant or a non-plant gene. The generation of such transgenic plants confers upon the plants the ability to respond to the presence of xenobiotics and other compounds which influence the promoter activity In considering transport substrates for GS-X pumps, the status of GSSG as an endogenous GS-conjugate (of GSH with itself) and its involvement in cellular responses to active oxygen species (AOS) should not be overlooked. The sulfhydryl group of GSH confers strong nucleophilicity and the facility for reacting with AOS, such as superoxide radicals ($O_2^-$), hydroxyl radicals (OH) and hydrogen peroxide. GSH is found in the majority of eukaryotes but in prokaryotes (eubacteria) it appears to be restricted to the cyanobacteria and purple bacteria (Fahey and Sundquist 1991, Adv. Enzymol. Relat. Mol. Biol. 64:1–53). Since the cyanobacteria are considered to be the first group of organisms capable of oxygenic photosynthesis and these and the purple bacteria probably gave rise to plant chloroplasts and mitochondria, respectively, it has been proposed that the emergence of the capacity for GSH biosynthesis was associated with the appearance of oxygenic and oxytrophic metabolism (approximately $4 \times 10^9$ years ago) to combat the attendant problem of AOS production. Most, if not all, of the factors known to elicit GST induction—pathogen attack, heavy metals, certain organic xenobiotics, wounding and ethylene—promote AOS production (Inze and Montagu 1995, Current Opinion in Biotech. 6:153–158). Intriguing, therefore, is the possibility that GS-X pumps arose from the need to detoxify AOS and the products of their action.

The feasibility of such a scheme has yet to be investigated systematically but a number of disparate observations are at least consistent with a close connection between oxidative stress and GS-X pump function: (i) All identified MRP-subclass transporters, including AtMRP1 and AtMRP2 recognize GSSG as a substrate. Studies of GS-X pumps originated from the discovery of ATP-dependent GSSG efflux from erythrocytes (Srivastava and Beutler 1969, J. Biol. Chem. 244:9–16). (ii) In *S. cerevisiae*, overexpression of yAP1, a bZIP transcription factor, not only activates the YCF1 and GSH 1 genes (Wemmie et al 1994, supra; Wu and Moye-Rowley 1994, supra), the latter of which encodes γ-glutamylcysteine synthetase, but also a panoply of oxidoreductases (DeRisi et al 1997, Science 278:680–686). Of the 17 genes whose mRNA levels are found to be increased by more than threefold on DNA microarrays by yAP1, more than two-thirds contain canonical upstream yAP1-binding sites (TTACTAA or TGACTAA), five bear homology to aryl-alcohol oxidoreductases and four to the general class of dehydrogenases/oxidoreductases (DeRisi et al 1997, supra). In view of the capacity of yAP1 overexpression to confer increased resistance to hydrogen peroxide, o-phenanthroline and heavy metals (Hirata et al 1994, Mol. Gen. Genet. 242:250–257), the fact that an appreciable fraction of the yAP1-regulated target genes identified against the yeast genome project database are oxidoreductases and coregulated with both YCF1 and GSH1, suggests that all of these genes play a protective role during oxidative stress. (iii) Two particularly harmful and early effects of AOS production are membrane lipid peroxidation. and oxidative DNA damage which yield highly toxic 4-hydroxyalkenals (Esterbauer et al 1991, Biochem. J. 208:129–140) and base propanols (Berhane et al 1994, Proc. Natl. Acad. Sci. USA 91:1480–1484), respectively. Although such a,b-unsaturated aldehydes (and their GS-conjugates) have not yet been screened against the GS-X pumps from plant sources, they are established substrates for mammalian GSTs (Berhane et al 1994, supra) and their glutathionated derivatives are transported at high efficiency by mammalian GS-X pumps (Ishikawa 1989, J. Biol. Chem. 264:17343–17348).

There is therefore also included in the invention a method of alleviating oxidative stress in a plant comprising intorducing into the cells of the plant DNA encoding a GS-X pump.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXPERIMENTAL EXAMPLES

The experimental examples described herein provide procedures and results for the isolation and characterization of yeast YCF1 and Arabidopsis AtMRP1 and AtMRP2 genes, gene products and various functions ascribed thereto. Further there is described data which establish that the Bz2 gene product exerts its effects on plant coloration via the GS-X pump.

The data which are now described establish that YCF1 is a vacuolar glutathione S-conjugate pump. The data establish that YCF1 is a membrane protein which is responsible for catalyzing MgATP-dependent, uncoupler-insensitive uptake of glutathione S-conjugates into the vacuole of wild type *S. cerevisiae*.

YCF1 encodes a protein responsible for resistance of yeast to the effects of cadmium. However, the mechanism by which resistance to $Cd^{2+}$ is effected was not understood until the present invention. The data presented herein demonstrate that YCF1 confers $Cd^{2+}$ resistance to yeast by effecting transport of $Cd^{2+}$ out of the cytosol via a YCF1 encoded vacuolar glutathione S-conjugate pump. Further, since YCF1 confers resistance to $Cd^{2+}$ through the transport of Cd.GS complexes or derivatives thereof, it is likely also capable of transporting other metal.GS-complexes. Examples of these other complexes include, but are not limited to, mercury (Hg), zinc (Zn), platinum (Pt) and arsenic (Ar). Both $Hg^{2+}$ and $Zn^{2+}$ form complexes with GSH which are analogous to those formed by $Cd^{2+}$ (Li et al., 1954, *J. Am. Chem. Soc.* 76:225–229; Kapoor et al., 1965, *Biochem. Biophys. Acta* 100:376–383; Perrin et al., 1971, *Biochem. Biophys. Acta* 230:96–104). In addition, MRP1 eliminates the $Pt^{2+}$ glutathionine complex bis(glutathionato) platinum from cancer cells (Ishikawa et al., 1994, *J Biol. Chem.* 269:29085–29093). Further, the MRP1 gene is overexpressed in cisplatin-resistant human leukemia HL-60 cells, which overexpression is associated with increased resistance to arsenite (Ishikawa et al., 1996, *J Biol. Chem.* 271:14981–14988). Both $Hg^{2+}$ and $Ar^{2+}$ are common environmental contaminants and $Zn^{2+}$ is an essential micronutrient.

According to the results of the present study, vacuolar membrane vesicles from wild type *S. cerevisiae* catalyze high rates of MgATP-dependent, uncoupler-insensitive S-conjugate transport, and the kinetics of the transporter involved are similar to those of the mammalian and plant vacuolar GS-X pumps. In addition, vacuole-deficient mutants of *S. cerevisiae* exhibit markedly increased sensitivity to cadmium, leading to the belief that one requirement for efficient elimination or detoxification of this metal is maintenance of a sizable vacuolar compartment.

It is known that *S. cerevisiae* yAP-1 transcription factor transcriptionally activates both the YCF1 gene and the GSH1 gene (Wemmie et al., 1994, *J Biol. Chem.* 269:32592–32597; Wu et al., 1994, *Mol. Cell. Biol.* 14:5832–5839). Since GSH1 encodes γ-glutamylcysteine synthetase, an enzyme critical for GSH synthesis, expression of the YCF1 gene and fabrication of one of the precursors for transport by the GS-X pump are coordinately regulated.

In the first set of experiments described below, transport of the model compounds DNP-GS and bimane-GS by isolated membrane vesicles and intact cells was examined.

Yeast Strains and Plasmids

Two strains of *S. cerevisiae* were used in these studies: DTY165 (MATα ura3-52 his6 leu2-3,-112 his3-Δ200 trp1-901 lys2-801 suc2-Δ) and the isogenic ycf1Δ mutant strain, DTY167 (MATα ura 3-52 his6 leu2-3,-112 his3-Δ200 trp 1-901 lys2-801 suc2-Δ, ycf1::hisG). The strains were routinely grown in rich (YPD) medium, or, when transformed with plasmid containing functional YCF1 gene, in synthetic complete medium (Sherman et al., 1983, *Methods in Yeast Genetics*, Cold Spring Harbor Laboratory, New York) or AHC medium (Kim et al., 1994, supra) lacking the appropriate amino acids. *Escherichia coli* strains XL1-blue (Stratagene) and DH11S were employed for the construction and maintenance of plasmid stocks (Ausubel et al., 1987, *Current Protocols in Molecular Biology*, Wiley, New York).

Plasmid pYCF1-HA, encoding epitope-tagged YCF1, was constructed in several steps. A 1.4-kb SalI-HindIII fragment, encompassing the carboxyl-terminal segment of the open reading frame of YCF1, from pIBIYCF1 (Szczypka et al., 1994, supra), was subcloned into pBluescript KS⁻. Single-stranded DNA was prepared and used as template to insert DNA sequence encoding the human influenza hemagglutinin 12CA5 epitope immediately before the termination codon of the YCF1 gene by oligonucleotide-directed mutagenesis. The sequence of the primer for this reaction, with the coding sequence for the 12CA5 epitope underlined, was 5'-GTTTCACAGTTTAA<u>AGCGTAGTCTGGGACGTCGTATGGGTA</u>ATTTTCATTG ACC-3' (SEQ ID NO: 12). After confirming the boundaries and fidelity of the HA-tag coding region by DNA sequencing, the 1.4-kb SalI-HindIII DNA fragment was exchanged with the corresponding wild type segment of pJAW50 (Wemmie et al., 1994, supra) to generate pYCF1-HA.

Isolation of Vacuolar Membrane Vesicles

For the routine preparation of vacuolar membrane vesicles, 15 ml of stationary phase cultures of DTY165 or DTY167 were diluted into 1-liter volumes of fresh YPD medium, grown for 24 hours at 30° C. to an $OD_{600\ nm}$ of approximately 0.8 and collected by centrifugation. After washing with distilled water, the cells were converted to spheroplasts with Zymolyase 20T (ICN) (Kim et al., 1994, supra) and intact vacuoles were isolated by flotation centrifugation of spheroplast lysates on Ficoll 400 step gradients as described by Roberts et al. (1991, *Methods. Enzymol.* 194:644–661). Both the spheroplast lysis buffer and Ficoll gradients contained 2 mg/ml bovine serum albumin, 1 μg/ml aprotinin, 1 μg/ml leupeptin, 1 μg/ml pepstatin, and 1 mM PMSF to minimize proteolysis. The resulting vacuole fraction was vesiculated in 5 mM $MgCl_2$, 25 mM KCl, 10 mM Tris-Mes (pH 6.9) containing 2 mg/ml bovine serum albumin, 1 μg/ml aprotinin, 1 μg/ml leupeptin, 1 μg/ml pepstatin, and 1 mM PMSF, pelleted by centrifugation at 37,000× g for 25 min, and resuspended in suspension medium (1.1 M glycerol, 2 mM dithiothreitol, 1 mM Tris-EGTA, 2 mg/ml bovine serum albumin, 1 μg/ml aprotinin, 1 μg/ml leupeptin, 1 μg/ml pepstatin, 1 mM PMSF, 5 mM Tris-Mes, pH 7.6) (Kim et al., 1995, *J. Biol. Chem.* 270:2630–2635).

In experiments involving cadmium transport, dithiothreitol and EGTA were removed from the suspension medium to prevent the attenuation of YCF1-dependent $Cd^{2+}$ transport otherwise exerted by these compounds. Vesiculated vacuolar membranes were subjected to three cycles of 50-fold dilution into simplified suspension medium (1.1 M glycerol, 5 mM Tris-Mes, pH 8.0), centrifugation at 100,000× g for 35 minutes and resuspension in the same medium before use.

For the experiment shown in FIG. 4, 1 ml of partially purified vacuolar membrane vesicles (1.1–1.2 mg of protein), prepared by Ficoll flotation, were subjected to further fractionation by centrifugation through a 30-ml linear 10–40% (w/v) sucrose density gradient at 100,000× g for 2 hours. Successive fractions were collected from the top of the centrifuge tube and, after determining sucrose concentration refractometrically, the fractions were diluted with suspension medium. The diluted fractions were sedimented at 100,000× g and resuspended in 100-μl aliquots of suspension medium for assay. For the immunoblots shown in FIG. 5 and the marker enzyme analyses shown in Table 4, crude microsomes were prepared by homogenization of spheroplasts in suspension medium and the sedimentation of total membranes at 100,000× g for 35 minutes.

Microsomes and purified vacuolar membranes that were to be employed for SDS-polyacrylamide gel electrophoresis and immunoblotting were washed free of bovine serum albumin by three rounds of suspension in suspension medium minus bovine serum albumin and centrifugation at 100,000× g for 35 minutes. The final membrane preparations were either used immediately or frozen in liquid nitrogen and stored at −85° C.

Measurement of Marker Enzyme Activities

α-Mannosidase was determined according to Opheim (1978, *Biochem. Biophys. Acta* 524:121–125) using p-nitrophenyl-α-D-mannopyranoside as substrate. NADPH-cytochrome c reductase was estimated as FMN-promoted reduction of NADPH (Kubota et al., 1977, *J Biol. Chem.* 81:197–201). GDPase was measured as the rate of liberation of $P_i$ from GDP (Yanagisawa et al., 1990, *J. Biol. Chem.* 265:19351–19355) in reaction buffer containing 0.05% (w/v) Triton X-100. V-ATPase, F-ATPase, and P-ATPase were assayed as bafilomycin $A_1$ (1 μM), azide (1 mM), and vanadate (100 μM) inhibited ATPase activity, respectively, at pH 8.0 (V-ATPase, F-ATPase) or pH 6.5 (P-ATPase) (Rea and Turner, 1990, *Methods Plant Biochem.* 3:385–405).

Measurement of DNP-GS Uptake

Unless otherwise indicated, [$^3$H]DNP-GS uptake was measured at 25° C. in 200 μl reaction volumes containing 3 mM ATP, 3 mM $MgSO_4$, 5 μM gramicidin-D, 10 mM creatine phosphate, 16 units/ml creatine kinase, 50 mM KC 1, 1 mg/ml bovine serum albumin, 400 mM sorbitol, 25 mM Tris-Mes (pH 8.0), and 66.2 μM [$^3$H]DNP-GS (8.7 mCi/mmol) (Li et al., 1995, supra). Gramicidin D was included in the uptake medium to abolish the H+electrochemical potential difference ($\Delta\mu_H+$) that would otherwise be established by the V-ATPase in medium containing MgATP. Uptake was initiated by the addition of vacuolar membrane vesicles (10–15 μg of membrane protein), brief mixing of the samples on a vortex mixer and uptake was then allowed to proceed for 1–60 minutes. Uptake was terminated by the addition of 1 ml of ice-cold wash medium (400 mM sorbitol, 3 mM Tris-Mes, pH 8.0) and vacuum filtration of the suspension through prewetted Millipore HA cellulose nitrate membrane filters (pore diameter, 0.45 μm). The filters were rinsed twice with 1 ml of ice-cold wash medium and air-dried, and radioactivity was determined by liquid scintillation counting in BCS mixture (Amersham Corp.). Non-energized [$^3$H]DNP-GS uptake and extravesicular solution trapped on the filters were enumerated by the same procedure except that ATP and $Mg^2$+were omitted from the uptake medium.

Fluorescence Microscopy

Cells were grown in YPD medium for 24 hours at 30° C. to an $OD_{600\ nm}$ of approximately 1.4, and 100 μl aliquots of the suspensions were transferred to 15 ml volumes of fresh YPD medium containing 100 μM syn-($ClCH_2$,$CH_3$)-1,5-diazabicyclo-[3.3.0]-octa-3,6-dione-2,8-dione (monochlorobimane) (Kosower et al., 1980, *J Am. Chem. Soc.* 102:4983–4993). After incubation for 6 hours, the cells were pelleted by centrifugation, washed twice with YPD medium lacking monochlorobimane, and viewed without fixation under an Olympus BH-2 fluorescence microscope equipped with a BP-490 UV excitation filter, AFC-0515 barrier filter, and Nomarski optics attachment.

Electrophoresis and Immunoblotting

Membrane samples were subjected to one-dimensional SDS-polyacrylamide gel electrophoresis on 7–12% (w/v) concave exponential gradient gels after delipidation with acetone:ethanol (Parry et al., 1989, *J Biol. Chem.* 264:20025–20032). The separated polypeptides were electrotransferred to 0.45 μm nitrocellulose filters at 60 V for 4 hours at 4° C. in a Mini Trans-Blot transfer cell (Bio-Rad) and reversibly stained with Ponceau-S (Rea et al., 1992, *Plant Physiol.* 100:723–732). The filters were blocked and incubated overnight with mouse anti-HA monoclonal antibody (20 μg/ml) (Boehringer-Mannheim). Immunoreactive bands were visualized by reaction with horseradish peroxidase-conjugated goat anti-mouse IgG (1/1000 dilution) (Boehringer-Mannheim) and incubation in buffer containing $H_2O_2$ (0.03% w/v), diaminobenzidine (0.6 mg/ml) and $NiCl_2$ (0.03% w/v) (Rea et al., 1992, supra).

Purification of Cadmium-Glutathione Complexes

Singly radiolabeled $^{109}$Cd.$GS_n$ and doubly radio-labeled $^{109}$Cd[$^3$H].$GS^n$ complexes were prepared by sequential gel-filtration and anion-exchange chromatography of the reaction products generated by incubating 20 mM $^{109}CdSO_4$ (78.4 mCi/mmol) with 40 mM GSH or 40 mM [$^3$H]GSH (240 mCi/mmol) in 15 ml 10 mM phosphate buffer (pH 8.0) containing 150 mM $KNO_3$ at 45° C. for 24 hours. For gel-filtration, 2 ml aliquots of the reaction mixture were applied to a column (40×1.5 cm ID) packed with water-equilibrated Sephadex G-1 5, eluted with deionized water and $^{109}$Cd and/or $^3$H in the fractions was measured by liquid scintillation counting. The fractions encompassed by each of the two $^{109}$Cd.$GS_n$ peaks identified were pooled, lyophilized and redissolved in 4 ml of loading buffer (5 mM Tris-Mes, pH 8.0). For anion-exchange chromatography, 0.5 ml aliquots of the resuspended lyophilizates from gel-filtration chromatography were applied to a Mono-Q HR5/5 column (Pharmacia) equilibrated with the same buffer. Elution was with a linear gradient of NaCl (0.5 ml/minute; 0–500 mM) dissolved in loading buffer. The individual fractions corresponding to the major peaks of $^{109}$Cd obtained from the Mono-Q column (one each for the peaks resolved by gel-filtration chromatography) were pooled, lyophilized and resuspended in 4 ml deionized water after liquid scintillation counting. Buffer salts were removed before transport measurements or mass spectrometry by passing the samples down a column (120×1.0 cm ID) packed with water-equilibrated Sephadex G-15.

Measurement of $^{109}Cd^{2+}$ Uptake

MgATP-energized, uncoupler-insensitive $^{109}Cd^{2+}$ uptake by vacuolar membrane vesicles was measured at 25° C. in 200 μl reaction volumes containing 3 mM ATP, 3 mM $MgSO_4$, 5 μM gramicidin-D, 10 mM creatine phosphate, 16 units/ml creatine kinase, 50 mM KCl, 400 mM sorbitol, 25 mM Tris-Mes (pH 8.0) and the indicated concentrations of $^{109}CdSO_4$, GSH or $^{109}$Cd- and/or $^3$H-labeled purified Cd.$GS_n$ complexes as described herein except that the wash media contained 100 μM $CdSO_4$ in addition to sorbitol (400 mM) and Tris-Mes (3 mM, pH 8.0).

Pretreatment of DTY165 Cells with $Cd^{2+}$ or 1-Chloro-2,4-dinitrobenzene

For studies on the inducibility of YCF1 expression and YCF1-dependent transport, DTY165 cells were grown in YPD medium (Sherman et al., 1983, supra) for 24 hours at 30° C. to an $OD_{600}$ nm of 1.0–1.2, pelleted by centrifugation and resuspended in fresh YPD medium containing $CdSO_4$ (200 PM) or 1-chloro-2,4-dinitrobenzene (CDNB). After washing in distilled water, total RNA was extracted and vacuolar membrane vesicles were prepared from the pretreated cells. Control RNA and membrane samples were prepared from DTY165 cells treated in an identical manner except that $CdSO_4$ and CDNB were omitted from the second incubation cycle.

RNase Protection Assays $Cd^{2+}$ and CDNB-elicited increases in YCF1 mRNA levels were assayed by RNase protection using 18S rRNA as an internal control. YCF1-specific probe was generated by PCR amplification of the full-length YCF1::HA gene, encoding human influenza hemagglutinin 12CA5 (HA) epitope-tagged YCF1, using plasmid pYCF1-HA as template. The forward YCF1-specific primer and backward primer containing the HA-tag coding sequence had the sequences 5'-AAACTGCAGATGGCTGGTAATCTTGTTTC-3' (SEQ ID NO: 13) and 5'-GCCTCTAGATCAAGCGTAGTCTGGGACGTCGTA TGGGTAATTTTCATTGA-3' (SEQ ID NO: 14), respectively. An 18S rRNA-specific probe was synthesized by PCR of S. cerevisiae genomic DNA using sense and antisense primers having the sequences 5'-AGATTAAGCCATGCATGTCT-3' (SEQ ID NO: 15) and 5'-TGCTGGTACCAGACTTGCCCTCC-3' (SEQ ID NO: 16), respectively. Both PCR products were individually subcloned into pCR$^{TM}$II vector (Invitrogen) to generate plasmids pCR-YCF1 and pCR-Y18S. After linearization of pCR-YCF1 and pCR-Y18S with AflI and NcoI, a 320-nucleotide YCF1-specific RNA probe and 220-nucleotide 18S rRNA-specific probe were synthesized using T7 RNA polymerase and SP6 RNA polymerase, respectively. Aliquots of total RNA, prepared as described (Kohrer et al., 1991, *Methods in Enzymol.* 194:390–398)), from control, $CdSO_4$- or CDNB-pretreated DTY165 cells were hybridized with a mixture of $^{32}$P-labeled YCF1 anti sense probe ($1\times10^6$ cpm) and 18S rRNA antisense probe ($5\times10^2$ cpm) and RNase protection (Teeter et al., 1990, *Mol. Cell. Biol.* 10:5728–5735) was assayed using an RPAII kit (Ambion).

Matrix-Assisted Laser Desorption Mass Spectrometry (MALD-MS)

The 109Cd.GS$_n$ complexes purified by gel-filtration and anion-exchange chromatography were adjusted to a final concentration of 2–5 mM (as Cd) with deionized water, mixed with an equal volume of sinapinic acid (10 mg/ml) dissolved in acetonitrile/$H_2$O/trifluoroacetic acid (70:30:0.1% (v/v)) and applied to the ion source of a PerSeptive Biosystems Voyager RP Biospectrometry Workstation. The instrument, which was equipped with a 1.3 m flight tube and variable two-stage ion source set at 30 kV, was operated in linear mode. Mass/charge (m/z) ratio was measured by time-of-flight after calibration with external standards.

Protein Estimations

Protein was estimated by a modification of the method of Peterson (1977, *Anal. Biochem.* 83:346–356).

Chemicals

S-(2,4-dinitrophenyl)glutathione (DNP-GS) was synthesized from 1-chloro-2,4-dinitrobenzene (CDNB) and GSH by the procedure of Kunst et al. (1983, 3 *Biochem. Biophys. Acta* 983:123–125) and (Li et al., 1995, supra). [$^3$H]DNP-GS (specific activity, 8.7 mCi/mmol) and bimane-GS were synthesized enzymatically and purified by a modification of the procedure of Kunst et al. (1983, supra) according to Li et al. (1995, supra). Metolachlor-GS was synthesized by general base catalysis and purified by reverse-phase high performance liquid chromatography (Li et al., 1995, supra).

GSH and CDNB were purchased from Fluka; AMP-PNP, aprotinin, ATP, creatine kinase (type I from rabbit muscle, 150–250 units/mg of protein), creatine phosphate, FCCP, oxidized glutathione (GSSG), S-methylglutathione, cysteinylglycine, cysteine, glutamate and gramicidin D, leupeptin, PMSF, verapamil, and vinblastine were from Sigma; monochlorobimane was from Molecular Probes; cellulose nitrate membranes (0.45-µm pore size, HA filters) were from Millipore; [$^3$H]glutathione[(glycine-2–3H]-L-Glu-Cys-Gly; 44 Ci/mmol) was from DuPont NEN; and $^{109}$CdSO$_4$ (78.44 Ci/mmol) was from Amersham Corp. Metolachlor was a gift from CIBA-Geigy, Greensboro, N.C. All other reagents were of analytical grade and purchased from Fisher, Fluka, or Sigma.

Sensitivity to CDNB

If the YCF1 gene product were to participate in the detoxification of S-conjugable xenobiotics, mutants deleted for this gene would be expected to be more sensitive to the toxic effects of these compounds than wild type cells. This is what was found (FIG. 1).

The isogenic wild type strain DTY165 and the ycf1Δ mutant strain, DTY167, were indistinguishable during growth in YPD medium lacking CDNB; both strains grew at the same rate after a brief lag. However, the addition of CDNB to the culture medium caused a greater retardation of the growth of DTY167 cells (FIG. 1B) than DTY165 cells (FIG. 1A). Inhibitory concentrations of CDNB resulted in a slower, more linear, growth rate for at least 24 hours for both strains, but DTY167 underwent growth retardation at lower concentrations than did DTY165. The optical densities of the DTY167 cultures were diminished by 65, 82, 85, and 91% by 40, 50, 60, and 70 µM CDNB, respectively, after 24 hours of incubation (FIG. 1B), whereas the corresponding diminutions for the DTY165 cultures were 14, 31, 59, and 92% (FIG. 1A). The increase in sensitivity to CDNB conferred by deletion of the YCF1 gene was similar to that seen with cadmium.

Impaired Vacuolar DNP-GS Transport

Vacuolar membrane vesicles purified from DTY165 cells exhibited high rates of MgATP-dependent [3H]DNP-GS uptake (FIG. 2). Providing that creatine phosphate and creatine kinase were included in the uptake media to ensure ATP regeneration, addition of 3 mM MgATP increased the initial rate of DNP-GS uptake by 122-fold to a value of 12.2 nmol/mg/minute. The same membrane fraction from DTY167 cells, although capable of similar rates of MgATP-independent DNP-GS uptake, was only 17-fold stimulated by MgATP and capable of an initial rate of uptake of only 1.7 nmol/mg/minute (FIG. 2).

Selective Impairment of Uncoupler-Insensitive Transport

Direct comparisons between vacuolar membrane vesicles from DTY165 and DTY167 cells demonstrated that deletion of the YCF1 gene selectively abolished MgATP-energized, $\Delta\mu_H$+-independent DNP-GS transport.

Agents that dissipate both the pH ($\Delta$pH) and electrical ($\Delta\psi$) components of the $\Delta\mu_H$+established by the V-ATPase (FCCP, gramicidin D) or directly inhibit the V-ATPase, itself (bafilomycin $A_1$), decreased MgATP-dependent DNP-GS uptake by vacuolar membrane vesicles from DTY165 cells from 77.7±1.0 nmol/mg/10 minutes to between 43.2±1.0 and 47.4±1.7 nmol/mg/10 minutes (Table 1). Ammonium chloride, which abolishes $\Delta$pH while leaving $\Delta\psi$ unaffected, on the other hand, did not inhibit DNP-GS uptake (Table 1). On the basis of these characteristics, the inability of uncouplers to markedly increase the inhibitions caused by V-ATPase inhibitors, alone, and the resistance of 50–60% of total uptake to inhibition by any one of these compounds (Table 1), DNP-GS uptake by vacuolar membranes from wild type cells is concluded to proceed via two parallel mechanisms: a V-ATPase inhibitor- and uncoupler-insensitive pathway that is directly energized by MgATP, and a $\Delta\mu_H$+-dependent, V-ATPase inhibitor-sensitive and uncoupler-sensitive pathway that is primarily driven by the inside-positive $\Delta\psi$ established by the V-ATPase.

Of these two pathways, the $\Delta\psi$-dependent pathway predominated in membranes from DTY167 cells (Table 1). FCCP, gramicidin D, and bafilomycin $A_1$ diminished net DNP-GS uptake by DTY167 vacuolar membranes from 15.4±0.4 nmol/mg/10 minutes to between 4.3±0.3 and 6.4±0.3 nmol/mg/10 minutes. Moreover, although the effects of FCCP or gramicidin D and V-ATPase inhibitors in combination were slightly greater than those seen when these agents were added individually, the transport remaining was only about 10% of that seen with wild type membranes and only 2–4-fold stimulated by MgATP. In conjunction with the negligible inhibitions seen with NH$_4$Cl, alone, indicating that $\Delta\psi$, not $\Delta$pH, is the principal driving force for the transport activity remaining in their vacuolar membranes, DTY167 cells are inferred to be preferentially impaired in MgATP-energized, $\Delta\mu_H$+-independent DNP-GS transport.

The nonhydrolyzable ATP analog, AMP-PNP, did not promote DNP-GS uptake by vacuolar membrane vesicles from either DTY165 or DTY167 cells (Table 1), indicating a requirement for hydrolysis of the γ-phosphate of ATP regardless of whether uptake was via the YCF1- or γψ-dependent pathway.

TABLE 1

Effects of MgATP, MgAMP-PNP, protonophores, ionophores and V-ATPase inhibitors on [$^3$H]DNP-GS uptake by vacuolar membrane vesicles purified from DTY165 and DTY167 cells
Uptake was measured for 10 minutes in standard uptake medium described herein containing 66.2 μM [$^3$H]DNP-GS plus the compounds indicated. MgATP (3 mM) was present throughout unless otherwise indicated, MgAMP-PNP, bafilomycin A$_1$, FCCP, gramicidin D, and NH$_4$Cl were added at concentrations of 3 mM, 0.5 μM, 5 μM, 5 μM and 1 mM, respectively
Values outside parentheses are means ± SE (n = 3–6); values inside parentheses are rates of uptake expressed as percentage of control

| | DNP-GS UPTAKE | |
|---|---|---|
| | DTY165 | DTY167 |
| ADDITIONS | (nmol/mg/10 minutes) | |
| Control | 77.7 ± 1.0 (100) | 15.4 ± 0.4 (100) |
| —MgATP | 2.2 ± 0.4 (2.8) | 1.5 ± 0.6 (9.7) |
| MgAMP-PNP(—MgATP) | 2.5 ± 0.5 (3.2) | 1.4 ± 0.3 (9.1) |
| FCCP | 47.4 ± 1.7 (61.0) | 6.4 ± 0.3 (41.8) |
| Gramicidin D | 45.8 ± 1.4 (58.9) | 5.8 ± 0.1 (37.7) |
| NH$_4$Cl | 69.1 ± 2.9 (88.9) | 14.9 ± 0.7 (96.8) |
| NH$_4$Cl ± gramicidin D | 42.6 ± 1.8 (54.8) | 4.1 ± 0.2 (26.6) |
| Bafilomycin A$_1$ | 43.2 ± 1.0 (55.6) | 4.3 ± 0.3 (27.9) |
| Bafilomycin A$_1$ ± gramicidin D | 39.2 ± 2.6 (50.5) | 3.8 ± 0.1 (24.7) |

Abolition of High Affinity, Uncoupler-insensitive Uptake

Figure 3A:
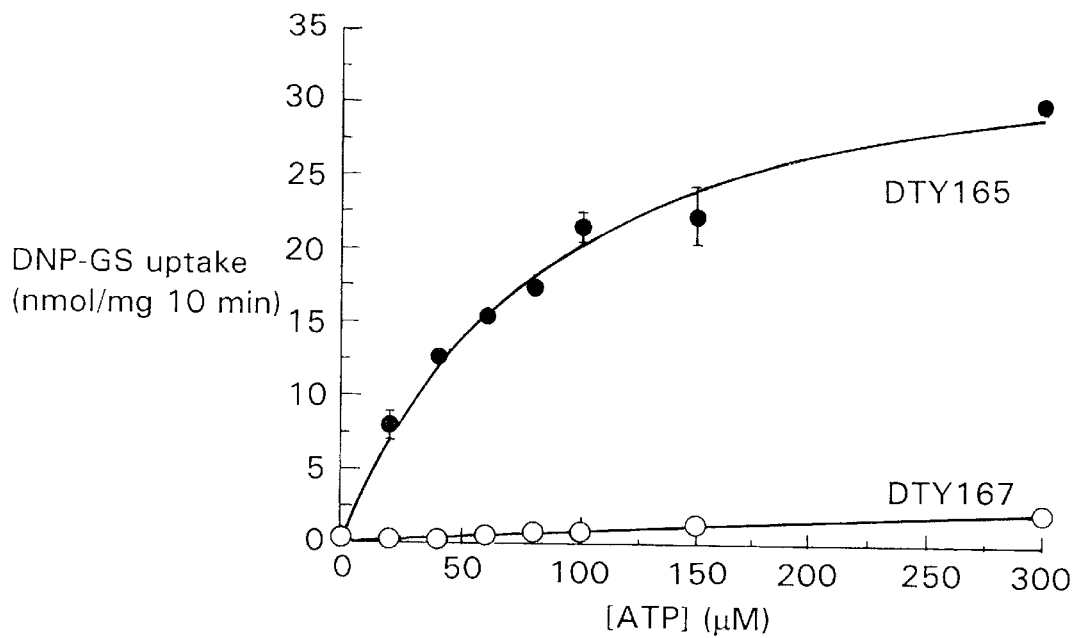
FIGS. 3A–3B are a series of graphs depicting the kinetics of uncoupler-insensitive [$^3$H]DNP-GS uptake by vacuolar membrane vesicles purified from DTY165 and DTY167 cells.
Figure 3B:
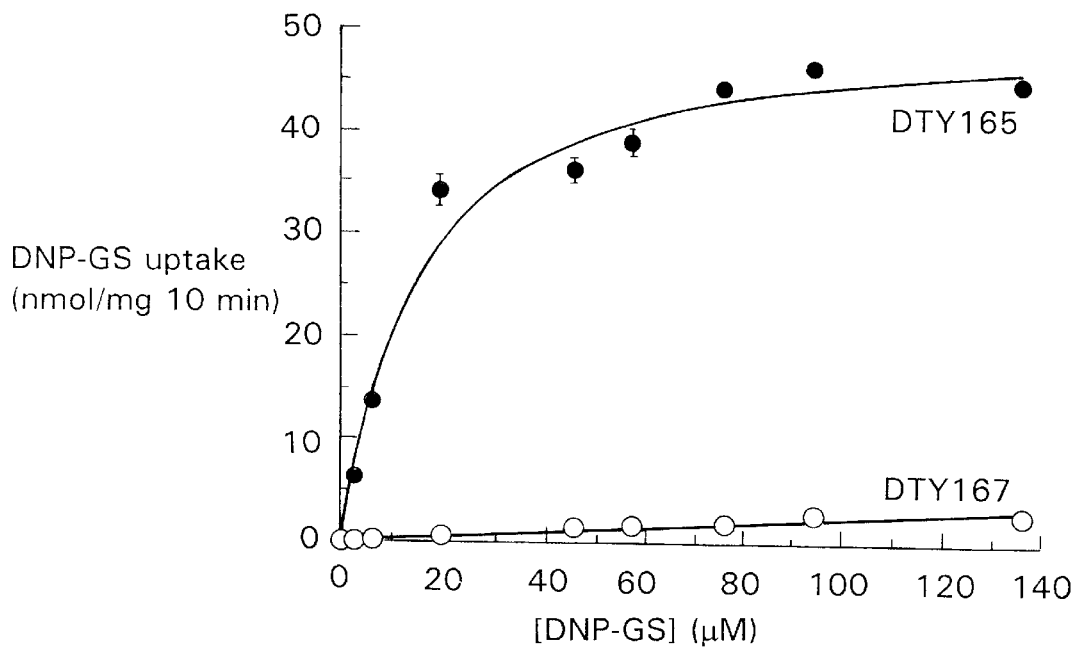
Figure 4A:
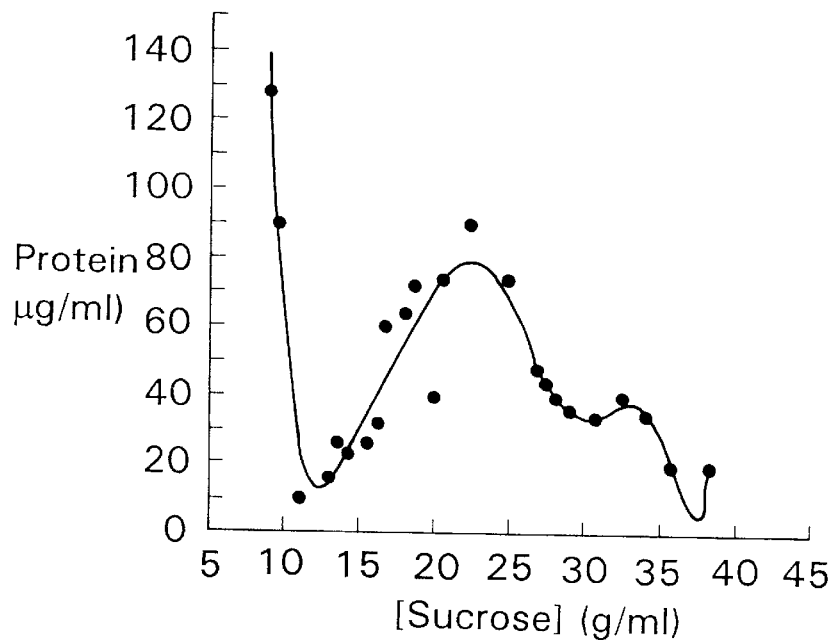
FIGS. 4A–4D are a series of graphs depicting sucrose density gradient fractionation of vacuolar membrane-enriched vesicles prepared from DTY165 cells. One ml (1.1 mg protein) of partially purified vacuolar membrane vesicles derived from vacuoles prepared by the Ficoll flotation technique were applied to a linear sucrose density gradient (10–40%, w/v) and analyzed for protein (FIG. 4A), α-mannosidase activity (FIG. 4B), V-ATPase activity (FIG. 4C), and MgATP-dependent, uncoupler-insensitive [$^3$H] DNP-GS uptake (FIG. 4D). [$^3$H]DNP-GS uptake and enzyme activity were assayed as described herein in Table 4 and the accompanying text.
Figure 4B:
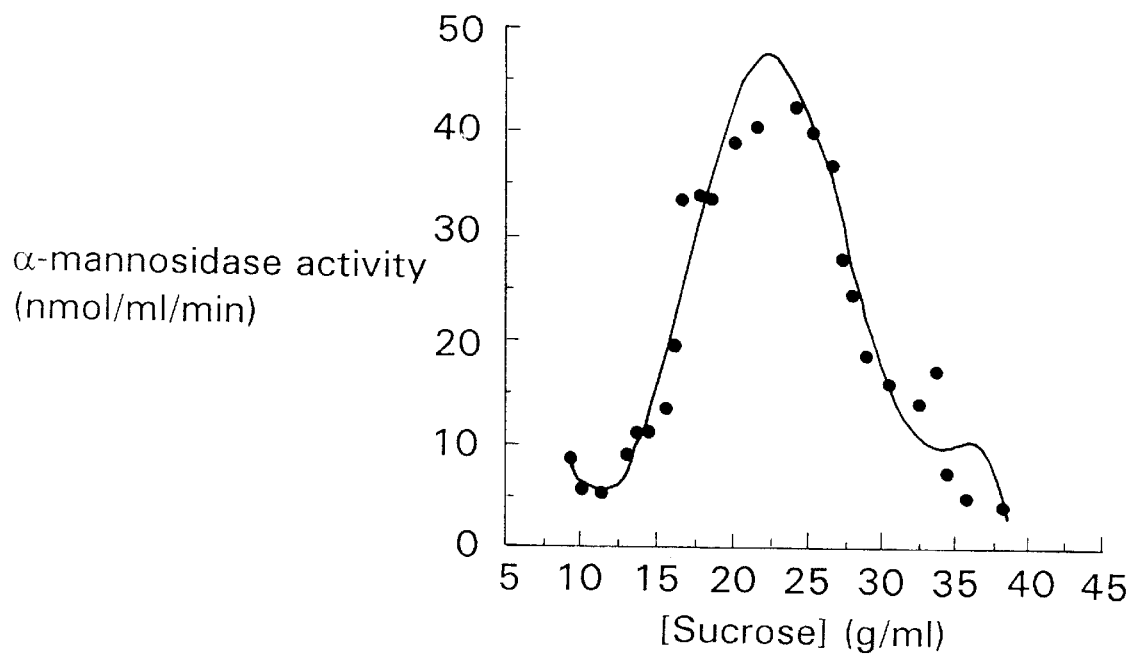
Figure 4C:
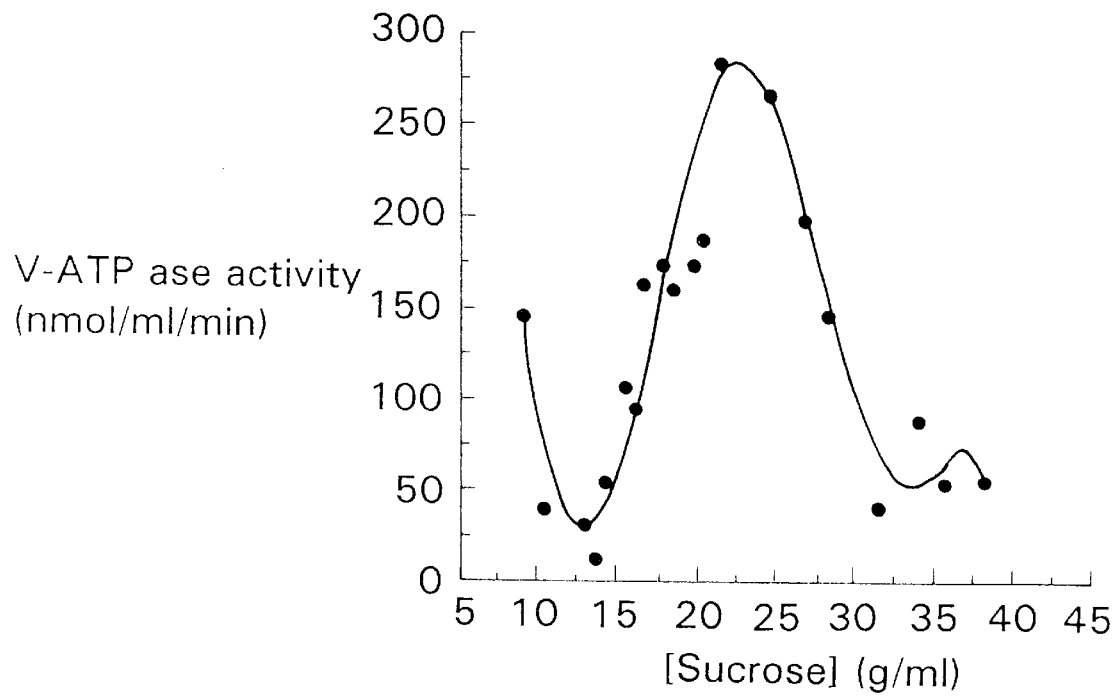
Figure 4D:
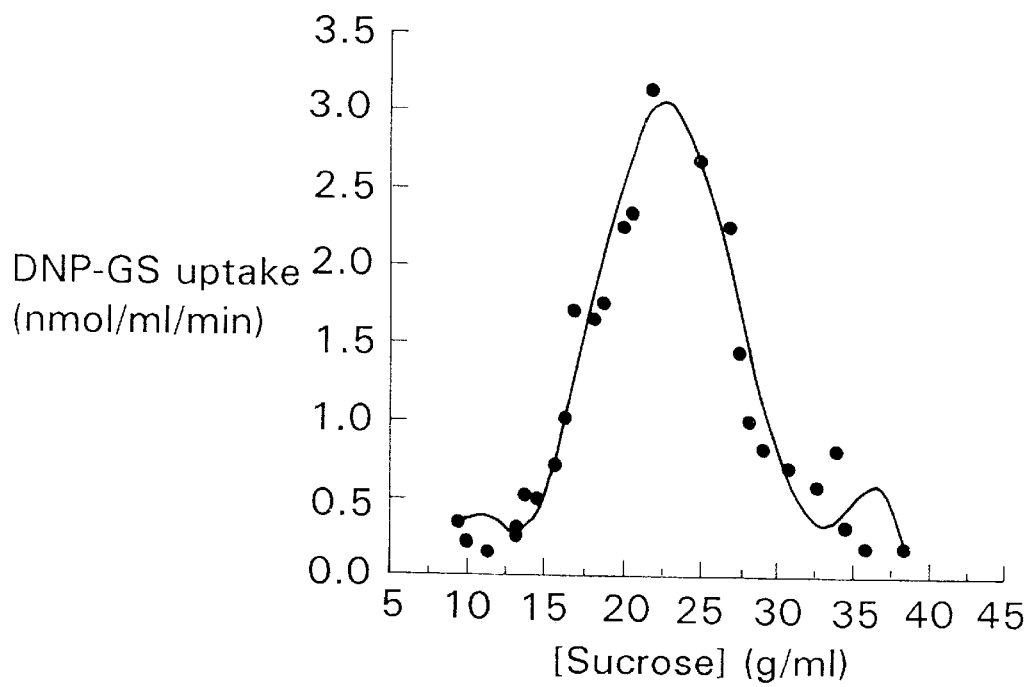

Examination of the concentration dependence of [$^3$H] DNP-GS uptake revealed a near total abolition of high affinity, MgATP-dependent, uncoupler-insensitive transport by vacuolar membrane vesicles from the ycf1Δ mutant strain (FIG. 3). When measured in the presence of uncoupler (gramicidin D), the rate of DNP-GS uptake by vacuolar membrane vesicles purified from DTY165 cells increased as a simple hyperbolic function of MgATP (FIG. 3A) and DNP-GS concentration (FIG. 3B) to yield K$_m$ values OF 86.5±29.5 μM (MgATP) and 14.1±7.4 μM (DNP-GS) and a V$_{max}$ of 51.0±16.3 nmol/mg/10 minutes (DNP-GS). By contrast, uncoupler-insensitive uptake by the corresponding membrane fraction from DTY167 cells was more than 15-fold slower over the entire concentration range, showed no evidence of saturation and increased as a linear function of both DNP-GS and MgATP concentration (FIG. 3).

Selective Inhibitors of YCF1-mediated Transport

MgATP-dependent, uncoupler-insensitive DNP-GS uptake by vacuolar membrane vesicles purified from DTY165 cells was sensitive to inhibition by vanadate, vinblastine, verapamil, GSSG and glutathione S-conjugates other than DNP-GS (Tables 2 and 3). One hundred μM concentrations of metolachlor-GS, azidophenacyl-GS and bimane-GS and 1 mM GSSG inhibited uptake by about 50% (Table 2), while vanadate, vinblastine, and verapamil exerted 50% inhibitions at concentrations of 179, 89 and 203 μM, respectively (Table 3). None of these agents significantly inhibited residual MgATP-dependent, uncoupler-insensitive DNP-GS uptake by vacuolar membrane vesicles from DTY167 cells (Tables 2 and 3).

TABLE 2

Effects of GSH, GSSG, and glutathione S-conjugates other than DNP-GS on MgATP-dependent, uncoupler-insensitive [$^3$H]DNP-GS uptake by vacuolar membrane vesicles purified from DTY165 and DTY167 cells. Uptake was measured as described for Table 1 except that 5 μM gramicidin D was included in all of the uptake media
Values outside parentheses are means ± SE (n = 3–6); values inside parentheses are rates of uptake expressed as percentage of control

| | DNP-GS UPTAKE | |
|---|---|---|
| | DTY165 | DTY167 |
| COMPOUND | (nmol/mg/10 minutes) | |
| Control | 47.9 ± 2.5 (100) | 6.5 ± 0.8 (100) |
| GSH (1 mM) | 50.6 ± 2.3 (105.6) | 4.6 ± 1.1 (70.8) |
| GSSG (1 mM) | 26.0 ± 0.9 (54.3) | 4.4 ± 0.4 (67.7) |
| Metolachlor-GS (100 μM) | 27.6 ± 0.9 (57.7) | 4.8 ± 0.7 (73.8) |
| Azidophenacyl-GS (100 μM) | 16.0 ± 1.4 (33.5) | 5.2 ± 0.3 (80.0) |
| Bimane-GS (100 μM) | 25.2 ± 1.1 (52.6) | 4.5 ± 0.4 (69.2) |

TABLE 3

Sensitivity Of MgATP-dependent, uncoupler-insensitive [$^3$H]DNP-GS uptake by vacuolar membrane vesicles purified from DTY165 and DTY167 cells to inhibition by vanadate, vinblastine, and verapamil
Uptake was measured as described in Table I except that 5 μM gramicidin D was included in all of the uptake media. The concentrations of the compounds causing 50% inhibition of uptake (I$_{50}$ values) were estimated by nonlinear least squares analysis after fitting the data to a single negative exponential (Marquardt, 1963, supra).

| | I$_{50}$ | |
|---|---|---|
| | DTY165 | DTY167 |
| Addition | μM | |
| Vanadate | 179.1 | Insensitive |
| Vinblastine | 88.8 | >500 |
| Verapamil | 202.6 | Insensitive |

Vacuolar Membrane Localization

The capacity for MgATP-dependent, uncoupler-insensitive [$^3$H]DNP-GS uptake strictly copurified with the vacuolar membrane fraction (Table 4). By comparison with crude microsomes (total membranes) prepared from whole spheroplast homogenates of DTY165 cells, vacuolar membrane vesicles derived from vacuoles purified by the Ficoll flotation technique were coordinately enriched for DNP-GS uptake and for both of the vacuolar membrane markers assayed, α-mannosidase and bafilomycin A$_1$-sensitive ATPase (V-ATPase) activity. The respective enrichments of MgATP-dependent, uncoupler-insensitive DNP-GS uptake, α-mannosidase and bafilomycin A$_1$-sensitive ATPase activity were 28-, 53- and 22-fold. By contrast, the vacuolar membrane fraction was 4.5-, 6.3-, 11.1- and 4.3-fold depleted of NADPH cytochrome c reductase (endoplasmic reticulum), latent GDPase (Golgi), vanadate-sensitive ATPase (plasma membrane), and azide-sensitive ATPase activity (mitochondrial inner membrane), respectively. Accordingly, when vacuolar membrane vesicles derived from Ficoll-flotated vacuoles were subjected to further fractionation on linear 10–40% (w/v) sucrose density gradients, MgATP-dependent, uncoupler-insensitive [$^3$H]DNP-GS uptake, α-mannosidase and bafilomycin A$_1$-sensitive ATPase activity were found to comigrate and exhibit identical density profiles (FIG. 4).

Oude Elferinketal., 1993, *Hepatology* 17:343–444; Ishikawa et al., 1994, *J Biol. Chem.* 269:29085–29093). The GS-X pumps of both animal and plant cells exhibit activity toward a broad range of S-conjugates, including bimane-GS

TABLE 4

Comparison of rates of MgATP-dependent, uncoupler-insensitive [$^3$H]DNP-GS transport and specific activities of marker enzymes in crude microsomes and vacuolar membrane vesicles prepared from DTY165 cells. Microsomes and vacuolar membrane vesicles were prepared from spheroplasts and the marker enzymes were assayed as described herein. Values shown are means ± SE(n = 3)

| PREPARATION | ACTIVITY | | |
|---|---|---|---|
| | DNP-GS UPTAKE nmol/mg/10 min | α-mannosidase nmol/mg/min | NADPH-cyt c reductase nmol/mg/min |
| Microsomes | 2.5 ± 0.3 | 6.3 ± 0.3 | 88.0 ± 1.3 |
| Vacuolar membrane | 69.9 ± 1.0 | 329.3 ± 3.2 | 19.3 ± 0.6 |
| Enrichment (-fold) | 27.96 | 52.27 | 0.22 |

| PREPARATION | ACTIVITY | | | |
|---|---|---|---|---|
| | V-ATPase umol/mg/h | GDPase | P-ATPase umol/mg/h | F-ATPase |
| Microsomes | 11.7 ± 6.3 | 35.0 ± 1.1 | 37.1 ± 4.6 | 155.6 ± 3.0 |
| Vacuolar membrane | 253.1 ± 15.8 | 5.5 ± 0.1 | 3.2 ± 1.6 | 35.1 ± 8.4 |
| Enrichment (-fold) | 21.63 | 0.16 | 0.09 | 0.23 |

Plasmid-encoded YCF1 Mediates Vacuolar DNP-GS Transport and CDNB Resistance

Figure 5B:
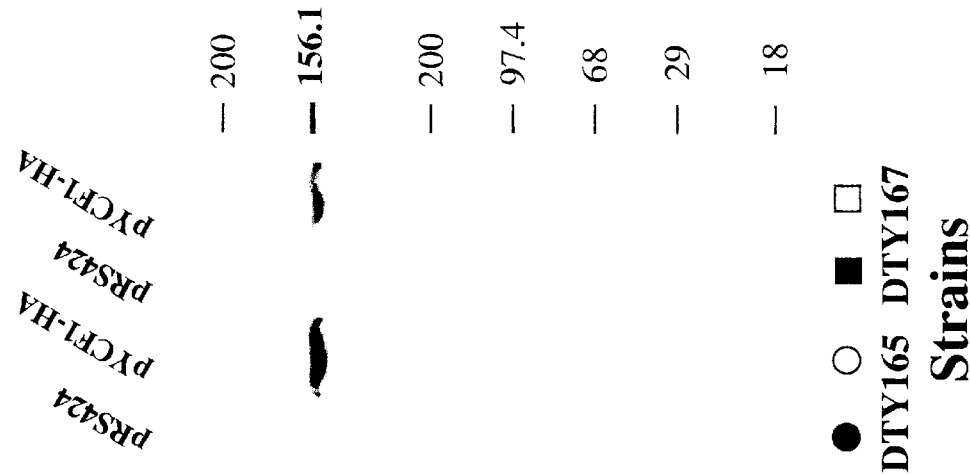
FIGS. 5A–5B include a graph (FIG. 5A) depicting the effect of transformation with pYCF1-HA or pRS424 on MgATP-dependent, uncoupler-insensitive [$^3$H]DNP-GS uptake by vacuolar membranes purified from DTY165 and DTY167 cells. Uptake was measured in standard uptake medium containing 66.2 $\mu$M [3H]DNP-GS and 5 $\mu$M gramicidin D. Also shown (FIG. 5B) is an image of a gel depicting immunoreaction of vacuolar membrane proteins prepared from pYCF1-HA-transformed and pRS424-transformed DTY165 and DTY167 cells with mouse monoclonal antibody raised against the 12CA5 epitope of human influenza hemagglutinin. All lanes were loaded with 25 $\mu$g of delipidated membrane protein and subjected to SDS-polyacrylamide gel electrophoresis and Western analysis as described herein. The $M_r$ of YCF1-HA (boldface type) and the positions of the $M_r$ standards are indicated on the figure.
Figure 5A:
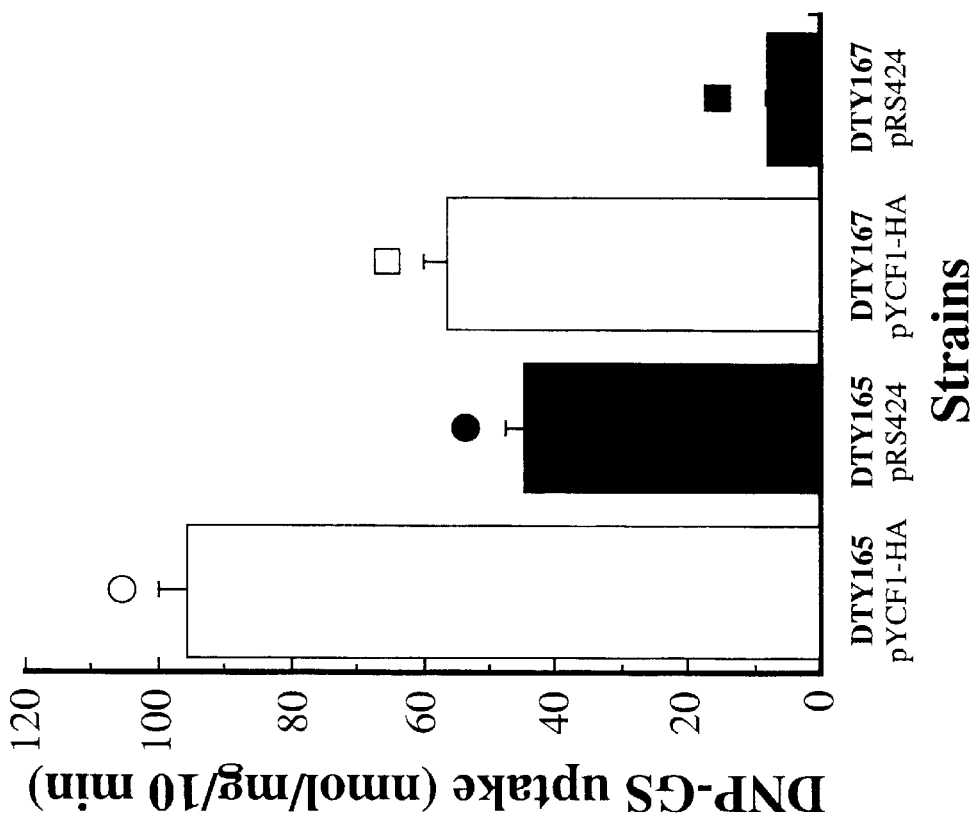

Immunoblots of vacuolar membranes from pYCF1-HA-transformed DTY165 or DTY167 cells, probed with mouse anti-HA monoclonal antibody, demonstrated incorporation of YCF1-HA polypeptide into the vacuolar membrane fraction (FIG. 5B). Immunoreaction with the 12CA5 epitope was not detectable in lanes loaded with membranes from pRS424-transformed cells but the same quantities of membranes prepared from pYCF1-HA-transformed cells yielded a single intensely immunoreactive band with an electrophoretic mobility (M$_r$=156,200) commensurate with a computed mass of 172 kDa for the fusion protein encoded by YCF1-HA (FIG. 5B).

Figure 6A:
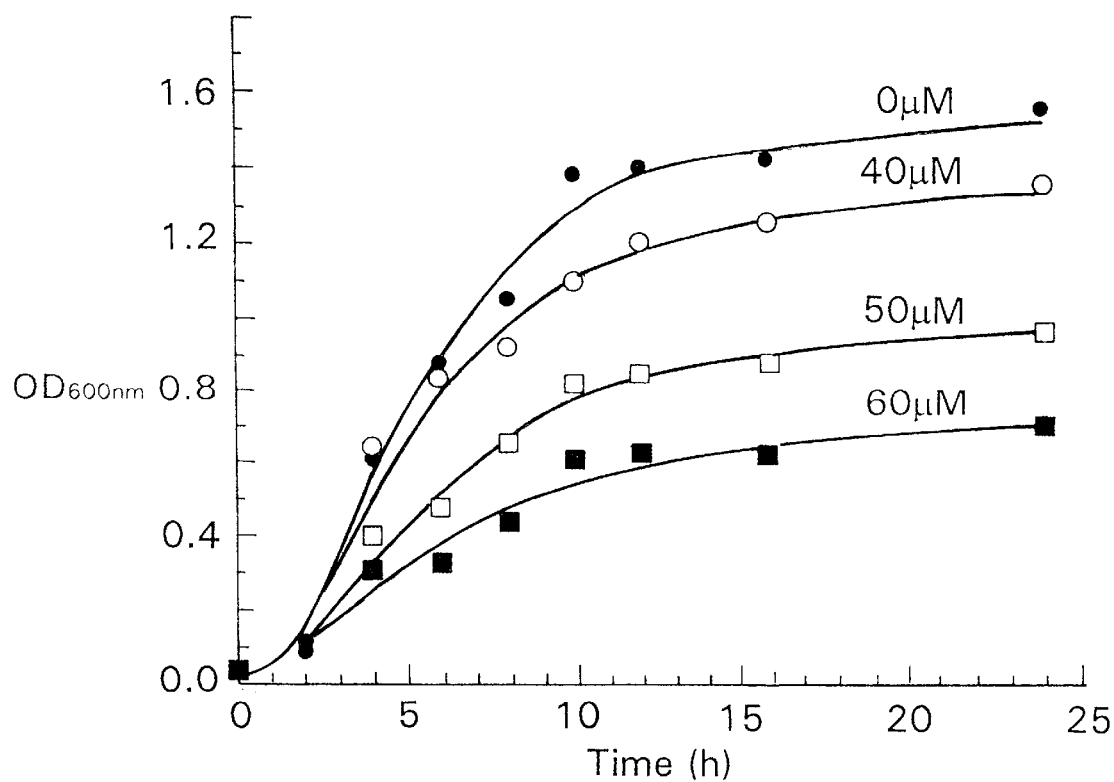
FIGS. 6A–6B are a series of graphs depicting transformation with pYCF1-HA (FIG. 6A) or pRS424 (FIG. 6B) on the sensitivity of DTY167 cells to growth retardation by CDNB. Cells were grown at 30° C. for 24 hours to an $OD_{600\ nm}$ of approximately 1.4 in AHC medium (Kim et al., 1994, Proc. Natl. Acad. Sci. USA 91:6128–6132) before inoculation of aliquots into 15 ml volumes of the same medium containing 0–60 $\mu$M CDNB. $OD_{600\ nm}$ was measured at the times indicated.
Figure 6B:
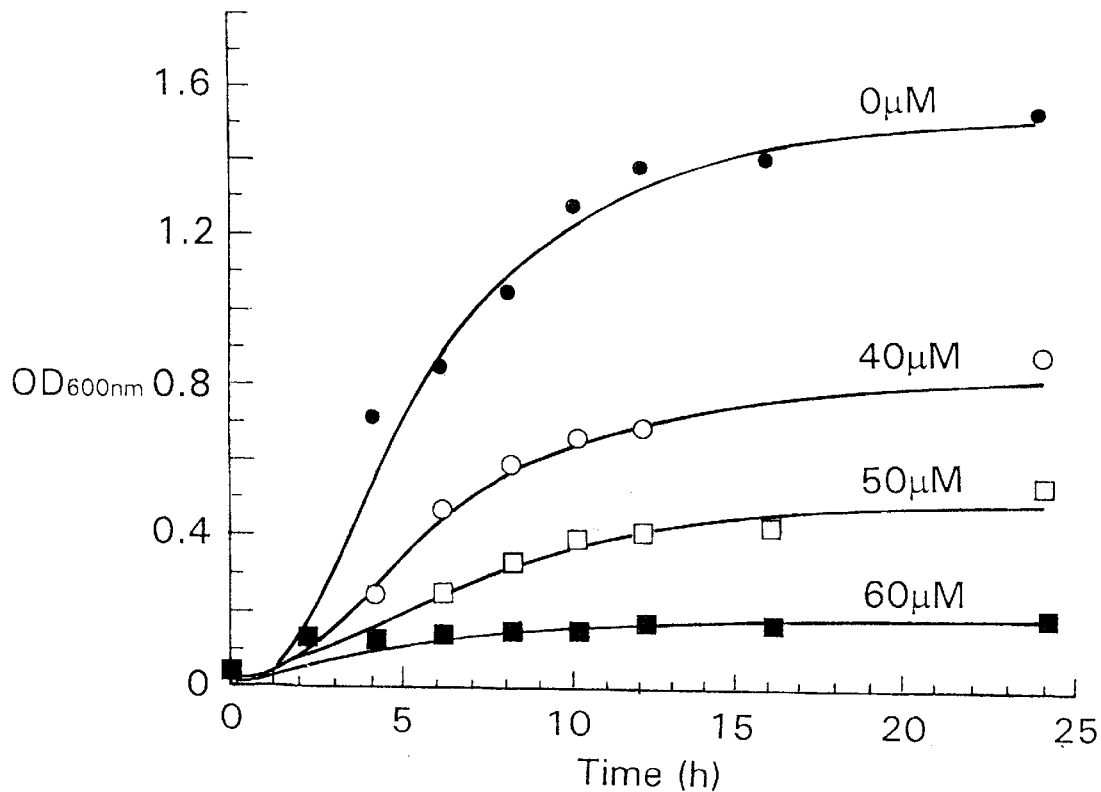

Direct participation of the plasmid-borne YCF1-HA gene product in DNP-GS transport and CDNB detoxification was verified by the finding that vacuolar membrane vesicles purified from pYCF1-HA-transformed DTY167 cells exhibited a 6-fold enhancement of MgATP-dependent, uncoupler-insensitive [$^3$H]DNP-GS uptake (FIG. 5A) which was accompanied by a decrease in the susceptibility of such transformants to growth retardation by exogenous CDNB (FIG. 6). Whereas pYCF1-HA-transformed DTY167 cells exhibited a similar resistance to growth retardation by CDNB as untransformed DTY165 cells (compare FIG. 6B with FIG. 1A), the same mutant strain showed neither increased vacuolar DNP-GS transport in vitro nor decreased susceptibility to CDNB in vivo after transformation with parental plasmid pRS424, lacking the YCF1-HA insert (FIG. 6B).

Vacuolar Accumulation of Bimane-GS In Vivo

Monochlorobimane, a membrane-permeant, nonfluorescent compound, is specifically conjugated with GSH by cytosolic glutathione S-transferases (GSTs) to generate the intensely fluorescent, membrane-impermeant S-conjugate, bimane-GS (Shrieve et al., 1988, *J Biol. Chem.* 263:14107–12114;

(Ishikawa et al., 1994, supra; Martinoia et al., 1993, supra), and DNP-GS uptake by the yeast enzyme is shown herein to be reversibly inhibited by this compound (Table 2). These data suggest competition between bimane-GS and DNP-GS for a common uptake mechanism. Exogenous monochlorobimane therefore satisfies the minimum requirements of a sensitive probe for monitoring the intracellular transport and localization of its S-conjugate.

Figure 8A:
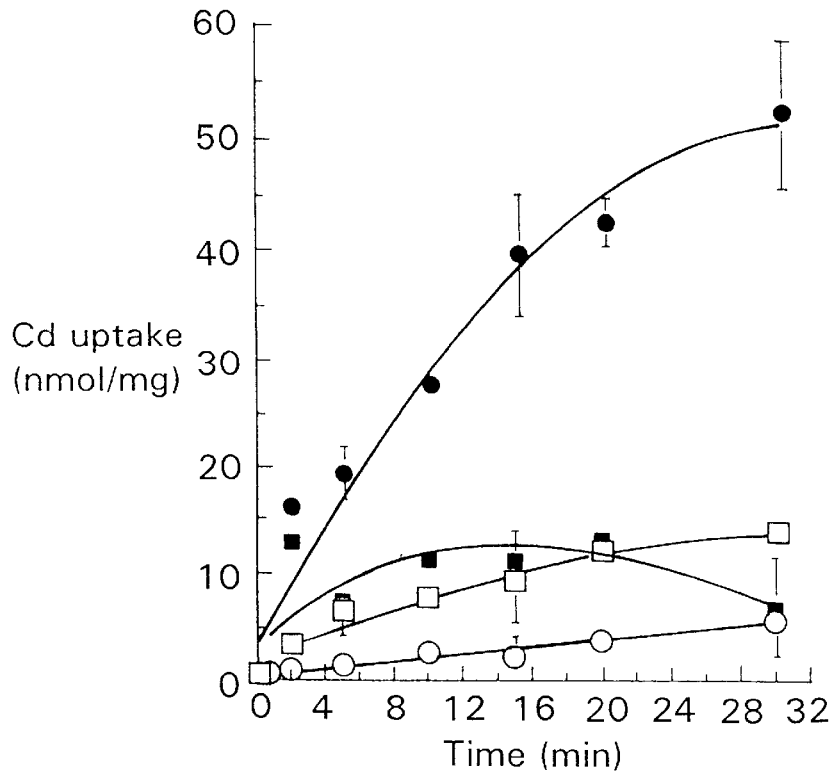
FIGS. 8A–8C are a series of graphs depicting uptake of $Cd^{2+}$ into vacuolar membrane vesicles purified from DTY165 and DTY167 cells. Uptake of $^{109}Cd^{2+}$ by DTY165 membranes (FIG. 8A) or DTY167 membranes (FIG. 8B) was measured in the absence of MgATP plus (○) or minus GSH (1 mM) (□) or in the presence of MgATP (3 mM) plus (●) or minus (■) GSH. $^{109}Cd_2SO_4$ and gramicidin-D were added at concentrations of 80 $\mu$M and 5 $\mu$M, respectively.
Figure 8B:
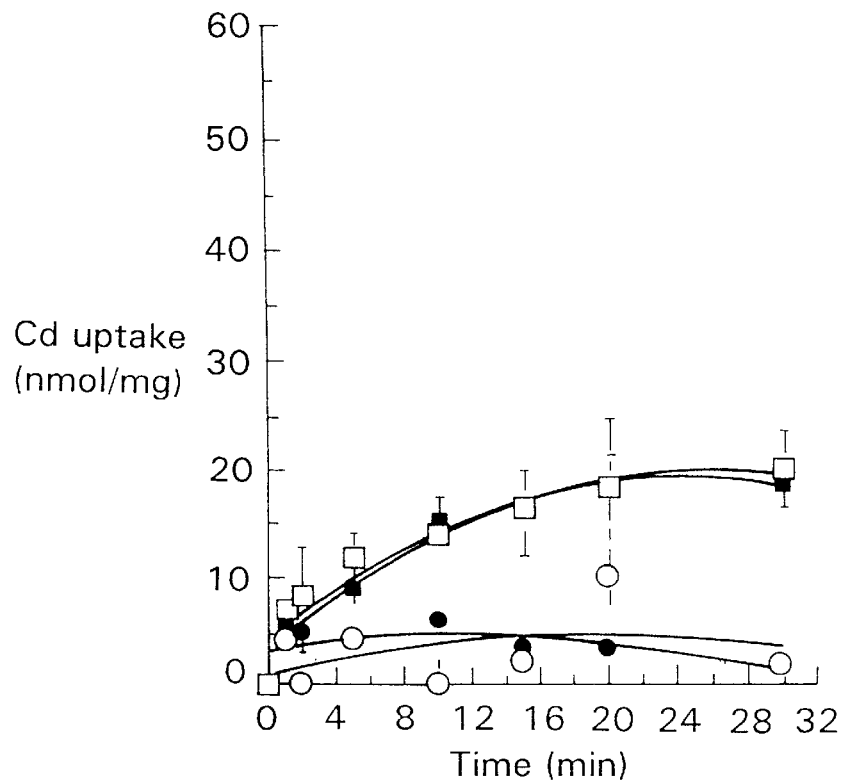

Fluorescence microscopy of DTY165 and DTY167 cells after incubation in growth medium containing monochlorobimane provides direct evidence that YCF1 contributes to the vacuolar accumulation of its glutathione S-conjugate by intact cells (FIG. 7). DTY165 cells exhibited an intense punctate fluorescence, corresponding to the vacuole as determined by Nomarski microscopy, after 6 hours of incubation with monochlorobimane (FIGS. 7A and 7C). The fluorescence associated with vacuolar bimane-GS was by comparison severely attenuated in most, and completely absent from many, DTY167 cells (FIGS. 7B and 7D).

ycf1Δ Mutants are Defective in GSH-Dependent Cd Transport Physiological (1 mM) concentrations of GSH (Kang, 1992, *Drug Metabolism and Disposition* 20:714–718) promoted Cd$^{2+}$ uptake by vacuolar membrane vesicles purified from the wild type strain DTY165 but not the ycf1Δ mutant strain DTY167 (FIG. 8). Addition of Cd$^{2+}$ (80 μM) to GSH-containing media elicited MgATP-dependent, uncoupler-insensitive $^{109}$Cd$^{2+}$ uptake rates of 4.5 and 0.8 nmol/mg/minute by DTY165 and DTY167 membranes, respectively (FIGS. 8A and 8B). Uptake by DTY165 membranes was diminished more than 9-fold by the omission of GSH (FIG. 8A) whereas uptake by DTY167 membranes was slightly stimulated (FIG. 8B).

Figure 8C:
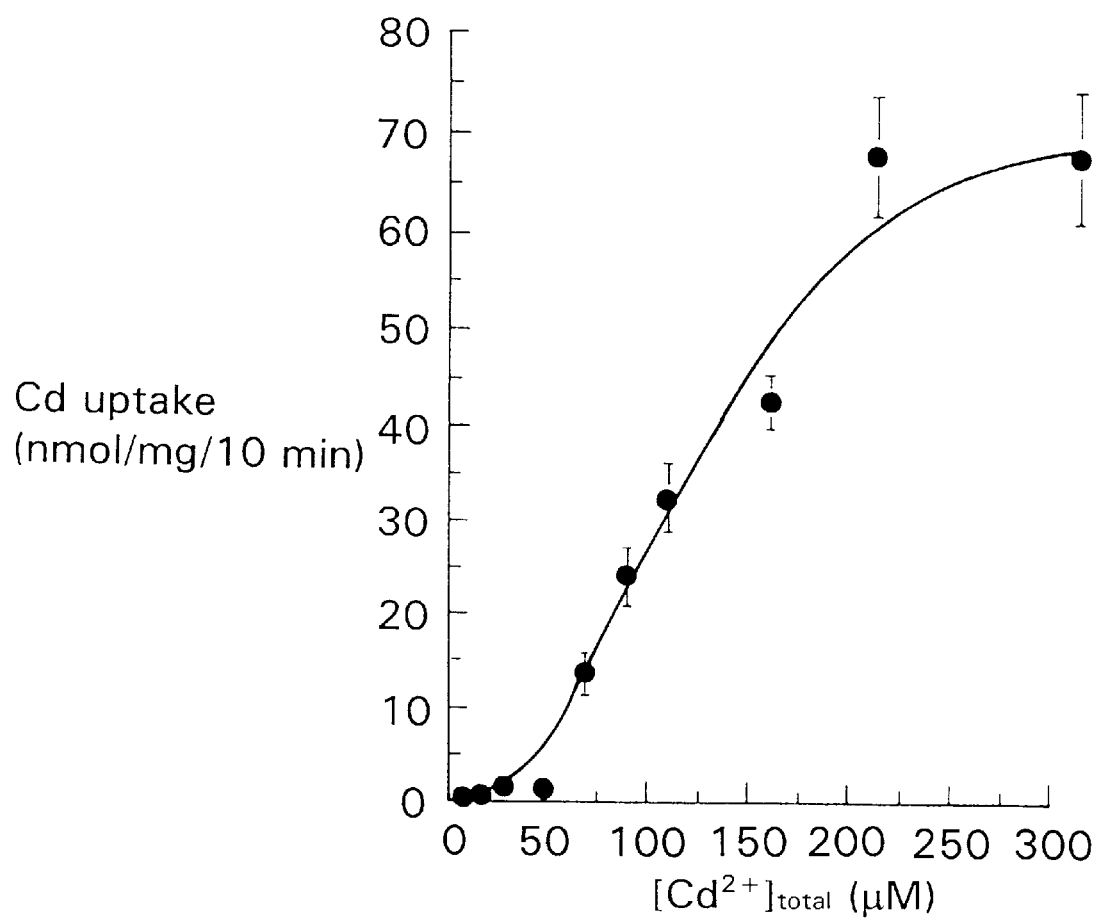

GSH maximally stimulated uptake within minutes (t$_{1/2}$<5 minutes) of the addition of Cd$^{230}$ to the uptake medium and uptake was sigmoidally dependent on Cd$^{2+}$ concentration, achieving half-maximal velocity at 120 μM (FIG. 8C).

Specific Requirement for GSH

The stimulatory action of GSH was abolished by the omission of MgATP from the assay medium (FIG. 8 and Table 5) and 1 mM concentrations of GSSG, S-methylglutathione, cysteinylglycine, cysteine or glutamate did not promote MgATP-dependent, uncoupler-insensitive $Cd^{2+}$ uptake by vacuolar membrane vesicles from either strain (Table 5).

TABLE 5

Effects of different GSH-related compounds on uncoupler-insensitive $^{109}$Cd uptake by vacuolar membrane vesicles purified from DTY165 or DTY167 cells, GSH, oxidized glutathione (GSSG), S-methylglutathione (GS-CH$_3$), cysteinylglycine, cysteine and glutamate were added at concentrations of 1 mM. MgATP, $^{109}$CdSO$_4$ and gramicidin-D were added at concentrations of 3 mM, 80 μM and 5 μM, respectively. Values shown are means ± SE (n = 3–6)

| | $^{109}$Cd UPTAKE (nmol/mg/10 minutes) | | | |
|---|---|---|---|---|
| | DTY165 | | DTY167 | |
| COMPOUND | −MgATP | +MgATP | −MgATP | +MgATP |
| $Cd^{2+}$ | 5.8 ± 2.4 | 5.6 ± 1.5 | 4.3 ± 1.3 | 4.6 ± 2.1 |
| $Cd^{2+}$ GSH | 4.2 ± 1.2 | 37.4 ± 4.5 | 3.3 ± 1.1 | 8.3 ± 2.7 |
| $Cd^{2+}$ GSSG | — | 5.1 ± 3.2 | — | 3.8 ± 2.3 |
| $Cd^{2+}$ GS-CH$_3$ | — | 4.5 ± 1.9 | — | 3.7 ± 3.1 |
| $Cd^{2+}$ Cys-Gly | — | 5.6 ± 3.2 | — | 6.9 ± 1.4 |
| $Cd^{2+}$ Cys | — | 7.0 ± 1.2 | — | 3.9 ± 1.0 |
| $Cd^{2+}$ Glu | — | 5.7 ± 1.1 | — | 5.2 ± 1.3 |

Purification of Transport-Active Complex

To determine the mode of action of GSH and the form in which $Cd^{2+}$ is transported, reaction mixtures initially containing $Cd^{2+}$ and GSH were fractionated and YCF1-dependent uptake was assayed.

Incubation of $^{109}Cd^{2+}$ with GSH and gel-filtration of the mixture on 109 Sephadex G-15 yielded two major Cd-labeled peaks: a low molecular weight peak (LMW-Cd.GS) and a high molecular weight peak (HMW-Cd.GS) (FIG. 9A). When rechromatographed on Mono-Q, LMW-Cd.GS and HMW-Cd.GS eluted at 0 (FIG. 9C) and 275 mM NaCl, respectively (FIG. 9B). Of these two $^{109}$Cd-labeled components, HMW-Cd.GS alone, underwent YCF1-dependent transport. MgATP-dependent, uncoupler-insensitive HMW-$^{109}$Cd.GS uptake by DTY165 membranes increased as a single Michaelian function of concentration ($K_m$, 39.1±14.1 μM; $V_{max}$, 157.2±60.7 nmol/mg/10 minutes) (FIG. 10A). By contrast, uptake of LMW-$^{109}$Cd.GS by DTY165 membranes was negligible at all of the concentrations examined (FIG. 10B). Vacuolar membranes from DTY167 cells transported neither HMW-09Cd.GS nor LMW-$^{109}$Cd.GS (FIGS. 10A and 10B).

Bis(glutathionato)cadmium Is the Transport-Active Complex

The transport-active complex, HMW-Cd.GS, was identified as bis(glutathionato)cadmium (Cd.GS$_2$) by three criteria: (i) The average Cd:GS molar ratio of the transported species, estimated from the $^{109}$Cd:$^3$H ratios of the HMW-Cd.GS peaks obtained after chromatography of reaction mixtures initially containing 109Cd2 and [$^3$H]GSH on Sephadex G-15 and Mono-Q were 0.44±0.09 and 0.49±0.17, respectively (Table 6). (ii) DTY165 membranes accumulated $^{109}$Cd and [3H]GS in a molar ratio of 0.49±0.01 when incubated in media containing HMW-$^{109}$Cd.[$^3$H]GS, MgATP and gramicidin-D (Table 6). (iii) The principal ion peak detected after MALD-MS of HMW-Cd.GS had an m/z ratio of 725.4±0.7, consistent with the molecular weight of bis(glutathionato)cadmium (724.6 Da, FIG. 11). The transport-inactive complex, LMW-Cd.GS, on the other hand, was tentatively identified as mono(glutathionato)cadmium on the basis of its smaller apparent molecular size (FIG. 9A), failure to bind Mono-Q (FIG. 9C) and Cd:GS ratio of 0.67 1 0.04 and 0.86±0.07 after chromatography on Sephadex G-15 and Mono-Q (Table 6), respectively.

While an m/z ratio of 725 for HMW-Cd.GS would be equally compatible with the transport of Cd.GSSG, this is refuted by two findings: (i) GSSG alone does not promote YCF1-dependent uptake (Table 5). (ii) The transport-active complex is probably a mercaptide. Pretreatment of HMW-Cd.GS with 2-mercaptoethanol inhibits MgATP-dependent, uncoupler-insensitive $Cd^{2\circ}$ uptake by DTY165 membranes by more then 80% (Table 6) and S-methylation abolishes the stimulatory action of GSH (Table 5).

TABLE 6

Molar Cd:GS ratios of LMW-Cd GS and HMW-Cd GS complexes fractionated by Sephadex G-15 and Mono-O chromatography (FIG. 9) before and after MgATP-dependent, uncoupler-insensitive uptake by vacuolar membrane vesicles purified from DTY165 and DTY167 cells. Cd:GS ratios were estimated from the $^{109}$Cd:[$^3$H] radioisotope ratios of samples prepared from $^{109}$CdSO$_4$ and [$^3$H]GSH. HMW-$^{109}$Cd.[$^3$H]GS was pretreated with 2-mercaptoethanol (2-ME) by heating a 1:4 mixture of HMW-$^{109}$Cd.[$^3$H]GS with 2-ME at 60° C. for 10 minutes before measuring $^{109}Cd^{2+}$ uptake. Uptake was measured using 50 μM concentrations (as Cd) of the complexes indicated in standard uptake medium containing 5 μM gramicidin-D. Values shown are means ± SE (n = 3–6)

| | $^{109}$Cd UPTAKE | | MOLAR RATIO Cd:GS | |
|---|---|---|---|---|
| | (nmol/mg/10 min) | | BEFORE | AFTER |
| FRACTION | DTY165 | DTY167 | UPTAKE | UPTAKE |
| Sephadex G-15 | | | | |
| HMW-Cd.GS | — | — | 0.44 ± 0.09 | — |
| LMW-Cd.GS | — | — | 0.67 ± 0.04 | — |
| Mono-Q | | | | |
| HMW-Cd.GS | 66.3 ± 2.7 | 5.6 ± 2.6 | 0.49 ± 0.17 | 0.49 ± 0.01 |
| LMW-Cd.GS | 4.4 ± 0.8 | 3.9 ± 1.4 | 0.86 ± 0.0j | — |
| After 2-ME | | | | |
| HMW-Cd.GS | 11.9 ± 2.4 | 4.4 ± 3.0 | — | — |

Cd.GS$_2$ Transport is Directly Energized by MgATP

Purification of Cd.GS$_2$ enabled the energy requirements of YCF1-dependent transport to be examined directly and confirmed that more than 83% of the MgATP-dependent, uncoupler-insensitive $Cd^{2+}$ transport measured using DTY165 membranes was mediated by YCF1. Agents that dissipate both the ΔpH and ΔΨ components of the H$^+$-electrochemical gradient established by the V-ATPase (FCCP, gramicidin-D) or directly inhibit the V-ATPase, itself (bafilomycin A$_1$), decreased MgATP-dependent Cd-GS$_2$ uptake by vacuolar membrane vesicles from DTY165 cells by 22% (Table 7). Ammonium chloride which abolishes ΔpH while leaving ΔΨ unaffected, on the other hand, inhibited uptake by only 15% (Table 7). From these results and the inability of uncouplers to markedly increase the inhibitions caused by V-ATPase inhibitors alone (Table 7), Cd.GS2 uptake by wild type membranes is inferred to proceed via a YCF1-dependent, MgATP-energized pathway that accounts for most of the transport measured and a YCF1-independent pathway, primarily driven by the H$^+$-gradient established by the V-ATPase, that makes a minor contribution to total uptake.

TABLE 7

Effects of uncouplers and V-ATPase inhibitors on uptake of bis(glutathionato)cadmium (Cd.GS$_2$) by vacuolar membrane vesicles purified from DTY165 and DTY167 cells. Uptake was measured in standard uptake medium containing 50 μM purified $^{109}$Cd.GS$_2$. Bafilomycin A$_1$, FCCP, gramicidin-D and NR$_4$Cl were added at concentrations of 0.5 μM, 5 μM, 5 μM, and 1 mM, respectively. Values outside parentheses are means ± SE (n = 3–6); values inside parentheses are rates of uptake expressed as percentage of control.

| ADDITION | $^{109}$Cd.GS$_2$ UPTAKE (nmol/mg/10 minutes) | |
|---|---|---|
| | DTY165 | DTY167 |
| Control | 105.8 ± 12.4 (100) | 17.3 ± 2.7 (100) |
| Gramicidin-D | 77.8 ± 6.4 (73.5) | 9.3 ± 2.0 (56.6) |
| FCCP | 62.2 ± 11.4 (58.8) | 10.2 ± 1.6 (59.0) |
| NH$_4$Cl | 89.8 ± 8.2(84.8) | 10.0 ± 1.7(57.8) |
| NH$_4$Cl+ gramicidin-D | 69.8 ± 12.0 (66.0) | 8.8 ± 2.2 (50.9) |
| Bafilomycin A$_1$ | 81.8 ± 6.0 (76.6) | 12.8 ± 3.6 (74.0) |
| Bafilomycin A$_1$ + gramicidin-D | 70.2 ± 12.2 (66.4) | 7.2 ± 2.4 (41.6) |

Cd.GS$_2$ Competes with DNP-GS for Transport

As would be predicted if Cd.GS$_2$ and the model organic GS-conjugate DNP-GS follow the same transport pathway, the K$_i$ for inhibition of MgATP-dependent, uncoupler-insensitive Cd.GS2 uptake by DNP-GS (11.3±2.1 μM; FIGS. 10A and 10C) coincided with the K$_m$ for DNP-GS transport (14.1±7.4 [μM).

Pretreatment with Cd$^{2+}$ or CDNB Increases YCF1 Expression

RNase protection assays of YCF1 expression in DTY165 cells and measurements of MgATP-dependent, uncoupler-insensitive 109Cd.GS$_2$ and [$^3$H]DNP-GS uptake by vacuolar membranes prepared from the same cells after 24 hour of growth in media containing CdSO$_4$ (200 μM) or the cytotoxic DNP-GS precursor, CDNB (150 μM), demonstrated a parallel increase in all three quantities. YCF1-specific mRNA levels were increased by 1.9- and 2.5-fold by pretreatment of DTY165 cells with CdSO$_4$ and CDNB, respectively (FIG. 12). The same pretreatments increased MgATP-dependent, uncoupler-insensitive $^{109}$Cd.GS$_2$ uptake into vacuolar membrane vesicles by 1.4- and 1.7-fold and [$^3$H] DNP-GS uptake by 1.6- and 2.8-fold (FIG. 12).

These investigations provide the first indication of the mechanism by which YCF1 confers Cd$^{2+}$ resistance in S. cerevisiae and its relationship to the transport of organic GS-conjugates by demonstrating that the integral membrane protein encoded by this gene specifically catalyzes the MgATP-energized uptake of bis(glutathionato)cadmium by vacuolar membrane vesicles.

The codependence of Cd-GS$_2$ and organic GS-conjugate transport on YCF1 is evident at multiple levels: (i) The ycf1Δ mutant strain, DTY167, is hypersensitive to Cd$^{2+}$ and CDNB in the growth medium and both hypersensitivities are alleviated by transformation with plasmid-borne YCF1. (ii) Vacuolar membrane vesicles purified from DTY167 cells are grossly impaired for MgATP-energized, uncoupler-insensitive organic GS-conjugate and GSH-promoted Cd$^{2+}$ uptake. (iii) Cd.GS$_2$, and organic GS-conjugates compete for the same uptake sites on YCF1. (iv) Factors that increase YCF1 expression elicit a parallel increase in Cd.GS$_2$ and organic GS-conjugate transport. Thus, a number of ostensibly disparate observations, the strong association between cellular GSH levels and Cd$^{2+}$ resistance (e.g., Singhal et al., 1987, FASEB J 1:220–223), the markedly increased sensitivity of vacuole deficient S. cerevisiae strains to Cd2+ toxicity, and the coordinate regulation of the yeast YCF1 and GSH1 genes, the latter of which encodes γ-glutamylcysteine synthetase (Wemmie et al., 1994, supra; Wu et al., 1994, supra), are now explicable in terms of a model in which YCF1 catalyzes the GSH-dependent vacuolar sequestration of Cd$^{2+}$ Further, at the biochemical level, YCF1 specifically catalyzes the transport of Cd.GS$_2$ as the data provided herein establish. In addition, at the cellular level, YCF1 confers resistance to and is induced by a spectrum of xenobiotics. Expression of YCF1 is increased by exposure of cells to glutathione-conjugable xenobiotics and Cd$^{2+}$. The close resemblance of YCF1 to MRP1, the capacity of YCF1 for both organic toxin and heavy metal transport, and its discovery in one of the most tractable and thoroughly molecularly characterized eukaryotes, S. cerevisiae, establishes that YCF1 is useful for manipulation of the transport of organic toxins and heavy metals in plants, mammals and yeast. Thus, according to the present invention, methods for overcoming, or at least diminishing, heavy metal contamination through bioremediation using native species or genetically engineered organisms are now possible.

Cloning of plant MRP1/YCF1 homologs

As described herein, the data presented herein establish that YCF1 encodes a protein functionally equivalent to human MRP1. There is next described the discovery that two plant genes, AtMRP1 and AtMRP2, from Arabidopsis encode MRP1/YCF1 homologs.

To isolate genes likely involved in glutathione S-conjugate transport from Arabidopsis thaliana, degenerate PCR primers corresponding to appropriate portions of human MRP1 (Cole et al., 1992, supra) and YCF1 (Szczypka et al., 1994, supra) were designed. Four degenerate primers were synthesized but only two of these yielded amplification products of the appropriate size that hybridized with MRP1 and YCF1. The sequences of the two primers were: 5'-GARAARGTIGGIATHGTIGGIMGIACIGGIGC-3' (MRP2) (SEQ ID NO: 17) and 5'-TCCATDATIGTRTTIARICKTGIGC-3'(MRP4) (SEQ ID NO: 18), where I=inosine, K=T or G, M=C or A and R=A or G. MRP2 corresponds to positions 1321–1331 and 1300–1310 in MRP1 and YCF1, respectively; MRP4 corresponds to positions 1486–1494 and 1466–1474. Database searches confirmed that the sequences of the peptides specified by MRP2 and MRP4 were specific to MRP1 and YCF1 but not any other ABC transporter in GenBank database release 90 (Altschul et al., 1990, J. Mol. Biol., 215: 403–410).

Degenerate PCR was performed using Arabidopsis genomic DNA as template. Amplification was for 45 cycles using the following thermal profile: 94° C. for 30 seconds, 50° C. for 30 seconds and 72° C. for 1 minute. A 0.6 kb PCR product was isolated, shown to hybridize strongly with a mixed probe encompassing the second NBF domain of MRP1 and YCF1, and was cloned into pCRII vector (Invitrogen).

Sequence analysis verified that the deduced translation product of the Arabidopsis PCR product exhibited greatest similarity to YCF1 and MRP1 plus an unidentified 1.7 kb Arabidopsis EST (ATTS 1246; Hofte et al., 1993, Plant J., 4: 1051–1061). In order to increase the likelihood of obtaining positive clones, a mixed probe consisting of the 0.6 kb PCR product and 1.6 kb EST was employed for further screens.

Eleven independent positive clones were obtained after screening approximately 3×10⁵ plaques of a size-fractionated (3–6 kb) Arabidopsis cDNA library constructed in λZAPII (Kieber et al., 1993, Cell, 72: 427–441) with the mixed probe. Restriction mapping confirmed that all 11 isolates corresponded to the same gene. The longest of these inserts, a 3.5 kb insert, designated AtMRP2, was subcloned and sequenced (FIG. 13).

Since this isolate of AtMRP2 was estimated to be missing approximately 1.5 kb of the 5' sequence of the ORF (assuming that the complete ORF of AtMRP2 is similar in size to the ORFs of human MRP1 and yeast YCF1), 500 bp of the most 5' sequence of AtMRP2 was used to probe two Arabidopsis bacterial artificial chromosome (BAC) libraries, UCD and TAMU (Choi et al., 1995, Weeds World, 2: 17–20) to isolate clones containing the missing sequence. This procedure yielded 8 BAC clones: U1L22, U8C12, U12A2, U23J22, U419, T9C22, TIB17 and T4K22. After digestion with HindIII, those fragments that hybridized with the 3.5 kb cDNA insert were introduced into pBluescript SK⁻ and sequenced. Two of these BAC clones (T1B17, T4K22) comprise a second MPR1 plant homolog, designated AtMRP1, while the remainder (U 1 L22, U8C12, U12A2, U23J22, U419, T9C22) comprise AtMRP2 (see below).

After establishing that an approximately 10 kb HindIII fragment from BAC clone U1L22 encompassed sequences identical to AtMRP2, a BglII restriction fragment comprising the first 3 kb of the BAC clone was used to rescreen approximately 2×10⁶ plaques from the Arabidopsis λZAPII cDNA library. Twenty six independent positive clones were obtained and the one containing the longest cDNA insert, 5.2 kb, was sequenced.

Sequence analysis demonstrated that the 5.2 kb cDNA was not identical to AtMRP2 but instead a very closely related gene. Designated AtMRP1 (FIG. 16), the 5.2 kb cDNA was 84.3% and 88.2% identical to AtMRP2 at the nucleotide and amino acid levels, respectively. Importantly, AtMRP1 is a full-length cDNA.

Having determined the complete sequence of the AtMRPF cDNA, it was possible to identify the initiation codon of the AtMRP2 genomic clone, design a specific 5'-UTR primer and amplify the remaining 5' end of AtMRP2 to generate a full-length cDNA. Thus, full-length cDNAs encoding AtMRP2 and AtMRP1 (FIGS. 13 and 16, respectively) and genomic clones corresponding to AtMRP2 and AtMRP1 have been generated (FIGS. 14 and 17, respectively). The deduced amino acid sequences of AtMRP2 and AtMRP1 are presented in FIGS. 15 and 18, respectively.

Expression of AtMRP1 in *Saccharomyces cerevisiae*

The experiments described below establish that AtMRP1 mediates the MgATP-dependent transport of GS-conjugates. The results of similar experiments on AtMRP2 demonstrate that this gene product has the same transport capability.

The data presented herein establishes that YCF1 from *Saccharomyces cerevisiae* encodes a 1,515 amino acid ATP-binding cassette (ABC) transporter protein which localizes to the vacuolar membrane and catalyzes MgATP-dependent GS-conjugate transport. Membrane vesicles from wild type (DTY165) cells contain two pathways for transport of the model GS-conjugate, DNP-GS: an MgATP-dependent, uncoupler-insensitive pathway and an electrically driven pathway. Membranes from the mutant strains DTY167 and DTY168, harboring a deletion of the YCF1 gene, are by contrast more than 90% impaired in MgATP-dependent, uncoupler-insensitive DNP-GS transport. Yeast strains lacking a functional YCF1 gene therefore represent a model system for probing the GS-conjugate transport function of plant YCF1/MRP1 homologs.

To test the transporter capacity of AtMRP1 (the first clone for which a full-length cDNA was obtained) for conferring GS-conjugate transport, yeast strain DTY168 (disrupted for the YCF1 gene) was transformed with an expression vector engineered to contain the coding sequence of AtMRP1. After selection of the transformants, membranes were prepared and assayed for MgATP-dependent, uncoupler-insensitive DNP-GS transport as described herein. The results establish that AtMRP1 catalyzes GS-conjugate transport in a manner indistinguishable from the vacuolar GS-X pump.

Construction of the expression vector

In order to constitutively express the AtMRP1 gene in *S. cerevisiae*, a derivative of the yeast-*E. coli* shuttle vector, pYES2 (Invitrogen), was constructed. Essentially, the 831 bp XbaI/NotI fragment encompassing the 3-phosphoglycerate kinase (PGK) promoter of plasmid pFL61 (Minet et al., 1992, Plant J. 2:417–422) was inserted between the SpeI/NotI restriction sites of pYES2. In so doing, the galactose-inducible yeast GAL] promoter of pYES2 was replaced by the constitutive yeast PGK promoter, pPGK. This plasmid, designated pYES3, is otherwise identical to pYES2. The gene to be expressed is inserted into the multiple cloning site located between the PGK promoter and CYC1 termination sequences.

Preliminary experiments had established that the 5' untranslated region (UTR) of the original AtMRP1 cDNA isolate diminished expression of the open reading frame in yeast. Thus, to maximize expression, the 127 bp 5'-UTR of AtMRP1 was removed. For this purpose, pBluescript SK⁻-AtMRP1 was digested with HpaI/SnaBI to delete 3045 bp of the internal sequence. The remaining 5 kb fragment from this digest was gel-purified and self-ligated to generate truncated AtMRP1 cDNA as a template for PCR. One hundred pmol of AtMRP1-Nco primer (5'-AAACCGGTGCGGCCGCCATGGGGTTTGAGCCGT-3') (SEQ ID NO: 19) and 100 pmol of T3 primer (5'-AATTAACCCTCACTAAAGGG-3') (SEQ ID NO: 20) were used to amplify a 2002 bp fragment of AtMRP1 using Pfu DNA polymerase (Stratagene). Amplification was for 30 cycles using the following thermal profile:

94° C. for 15 seconds; 50° C. for 15 seconds; and 72° C. for 3.5 minutes.

The PCR product was gel-purified, digested with SpeI and cloned into the EcoRV/SpeI sites of pBluescript SK⁻ to generate pSK⁻ AtMRP1-Nco2. The 1227 bp SphI/SpeI fragment of this construct was then exchanged with the 4363 bp SphI/SpeI fragment of pBluescript pSK⁻ AtMRP1 to generate pSK¹ AtMRP1-Nco5. pYES-AtMRP1, lacking the 5' UTR, was constructed by digesting pSK⁻ AtMRP1-Nco5 with XhoI/SpeI to obtain a 5049 bp truncated AtMRP1 gene fragment which was cloned into the XhoI/XbaI sites of pYES3. One kb of the 5' sequence of the AtMRP1 insert of pYES3-AtMRP1 was analyzed and was found to match exactly the sequence of the original cDNA clone.

Transformation of Yeast

*S. cerevisiae* strain DTY168 (MATα his6, leu2-3, -112, ura3-52 ycf1::hisG) was transformed with pYES3-AtMRP1 or empty vector lacking the AtMRP1 insert (pYES3) by the LiOAc/PEG method (Giest et al., 1991, Yeast 7:253–263) and selected for uracil prototrophy by plating on AHC medium containing tryptophan (Kim et al., 1994, supra).

Isolation of membrane vesicles

For the preparation of membrane vesicles, 15 ml volumes of stationary phase cultures of the transformants were diluted into 1 L of fresh AHC medium and grown to an $OD_{600\,nm}$ of about 1.2. Membrane vesicles were purified as described herein and in Kim et al. (1995, supra).

Measurement of DNP-GS uptake

DNP-GS uptake was measured as described herein in 200 μl reaction volumes containing 3 mM ATP, 3 mM $MgSO_4$, 5 μM gramicidin-D, 10 mM creatine phosphate, 16 units/ml creatine kinase, 50 mM KCl, 1 mg/ml BSA, 400 mM sorbitol, 25 mM Tris-Mes (pH 8.0) and the indicated concentrations of [$^3$H]DNP-GS (17.4 mCi/mmol). Gramicidin-D (uncoupler) was included to abolish the $H^+$-electrochemical potential difference that would otherwise be established by the V-ATPase in media containing MgATP.

The results of this study

Membrane vesicles purified from pYES3-AtMRP1-transformed DTY168 cells exhibit an approximately 4-fold increase in MgATP-dependent, uncoupler-insensitive [$^3$H] DNP-GS uptake by comparison with membrane vesicles purified from DTY168 cells transformed with empty vector (FIG. 19). When measured at a DNP-GS concentration of 61.3 μM, the initial rates of uptake by membrane vesicles purified from pYES3-AtMRP1-transformed and pYES3-transformed cells were 0.4 nmol/mg/minute and 0.1 nmol/mg/minute, respectively (FIG. 19).

The concentration dependence and vanadate inhibitility of uptake verify direct participation of AtMRP1. MgATP-dependent, uncoupler-insensitive uptake by membrane vesicles purified from the pYES3-AtMRP1 transformants increases as a single hyperbolic function of DNP-GS concentration to yield $K_m$ and $V_{max}$ values of 48.7±15.4 μM and 6.0±1.7 nmol/mg/10 minutes, respectively (FIG. 19). pYES3-AtMRP1-dependent DNP-GS uptake decreases as a single exponential function of the concentration of the phosphoryl transition state analog vanadate, to yield an $I_{50}$ of 8.3±3.3 μM (FIG. 20). By contrast, the apparent $K_m$ for DNP-GS uptake by membrane vesicles purified from pYES3-transformed DTY168 cells is in excess of 500 μM and uptake is insensitive to vanadate.

On the basis of its sequence characteristics and the results of these experiments, AtMRP1 encodes the vacuolar GS-X pump. The increases in uptake following the introduction of plasmid borne AtMRP1 into yeast (ca. 4 nmol/mg/20 minutes) are commensurate with the rates of MgATP-dependent, uncoupler-insensitive DNP-GS uptake measured in vacuolar membrane vesicles purified from plant sources (2.3, 3.8, 18.2, 5.8, and 2.1 nmol/mg/20 minutes for Arabidopsis leaf, Arabidopsis root, *Beta vulgaris* storage root, *Vigna radiata* hypocotyl and *Zea mays* root, respectively) (Table III in Li et al., 1995, supra). The $K_m$ for DNP-GS transport by heterologously expressed AtMRP1 is similar to that reported for the endogenous GS-X pump of plant vacuolar membranes (81.3±41.8 μM, Li et al., 1995, supra). The $I_{50}$ for inhibition of AtMRP1-dependent DNP-GS transport by vanadate coincides with the $I_{50}$ for inhibition of the endogenous vacuolar GS-X pump of plant cells (7.5±3.9 μM, Li et al., 1995, supra).

Having confirmed that the endogenous vacuolar GS-X pump of S. cerevisiae is lacking in the ycf1Δ mutant strains, DTY168 and DTY167 (Li et al., 1995, supra), and in any case has a markedly lower $K_m$ for DNP-GS and is 6 to 8-fold less sensitive to vanadate than the plant cognate, these findings establish that AtMRP1 per se is responsible for the MgATP-dependent, uncoupler-insensitive transport measured in these experiments. Given that heterologous expression of AtMRP1 alone is sufficient for DNP-GS transport in DTY168 cells, it is concluded that one of the GS-X pumps of Arabidopsis has been cloned in its entirety.

Sequence comparisons of MRP1, cMOAT, YCF1, AtMRP1 and AtMRP2 with other members of the ABC transporter superfamily reveal two major subgroups. One group contains MRP1, cMOAT, YCF1, AtMRP1, AtMRP2 and the Leishmania P-glycoprotein-related molecule (Lei/PgpA). The other group contains the MDRs, the major histocompatibility complex transporters and STE6. However, of all the ABC transporters defined to date, cMOAT, YCF1, AtMRP1 and AtMRP2 exhibit the closest resemblance to each other. Unlike the similarities between the GS-X pump subgroup, Lei/PgpA and CFTR, which center on the nucleotide binding folds (NBFs), the similarities between the GS-X pump members cMOAT, YCF1, AtMRP1 and AtMRP2 are found throughout the sequence. GS-X family members are 40–45% identical (60–65% similar) at the amino acid level, possess NBFs with an equivalent spacing of conserved residues and are colinear with respect to the location, extent and alteration of putative transmembrane spans and extramembrane domains. Two features of members of the GS-X pump family that distinguish them from other ABC transporters are their possession of a central truncated CFTR-like regulatory domain rich in charged amino acid residues and an approximately 200 amino acid residue N-terminal extension.

A hydropathy aligment of AtMRP1, AtMRP2, YCF1, HmMRP1, and RtCMOAT is shown in FIG. 21. Note the following: (i) The almost exact equivalence of AtMRP1 and AtMRP2 with respect to the alternation of hydrophobic and hydrophilic stretches. (ii) The close correspondence of AtMRP1 and AtMRP2 with all of the other members of the MRP1 /YCF1/cMOAT subclass of ABC transporters in terms of the overall hydropathy profiles. (iii) The "signature" profile for the N-terminal 200 amino acid residues of all of the sequences shown, which is unique to the MRP1/YCF1/cMOAT subclass. Hydropathy was computed according to Kyte and Doolittle (1982, *J Mol. Biol.* 46:105–132) over a running window of 15 amino acid residues. Hydrophobic stretches of sequence fall below the line and hydrophilic stretches fall above the line.

In FIG. 22 there is depicted domain comparisons between AtMRP1, ScYCF1, HmMRP1, RtCMOAT, RbEBCR and HmCFTR. The domains indicated are the N-terminal extension ($NH_2$), first and second transmembrane spans (TM1 and TM2, respectively), first and second nucleotide binding folds (NBF1 and NBF2, respectively), putative CFTR-like regulatory domain (R), and the C-terminus (COOH). This comparison is also tabulated in Tables 8 and 9.

TABLE 8

Identity and similarity analysis of putative domains of AtMRP1 against AtMRP2 ScYCF1, HmMRP1, RtCMOAT, HmCFTR and RbEBCR, ScYCF1, *Saccharomyces cerevisiae* YCF1; HmMRP1, human MRP1; RtCMOAT, rat cMOAT; HmCFTR, human CFTR; RbEBCR, rabbit EBCR. The domains identified are N-terminal extension ($NH_2$), transmembrane segments 1 and 2 (TM1 and TM2, respectively), CFTR-like regulatory domain (R), nucleotide binding folds 1 and 2 (NBF1 and NBF2, respectively) and C-terminus (COOH). Similarity was calculated as described herein over the sequence segments indicated in Table 9

| SEQUENCE | DOMAIN | OVERALL | $NH_2$ | TM1 | NBFI |
|---|---|---|---|---|---|
| AtMRP2 | Identity | 87.0 | 74.4 | 90.4 | 92.1 |
|  | Similarity | 93.7 | 85.2 | 96.1 | 96.7 |
| ScYCF1 | Identity | 36.1 | 13.3 | 32.2 | 50.0 |
|  | Similarity | 55.4 | 32.9 | 52.6 | 75.0 |
| HmMRP1 | Identity | 41.5 | 16.2 | 37.4 | 58.0 |
|  | Similarity | 63.3 | 34.8 | 57.5 | 78.7 |

TABLE 8-continued

Identity and similarity analysis of putative domains of AtMRP1 against AtMRP2 ScYCF1, HmMRP1, RtCMOAT, HmCFTR and RbEBCR, ScYCF1, *Saccharomyces cerevisiae YCF1*; HmMRP1, human MRP1; RtCMOAT, rat cMOAT; HmCFTR, human CFTR; RbEBCR, rabbit EBCR. The domains identified are N-terminal extension (NH$_2$), transmembrane segments 1 and 2 (TM1 and TM2, respectively), CFTR-like regulatory domain (R), nucleotide binding folds 1 and 2 (NBF1 and NBF2, respectively) and C-terminus (COOH). Similarity was calculated as described herein over the sequence segments indicated in Table 9

| | | | | | |
|---|---|---|---|---|---|
| RtCMOAT | Identity | 38.6 | 19.6 | 33.8 | 58.7 |
| | Similarity | 60.2 | 36.7 | 61.0 | 80.0 |
| HmCFTR | Identity | 29.2 | 0 | 22.8 | 40.7 |
| | Similarity | 55.1 | 0 | 47.8 | 62.0 |
| RbEBCR | Identity | 38.9 | 17.2 | 34.5 | 62.4 |
| | Similarity | 60.4 | 34.9 | 61.6 | 82.6 |
| SEQUENCE | DOMAIN | R | TM2 | NBF2 | COOH |
| AtMRP2 | Identity | 80.5 | 86.9 | 91.3 | 89.4 |
| | Similarity | 89.8 | 94.2 | 96.5 | 94.4 |
| ScYCF1 | Identity | 33.9 | 34.7 | 34.7 | 58.1 |
| | Similarity | 59.5 | 57.9 | 57.9 | 71.8 |
| HmMRP1 | Identity | 31.6 | 31.9 | 61.9 | 48.3 |
| | Similarity | 50.4 | 56.3 | 72.8 | 69.0 |
| RtCMOAT | Identity | 33.9 | 34.4 | 60.7 | 50.0 |
| | Similarity | 50.0 | 58.8 | 75.7 | 67.2 |
| HmCFTR | Identity | 45.7 | 22.3 | 39.5 | 28.1 |
| | Similarity | 75.0 | 51.3 | 61.6 | 58.4 |
| RbEBCR | Identity | 35.6 | 34.1 | 61.9 | 43.0 |
| | Similarity | 51.7 | 59.1 | 74.0 | 62.7 |

TABLE 9

Positions and sizes of segments of sequence analyzed in Table 8

| SEQUENCE | DO-MAIN | OVER-ALL | NH$_2$ | TM1 | NBF1 |
|---|---|---|---|---|---|
| AtMRP1 | Position | | 1–223 | 224–631 | 634–782 |
| | Size | 1622 | 223 | 407 | 148 |
| AtMRP2 | Position | | 1–223 | 224–631 | 634–782 |
| | Size | 1622 | 223 | 407 | 148 |
| ScYCF1 | Position | | 1–210 | 211–645 | 646–787 |
| | Size | 1515 | 210 | 435 | 142 |
| HmMRP1 | Position | | 1–240 | 241–660 | 661–810 |
| | Size | 1531 | 240 | 420 | 150 |
| RtCMOAT | Position | | 1–192 | 193–648 | 649–799 |
| | Size | 1540 | 192 | 456 | 151 |
| HmCFTR | Position | | 0 | 1–440 | 441–590 |
| | Size | 1481 | 0 | 440 | 150 |
| RbEBCR | Position | | 1–193 | 194–651 | 652–800 |
| | Size | 1562 | 193 | 458 | 149 |
| SEQUENCE | DOMAIN | R | TM2 | NBF2 | COOH |
| AtMRP1 | Position | 783–900 | 901–1244 | 1245–1417 | 1418–1622 |
| | Size | 117 | 343 | 172 | 205 |
| AtMRP2 | Position | 783–905 | 906–1249 | 1250–1422 | 1423–1622 |
| | Size | 122 | 343 | 172 | 200 |
| ScYCF1 | Position | 788–936 | 937–1279 | 1280–1453 | 1454–1515 |
| | Size | 149 | 343 | 174 | 163 |
| HmMRP1 | Position | 811–960 | 961–1300 | 1301–1473 | 1474–1531 |
| | Size | 150 | 340 | 173 | 59 |
| RtcMOAT | Position | 800–960 | 961–1302 | 1303–1476 | 1477–1541 |
| | Size | 161 | 342 | 174 | 65 |
| HmCFTR | Position | 591–847 | 848–1217 | 1218–1389 | 1390–1481 |
| | Size | 256 | 371 | 172 | 92 |
| RbEBCR | Position | 801–961 | 962–1304 | 1305–1477 | 1478–1562 |
| | Size | 161 | 343 | 173 | 86 |

As is apparent from the data presented above, there is significant homology between similar domains among AtMRP-related proteins. In particular, the N-terminal and R domains share significant homology among the AtMRP-related proteins tested. These data establish that in addition to primary sequence, the secondary structure of the molecule plays a significant role in GS-X pump function.

It should be appreciated that AtMRP1 and AtMRP2 constitute a family of genes in Arabidopsis, wherein various members of the family have different substrate specificities as demonstrated by the next set of experiments.

Substrate Preferences of AtMRP1 and AtMRP2

To examine the substrate preferences of AtMRP1 and AtMRP2, the following experiments were performed.

Isolation of Bn-NCC-1

[$^{14}$C]Bn-NCC-1 (33.3 mCi/mmol) was extracted from senescent cotyledons of rape (*Brassica napus*) and was purified by preparative HPLC (Krautler et al., 1992, *Plant Physiol. Biochem.* 30:333–346). Determination of the purity of the final preparation by analytical HPLC and enumeration of concentration and specific radioactivity (33.3 mCi/mmol) were performed according to Hinder et al. (1966, *J Biol. Chem.* 271:27233–27236). Unlabeled Bn-NCC-1 was isolated from fully senescent cotyledons of excised shoots that had been maintained in complete darkness for 1 week.

Measurement of transport

Cells were grown and vacuolar membrane-enriched vesicles were prepared as described (Kim et al., 1995, *J Biol. Chem.* 270:2630–2635-). Uptake of [$^{14}$C]Bn-NCC-1, [$^3$H]C3G-GS, [$^3$H]DNP-GS, [$^3$H]GSSG, [$^{14}$C]metolachlor or [$^3$H]taurocholate was measured routinely in 200 μl reaction volumes containing membrane vesicles (10–20 g protein), 3 mM ATP, 3 μmM MgSO$_4$, 5 μM gramicidin-D, 10 mM creatine phosphate, 16 units/ml creatine phosphate kinase, 50 mM KCl, 1 mg/ml BSA, 400 mM sorbitol, 25 mM Tris-Mes (pH 8.0) and the indicated concentrations of transport substrate. Uptake was terminated by the addition of 1 ml ice-cold wash medium (400 mM sorbitol/3 mM Tris- Mes, pH 8.0) and vacuum filtration of the suspension through prewetted Millipore HA cellulose nitrate filters (pore size 0.45 μm). The filters were rinsed twice with wash medium, and the retained radioactivity was determined by liquid scintillation counting. Nonenergized uptake was estimated by the same procedure except that ATP was omitted from the uptake medium.

The effect of taurocholate on the release of [$^3$H]DNP-GS from membrane vesicles that had been allowed to mediate AtMRP2-dependent accumulation of this compound during a preceding uptake period was determined. This was accomplished by rapid depletion of ATP from the uptake medium using a hexokinase trap (glucose+ATP–>glucose-6-phosphate+ADP) and measurements of the decrease in vesicular radiolabel in the presence or absence of taurocholate. Membranes from DTY168/pYES3-AtMRP2 cells were incubated for 10 minutes in standard uptake medium containing 61.3 μM [$^3$H]DNP-GS after which time 200 mM glucose and 50 units/ml hexokinase (Type F-300 from baker's yeast) were added. After incubation for a further 2 minutes, taurocholate (50 μM) or Triton X-100 (9.01% v/v) was added and release of vesicular [$^3$H]DNP-GS was measured as described. Control samples were treated identically except that no additions were made after the initial 10 minute incubation period.

Substrate Preferences

The absence of AtMRP2-dependent transport from DTY168 and DTY168/pYES3 membranes and the selective inhibition of this system by micromolar concentrations of vanadate, established that AtMRP2-dependent transport may be measured in two ways. This may be accomplished by assessing the difference between the rates of MgATP-dependent, uncoupler-insenstitive uptake by DTY168/pYES3-AtMRP2 membranes by comparison with DTY168 or DTY168/pYES3 membranes, or by assessing the vanadate-sensitive component of MgATP-dependent, uncoupler-insensitive uptake by DTY168/pYES3-AtMRP2 membranes. Because the results were qualitatively and quantitatively similar whichever method was used, "AtMRP2-dependent" transport as used in this section refers to uptake which is measured as the increment consequent on transformation of DTY168 cells with pYES3-AtMRP2 versus pYES3.

Application of this methodology to vacuolar membrane-enriched vesicles purified from pYES3-AtMRP2- versus pYES3-transformed DTY168 cells and expansion of the transport assays to measurements of the concentration dependence of [$^3$H]DNP-GS, [$^3$H]GSSG, [$^{14}$C]metolachlor-GS, [$^{14}$C]Bn-NCC-1 and [$^3$H]taurocholate uptake, demonstrated that the substrate preferences and maximal transport capacities of AtMRP2 and AtMRP1 differed markedly. While uptake of all of the GSH derivatives examined conformed to Michaelis-Menten kinetics, the $V_{max}$ values for AtMRP2-dependent uptake were consistently serveral-fold greater than those for AtMRP1-dependent uptake. The $V_{max}$ values for AtMRP2-dependent uptake of [$^3$H]DNP-GS, [3H]GSSG and [$^{14}$C]metolachlor-GS were 16.3±3.1, 38.1±3.2 and 136.0±28.1 nmol/mg/10 min, respectively; the corresponding values for AtMRP1 were 8.2±1.6, 6.8±1.1 and 17.5±5.2 nmol/mg/10 min. With the exception of [$^3$H] GSSG whose $K_m$ for AtMRP1-dependent uptake (21.9.2±58.3 μM) was three times greater than that for AtMRP2-dependent uptake (73.0±15.1 μM), the $K_m$ values estimated for AtMRP2 and AtMRP1 were very similar (65.7±29.8 versus 63.6±36.5 μM for metolachlor-GS).

Single concentration (50 μM) measurements of uptake of the glutathionated anthocyanin, cyanin-3-glucoside-GS (C3G-GS), demonstrated an approximately 6-fold greater capacity of AtMRP2 for transport of this compound (rate= 48.4±2.2 nmol/mg/10 min) by comparison with AtMRP1 (rate=7.9±0.7 mol/mg/10 min).

In no case was MgATP-dependent, uncoupler-insensitive uptake of the unconjugated precursors of the GS-compounds, DNP, GSH, metolachlor and C3G detectable.

Neither AtMRP2 nor AtMRP1 catalyzed the uptake of [$^3$H]taurocholate. Transformation of DTY168 cells with either pYES3-AtMRP2 or pYES3-AtMRP1 conferred little or no increase in the capacity of vacuolar membrane-enriched vesicles for [$^3$H]taurocholate uptake over that measured with vesicles prepared from pYES3-transformed cells. The results of these experiments are presented in Table 10.

TABLE 10

Kinetic parameters for uncoupler-insensitive AtMRP1- and AtMRP2-dependent transport of GS-derivatives, Bn-NCC-1 and taurocholate.

| Com- | AtMRP1 | | AtMRP2 | |
|---|---|---|---|---|
| pound | $K_m$ | $V_{max}$ | $K_m$ | $V_{max}$ |
| DNP-GS | 73.8 ± 18.8 | 8.2 ± 1.6 | 65.7 ± 29.8 | 16.3 ± 3.1 |
| GSSG | 219.2 ± 58.3 | 6.8 ± 1.1 | 73.0 ± 15.1 | 38.1 ± 3.2 |
| Meto-lachlor-GS | 63.6 ± 36.5 | 17.5 ± 5.2 | 75.1 ± 31.6 | 136.0 ± 28.1 |
| Bn-NCC-1 | Linear | | 15.2 ± 2.3 | 63.1 ± 2.5 |
| Tauro-cholate | Linear | | Linear | |

MgATP-dependent, uncoupler-insensitive uptake by DTY168/pYES3-AtMRP1, DTY168/pYES3-AtMRP2 and DTY168/pYES3 membranes was measured as described herein. The $K_m$ and $V_{max}$ values were estimated by fitting the data to a single Michaelis-Menten function by nonlinear least squares analysis. Values shown are means ±SE.

The 2- to 8-fold greater capacity of AtMRP2 versus AtMRP1 for transport of the compounds examined was not attributable to differences in the levels of expression of their cDNAs from the PGK gene promoter of pYES3. Quantitative RT-PCR of equivalent amounts of total RNA extracted from DTY168/pYES3-AtMRP2 and DTY168/pYES3-AtMRP1 cells yielded similar levels of the 800 bp PCR amplification product predicted from the sequences of the oligonucleotide primers used. Since neither amplification product was generated when PCR was performed without reverse transcription or when total RNA from DTY168/pYES3 cells was employed as template, contamination by genomic DNA and/or RT-PCR of transcripts other than those from AtMRP2 or AtMRP1, respectively, was not responsible for the observed results.

Anomalous interactions between candidate transport substrates

Two critical properties of AtMRP2 were its capacity for the simultaneous transport of GS-conjugates and Bn-NCC-1 and its pronounced sensitivity to inhibition by taurocholate. Simultaneous measurements of [$^{14}$C]Bn-NCC-1 and [$^3$H] DNP-GS uptake by membrane vesicles purified from DTY168/pYES3-AtMRP2 cells revealed parallel accumulation of both compounds with little or no interference of the transport of one by the other. AtMRP2-dependent uptake of [$^{14}$C]Bn-NCC-1 at an extravesicular concentration equivalent to its $K_m$ value (15 μM,) was nearly three times less sensitive to DNP-GS than would be predicted if this GS-conjugate were a competitior. If DNP-GS were a simple competitive inhibitor such that its Km value (66 μM) approximated its $K_i$ value for the inhibition of BN-NCC-1 uptake, 120 μM DNP-GS would be expected to inhibit [$^{14}$C]Bn-NCC-1 uptake by 48% but this was not observed. DNP-GS concentrations in excess of 120 μM decreased [$^{14}$C]Bn-NCC-1 uptake by less than 18%. Reciprocally, the concentration-dependence of AtMRP2-mediated [$^3$H]DNP- GS uptake was not affected appreciably by Bn-NCC-1. The $K_m$ and $V_{max}$ values for AtMRP2-dependent [$^3$H]DNP-GS uptake in the presence of 15 µM Bn-NCC-1 (80.5±28.6 µM and 18.3±1.6 nmol/mg/10/min) were similar to those measured in its absence.

Although neither AtMRP2 nor AtMRP1 transported taurocholate, AtMRP2-mediated transport was selectively inhibited by this compound. AtMRP1-dependent [$^3$H]DNP-GS uptake was relatively insensitive to taurocholate ($I_{50}$>250 µM) but the uptake of both [$^3$H]DNP-GS and [$^{14}$C]Bn-NCC-1 by AtMRP2 was strongly inhibited ($I_{50(DNP\text{-}GS\ uptake)}$=27±1.3 µM; $I_{50(Bn\text{-}NCC\text{-}1\ uptake)}$=49.5±0.3 µM).

Taurocholate at the concentrations employed appeared to exert is effect on AtMRP2-mediated transport by inhibiting pump activity directly rather than by increasing background membrane permeability and decreasing net influx by increasing passive DNP-GS efflux. Addition of taurocholate at a concentration (50 µM) sufficient to inhibit AtMRP2-dependent [$^3$H]DNP-GS uptake by 70% to DTY168/pYES3-AtMRP2 vesicles that had accumulated [$^3$H]DNP-GS for 10 minutes before arresting pump action by ATP depletion using a hexokinase trap, did not accelerate the efflux of intravesicular $^3$H-label over that measured on vesicles subject to a hexokinase trap in the absence of taurocholate. Imposition of a hexokinase trap and addition of a concentration of detergent (Triton X-100; 0.01% v/v) known to permeate these membranes (Zhen et al., 1997, *J Biol. Chem.* 272:22340–22348), on the other hand, increased the rate and extent of release of the [$^3$H]DNP-GS accumulated during the preceding 10 minute uptake period by more than 3-fold versus DTY168/pYES3-AtMRP2 vesicles treated with hexokinase alone or hexokinase plus taurocholate.

The high capacity of AtMRP2 for the transport of large amphipathic anions other than GS-conjugates (i.e., Bn-NCC demonstrates that one pump can assume more than one of the several ABC transporter-like functions identified in plants to date. In the case of AtMRP2, this includes transport activity directed to a broad-range GS-conjugate pump and a chlorophyll metabolite pump. Thus, one the one hand, the high capacity of heterologously expressed AtMRP2, and to a lesser extent AtMRP1, for the transport of metolachlor-GS, and by extension GS-conjugates of other herbicides to glutathionation, is consistent with the molecular identification of transporters capable of removing these and related compounds from the cytosol. On the other hand, the high capacity of AtMRP2 for the transport of Bn-NCC is consistent with the identification of an element capable of contributing to the further metabolism and eventual removal of tetrapyrrole derivatives generated during leaf senescence from the cytosol.

Vacuolar uptake of glutathionated medicarpin by the glutathione conjugate pump

A key event in the disease resistance response of legumes is the rapid and localized accumulation of isoflavonoid phytoalexins. Accordingly, most studies of plant-pathogen interactions in the Leguminosae have centered on the enzymology and molecular biology of the isoflavonoid biosynthetic pathway (Dixon et al., 1995, *Physiol. Plant* 93:385). However, the mechanism and sites of intracellular accumulation of these compounds is not understood. Since many isoflavonoid phytoalexins are as toxic to the host plant as they are to its pathogens, it is essential that they are accumulated in the plant in a site which is sequestered (i.e., isolated) from the cytoplasm. The following experiments describe uptake of free [3H]medicarpin by vacuolar membrane vesicles purified from etiolated hypocotyls of mung bean (*Vigna radiata*). This uptake is slow and relatively insensitive to MgATP. However, after incubation with glutathione and a total glutathione-S-transferase preparation from maize (*Zea mays*), [$^3$H]medicarpin uptake occurs at a rate which is 8-fold faster in the presence, as opposed to the absence of MgATP. MgATP-dependent uptake of glutathione/glutathione-S-transferase pretreated [$^3$H]medicarpin is only slightly inhibited by uncoupler (gramicidin D), but is strongly inhibited by vanadate and the model glutathione-S-conjugate, S-(2,4-dinitrophenyl) glutathione. These results demonstrate that the MgATP-energized glutathione-conjugate pump identified herein in the membrane preparation is capable of high affinity, high capacity transport of glutathionated isoflavonoid phytoalexins. The experimental procedures and results of these experiments are now described.

Preparation of [$^3$H]medicarpin

[$^3$H]medicarpin was produced by base-catalyzed tritium exchange from $^3$H$_2$O using unlabeled medicarpin isolated from fenugreek (*Trigonella foenumgraecum*) seedlings exposed to 3 mM CuCl$_2$.

GST purification and conjugation of medicarpin

Two-week old maize (*Zea mays*) B73N seedlings were grown under continuous light at 21° C. Twenty four hours prior to harvesting, the seedlings were exposed to a mild treatment with 2,4-dichlorophenoxyacetic acid and atrazine to stimulate GST expression (Timmerman, 1989, *Physiol. Plant* 77:465). Two-gram samples of root and shoot tissue were ground to homogeneity in 50 ml of 500 mM sodium phosphate buffer, pH 7.8 (Buffer A). The extract was centrifuged at 7,000× g for 10 minutes at 4° C. and the resulting supernatant was filtered through Miracloth and mixed with 2 ml of S-hexylglutathione-conjugated agarose beads (Sigma). After incubation for 5 minutes at 21° C., the beads were sedimented by centrifugation at 500 x g at 4° C. The supernatant was discarded and the beads were resuspended in 2.5 ml of prechilled Buffer A and centrifuged again. Bound GST was eluted by resuspension of the beads in 2 ml Buffer B (20 mM GSH, 500 mM sodium phosphate, pH 7.8) and incubation for 5 minutes at 21° C. The beads were sedimented by centrifugation at 500× g and the supernatant was assayed for GST activity (Mannervick et al., 1981, *Methods Enzymol.*, 77:231).

[3H]medicarpin (0.5 µCi, 4.5 Ci/mol) was conjugated with GSH by incubation with 25 µl of total purified maize GSTs for 3 hours at 21° C. in the dark. Control, unconjugated samples were prepared by mixing [$^3$H]medicarpin (0.5 µCi) with cold Buffer B and immediately freezing the mixture in liquid nitrogen.

Synthesis of S-(2,4-dinitrophenyl)glutathione (DNP-GS)

DNP-GS was synthesized from 1-chloro-2,4-dinitrobenzene and GSH by a modification of the enzymatic procedure of Kunst et al., (1989, *Biochim. Biophys. Acta* 983:123; Li et al., 1995, supra).

Preparation of vacuolar membrane vesicles

Vacuolar membrane vesicles were purified from etiolated hypocotyls of *V. radiata* cv. Berken as described (Li et al., *Plant Physiol.* 109: 1257, Li et al., 1995, supra).

Measurement of uptake

Unless otherwise indicated, [$^3$H]medicarpin or [3H]medicarpin-GS uptake was measured at 25° C. in 200 µl reaction volumes containing 3 mM ATP, 3 mM MgSO$_4$, 10 mM creatine phosphate, 16 U/ml creatine kinase, 50 mM KCl, 0.1% (w/v) BSA, 400 mM sorbitol and 25 mM Tris-Mes buffer, pH 8.0. Uptake was initiated by the addition of 12 µl membrane vesicles (30–40 µg protein) and brief mixing of the samples on a vortex mixer. Uptake was terminated by the addition of 1 ml ice-cold wash medium (400 mM sorbitol, 3 mM Tris-Mes, pH 8.0) and vacuum filtration of the suspension through prewetted HA cellulose nitrate filters (pore diameter 0.45 µm). The filters were rinsed twice with a 1 ml ice-cold wash medium, air-dried and radioactivity was determined by liquid scintillation counting.

Protein estimations and source of commercial chemicals was as described herein.

Results

Appreciable MgATP-dependent uptake of [$^3$H] medicarpin by vacuolar membrane vesicles purified from etiolated hypocotyls of mung was dependent on preincubation of this compound with GSH and GSTs. Free [$^3$H] medicarpin incubated in the presence of GSH in the absence of GSTs was taken up at 16.7±3.6 and 7.4±1.3 nmol/mg/20 minutes in the presence and absence of MgATP, respectively (FIG. 25). In contrast, [$^3$H]medicarpin-GS synthesized by incubating [$^3$H]medicarpin with GSH in the presence of affinity-purified maize GSTs, was taken up at 81.0±13.3 and 11.3±0.4 nmol/mg/20 minutes in the presence and absence of MgATP, respectively (FIG. 25).

MgATP-dependent [$^3$H]medicarpin-GS uptake was strongly inhibited by vanadate and DNP-GS but was relatively insensitive to uncouplers. Whereas inclusion of vanadate (10 μM) or DNP-GS (100 μM) in the assay medium inhibited [$^3$H]medicarpin uptake by more than 85%, addition of the ionophore, gramicidin D, diminished uptake by only 17% (Table 11).

TABLE 11

Effects of different inhibitors on [$^3$H]medicarpin-GS uptake by vacuolar membrane vesicles. [$^3$H]medicarpin-GS was added at a concentration of 65 μM. MgATP was either omitted (−MgATP) or added at a concentration of 3 mM (+MgATP). Gramicidin-D, vanadate and DNP-GS were added at concentrations of 5 μM, 10 μM and 100 μM, respectively. Values outside parentheses are means ± SE (n = 3); values inside parentheses are rates of uptake expressed as percentage of control

| TREATMENT | [$^3$H]Medicarpin-GS Uptake (nmol/mg/10 minutes) | |
|---|---|---|
|  | +MgATP | −MgATP |
| Control | 85.6 ± 13.3 (100) | 16.7 ± 6.0 (100) |
| + Gramicidin-D | 71.2 ± 3.0 (83.2) | 13.2 ± 2.1 (79.0) |
| + Gramicidin-D + vanadate | 12.9 ± 0.9 (15.1) | 17.4 ± 0.5 (104.2) |
| + Gramicidin-D + DNP-GS | 11.7 ± 2.8 (13.7) | 5.6 ± 3.1 (33.5) |

MgATP-dependent, uncoupler-insensitive uptake increases as a single Michaelian function of [$^3$H]medicarpin-GS concentration to yield $K_m$ and $V_{max}$ values of 21.5±15.5 μM and 77.8±23.3 nmol/mg/20 minutes, respectively (FIG. 26).

Direct involvement of the GS-X pump in the accumulation of [$^3$H]medicarpin-GS by vacuolar membrane vesicles is therefore evident at three levels: (i) Glutathionation of medicarpin selectively increases MgATP-dependent uptake. MgATP-independent uptake is marginally affected by glutathionation but MgATP-dependent uptake is stimulated by approximately six-fold confirming that medicarpin-GS is the transported species and MgATP is the energy source. (ii) Uptake is directly energized by MgATP. The inability of uncoupler to markedly inhibit [3H]medicarpin-GS uptake implies that the H$^+$-electrochemical gradient that would otherwise be established by the vacuolar H$^+$-ATPase in the presence of MgATP does not drive uptake. Rather, the pronounced inhibition of MgATP-dependent uptake exerted by vanadate agrees with the notion that GS-X-mediated uptake is strictly dependent on ATP hydrolysis and formation of a phosphoenzyme intermediate (Martinoia et al. 1993, supra; Li et al., 1995, supra), (iii) [$^3$H]medicarpin-GS and the model GS-X pump substrate DNP-GS, whose transport has been exhaustively analyzed in this system as described herein, compete for uptake indicating that both are transported by the same moiety.

The efficacy of medicarpin-GS as a substrate for the vacuolar GS-X pump is striking. Even though the $K_m$ for medicarpin-GS uptake is undoubtedly an overestimate, since the yield from the conjugation reaction was not enumerated, it is nevertheless 2 to 25-fold lower than those estimated previously for DNP-GS, C3G-GS (80 and 46 IM in this system), glutathione-S-N-ethylmaleimide (500 μM) and metolachlor-GS (40–60 μM, barley vacuoles; Martinoia et al., 1993, supra). Moreover, the capacity of the GS-X pump for medicarpin-GS uptake is high ($V_{max}$=78 nmol/mg/20 minutes) versus DNP-GS ($V_{max}$=12 nmol/mg/20 minutes) and comparable to that estimated for C3G-GS ($V_{max}$=45 nmol/mg/minute). Thus, while maize anthocyanin was the first natural substrate shown to be vacuolarly sequestered through the concerted actions of cystolic GSTs and the vacuolar GS-X pump in plants (Marrs et al., 1995, Nature, 375:397 and data contained herein), medicarpin, and presumably other isoflavonoid phytoalexins, is equally strong a candidate.

These data suggest that the GSTs which are induced following the hypersensitive response to avirulent fungal pathogens likely serve to facilitate the vacuolar storage of antimicrobial compounds in the healthy cells surrounding the lesion.

Transport of glutathionated anthocyanins and auxins by the vacuolar GS-X pump of plant cells The data which are now described demonstrate that the vacuolar GS-X pumps of corn (Zea mays) roots and etiolated hypocotyls of mung bean (Vigna radiata) transport the anthocyanin cyanidin-3-glucoside (C3G), and the phytohormone, indole-3-acetic acid (IAA), after conjugation with glutathione. Whereas the unconjugated forms of these compounds undergo negligible uptake into vacuolar membrane vesicles, both C3G-GS and IAA-GS are subject to high rates of MgATP-dependent, uncoupler-insensitive uptake (FIG. 27 and Table 12). IAA-GS and C3G-GS uptake approximates Michaelis-Menten kinetics to yield $K_m$ values in the micromolar range and $V_{max}$ values 7- to 40-fold greater than those measured with the artificial transport substrate, DNP-GS (Table 12 and Li et al., 1995, supra). Uptake of both conjugates is inhibited by DNP-GS and vanadate in a manner consistent with mediation by the GS-X pump (FIG. 27 and Table 13). In contrast, glutathionated abscissic acid (ABA-GS) is a poor substrate for the GS-X pump: uptake is relatively slow and only saturates at high substrate concentrations (FIG. 27 and Table 13).

TABLE 12

Summary of kinetic parameters for MgATP-dependent, uncoupler-insensitive uptake of C3G-GS, IAA-GS and ABA-GS by vacuolar membrane vesicles purified from etiolated hypocotyls of V. radiata and roots of Z. mays. Kinetic parameters ($K_m$, [M; $V_{max}$, nmol/mg/10 min) were computed from the data shown in FIG. 27 by nonlinear least squares analysis. Values shown are means ± SE.

|  | C3G-GS | | IAA-GS |
|---|---|---|---|
| PARAMETER | V. radiata | Z. mays | V. radiata |
| $K_m$ | 45.7 ± 14.0 | 39.5 ± 16.6 | 36.0 ± 16.7 |
| $V_{max}$ | 45.3 ± 6.5 | 79.1 ± 14.7 | 17.7 ± 5.8 |

|  | IAA-GS | ABA-GS | |
|---|---|---|---|
| PARAMETER | Z. mays | V. Radiata | Z. mays |
| $K_m$ | 47.7 ± 19.6 | >1000 | 128.8 ± 79.1 |
| $V_{max}$ | 30.0 ± 4.9 | 22.9 ± 9.2 | 4.0 ± 1.4 |

It has been known for some time that the characteristic bronze coloration of Bronze-2 (bz2) mutants is a consequence of the accumulation of cyanidin-3-glucoside in the cytosol. In wild type (Bz2) plants, anthocyanins are transported into the vacuole and become purple or red whereas in bz2 plants, anthocyanin is restricted to the cytoplasm where it is oxidized to a brown ("bronze") pigment. However, until the present invention, the exact molecular basis of this lesion was unknown. Since Bz2 encodes a GST responsible for conjugating anthocyanin with GSH (Marrs et al., 1995) and glutathionated anthocyanins are transported by the vacuolar GS-X pump, the experiments described herein explain the bronze phenotype. Being defective in the glutathionation of anthocyanins, bz2 mutants are unable to pump these pigments from the cytosol into the vacuole lumen; a conclusion borne out by the ability of the GS-X pump inhibitor, vanadate, to phenocopy the bz2 lesion in wild type protoplasts and the efficacy of cyanidin-3-glucoside-GS as a substrate for the plant vacuolar GS-X pump in vitro, as the data presented herein establish.

The concept underlying the above-described experiments on phytohormones is that they may be subject to metabolic interconversions and compartmentation analogous to those deduced for anthocyanins. On the one hand, it is now established that C3G must be glutathionated before it can be transported into the vacuole. On the other hand, it is evident that most of the vacuolar anthocyanins of intact plants are not stored in this form. Instead, they are subject to long term storage as their malonyl derivatives. It is therefore apparent that while C3G-GS is a short-lived but necessary intermediate for vacuolar anthocyanin compartmentation, it is not the terminal product of this process. The experiments with auxins further illustrate this principle by demonstrating that IAA is susceptible to glutathionation and that the resultant IAA-GS conjugate is transported by the vacuolar GS-X pump in a MgATP-dependent, uncoupler-insensitive, vanadate-inhibitible manner. Thus, even though IAA-GS derivatives have not been detected in planta, this does not exclude the possibility that they are short-lived transport intermediates necessary for subsequent vacuolar processing of this class of compounds.

TABLE 13

Concentrations of DNP-GS and vanadate required to inhibit MgATP-dependent, uncoupler-insensitive uptake of C3G-GS, IAA-GS and ABA-GS by 50% ($I_{50}$ values) by vacuolar membrane vesicles purified from etiolated hypocotyls of *V. radiata* and roots of *Z. mays*. $I_{50}$ values ($\mu$M) were estimated by nonlinear least squares analysis after fitting the data to a single negative exponential. ND, not determined.

|  | C3G-GS | IAA-GS | ABA-GS |
| --- | --- | --- | --- |
| COMPOUND | *V. radiata* | *Z. mays* | *V. radiata* |
| Vanadate | 7.9 | 8.2 | 6.5 |
| DNP-GS | 103.5 | 112.4 | 124.2 |
| COMPOUND | *Z. mays* | *V. radiata* | *Z. mays* |
| Vanadate | 5.5 | ND | >150 |
| DNP-GS | 109.8 | ND | 231.5 |

Generation of a Transgenic Plant Comprising a Transgene Encoding a GS-X Pump

To generate a transgenic plant comprising a gene encoding YCF1, the following experiments were performed. The binary vector pROK-YCF1, encoding wild type YCF1 was constructed. The sense orientation of the inserts with respect to the CaMV 35S promoter of pROK (Baulscombe et al., 1986, *Nature* 321:446–449) was confirmed and these constructs, as well as empty vector (PROK) controls, were transformed into Agrobacterium strain C58 by electroporation (Ausubel et al., 1992, *Current Protocols in Molecular Biology*, pp 27–28).

Kanamycin-resistant Agrobacterium transformants were isolated, the integrity of the constructs in the bacterial recipient was established by PCR and Arabidopsis roots were inoculated with the transformants (Huang et al., 1992, *Plant Mol. Biol.* 10:372–384). The resulting rosette shoots generated on selective medium were transferred to root-inducing medium for regeneration. Stable insertion of the sense strands and constitutive expression of YCF1 and YCF1::HA was demonstrated in the kanamycin-resistant Arabidopsis transformants, by probing Southern blots with YCF1 and pROK sequences and by Northern analyses, respectively.

An association between YCF1 expression and altered xenobiotic resistance was tested by screening multiple T2 generation pROK-YCF1, pROK-YCF1-HA and pROK empty vector transformant lines for tolerance to cadmium salts and the GS-conjugable xenobiotic 1-chloro-2,4-dinitrobenzene (CDNB). CDNB has three advantages for studies of this type: (i) It is an established plant toxin (Li et al., 1995, *Plant Physiol.* 109:117–185); (ii) The kinetics of transport of its glutathionated derivative, DNP-GS, as well characterized for YCF1 (Li et al., 1996, *J. Biol. Chem.* 271:6509–6517) and the endogenous GS-X pump (Li et al., 1995, *Plant. Physiol.* 107:1257–1268; Li et al., 1995, *Plant Physiol.* 109:117–185). (iii) DNP-GS is the only known immediate metabolite of CDNB in vivo (Li et al., 1995, *Plant Physiol.* 109:117–185).

Methods similar to those described by Howden et al. (Howden et al., 1992, *Plant Physiol.* 99:100–107; Howden et al., 1995, *Plant Physiol.* 107:1059–1066; Howden et al., 1995, *Plant Physiol.* 107:1067–1073) were applied to the initial characterization of the transformants. T2 seeds were first sown in rows on $Cd^{2+}$-free and CDNB-free medium in Petri dishes standing on edge so that the roots grew vertically down the surface of the agar. Three to 4 days after germination, the seeds were transferred, again in rows, to media containing a range of $CdSO_4$ or CDNB concentrations. After rotating the Petri dishes though 180° and allowing growth for another 24–48 hours, the seedlings were scored for hook length. The results of this study are shown in FIG. 28. It is evident from the data presented therein that transgenic Arabiposis plants comprising YCF1 acquire increased resistance to cadmium salts and the organic cytotoxin, CDNB.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
    (A) LENGTH: 5232 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:1:

```
TTATGAAAAT TTATTATTTT TGTTGCTATG GTTTTTTGGA ATTAGAAGCT CATTTCAAAG      60
TTGTTGATTT TCTTTGCAGG GTAGGGAATT GGTGTGGTAG CTTGTGATGC ACTGTGTTTG     120
AGGGAAAGGA AAGGATAACG ATGGGGTTTG AGTTTATTGA ATGGTATTGT AAGCCGGTGC     180
CTAATGGTGT GTGGACTAAA ACAGTGGCTA ATGCATTTGG TGCATACACG CCTTGTGCTA     240
CTGACTCTTT TGTGCTTGGT ATCTCTCAAC TGGTTCTGTT GGTTCTGTGC CTGTATCGTA     300
TATGGCTCGC CTTAAAGGAT CACAAGGTGG AGAGGTTCTG TTTGAGGTCG AGATTGTATA     360
ACTATTTCCT GGCTTTGTTG GCTGGTATGC TACTGCTGAG CCTTTGTTTA GATTGATCAT     420
GGGGATTTCA GTTTTAGATT TTGATGGACC TGGACTTCCT CCTTTTGAGG CATTCGGATT     480
GGGTGTCAAA GCTTTTGCTT GGGGCGCTGT AATGGTCATG ATTTTAATGG AAACTAAAAT     540
TTACATCCGT GAACTCCGTT GGTATGTCAG GTTTGCTGTC ATATATGCTC TTGTGGGGGA     600
TATGGTCTTG TTAAATCTTG TTCTCTCAGT CAAGGAGTAC TATAGCAGTT ATGTTCTGTA     660
TCTCTACACA AGCGAAGTGG GAGCTCAGGT TCTGTTTGGA ATTCTCTTGT TTATGCATCT     720
TCCCAATTTG GATACTTACC CTGGCTACAT GCCAGTGCGG AGTGAAACTG TGGATGATTA     780
TGAGTATGAA GAGATTTCTG ATGGACAACA AATATGCCCT GAGAAGCATC CAAATATATT     840
TGACAAAATC TTCTTCTCAT GGATGAATCC CTTGATGACT TTGGGATCTA AAAGGCCTCT     900
AACAGAGAAG GATGTGTGGT ATCTAGACAC TTGGGATCAG ACTGAAACTC TGTTCACGAG     960
TTTCCAGCAT TCCTGGGATA AGAACTACA AAAGCCGCAA CCGTGGCTGT TGAGAGCATT    1020
GAACAATAGC CTGGGAGGAA GGTTTTGGTG GGGAGGATTT TGGAAGATCG GAATGATTG    1080
CTCACAGTTT GTGGGACCTC TTTTACTGAA TCAACTCTTA AAGTCAATGC AAGAGGATGC    1140
GCCAGCTTGG ATGGGTTACA TCTATGCGTT CTCAATCTTT GGTGGAGTGG TGTTCGGGGT    1200
GCTATGTGAA GCTCAATATT TCCAGAATGT CATGCGTGTT GGTTACCGAC TGAGATCTGC    1260
TCTGATTGCT GCTGTGTTCC GCAAATCGTT GAGGTTAACT AATGAAGGTC GTAGAAAGTT    1320
TCAAACAGGA AAGATAACCA ACTTAATGAC GACTGATGCC GAATCTCTTC AGCAAATATG    1380
CCAATCACTT CATACCATGT GGTCGGCTCC ATTTCGTATA ATTATAGCAC TGATTCTCCT    1440
CTATCAGCAA TTGGGTGTTG CCTCGCTCAT TGGTGCATTG TTGTTGGTCC TTATGTTCCC    1500
TTTACAGACT GTTATTATAA GCAAAATGCA GAAGCTGACA AAGGAAGGTC TGCAGCGTAC    1560
TGACAAGAGA ATTGGCCTTA TGAATGAAGT TTTAGCTGCA ATGGATACAG TAAAGTGTTA    1620
TGCTTGGGAA AACAGTTTCC AGTCCAAGGT CCAAACTGTA CGTGATGATG AATTATCTTG    1680
GTTCCGGAAA TCACAGCTCC TGGGAGCGTT GAATATGTTC ATACTGAATA GCATTCCTGT    1740
TCTTGTGACT ATTGTTTCAT TTGGTGTGTT CACATTACTT GGAGGAGACC TGACCCCTGC    1800
AAGAGCATTT ACGTCACTCT CTCTCTTTGC TGTGCTTCGT TTCCCTCTCT TCATGCTTCC    1860
AAACATTATA ACTCAGGTGG TAAATGCTAA TGTATCCTTA AAACGTCTTG AGGAGGTATT    1920
GGCGACAGAA GAAAGAATTC TCTTACCAAA TCCTCCCATT GAACCTGGAG AGCCAGCCAT    1980
CTCAATAAGA AATGGATATT TCTCTTGGGA TTCTAAGGGG GATAGGCCGA CGTTGTCAAA    2040
```

```
TATCAACTTG GATGTACCTC TTGGCAGCCT AGTTGCTGTG GTTGGTAGTA CAGGCGAAGG      2100

AAAAACCTCT CTAATATCTG CTATCCTTGG TGAACTTCCT GCAACATCTG ATGCAATAGT      2160

TACTCTCAGA GGATCAGTTG CTTATGTTCC ACAAGTTTCA TGGATCTTTA ATGCAACAGT      2220

ACGCGACAAT ATACTGTTTG GTTCTCCTTT CGACCGTGAA AAGTATGAAA GGGCCATTGA      2280

TGTGACTTCA CTGAAGCATG ACCTAGAGTT ACTGCCTGGT GGTGATCTCA CGGAGATTGG      2340

AGAAAGAGGT GTTAATATCA GTGGAGGACA GAAGCAGAGG GTTTCCATGG CTAGGGCCGT      2400

TTACTCAAAT TCAGATGTGT ACATCTTTGA TGACCCGTTA AGTGCCCTTG ATGCTCATGT      2460

TGGTCAACAG GTTTTTGAAA AATGCATAAA AAGAGAACTG GGGCAGAAAA CGAGAGTTCT      2520

TGTTACAAAC CAGCTCCACT TCCTATCACA AGTGGACAGA ATTGTACTTG TGCATGAAGG      2580

CACAGTGAAA GAGGAAGGAA CATATGAAGA GCTATCCAGT AATGGCCCTT TGTTCCAGAG      2640

GCTAATGGAA AATGCAGGGA AGGTGGAAGA ATATTCAGAA GAAAATGGAG AAGCTGAGGC      2700

AGATCAAACA GCGGAACAAC CAGTTGCGAA TGGGAACACA AATGGTCTTC AAATGGATGG      2760

AAGTGACGAT AAAAAATCCA AAGAAGGAAA TAAAAAAGGA GGGAAAATCTG TCCTCATCAA      2820

GCAAGAAGAA CGTGAAACCG GAGTTGTAAG TTGGAGAGTC CTGAAGAGGT ACCAGGATGC      2880

ACTTGGAGGG GCATGGGTAG TGATGATGCT CCTTTTATGT TACGTCTTAA CAGAAGTATT      2940

TCGGGTTACT AGCAGCACGT GGTTGAGTGA GTGGACTGAT GCAGGAACTC CAAAGAGTCA      3000

TGGACCCCTT TTCTACAATC TCATATATGC ACTTCTCTCG TTTGGACAGG TTTTGGTGAC      3060

ATTGACCAAT TCATATTGGT TGATTATGTC CAGTCTTTAT GCAGCTAAGA AGTTACACGA      3120

CAATATGCTT CATTCCATAC TGAGGGCCCC GATGTCCTTC TTCCATACCA ATCCGCTAGG      3180

ACGGATAATC AATCGATTCG CAAAAGATCT GGGTGATATT GATCGAACTG TGGCCGTCTT      3240

TGTAAACATG TTTATGGGTC AAGTCTCACA GCTTCTTTCA ACTGTAGTGT TGATTGGCAT      3300

TGTAAGCACT TTGTCCTTGT GGGCCATCAT GCCCCTCCTG GTCTTGTTTT ATGGAGCTTA      3360

TCTTTATTAT CAGAACACAG CCCGTGAGGT TAAGCGTATG GATTCAATTT CAAGATCGCC      3420

TGTTTATGCA CAGTTTGGAG AGGCATTGAA TGGCTTATCA ACTATCCGTG CTTACAAAGC      3480

ATATGATCGT ATGGCTGATA TCAACGGAAG ATCAATGGAT AATAACATCA GATTCACTCT      3540

TGTCAACATG GGTGCCAATC GGTGGCTTGG AATCCGTTTA GAAACTCTGG GTGGTCTTAT      3600

GATATGGCTG ACAGCATCGT TGCTGTCAT GCAGAATGGA AGAGCGGAGA ACCAACAGGC      3660

ATTTGCATCT ACAATGGGTT TGCTTCTCAG TTATGCCTTA AATATTACTA GCTTGTTAAC      3720

AGGTGTTCTG AGACTTGCGA GTTTGGCTGA GAATAGTCTA AACGCGGTCG AGCGTGTTGG      3780

CAATTATATA GAGATTCCGC CAGAGGCTCC GCCTGTCATT GAGAACAACC GTCCACCTCC      3840

TGGATGGCCA TCATCTGGAT CCATAAAGTT TGAGGATGTT GTTCTCCGTT ACCGCCCTCA      3900

GTTACCGCCT GTGCTTCATG GGGTTTCTTT CTTCATTCAT CCAACAGATA AGGTGGGGAT      3960

TGTTGGAAGG ACTGGTGCTG GAAAGTCAAG CCTGTTGAAT GCATTGTTTA GAATTGTGGA      4020

GGTGGAAGAA GGAAGGATCT TAATCGATGA TTGTGACGTT GGAAAGTTTG GACTGATGGA      4080

CCTACGTAAA GTGCTCGGAA TCATTCCACA GTCACCGGTT CTTTTCTCAG GAACTGTGAG      4140

GTTCAATCTT GATCCATTTG GTGAACACAA TGATGCTGAT CTTTGGGAAT CTCTAGAGAG      4200

GGCACACTTG AAGGATACCA TCCGCAGAAA TCCTCTTGGT CTTGATGCTG AGGTCTCTGA      4260

GGCAGGAGAG AATTTCAGCG TGGGACGAG GCAATTGTTG AGTCTTTCAC GTGCGCTGTT      4320

ACGGAGATCT AAGATACTCG TCCTTGATGA AGCAACTGCT GCTGTAGATG TTAGAACCGA      4380

TGCCCTCATT CAGAAGACTA TCCGAGAAGA ATTCAAGTCA TGCACGATGC TCATTATCGC      4440
```

```
TCACCGTCTC AATACCATCA TTGACTGTGA CAAAATTCTC GTGCTTGATT CTGGAAGAGT    4500

TCAAGAATTC AGTTCACCGG AGAACCTTCT TTCAAATGAA GGAAGCTCTT TCTCCAAGAT    4560

GGTTCAAAGC ACTGGAGCTG CAAATGCTGA GTACTTGCGT AGTTTAGTAC TCGACAACAA    4620

GCGTGCCAAA GATGACTCAC ACCACTTACA AGGCCAAAGG AAATGGCTGG CTTCTTCTCG    4680

CTGGGCTGCA GCCGCTCAGT TTGCTCTGGC TGCGAGTCTT ACTTCGTCGC ACAACGATCT    4740

TCAAAGCCTT GAAATTGAAG ATGACAGCAG CATTTTGAAG AGAACAAACG ATGCAGTTGT    4800

GACTCTGCGC AGTGTTCTCG AGGGGAAACA CGACAAAGAG ATTGCAGAGT CGCTTGAGGA    4860

ACATAATATC TCTAGAGAGG GATGGTTGTC ATCACTCTAT AGAATGGTAG AAGGGCTTGC    4920

AGTGATGAGC AGATTGGCAA GGAACCGAAT GCAACAACCG GATTACAATT TCGAAGGAAA    4980

TACATTTGAC TGGGACAACG TCGAGATGTA GATAAGTTCA TGTTAAACTA GGAATCATTG    5040

TCTCTTCCGT AAGAAACATA TATTTATCTT AACCAAAATT ATTAGTTTGG TTTCCATTTC    5100

ATAAACTTAA TTTTCACCTG CAAAGAAAAT CAAACCCTGT TGTGTTCTTC GTGATAAGTA    5160

GAGAAATTAC TTGAGTATCC TTCTAACTCA AAAAAAAAAA AAAAAAAAAA AAAAAAAAA    5220

AAAAAAAAAA AA                                                         5232

(2) INFORMATION FOR SEQ ID NO:2:

(i) SEQUENCE CHARACTERISTICS:
        (A) LENGTH: 9936 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

GACTCGATAC CATCTTAAAT GCAGAGTCTT TTCGTGATAA TAAAATTATG GATTCGTTTC      60

AAAGTTTTTT TTTTTTCGTA TGGAAAACAC TTGAGCTCTC TCAATCTTGT AGTCTTGACT     120

CTTGATGATT CTTCTATGTT CTCGTTGTGA TTGCTTGTCA CTGTTCTATC TTTATATATG     180

ATTAAATGCA ATTTTGCCCC TTTTTACGCG CGAATGTATT TATTATCTTT CGCACTCTGG     240

GTCCATTTCT TGTCACTTGA GCACATAATG ATTGATTTAT GACTTTTTAA AGTTATGAAA     300

ATTTATTATT TTTGTTGCTA TGGTTTTTTG GAATTAGAAG CTCATTTCAA AGTTGTTGAT     360

TTTCTTTGCA GGGTAGGGAA TTGGTGTGGT AGCTTGTGAT GCACTGTGTT TGAGGGAAAG     420

GAAAGGATAA CGATGGGGTT TGAGTTTATT GAATGGTATT GTAAGCCGGT GCCTAATGGT     480

GTGTGGACTA AAACAAGTGG CTAATGCATT TGGTGCATAC ACGCCTTGTG CTACTGACTC     540

TTTTGTGCTT GGTATCTCTC AACTGGTTCT GTTGGTTCTG TGCCTGTATC GTATATGGCT     600

CGCCTTAAAG GATCACAAGG TGGAGAGGTT CTGTTTGAGG TCGAGATTGT ATAACTATTT     660

CCTGGCTTTG TTGGCTGCGT ATGCTACTGC TGAGCCTTTG TTTAGATTGA TCATGGGGAT     720

TTCAGTTTTA GATTTGATG GACCTGGACT TCCTCCTTTT GAGGTGCTTT ATTTTCTGTT     780

CCTTATTCTT TATCTTTTAG TTTGTTGTGT ATGTTTTACC TGAAACATGC TATTGTTTGT     840

GTGATTTCTT TGGCAGGCAT TCGGATTGGG TGTCAAAGCT TTTGCTTGGG GCGCTGTAAT     900

GGTCATGATT TTAATGGAAA CTAAAATTTA CATCCGTGAA CTCCGTTGGT ATGTCAGGTT     960

TGCTGTCATA TATGCTCTTG TGGGGATAT GGTCTTGTTA AATCTTGTTC TCTCAGTCAA    1020

GGAGTACTAT AGCAGGTTGG TACAATTTTG GAGTTACTTT GGTTTATTGA AGTCATTGTT    1080

CTTCTTCTAC AGGGTGAATT CATGTTTTGT TTTCATTGCA GTTATGTTCT GTATCTCTAC    1140
```

```
ACAAGCGAAG TGGGAGCTCA GGTTAGCTCA CTTGGACTCC TTTAGAGAGT CCAGAATCCT    1200

AGCATGTGCT ATGATTATAA ATCAGAATCC GATACAGTTT GTTTTCTAAC ATCTTAAGAG    1260

GGTGAATTTT GGTTTTACTT CAGGTTCTGT TTGGAATTCT CTTGTTTATG CATCTTCCCA    1320

ATTTGGATAC TTACCCTGGC TACATGCCAG TGCGGAGTGA AACTGTGGAT GATTATGAGT    1380

ATGAAGAGAT TTCTGATGGA CAACAAATAT GCCCTGAGAA GCATCCAAAT ATATTTGACA    1440

GTAAGTCACT CTACATGATT TTCATTTGGT CGCCTGGCTG AAACTTATAA TTAGTAATCA    1500

TAATTTGCAA ACATCGTCTC TGACTTTTGT TCAGATTGAT CATGGGGATT TAGGTTTTGA    1560

AATTTCACCT GATTTCCTTC TTCCAATTTC CTTGTTTGGT CACAGAAATC TTCTTCTCAT    1620

GGATGAATCC CTTGATGACT TTGGGATCTA AAAGGCCTCT AACAGAGAAG GATGTGTGGT    1680

ATCTAGACAC TTGGGATCAG ACTGAAACTC TGTTCACGAG GTACTTCTAA CAATAATTAT    1740

ATCTCTTAAA ATGTATATTA CTGAATTGGC TATTTGATAT TTTCTGTATC CTTTTTAGTT    1800

TCCAGCATTC CTGGGATAAG GAACTACAAA AGCCGCAACC GTGGCTGTTG AGAGCATTGA    1860

ACAATAGCCT GGGAGGAAGG TAGATAGATT TTCTCACCTT ATCGTGCTGT GTTCTCATCT    1920

CTTTTGAGTT TTGAGTATGA TTAGATAGTG CTGGATTTCA CTGTGATGTG CAGATGTTTA    1980

AGTGATCTCT TGAAAGAACC ATCAGGTTTT TAGAATGTGT AGGAAGCAAG ATCAGAATAT    2040

TTCTACTTAT TTAATGTTAG TTGTTTGCTA TAGCAGCTTA ACACATTTCC ATCTTATCAT    2100

AGGCAATCAT GCTTGCTTTC GTACTCTTAT AAATTTAAGA CATAGGGGAT ACAACTTTTA    2160

CTGTAGATTG GTTAAATATG TTTTTTTTTC TTGGTTCATA TTGCTTAAGC ATTATTTCGT    2220

TTGTTAACTA CATGTCGTAT GGGGATCTAA TTTTTTGAAT TTTGTAGGTT TTGGTGGGGA    2280

GGATTTTGGA AGGTATTTTC GTCTACCTCT TTCTCTTTTA TTCGTGCTTC CAGAGTCTTT    2340

CCTCTCTTTT ATTCATATGA TCACAGGTTC TGCGTCATGT TGGATAACCT TCTGTCACGT    2400

GGAAGTCATT TATAATTTAC ATGGTGTTAC AGATTATTAG AAGGAACTAG TGGGTTCTTA    2460

GTTTTTCTTT ATCAATTCAT TGTACTTGAA CATATTTATT TACATTTGTA TGCACAGATC    2520

GGGAATGATT GCTCACAGTT TGTGGGACCT CTTTTACTGA ATCAACTCTT AAAGGTTTGT    2580

TCTTTTCTTG GCAGATTCGG AAACCTATTA TTGGTTCAAT ATTCTTATCT GACAATATCT    2640

CTCATTTTGG ATGTCAAACT ATATACAGTC AATGCAAGAG GATGCGCCAG CTTGGATGGG    2700

TTACATCTAT GCGTTCTCAA TCTTTGGTGG AGTGGTATGA AATGAAGTCC TCTTTCTCTC    2760

TCTCTCTCTG TCTATTTGGA CTCTCTTCTA TCAACTTGTG AAACTGACAC TTGTTATACT    2820

TCTGTATGTT TGGTCTAAGG TTCTTCTAAA CTGATTATAA TAGCAACACT AGATGTCCCC    2880

TAATGCCACT TTTTGATTTT GTTGCTCTTG GATTTTTTGC GTCTGTTAGA TAGGTTCTGA    2940

CTTTATCTAG TGTAGGGTGA TACTTAAAGC TACAAACTCA TCGAGTGACT GATGTTGATG    3000

ACAACGTTTC TAGGTGTTCG GGGTGCTATG TGAAGCTCAA TATTTCCAGA ATGTCATGCG    3060

TGTTGGTTAC CGACTGAGAT CTGCTCTGGT AAATTTTAAA TTTGCTACCC TGACGTTCTT    3120

CCTTTGCCAT ATGTTTTTGG TGCAGATATG TTTGCTGATA GCATGATTCC CAGTATCTTG    3180

TATAGGAATA AGTATATCAA CATGGTTTCT TTATCCTCTA TATATGATGC ATAAATAAGC    3240

CTTGTGCCAA AAGTTTAGGA ATAAGTTTGT GTTGCTTCAG ATGATTGAGT ATGCTGTTTT    3300

TATTTCTGGA AATTTCCACC ATTTTCAGAT CCTTTCACTA GAGAAATACA AATTTAGCTG    3360

TATTTCCTGA TTCAGTTCAT CGTTTTCTGC GTTTGTAGTG GAGTGAAATT AGCTTGTACG    3420

AAATGGAAGA TATTTTGAAC ACAGATGATT TTTAAAATTG GTCTTCCTGT TGATGACTGT    3480
```

-continued

```
TTTTTTTTTA GATTGCTGCT GTGTTCCGCA AATCGTTGAG GTTAACTAAT GAAGGTCGTA      3540

GAAAGTTTCA AACAGGAAAG ATAACCAACT TAATGACGAC TGATGCCGAA TCTCTTCAGG      3600

TGAGTATCCC TTTCATATTT TCGAATTCAA GTTTGCATGT TTCTCTATAT CATAGTTGCA      3660

GGGCTGTTAA CATCCGGATC TTGAATATTT ATTTTTGTCC GCAGCTGGTA TTGAGTGGGT      3720

TACAGTTACT TTTTATGTTC GGTAATAGAA GTTGGATTTA CTTAGAAATG ATTTCCAGCA      3780

TACTGATCTA CTGAATCTGT TTGTTAGGTC TAAGATTGGC TATGAATAGT GATTGCATTT      3840

TCATTTCTAG CTAGCACTTT GTTATCATTG AATTTTTCTT TCTTCTTTTT TATTTTGTTT      3900

CTTATGCCAA CTTAAACTGT GTCTTGTTTA ATGTTTTCGT CTTAACTGTG TCTGGTATCA      3960

ATATTGTTAT CTAATCAACC AGATGTACTT TGTACTAATT TTTCCATTTT CTGTGGCAGC      4020

AAATATGCCA ATCACTTCAT ACCATGTGGT CGGCTCCATT TCGTATAATT ATAGCACTGA      4080

TTCTCCTCTA TCAGCAATTG GGTGTTGCCT CGCTCATTGG TGCATTGTTG TTGGTCCTTA      4140

TGTTCCCTTT ACAGGTACAT GACTTCTAAA TTTCCTCATT TTTTTTCCTT TGTAGCTTAT      4200

TTTTCTCTAT ACTGTTCGCT TGTTCATTCG TACTCCTAAA GGCTACTTCT TCTTCGTCTC      4260

CTGAACTTGT TCTCTGTTTT CTTAAAACAG ACTGTTATTA TAAGCAAAAT GCAGAAGCTG      4320

ACAAAGGAAG GTCTGCAGCG TACTGACAAG AGAATTGGCC TTATGAATGA AGTTTTAGCT      4380

GCAATGGATA CAGTAAAGTA AGAAATTCTA GAACCAATTT TGTTAACATA GTTATTAATT      4440

TGCAGGAAAC TTGTACTAAA CCAAAATGCT ACAGGTGTTA TGCTTGGGAA AACAGTTTCC      4500

AGTCCAAGGT CCAAACTGTC GTGATGATGA ATTATCTTGG TTCCGAAAAT CACAGCTCCT      4560

GGGAGCGGTA TGACTACAGC GTAGTTACTT TTGTTTTTCC TCTAATTATT GTATATTTCT      4620

AACTCTTGCT TGGTCTTGTC TTGTTTTGCA GTTGAATATG TTCATACTGA ATAGCATTCC      4680

TGTTCTTGTG ACTATTGTTT CATTTGGTGT GTTCACATTA CTTGGAGGAG ACCTGACCCC      4740

TGCAAGAGCA TTTACGTCAC TCTCTCTCTT TGCTGTGCTT CGTTTCCCTC TCTTCATGCT      4800

TCCAAACATT ATAACTCAGG TGATTTCTTA AATATGTTGT TGCAATGCAT GTGTATTAAG      4860

TAGAACTGTT AGTGCTTGTA GTAACTGTCG TTTGGTTATC AAATCCATGA CTTATATTTC      4920

GAATTTACAT GCTGGAGGGT ATCCTTGCTG GTGCCAGAAA CAGATGCCGA TGCTGACTAG      4980

TTTTCACTTG TAGGTGGTAA ATGCTAATGT ATCCTTAAAA CGTCTTGAGG AGGTATTGGC      5040

GACAGAAGAA AGAATTCTCT TACCAAATCC TCCCATTGAA CCTGGAGAGC CAGCCATCTC      5100

AATAAGAAAT GGATATTTCT CTTGGGATTC TAAGGTGTCG CTTGGCTATT CTATACCATG      5160

TTCCTTCTTT CGCTTCTCTC ATTACCTTTA TCCATAGAAA GTACAAAAAT CGAGCTAACC      5220

CTATGTATCT ACAGGGGGAT AGGCCGACGT TGTCAAATAT CAACTTGGAT GTACCTCTTG      5280

GCAGCCTAGT TGCTGTGGTT GGTAGTACAG GCGAAGGAAA AACCTCTCTA ATATCTGCTA      5340

TCCTTGGTGA ACTTCCTGCA ACATCTGATG CAATAGTTAC TCTCAGAGGA TCAGTTGCTT      5400

ATGTTCCACA AGTTTCATGG ATCTTTAATG CAACAGTATG TTCTTCTTTT CTTTGACTTT      5460

TAAGTTGGGC TGACGTTGCA AATTTTTCTG TTGTACATAA TGTTAAATGT ATTTTCTGTC      5520

TTTTATAGTA GAACAATATG TGTTCTCAAA TGCGTCAGTT ACTTCACCAA CTTAGTGGAA      5580

ACCTTCTTCA ATATTTGATT CTCTAAGCTA TTTTGAACAG AAGACTGATA TGCATTTTCT      5640

TATAAAAATT TGTAGGTACG CGACAATATA CTGTTTGGTT CTCCTTTCGA CCGTGAAAAG      5700

TATGAAAGGG CCATTGATGT GACTTCACTG AAGCATGACC TAGAGTTACT GCCTGTAAGT      5760

TTTGAGGAGA GCTTCGTGGA GTTGATAACA AGGATTTGTC TTGCCTGTTC TCGTGTTGCT      5820

AAGTTTGTTT CAACCTCTTT CTCTTGCTTA ATAGGGTGGT GATCTCACGG AGATTGGAGA      5880
```

-continued

```
AAGAGGTGTT AATATCAGTG GAGGACAGAA GCAGAGGGTT TCCATGGCTA GGGCCGTTTA    5940

CTCAAATTCA GATGTGTACA TCTTTGATGA CCCGTTAAGT GCCCTTGATG CTCATGTTGG    6000

TCAACAGGTA CTAACTCATT GATTCTCTTT GATAAGGCTA GTCTATTTCA TTTTTGAATT    6060

TATCTAACAT TTTTGTGTCT GGTCATTATG GAATACTGT CAGTCTGATT TCTAGGAATA     6120

TTGTTTCAGG TTTTTGAAAA ATGCATAAAA AGAGAACTGG GGCAGAAAAC GAGAGTTCTT    6180

GTTACAAACC AGCTCCACTT CCTATCACAA GTGGACAGAA TTGTACTTGT GCATGAAGGC    6240

ACAGTGAAAG AGGAAGGAAC ATATGAAGAG CTATCCAGTA ATGGGCCTTT GTTCCAGAGG    6300

GTAATGGAAA ATGCAGGGAA GGTGGAAGAA TATTCAGAAG AAAATGGAGA AGCTGAGGCA    6360

GACCAAACAG CGGAACAACC AGTTGCGAAT GGGAACACAA ATGGTCTTCA AATGGATGGA    6420

AGTGACGATA AAAAATCCAA AGAAGGAAAT AAAAAAGGAG GGAAATCTGT CCTCATCAAG    6480

CAAGAAGAAC GTGAAACCGG AGTTGTAAGT TGGAGAGTCC TGAAGAGGTA ACTTGAACAT    6540

TTGGCTTTTG CAATCTTACT ATTTGTTTGC AACTTTCCCC ATACTCGATC CAAGAGGTCC    6600

ATTCATTTGT GGTGTTTCAC AACAAACTAG CATGTTCCTT ATGTTTTTAG GCTGAACTAT    6660

ACCTTTGCGG GATATCAGAA TGACTTTTCC AGGCTTTCAA TGTTTTCAGG TACCAGGATG    6720

CACTTGGAGG GGCATGGGTA GTGATGATGC TCCTTTTATG TTACGTCTTA ACAGAAGTAT    6780

TTCGGGTTAC TAGCAGCACG TGGTTGAGTG AGTGGACTGA TGCAGGAACT CCAAAGAGTC    6840

ATGGACCCCT TTTCTACAAT CTCATATATG CACTTCTCTC GTTTGGACAG GTATGAGTTA    6900

TGTTTGCTTG ATGGATGAGT GAAGATTTGA TATAATCTTG ACCTCATGAT ATAACATATA    6960

TAGCTGAAAC CTGACCAGCT TAGAAAGATC TTATATAATT CTACTTTTGT GATTTTACTT    7020

TGAGAATCCA AAGGTGGAGG TAGAAAAGGT TAGTAAAGAA TTGATTTTTT TGCTGAGACT    7080

CTTTCTTCTT GCTTACAGGT TTTGGTGACA TTGACCAATT CATATTGGTT GATTATGTCC    7140

AGTCTTTATG CAGCTAAGAA GTTACACGAC AATATGCTTC ATTCCATACT GAGGGCCCCG    7200

ATGTCCTTCT TCCATACCAA TCCGCTAGGA CGGATAATCA ATCGATTCGC AAAAGATCTG    7260

GGTGATATTG ATCGAACTGT GGCCGTCTTT GTAAACATGT TTATGGGTCA AGTCTCACAG    7320

CTTCTTTCAA CTGTAGTGTT GATTGGCATT GTAAGCACTT TGTCCTTGTG GGCCATCATG    7380

CCCCTCCTGG TCTTGTTTTA TGGAGCTTAT CTTTATTATC AGGTAATGTA CCTTCTGACC    7440

GCAGCATTTA AATAACTGAG ATTAAGTGAC AGAAAGAGAA AAGGCACAG ATGATGGATG     7500

TTACACATAC TTTTTTAGCC TCATTTGTCA TGTCTGAGTT CGTTTGGTGC TTAAGCTATC    7560

TACACTCATC TGTCACCAAA AATCATGCTG TATATGTTGT GTGTTAAATA TTTTTCTTAT    7620

TGCAGAACAC AGCCCGTGAG GTTAAGCGTA TGGATTCAAT TTCAAGATCG CCTGTTTATG    7680

CACAGTTTGG AGAGGCATTG AATGGCTTAT CAACTATCCG TGCTTACAAA GCATATGATC    7740

GTATGGCTGA TATCAACGGA AGATCAATGG ATAATAACAT CAGATTCACT CTTGTCAACA    7800

TGGGTGCCAA TCGGTGGCTT GGAATCCGTT TAGAAACTCT GGGTGGTCTT ATGATATGGC    7860

TGACAGCATC GTTTGCTGTC ATGCAGAATG GAAGAGCGGA GAACCAACAG GCATTTGCAT    7920

CTACAATGGG TTTGCTTCTC AGTTATGCCT TAAATATTAC TAGCTTGTTA ACAGGTGTTC    7980

TGAGACTTGC GAGTTTGGCT GAGAATAGTC TAAACGCGGT CGAGTGTTGG CAATTATATA    8040

GAGATTCCGC CAGAGGTCCG CCTGTCATTG AGAACAACCG TCCACCTCCT GGATGGCCAT    8100

CATCTGGATC CATAAAGTTT GAGGATGTTG TTCTCCGTTA CCGCCCTCAG TTACCGCCTG    8160

TGCTTCATGG GGTTTCTTTC TTCATTCATC CAACAGATAA GGTGGGGATT GTTGGAAGGA    8220
```

```
CTGGTGCTGG AAAGTCAAGC CTGTTGAATG CATTGTTTAG AATTGTGGAG GTGGAAAAAG      8280

GAAGGATCTT AATCGATGAT TGTGACGTTG GAAAGTTTGG ACTGATGGAC CTACGTAAAG      8340

TGCTCGGAAT CATTCCACAG TCACCGGTTC TTTTCTCAGG AACTGTGAGG TTCAATCTTG      8400

ATCCATTTGG TGAACACAAT GATGCTGATC TTTGGGAATC TCTAGAGAGG GCACACTTGA      8460

AGGATACCAT CCGCAGAAAT CCTCTTGGTC TTGATGCTGA GGTATTCAGT TGCTGCCTAT      8520

ATTGATATGA AGTCTCATTT TTTAAGTGGT AATAACTGAT TTTCAATCTT TGTTCAGGTC      8580

TCTGAGGCAG GAGAGAATTT CAGCGTGGGA CAGAGGCAAT TGTTGAGTCT TCACGTGCG      8640

CTGTTACGGA GATCTAAGAT ACTCGTCCTT GATGAAGCAA CTGCTGCTGT AGATGTTAGA      8700

ACCGATGCCC TCATTCAGAA GACTATCCGA GAAGAATTCA AGTCATGCAC GATGCTCATT      8760

ATCGCTCACC GTCTCAATAC CATCATTGAC TGTGACAAAA TTCTCGTGCT TGATTCTGGA      8820

AGAGTATGAT TTTAAACACT CTCTCTCTTT CAATCTCACA CTCTCCTTGT TTCTCAGCTA      8880

ACCTGTTCTA TTCCAATTTG TTAACTCAGG TTCAAGAATT CAGTTCACCG GAGAACCTTC      8940

TTTCAAATGA AGGAAGCTCT TTCTCCAAGA TGGTTCAAAG CACTGGAGCT GCAAATGCTG      9000

AGTACTTGCG TAGTTTAGTA CTCGACAACA AGCGTGCCAA AGATGACTCA CACCACTTAC      9060

AAGGCCAAAG GAAATGGCTG GCTTCTTCTC GCTGGGCTGC AGCCGCTCAG TTTGCTCTGG      9120

CTGCGAGTCT TACTTCGTCG CACAACGATC TTCAAAGCCT TGAAATTGAA GATGACAGCA      9180

GCATTTTGAA GAGAACAAAC GATGCAGTTG TGACTCTGCG CAGTGTTCTC GAGGGGAAAC      9240

ACGACAAAGA GATTGCAGAG TCGCTTGAGG AACATAATAT CTCTAGAGAG GGATGGTTGT      9300

CATCACTCTA TAGAATGGTA GAAGGTAAAC CAAATATGCA TCTCTACAAA TGCTTATGCA      9360

AAATCTTAAT CACCACACTG AAACATTAAA GTCAAATCGT GCTCTTATAT TGCAAGCCTG      9420

CTTTCCGCTG TCTACGTTTC AGGGCTTGCA GTGATGAGCA GATTGGCAAG GAACCGAATG      9480

CAACAACCGG ATTACAATTT CGAAGGAAAT ACATTTGACT GGGACAACGT CGAGATGTAG      9540

ATAAGTTCAT GTTAAACTAG GAATCATTGT CTCTTCCGTA AGAAACATAT ATTTATCTTA      9600

ACCAAAATTA TTAGTTTGGT TTCCATTTCA TAAACTTAAT TTTCACCTGC AAAGAAAATC      9660

AAACCCTGTT GTGTTCTTCG TGATAAGTAG AGAAATTACT TGAGTATCCT TCTAACTCAT      9720

AAATGGGATC TCATGATTCA TGAACAAGCA GCAACACAAT AATACCCTTT TCAGATTTTG      9780

GAGCTGGACA AAGTTGTTAA GTTGAGTTTC TCTTACAGTC ATTCATATAC AAAAACCTCT      9840

TCGACTGAAG CACCAAGAAA GAAACAAACA TCAAAAGGGA ATGAGGTCTT TTCTTAGGGC      9900

TGAGATCATC GGAATGTGGG AGTGCGGAAC ACGACC                                9936
```

(2) INFORMATION FOR SEQ ID NO:3:

(i) SEQUENCE CHARACTERISTICS:
        (A) LENGTH: 1621 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Gly Phe Glu Phe Ile Glu Trp Tyr Cys Lys Pro Val Pro Asn Gly
1               5                   10                  15

Val Trp Thr Lys Thr Val Ala Asn Ala Phe Gly Ala Tyr Thr Pro Cys
            20                  25                  30

Ala Thr Asp Ser Phe Val Leu Gly Ile Ser Gln Leu Val Leu Leu Val
        35                  40                  45
```

-continued

```
Leu Cys Leu Tyr Arg Ile Trp Leu Ala Leu Lys Asp His Lys Val Glu
 50                      55                  60

Arg Phe Cys Leu Arg Ser Arg Leu Tyr Asn Tyr Phe Leu Ala Leu Leu
 65                  70                  75                  80

Ala Ala Tyr Ala Thr Ala Glu Pro Leu Phe Arg Leu Ile Met Gly Ile
                 85                  90                  95

Ser Val Leu Asp Phe Asp Gly Pro Gly Leu Pro Pro Phe Glu Ala Phe
            100                 105                 110

Gly Leu Gly Val Lys Ala Phe Ala Trp Gly Ala Val Met Val Met Ile
        115                 120                 125

Leu Met Glu Thr Lys Ile Tyr Ile Arg Glu Leu Arg Trp Tyr Val Arg
    130                 135                 140

Phe Ala Val Ile Tyr Ala Leu Val Gly Asp Met Val Leu Leu Asn Leu
145                 150                 155                 160

Val Leu Ser Val Lys Glu Tyr Tyr Ser Ser Tyr Val Leu Tyr Leu Tyr
                165                 170                 175

Thr Ser Glu Val Gly Ala Gln Val Leu Phe Gly Ile Leu Leu Phe Met
            180                 185                 190

His Leu Pro Asn Leu Asp Thr Tyr Pro Gly Tyr Met Pro Val Arg Ser
        195                 200                 205

Glu Thr Val Asp Asp Tyr Glu Tyr Glu Glu Ile Ser Asp Gly Gln Gln
    210                 215                 220

Ile Cys Pro Glu Lys His Pro Asn Ile Phe Asp Lys Ile Phe Phe Ser
225                 230                 235                 240

Trp Met Asn Pro Leu Met Thr Leu Gly Ser Lys Arg Pro Leu Thr Glu
                245                 250                 255

Lys Asp Val Trp Tyr Leu Asp Thr Trp Asp Gln Thr Glu Thr Leu Phe
            260                 265                 270

Thr Ser Phe Gln His Ser Trp Asp Lys Glu Leu Gln Lys Pro Gln Pro
        275                 280                 285

Trp Leu Leu Arg Ala Leu Asn Asn Ser Leu Gly Gly Arg Phe Trp Trp
    290                 295                 300

Gly Gly Phe Trp Lys Ile Gly Asn Asp Cys Ser Gln Phe Val Gly Pro
305                 310                 315                 320

Leu Leu Leu Asn Gln Leu Leu Lys Ser Met Gln Glu Asp Ala Pro Ala
                325                 330                 335

Trp Met Gly Tyr Ile Tyr Ala Phe Ser Ile Phe Gly Val Val Phe
            340                 345                 350

Gly Val Leu Cys Glu Ala Gln Tyr Phe Gln Asn Val Met Arg Val Gly
        355                 360                 365

Tyr Arg Leu Arg Ser Ala Leu Ile Ala Ala Val Phe Arg Lys Ser Leu
    370                 375                 380

Arg Leu Thr Asn Glu Gly Arg Arg Lys Phe Gln Thr Gly Lys Ile Thr
385                 390                 395                 400

Asn Leu Met Thr Thr Asp Ala Glu Ser Leu Gln Gln Ile Cys Gln Ser
                405                 410                 415

Leu His Thr Met Trp Ser Ala Pro Phe Arg Ile Ile Ile Ala Leu Ile
            420                 425                 430

Leu Leu Tyr Gln Gln Leu Gly Val Ala Ser Leu Ile Gly Ala Leu Leu
        435                 440                 445

Leu Val Leu Met Phe Pro Leu Gln Thr Val Ile Ile Ser Lys Met Gln
    450                 455                 460
```

-continued

```
Lys Leu Thr Lys Glu Gly Leu Gln Arg Thr Asp Lys Arg Ile Gly Leu
465                 470                 475                 480

Met Asn Glu Val Leu Ala Ala Met Asp Thr Val Lys Cys Tyr Ala Trp
            485                 490                 495

Glu Asn Ser Phe Gln Ser Lys Val Gln Thr Val Arg Asp Asp Glu Leu
                500                 505                 510

Ser Trp Phe Arg Lys Ser Gln Leu Leu Gly Ala Leu Asn Met Phe Ile
        515                 520                 525

Leu Asn Ser Ile Pro Val Leu Val Thr Ile Val Ser Phe Gly Val Phe
    530                 535                 540

Thr Leu Leu Gly Gly Asp Leu Thr Pro Ala Arg Ala Phe Thr Ser Leu
545                 550                 555                 560

Ser Leu Phe Ala Val Leu Arg Phe Pro Leu Phe Met Leu Pro Asn Ile
            565                 570                 575

Ile Thr Gln Val Val Asn Ala Asn Val Ser Leu Lys Arg Leu Glu Glu
                580                 585                 590

Val Leu Ala Thr Glu Glu Arg Ile Leu Leu Pro Asn Pro Pro Ile Glu
            595                 600                 605

Pro Gly Glu Pro Ala Ile Ser Ile Arg Asn Gly Tyr Phe Ser Trp Asp
            610                 615                 620

Ser Lys Gly Asp Arg Pro Thr Leu Ser Asn Ile Asn Leu Asp Val Pro
625                 630                 635                 640

Leu Gly Ser Leu Val Ala Val Val Gly Ser Thr Gly Glu Gly Lys Thr
                645                 650                 655

Ser Leu Ile Ser Ala Ile Leu Gly Glu Leu Pro Ala Thr Ser Asp Ala
            660                 665                 670

Ile Val Thr Leu Arg Gly Ser Val Ala Tyr Val Pro Gln Val Ser Trp
            675                 680                 685

Ile Phe Asn Ala Thr Val Arg Asp Asn Ile Leu Phe Gly Ser Pro Phe
    690                 695                 700

Asp Arg Glu Lys Tyr Glu Arg Ala Ile Asp Val Thr Ser Leu Lys His
705                 710                 715                 720

Asp Leu Glu Leu Leu Pro Gly Gly Asp Leu Thr Glu Ile Gly Glu Arg
                725                 730                 735

Gly Val Asn Ile Ser Gly Gly Gln Lys Gln Arg Val Ser Met Ala Arg
                740                 745                 750

Ala Val Tyr Ser Asn Ser Asp Val Tyr Ile Phe Asp Asp Pro Leu Ser
            755                 760                 765

Ala Leu Asp Ala His Val Gly Gln Gln Val Phe Glu Lys Cys Ile Lys
    770                 775                 780

Arg Glu Leu Gly Gln Lys Thr Arg Val Leu Val Thr Asn Gln Leu His
785                 790                 795                 800

Phe Leu Ser Gln Val Asp Arg Ile Val Leu Val His Glu Gly Thr Val
                805                 810                 815

Lys Glu Glu Gly Thr Tyr Glu Glu Leu Ser Ser Asn Gly Pro Leu Phe
            820                 825                 830

Gln Arg Leu Met Glu Asn Ala Gly Lys Val Glu Glu Tyr Ser Glu Glu
            835                 840                 845

Asn Gly Glu Ala Glu Ala Asp Gln Thr Ala Glu Gln Pro Val Ala Asn
            850                 855                 860

Gly Asn Thr Asn Gly Leu Gln Met Asp Gly Ser Asp Asp Lys Lys Ser
865                 870                 875                 880

Lys Glu Gly Asn Lys Lys Gly Gly Lys Ser Val Leu Ile Lys Gln Glu
```

-continued

```
                885                 890                 895
Glu Arg Glu Thr Gly Val Val Ser Trp Arg Val Leu Lys Arg Tyr Gln
                    900                 905                 910

Asp Ala Leu Gly Gly Ala Trp Val Val Met Met Leu Leu Leu Cys Tyr
                915                 920                 925

Val Leu Thr Glu Val Phe Arg Val Thr Ser Ser Thr Trp Leu Ser Glu
    930                 935                 940

Trp Thr Asp Ala Gly Thr Pro Lys Ser His Gly Pro Leu Phe Tyr Asn
945                 950                 955                 960

Leu Ile Tyr Ala Leu Leu Ser Phe Gly Gln Val Leu Val Thr Leu Thr
                965                 970                 975

Asn Ser Tyr Trp Leu Ile Met Ser Ser Leu Tyr Ala Ala Lys Lys Leu
            980                 985                 990

His Asp Asn Met Leu His Ser Ile Leu Arg Ala Pro Met Ser Phe Phe
        995                 1000                1005

His Thr Asn Pro Leu Gly Arg Ile Ile Asn Arg Phe Ala Lys Asp Leu
    1010                1015                1020

Gly Asp Ile Asp Arg Thr Val Ala Val Phe Val Asn Met Phe Met Gly
1025                1030                1035                1040

Gln Val Ser Gln Leu Leu Ser Thr Val Val Leu Ile Gly Ile Val Ser
                1045                1050                1055

Thr Leu Ser Leu Trp Ala Ile Met Pro Leu Leu Val Leu Phe Tyr Gly
            1060                1065                1070

Ala Tyr Leu Tyr Tyr Gln Asn Thr Ala Arg Glu Val Lys Arg Met Asp
        1075                1080                1085

Ser Ile Ser Arg Ser Pro Val Tyr Ala Gln Phe Gly Glu Ala Leu Asn
    1090                1095                1100

Gly Leu Ser Thr Ile Arg Ala Tyr Lys Ala Tyr Asp Arg Met Ala Asp
1105                1110                1115                1120

Ile Asn Gly Arg Ser Met Asp Asn Asn Ile Arg Phe Thr Leu Val Asn
                1125                1130                1135

Met Gly Ala Asn Arg Trp Leu Gly Ile Arg Leu Glu Thr Leu Gly Gly
            1140                1145                1150

Leu Met Ile Trp Leu Thr Ala Ser Phe Ala Val Met Gln Asn Gly Arg
        1155                1160                1165

Ala Glu Asn Gln Gln Ala Phe Ala Ser Thr Met Gly Leu Leu Leu Ser
    1170                1175                1180

Tyr Ala Leu Asn Ile Thr Ser Leu Leu Thr Gly Val Leu Arg Leu Ala
1185                1190                1195                1200

Ser Leu Ala Glu Asn Ser Leu Asn Ala Val Glu Arg Val Gly Asn Tyr
                1205                1210                1215

Ile Glu Ile Pro Pro Glu Ala Pro Val Ile Glu Asn Asn Arg Pro
            1220                1225                1230

Pro Pro Gly Trp Pro Ser Ser Gly Ser Ile Lys Phe Glu Asp Val Val
    1235                1240                1245

Leu Arg Tyr Arg Pro Gln Leu Pro Pro Val Leu His Gly Val Ser Phe
    1250                1255                1260

Phe Ile His Pro Thr Asp Lys Val Gly Ile Val Gly Arg Thr Gly Ala
1265                1270                1275                1280

Gly Lys Ser Ser Leu Leu Asn Ala Leu Phe Arg Ile Val Glu Val Glu
                1285                1290                1295

Glu Gly Arg Ile Leu Ile Asp Asp Cys Asp Val Gly Lys Phe Gly Leu
            1300                1305                1310
```

```
Met Asp Leu Arg Lys Val Leu Gly Ile Ile Pro Gln Ser Pro Val Leu
    1315                1320                1325
Phe Ser Gly Thr Val Arg Phe Asn Leu Asp Pro Phe Gly Glu His Asn
    1330                1335                1340
Asp Ala Asp Leu Trp Glu Ser Leu Glu Arg Ala His Leu Lys Asp Thr
1345                1350                1355                1360
Ile Arg Arg Asn Pro Leu Gly Leu Asp Ala Glu Val Ser Glu Ala Gly
                1365                1370                1375
Glu Asn Phe Ser Val Gly Gln Arg Gln Leu Leu Ser Leu Ser Arg Ala
                1380                1385                1390
Leu Leu Arg Arg Ser Lys Ile Leu Val Leu Asp Glu Ala Thr Ala Ala
                1395                1400                1405
Val Asp Val Arg Thr Asp Ala Leu Ile Gln Lys Thr Ile Arg Glu Glu
                1410                1415                1420
Phe Lys Ser Cys Thr Met Leu Ile Ile Ala His Arg Leu Asn Thr Ile
1425                1430                1435                1440
Ile Asp Cys Asp Lys Ile Leu Val Leu Asp Ser Gly Arg Val Gln Glu
                1445                1450                1455
Phe Ser Ser Pro Glu Asn Leu Leu Ser Asn Glu Gly Ser Ser Phe Ser
                1460                1465                1470
Lys Met Val Gln Ser Thr Gly Ala Ala Asn Ala Glu Tyr Leu Arg Ser
                1475                1480                1485
Leu Val Leu Asp Asn Lys Arg Ala Lys Asp Ser His His Leu Gln
                1490                1495                1500
Gly Gln Arg Lys Trp Ala Ser Ser Arg Trp Ala Ala Ala Ala Gln Phe
1505                1510                1515                1520
Ala Leu Ala Ala Ser Leu Thr Ser Ser His Asn Asp Leu Gln Ser Leu
                1525                1530                1535
Glu Ile Glu Asp Asp Ser Ser Ile Leu Lys Arg Thr Asn Asp Ala Val
                1540                1545                1550
Val Thr Leu Arg Ser Val Leu Glu Gly Lys His Asp Lys Glu Ala Glu
                1555                1560                1565
Ser Leu Glu Glu His Asn Ile Ser Arg Glu Gly Trp Leu Ser Ser Leu
                1570                1575                1580
Tyr Arg Met Val Glu Gly Leu Ala Val Met Ser Arg Leu Ala Arg Asn
1585                1590                1595                1600
Arg Met Gln Gln Pro Asp Tyr Asn Phe Glu Gly Asn Thr Phe Asp Trp
                1605                1610                1615
Asp Asn Val Glu Met
                1620
```

(2) INFORMATION FOR SEQ ID NO:4:

(i) SEQUENCE CHARACTERISTICS:
        (A) LENGTH: 5175 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

```
GAATTCGCGG CCGCCGGCGA ATTTGCACTC TTTACCTCTC TTTGACTCCG TGAGATTCGA      60

GGATTGTTAG TTTCTTGTGA TGTGTAGTCT TTGAAGCAGG GGATTTTTAT TGTATTGAGG     120

AAGAAGATGG GGTTTGAGCC GTTGGATTGG TATTGCAAGC CGGTGCCGAA TGGTGTGTGG     180
```

```
ACTAAAACTG TGGATTATGC GTTTGGTGCA TACACGCCTT GTGCTATTGA CTCTTTTGTG    240

CTTGGTATCT CTCATCTGGT TCTGTTGATT CTGTGTCTTT ATCGCTTGTG GCTCATCACG    300

AAGGATCACA AAGTGGATAA GTTCTGCTTG AGGTCTAAAT GGTTTAGCTA TTTTCTGGCT    360

CTTTTGGCTG CTTATGCTAC TGCGGAGCCT TTGTTTAGAT TGGTCATGAG GATCTCTGTT    420

TTGGATTTGG ATGGAGCTGG GTTTCCTCCC TATGAGGCGT TTATGTTGGT CCTTGAGGCT    480

TTTGCTTGGG GTTCTGCTTT GGTCATGACT GTTGTGGAAA CTAAAACGTA TATCCATGAA    540

CTCCGTTGGT ATGTCAGATT CGCTGTCATT TATGCTCTTG TGGGAGACAT GGTGTTGTTA    600

AATCTTGTTC TCTCTGTTAA GGAGTACTAT GGCAGTTTTA AACTGTATCT TTACATAAGC    660

GAGGTGGCAG TTCAGGTTGC ATTTGGAACC CTCTTGTTTG TGTATTTCCC TAATTTGGAC    720

CCTTACCCTG GTTACACACC AGTTGGGACT GAAAATTCCG AGGATTACGA GTATGAAGAG    780

CTTCCTGGAG GAGAAAATAT ATGTCCTGAG AGGCATGCAA ATTTATTTGA CAGTATCTTC    840

TTCTCATGGT TGAACCCATT GATGACTCTG GGATCAAAAC GACCTCTCAC CGAGAAGGAT    900

GTATGGCATC TGGACACTTG GGATAAAACT GAAACTCTTA TGAGGAGCTT CCAGAAGTCC    960

TGGGATAAGG AACTAGAAAA GCCCAAACCG TGGCTTTTGA GAGCACTGAA CAACAGCCTT   1020

GGGGGAAGGT TTTGGTGGGG TGGCTTTTGG AAGATTGGGA ATGACTGTTC ACAGTTCGTG   1080

GGGCCTCTTC TACTGAATGA GCTCTTAAAG TCAATGCAAC TTAATGAACC AGCGTGGATA   1140

GGTTACATCT ATGCAATCTC AATCTTTGTT GGAGTGGTAT TGGGGGTTTT ATGTGAAGCT   1200

CAGTATTTCC AAAATGTGAT GCGTGTTGGT TACCGGCTTA GGTCTGCACT GATTGCTGCT   1260

GTGTTCCGAA AATCTTTGAG GCTAACTAAT GAGGGGCGGA AGAAGTTTCA AACAGGAAAA   1320

ATAACAAACT TAATGACTAC TGATGCTGAG TCGCTGCAGC AAATCTGCCA ATCACTTCAT   1380

ACCATGTGGT CGGCGCCATT TCGTATAATT GTAGCACTGG TTCTCCTCTA TCAACAATTG   1440

GGTGTTGCCT CGATCATTGG TGCATTGTTT CTTGTCCTTA TGTTCCCCAT ACAGACTGTT   1500

ATTATAAGCA AAACGCAGAA GTTAACAAAA GAAGGGTTGC AGCGTACTGA CAAGAGAATT   1560

GGCCTAATGA ATGAGGTTTT AGCGGCAATG GATACAGTGA AGTGTTACGC TTGGGAAAAC   1620

AGTTTTCAGT CCAAGGTTCA AACTGTACGT GATGATGAAT TATCTTGGTT CCGGAAAGCA   1680

CAACTCCTGT CAGCGTTCAA TATGTTCATA CTAAACAGCA TCCCTGTCCT CGTGACTGTT   1740

GTTTCATTTG GTGTGTTCTC ATTGCTTGGA GGAGATCTGA CACCTGCAAG AGCGTTTACG   1800

TCACTCTCTC TATTTTCTGT GCTTCGCTTC CCTTTATTCA TGCTTCCAAA CATTATAACT   1860

CAGATGGTAA ATGCTAATGT ATCCTAAACC GTTTGGAGGA GGTACTGTCA ACCGAAGAGA   1920

GAGTTCTCTT ACCGAATCCT CCCATTGAAC CTGGACAGCC AGCTATCTCA ATAAGAAATG   1980

GATACTTCTC CTGGGATTCA AAGGCGGATA GGCCAACATT GTCAAACATC AACCTGGACA   2040

TACCTCTTGG CAGCCTAGTT GCGGTAGTTG GCAGCACAGG AGAAGGAAAA ACCTCCCTGA   2100

TATCTGCTAT GCTTGGGAA CTTCCTGCAA GATCTGATGC GACTGTTACT CTTAGAGGAT   2160

CAGTCGCTTA TGTTCCACAA GTTTCATGGA TCTTTAACGC AACAGTACGT GACAATATAT   2220

TGTTTGGGGC TCCTTTTGAC CAAGAAAAAT ATGAAAGGGT GATTGATGTG ACAGCACTCC   2280

AGCATGACCT TGAGTTACTG CCTGGAGGTG ACCTCACGGA GATCGGAGAA AGGGGTGTTA   2340

ACATCAGTGG GGGACAAAAG CAGAGGGTTT CTATGGCTAG GCCGTTTAC TCAAATTCAG    2400

ACGTGTGCAT CTTAGATGAA CCATTGAGTG CCCTTGATGC GCATGTTGGT CAGCAGGTTT   2460

TTGAAAAATG CATAAAAAGG GAACTAGGGC AGACAACGAG AGTACTTGTT ACAAATCAGC   2520
```

```
TCCACTTCCT ATCACAAGTG GATAAAATCC TACTTGTCCA TGAGGGAACA GTAAAAGAGG      2580

AAGGAACATA TGAAGAATTA TGCCATAGTG GCCCGTTGTT CCCGAGGTTA ATGGAAAATG      2640

CAGGGAAGGT TGAAGATTAT TCCGAAGAAA ATGGAGAAGC TGAAGTACAT CAAACATCTG      2700

TAAAACCAGT TGAAAATGGG AACGCTAATA ATCTGCAGAA GGATGGAATC GAGACAAAGA      2760

ATTCCAAAGA AGGAAACTCT GTTCTTGTCA AACGAGAAGA ACGTGAAACT GGAGTTGTGA      2820

GTTGGAAAGT CCTGGAGAGG TACCAGAATG CACTTGGAGG TGCATGGGTA GTGATGATGC      2880

TCGTTATATG CTACGTCTTG ACTCAAGTAT TTCGGGTTTC AAGCATCACT TGGTTGAGTG      2940

AGTGGACTGA TTCAGGAACC CCAAAGACTC ATGGACCCCT ATTCTATAAT ATTGTCTATG      3000

CGCTTCTTTC GTTTGGACAG GTCTCTGTGA CATTGATCAA TTCATATTGG TTGATTATGT      3060

CCAGTCTATA TGCAGCTAAA AAGATGCATG ATGCTATGCT TGGTTCCATA CTAAGGGCTC      3120

CAATGGTGTT CTTTCAAACC AATCCATTAG ACGGATAAT CAATCGATTT GCAAAAGATA      3180

TGGGAGATAT TGATCGAACT GTGGCAGTCT TTGTAAACAT GTTTATGGGT TCAATCGCAC      3240

AGCTTCTTTC AACTGTTATC TTGATTGGCA TTGTCAGCAC TCTGTCCCTG TGGGCCATCA      3300

TGCCCCTGTT GGTCGTGTTC TATGGAGCTT ATCTGTATTA CCAGAACACA TCTCGGGAAA      3360

TTAAACGTAT GGATTCCACT ACAAGATCGC CAGTTTATGC TCAATTTGGT GAGGCATTGA      3420

ATGGACTATC TAGTATCCGT GCTTATAAAG CATATGACAG GATGGCTGAA ATTAATGGAA      3480

GGTCAATGGA CAATAACATC AGATTCACAC TTGTAAACAT GGCTGCAAAT CGGTGGCTGG      3540

GAATCCGTTT GGAAGTTTTG GGAGGTCTCA TGGTTTGGTG GACTGCTTCA TTAGCCGTCA      3600

TGCAGAACGG AAAGGCAGCG AACCAACAAG CATATGCATC TACGATGGGT TTGCTTCTCA      3660

GTTATGCGTT AAGCATTACC AGCTCTTTAA CAGCTGTACT GAGACTCGCG AGTCTAGCTG      3720

AGAATAGTTT AAACTCGGTT GAGCGTGTTG GAAATTATAT CGAGATACCA TCAGAGGCTC      3780

CATTGGTCAT TGAAAACAAC CGTCCACCTC CCGGATGGCC ATCATCTGGA TCCATAAAAT      3840

TTGAGGATGT TGTTCTTCGT TACCGCCCTG AGTTACCTCC TGTTCTTCAT GGAGTTTCGT      3900

TCTTGATTTC TCCAATGGAT AAGGTGGGAA TTGTTGGGAG GACAGGCGCT GGGAAATCAA      3960

GCCTCTTAAA TGCCTTATTC AGGATTGTGG AGCTGGAAAA AGGAAGGATT TTAATTGATG      4020

AATGCGACAT TGGAAGATTT GGACTGATGG ACCTACGTAA AGTGGTCGGA ATTATACCGC      4080

AAGCGCCAGT TCTTTTCTCA GGTACCGTGA GATTCAATCT TGACCCATTT AGTGAACACA      4140

ACGACGCCGA TCTCTGGGAA TCTCTTGAGA GGGCACACTT GAAAGATACT ATCCGCAGAA      4200

ATCCTCTTGG TCTTGATGCT GAGGTAACTG AGGCAGGAGA GAATTTCAGT GTTGGACAGA      4260

GACAGTTGTT GAGTCTTGCA CGTGCATTGT TACGAAGATC TAAGATACTT GTTCTTGATG      4320

AAGCAACTGC TGCAGTTGAC GTAAGAACTG ATGTTCTCAT CCAAAAGACC ATCCGAGAAG      4380

AATTCAAGTC ATGCACAATG CTAATCATCG CTCATCGTCT CAATACTATC ATCGACTGTG      4440

ACAAAGTTCT TGTCCTTGAT TCTGGAAAAG TTCAGGAATT CAGTTCACCG GAGAATCTTC      4500

TTTCAAATGG AGAAAGTTCT TTCTCGAAGA TGGTTCAAAG TACAGGAACT GCAAACGCGG      4560

AGTACTTACG TAGTATAACA CTAGAGAACA AACGTACCAG AGAAGCTAAC GGTGATGATT      4620

CACAACCTTT AGAAGGTCAA AGGAAATGGC AAGCTTCTTC TCGTTGGGCT GCAGCTGCTC      4680

AATTTGCATT GGCTGTGAGC CTCACTTCAT CTCACAACGA CCTCCAAAGC CTTGAAATCG      4740

AAGATGATAA CAGTATTTTG AAGAAAACAA AGGACGCCGT CGTCACTTTA CGCAGTGTCC      4800

TTGAAGGGAA ACATGATAAA GAGATTGAAG ACTCTCTAAA CCAAAGTGAC ATCTCTAGAG      4860

AGCGTTGGTG GCCATCTCTT TACAAAATGG TCGAAGGGCT TGCCGTGATG AGCAGATTGG      4920
```

```
CGAGGAACAG AATGCAACAC CCGGATTACA ATTTAGAAGG GAAATCGTTT GACTGGGACA      4980

ATGTCGAGAT GTAAACGATG AAAGGCTTAC ACTAATAGAC CTAAAACTCC CATTTTGATG      5040

GAACTTTTAT TTGTATTGCT TGGGATACAC GTAACAAAAT GCCCATTAAT CGTGGTGTAA      5100

CTATATAGGC TATGCTTCTT TTGGGAAAAA GAGAGTTTGA TTACAGAGGA TGTGATGATA      5160

ACACAATTGG AATTC                                                      5175

(2) INFORMATION FOR SEQ ID NO:5:

(i) SEQUENCE CHARACTERISTICS:
        (A) LENGTH: 10342 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

GGGAGGTTTG GTTTTTTCCC TATCAATCGA ATTCCATTTC GTGCTCGTAA CGTGGATTTT        60

GGTAGATTTT TTTTAGGGGG ATGGAAACTT GTTTATTATC TATAGATGAT GATTTTGTTT       120

TCTCCATGAG AATGTATGCT TTTAAACTTT TTTTTTTTTG TTTTTTGCCT TCGGAGCTAA       180

CTTTGGGGGC TGGTCTCGGT CTCTGTTTTC TCTCCACTAA AAAGATAAAA AGCTTTTGCC       240

ATCTTTTTTT TTTTCTCAAT AATCTATCAC ATCGTTTTTT TTCTTTGTTT TTTTCTCCAT       300

TTGTCTTCAT TGAGTTCATA GCCACATAAT TATTGATTTC TTTTTCTTTT AGTGTTTCTG       360

TTACTGATGC GTTTCATTAT TTATACTTCT CACTTGCAGA TTCGAGGATT GTTAGTTTCT       420

TGTGATGTGT AGTCTTTGAA GCAGGGGATT TTTATTGTAT TGAGGAAGAA GATGGGGTTT       480

GAGCCGTTGG ATTGGTATTG CAAGCCGGTG CCGAATGGTG TGTGGACTAA AACTGTGGAT       540

TATGCGTTTG GTGCATACAC GCCTTGTGCT ATTGACTCTT TTGTGCTTGG TATCTCTCAT       600

CTGGTTCTGT TGATTCTGTG TCTTTATCGC TTGTGGCTCA TCACGAAGGA TCACAAAGTG       660

GATAAGTTCT GCTTGAGGTC TAAATGGTTT AGCTATTTTC TGGCTCTTTT GGCTGCTTAT       720

GCTACTGCGG AGCCTTTGTT TAGATTGGTC ATGAGGATCT CTGTTTTGGA TTTGGATGGA       780

GCTGGGTTTC CTCCCTATGA GGTGTGTTAT CACTTTGCTG TTTTGTTGAT GTTGTTCTCC       840

TTCTGTATGT TTTTTCCTGA GAGATGCTGT TGTTTTGTGC TTTATTTGGC AGGCGTTTAT       900

GTTGGTCCTT GAGGCTTTTG CTTGGGGTTC TGCTTTGGTC ATGACTGTTG TGGAAACTAA       960

AACGTATATC CATGAACTCC GTTGGTATGT CAGATTCGCT GTCATTTATG CTCTTGTGGG      1020

AGACATGGTG TTGTTAAATC TTGTTCTCTC TGTTAAGGAG TACTATGGCA GGTTGGTAAA      1080

TTTGCAGTCT GTATGGTTTA TGCAATTTTG TTTCCCTGGT CTGGCACGAT GAACTTATAT      1140

GCGTCATTTT TTTTTTGTTT TTGGCAGTTT TAAACTGTAT CTTTACATAA GCGAGGTGGC      1200

AGTTCAGGTT TGCACTTTAA AACTCCTTTT TGCATTCTCC AAACTACTCT TTACCATGTG      1260

CTGTATCTAA GTCACACTGT AAATGATACA ACTTTGTTTT TATAATGACG TTAAGGATGG      1320

TTTTTGGATC CAGGTTGCAT TTGGAACCCT CTTGTTTGTG TATTTCCCTA ATTTGGACCC      1380

TTACCCTGGT TACACACCAG TTGGGACTGA AAATTCCGAG GATTACGAGT ATGAAGAGCT      1440

TCCTGGAGGA GAAAATATAT GTCCTGAGAG GCATGCAAAT TTATTTGACA GTATGTCACT      1500

CTACACTTCT CATTCCCTAC TTTGTTTTTA TAGGTGCATT TTCTATTTTA ATTGTGAGAA      1560

TTGCCACCGC ATCTTTTATC ACTTTTCTGC ACTTACTACC TATCTAAGTT GGTTATTTAT      1620

GCAGAGCTTA AATATTTCCC TGGAATTGTA AATTTTCTTA TGGAGTGCTA ATACGTAGTA      1680
```

```
GGTCATTAAA ATTGTTTCCG CAGAGAGTAG TCTATAGTCT CTTCAAAATT TTTTTTTGAC    1740

TTATCCTCCC GTTCTCCCTA GAAATGAACT TATGATTTGT GACTGTGCCG AGGTTTTTGC    1800

TTAGTGATCA TCACTTCGAC TAAGCTGCAA CATTTTATAT AGTATATTCG TCAACATTTG    1860

TCAAACTTTG ACTATTATGT TCCTTCTTAC CCTTGTCTTT CAACCCACAG GTATCTTCTT    1920

CTCATGGTTG AACCCATTGA TGACTCTGGG ATCAAAACGA CCTCTCACCG AGAAGGATGT    1980

ATGGCATCTG GACACTTGGG ATAAAACTGA AACTCTTATG AGGAGGTATA TTTTAATAAA    2040

TAACAACTGT TCTCATACTG TCTATGACTG GCATGGTTGC GTGACATATT TTTATCTCAT    2100

TTTTTAGCTT CCAGAAGTCC TGGGATAAGG AACTAGAAAA GCCCAAACCG TGGCTTTTGA    2160

GAGCACTGAA CAACAGCCTT GGGGGAAGGT AAACAAAAAC TTCTTCACAG TCATGTGTTT    2220

TCATCTTTTT GGGCTTTGAC ATGATGTGTG ATTTGTAAAA GGAAGCATTT GGTTGTAATA    2280

ATAAATGCAT TATGAATAAC TAGAAGCTGA GAAATCTGTT ATGGCTGTGA CTTCAAGTAT    2340

GTTTTGATGC GTGTCGAGTT GAATAAGAAA TGTGTTACTT TTCTGGTTAT AATCTGCCAT    2400

AGATACTTTC CATCCTTATG GACTGTCTGT TTCTGCATTT TGTAGGTTTT GGTGGGGTGG    2460

CTTTTGGAAG GTACTTTTGT ACTCTTTATT GTGTTTTATT CTTTATTCTG AAACAGTCTT    2520

TTCCTTGTCT ATTTGATAAT ATTGATGGCT TCTGAGGTCT TAGTTTTCCT AAATGGTGTG    2580

TTTTGTAACT GTTTAATCTT GACATTTCAA TCTAAATTGT ATCATAGATT GGGAATGACT    2640

GTTCACAGTT CGTGGGGCCT CTTCTACTGA ATGAGCTCTT AAAGGTTTGT TCCTTTACTT    2700

CTTTTTACCC CGTGCACATT GTGCTTGAAC CTATTTAACA CAATGCTTTG TAATTTTTCC    2760

ATTCACATGG ATCTTTGAGA TGGATTCATA TTCCTACTGG CTCGAATAAG TGTTTAAACG    2820

TTCTTGATAG ATTCAAAATC CTATCATCCT TTGAATATTA TGTTCTGACG ATATCTCACA    2880

ATGTCTCCTT TAACTTTCCG CAGTCAATGC AACTTAATGA ACCAGCGTGG ATAGGTTACA    2940

TCTATGCAAT CTCAATCTTT GTTGGAGTGG TATGCAACAA ATTCTCTTTT TCTTCGCTGC    3000

CTTTATTATT CTCTTGCATG GACTGCAAAG GATATGAAAC AAAAACTCTA CTTTCCTTGG    3060

ATTCTTTTCT TTCTTGCTAG GACTTCATGG TATTTTTGGT CTAGAGTAGA TGCTACGAAT    3120

TGTAGGACCA GTTTAATTTT CTTAAGCTGA AAGTAATCTC TGTGCGATTC GATTGTATTA    3180

GAAAATAGCC TGATTCTACT CTTAGAGTTA GTTTTTTTTG TTTGTTAATA CATTTGCATG    3240

TTGAAAAGGT TTTGTTTAAT GTAGGTCAAG GTGACACTTG ACCAATGGAC TCCTTGATCG    3300

CTTGATGTTG ATGTTGACAT TTTCAGGTAT TGGGGGTTTT ATGTGAAGCT CAGTATTTCC    3360

AAAATGTGAT GCGTGTTGGT TACCGGCTTA GGTCTGCACT GGTAAGAAAA AGTTTCACAT    3420

GAATTATCTT TTGCTACTTA GTTTTTCTTT TTGCTCTGCT TCTCATGTTT TGATGCAATA    3480

CCTGTACTGT TATGTCTGTT GAAAGCTATA GCAGATGCTT ATAGATTGCT TCATTCTGCT    3540

GATGAATTCT CCCTTAATAG ATTGCTGCTG TGTTCCGAAA ATCTTTGAGG CTAACTAATG    3600

AGGGGCGGAA GAAGTTTCAA ACAGGAAAAA TAACAAACTT AATGACTACT GATGCTGAGT    3660

CGCTGCAGGT GTATCTTTGT TACCTTTACT CTCTTTAGCC TTGTCTGTTT CTTGATATAA    3720

ATTTACACTG CATAGTTGTA TATCTACCTC AAAATATGAG TCTTAGATGC AATTTACCAA    3780

GATAGTCTTT TTCCTGCAAC TGACGACTGA ATCTGAAGCT TATTCTAAGA TTCTAGAAAT    3840

CCTAAGAGTT GTGATTACAT TTTCAACACC CTTGTTCTTT TGTTGCCGTT GTAGGATTTG    3900

ATTTTCCTTT ATTAGCCAAT AAACCTTTAA TTCGCTTGAT TTGTAGAAAA AAGTTACCTT    3960

TGAACAGTGC TTTTATCTAA GCTCTTGCTT GAAATCAAAG TGTTTATCTA GCTGATAGCT    4020
```

-continued

```
GTTCTTTTTC CCTAACGTTT CTCTTGTGTG TGACAGCAAA TCTGCCAATC ACTTCATACC      4080

ATGTGGTCGG CGCCATTTCG TATAATTGTA GCACTGGTTC TCCTCTATCA ACAATTGGGT      4140

GTTGCCTCGA TCATTGGTGC ATTGTTTCTT GTCCTTATGT TCCCCATACA GGTTCGTATA      4200

TCTTAATAAT TCCCCATTCT CTTTGCGCTG TCGGTTTTTT TTTCCTTTTG ATTGCTTATT      4260

TCTCATTTGC TTTTCACACC AATGAAAATG ATTCATTTCC TCCGTTTATT TGGTTGAAAC      4320

AGACTGTTAT TATAAGCAAA ACGCAGAAGT TAACAAAAGA AGGGTTGCAG CGTACTGACA      4380

AGAGAATTGG CCTAATGAAT GAGGTTTTAG CGGCAATGGA TACAGTGAAG TACGATACTT      4440

TGGAAGCCTG AAACCTAATA TTTATTTTCT TGCATAGTTG GAAGTTTGTG GCAGTGTTTA      4500

ACTATCTCAC TAAACCAAAA TACTGTAGGT GTTACGCTTG GGAAAACAGT TTTCAGTCCA      4560

AGGTTCAAAC TGTACGTGAT GATGAATTAT CTTGGTTCCG GAAAGCACAA CTCCTGTCAG      4620

CGGTATGGCT TGAGTGCAGT GACTGTTATA TTAATTGATT TTATAGACCG TATGCATGAT      4680

GTGCATAGTT GTCTTGGTCA TTTACTTGTC GCTCTCCTAA CGGTATGATT GTATACAAGG      4740

ACAAATCCAA GTTGCTCGTC TTTTTAAATG CCTTTGACCA TTTTGAGAAT GGTATCCATC      4800

AATATGTGTT TAGGCATTTT CTGTACTATT TTCTAGTTCA TTGAACATTG ATTCAGTTGT      4860

TTCGGGCATG TGTAGCAGCA TTCATGCATG ATCTTTAACA TATATTGCAT TAATGTTTCT      4920

GACTCATTCT TGGTCTTCTA TTTGCTCTGC AGTTCAATAT GTTCATACTA AACAGCATCC      4980

CTGTCCTCGT GACTGTTGTT TCATTTGGTG TGTTCTCATT GCTTGGAGGA GATCTGACAC      5040

CTGCAAGAGC GTTTACGTCA CTCTCTCTAT TTTCTGTGCT TCGCTTCCCT TTATTCATGC      5100

TTCCAAACAT TATAACTCAG GTGATTTCCT TAAAATGTTT CTTGAACCAT GTTTTCATGT      5160

CCAGTACTGA ATAATGTGGC ATCATAGTAA TGATTGCTTC TGATTGCTCT TTTAATTTTC      5220

CATCTCTACC TCTTTTTCTA GACCAGTCGT TGTCATAATG TTTTTGCAGA TGCTGACCAG      5280

GCTTTACTTT TGTAGATGGT AAATGCTAAT GTATCCTTAA ACCGTTTGGA GGAGGTACTG      5340

TCAACCGAAG AGAGAGTTCT CTTACCGAAT CCTCCCATTG AACCTGGACA GCCAGCTATC      5400

TCAATAAGAA ATGGATACTT CTCCTGGGAT TCAAAGGTCT TCTTTGTCTA TTTTATCACA      5460

TGTTCTTACT TCTATTAGTT TCTATCATTA CATATTGTCA ATGAAGTACA AAAAGTGAGC      5520

TAGAAGTATA CATATGCAGG CGGATAGGCC AACATTGTCA AACATCAACC TGGACATACC      5580

TCTTGGCAGC CTAGTTGCGG TAGTTGGCAG CACAGGAGAA GGAAAAACCT CCCTGATATC      5640

TGCTATGCTT GGGGAACTTC CTGCAAGATC TGATGCGACT GTTACTCTTA GAGGATCAGT      5700

CGCTTATGTT CCACAAGTTT CATGGATCTT TAACGCAACA GTAAGTTTAT ATATGCTACT      5760

CAGTTTATAG TATGGTTCTC AATGCGAAAA TGTCAAATTC TCCTCTTGGA TTGTTACTTA      5820

TTTTGTATGT ATTTTATGTT TTGTATATGA TGATGTGTGC TTTTAGATAC GTCCACATGC      5880

TGATGGTTGT AATTAACATC GCGTAGGTAC GTGACAATAT ATTGTTTGGG GCTCCTTTTG      5940

ACCAAGAAAA ATATGAAAGG GTGATTGATG TGACAGCACT CCAGCATGAC CTTGAGTTAC      6000

TGCCTGTAAG TTTTGTGGAG AGTTACTTAG CCATGTGCAT TGAAAATTTC CTGAGGTGAA      6060

ACGAACCTTG AAATCTGTTG GTGCGATGTA AATCGAAAAA ACTGAATTGC ATCAGTTCTG      6120

TTGATAGCAT GTACTTCTAT TTTCTAGTGC TCAGGTATCT AAGCTTGTTT CCTCTTCTTT      6180

CTCTTGATTG ATAGGGAGGT GACCTCACGG AGATCGGAGA AAGGGGTGTT AACATCAGTG      6240

GGGGACAAAA GCAGAGGGTT TCTATGGCTA GGGCCGTTTA CTCAAATTCA GACGTGTGCA      6300

TCTTAGATGA ACCATTGAGT GCCCTTGATG CGCATGTTGG TCAGCAGGTA AACTAGCCAT      6360

AGGCTCTTTT GGATAGAACA ATACTTTGTT TTTCTTTCAA TTTTGCAAAT CGTGAACTCT      6420
```

```
ATAACGTTTT GTTTTTCAAT CTGCATGGAT ATTCTACTTC TTGTTTGCCA CGGATCTCTG    6480

CCATATACTA CTTTTAAGCA AACATTGTTA TCTGATGTTC GAAACTGGCT GTTATATATA    6540

GGTTTTTGAA AAATGCATAA AAAGGGAACT AGGGCAGACA ACGAGAGTAC TTGTTACAAA    6600

TCAGCTCCAC TTCCTATCAC AAGTGGATAA AATCCTACTT GTCCATGAGG GAACAGTAAA    6660

AGAGGAAGGA ACATATGAAG AATTATGCCA TAGTGGCCCG TTGTTCCCGA GGTTAATGGA    6720

AAATGCAGGG AAGGTTGAAG ATTATTCCGA AGAAAATGGA GAAGCTGAAG TACATCAAAC    6780

ATCTGTAAAA CCAGTTGAAA ATGGGAACGC TAATAATCTG CAGAAGGATG GAATCGAGAC    6840

AAAGAATTCC AAAGAAGGAA ACTCTGTTCT TGTCAAACGA GAAGAACGTG AAACTGGAGT    6900

TGTGAGTTGG AAAGTCCTGG AGAGGTAAGT TGGCATTCGG ATTTTTGCTC TTTCTTGTTG    6960

TGTTGTTGCA GTATTCCTTT CTATCGACAG TGGAAATATC CGTAAATAAG ACATATTCTT    7020

TGGTTTAGAG CAATATGTCA ATTTATCTGT GGTGTTTCTT TACTACAAAA TGGATATATA    7080

TTGTTTGACT CGCTCTATTC ATATTCATAC AAAATGTATA TATATTTTCC GTATTAAGGT    7140

TCGTATTGTA AAGCCATTGT AATAACTTGT GAGGTGTCAC CATGTTCCAG GTACCAGAAT    7200

GCACTTGGAG GTGCATGGGT AGTGATGATG CTCGTTATAT GCTACGTCTT GACTCAAGTA    7260

TTTCGGGTTT CAAGCATCAC TTGGTTGAGT GAGTGGACTG ATTCAGGAAC CCCAAAGACT    7320

CATGGACCCC TATTCTATAA TATTGTCTAT GCGCTTCTTT CGTTTGGACA GGTATGAGTT    7380

GCATTTGGCA AATGTTTGAG TCGGTATCTT CATGATCGGA TAACAATATA TAACTGAACA    7440

TTAAAGGCTG ATCAGTTAAG AATATACACC ATGTTTCTTC TGCGCCAAAG TATCGAGCAA    7500

ACAAAATGGA AAATAAAAGG ATACAGAGAG CAAAACGTTT ATTGCTAACA CGTATTTCTG    7560

CGGGGGTTTG TCAGGTCTCT GTGACATTGA TCAATTCATA TTGGTTGATT ATGTCCAGTC    7620

TATATGCAGC TAAAAAGATG CATGATGCTA TGCTTGGTTC CATACTAAGG GCTCCAATGG    7680

TGTTCTTTCA AACCAATCCA TTAGGACGGA TAATCAATCG ATTTGCAAAA GATATGGGAG    7740

ATATTGATCG AACTGTGGCA GTCTTTGTAA ACATGTTTAT GGGTTCAATC GCACAGCTTC    7800

TTTCAACTGT TATCTTGATT GGCATTGTCA GCACTCTGTC CCTGTGGGCC ATCATGCCCC    7860

TGTTGGTCGT GTTCTATGGA GCTTATCTGT ATTACCAGTG TAACCTACAT ACTTTTTAAA    7920

CGCAATGCTA TCTACATTCA TGACTACAGA TCGAGACATG GAAAACTGAG ACCAAAAGGA    7980

ACACTGATTG TGTCATATCT GTTGTGTCAT AACCTGATTT TTCCTTATTG TAGAACACAT    8040

CTCGGGAAAT TAAACGTATG GATTCCACTA CAAGATCGCC AGTTTATGCT CAATTTGGTG    8100

AGGCATTGAA TGGACTATCT AGTATCCGTG CTTATAAAGC ATATGACAGG ATGGCTGAAA    8160

TTAATGGAAG GTCAATGGAC AATAACATCA GATTCACACT TGTAAACATG GCTGCAAATC    8220

GGTGGCTGGG AATCCGTTTG GAAGTTTTGG GAGGTCTCAT GGTTTGGTGG ACTGCTTCAT    8280

TAGCCGTCAT GCAGAACGGA AAGGCAGCGA ACCAACAAGC ATATGCATCT ACGATGGGTT    8340

TGCTTCTCAG TTATGCGTTA AGCATTACCA GCTCTTTAAC AGCTGTACTG AGACTCGCGA    8400

GTCTAGCTGA GAATAGTTTA AACTCGGTTG AGCGTGTTGG AAATTATATC GAGATACCAT    8460

CAGAGGCTCC ATTGGTCATT GAAAACAACC GTCCACCTCC CGGATGGCCA TCATCTGGAT    8520

CCATAAAATT TGAGGATGTT GTTCTTCGTT ACCGCCCTGA GTTACCTCCT GTTCTTCATG    8580

GAGTTTCGTT CTTGATTTCT CCAATGGATA AGGTGGGAAT TGTTGGGAGG ACAGGCGCTG    8640

GGAAATCAAG CCTCTTAAAT GCCTTATTCA GGATTGTGGA GCTGGAAAAA GGAAGGATTT    8700

TAATTGATGA ATGCGACATT GGAAGATTTG GACTGATGGA CCTACGTAAA GTGGTCGGAA    8760
```

```
TTATACCGCA AGCGCCAGTT CTTTTCTCAG GTACCGTGAG ATTCAATCTT GACCCATTTA    8820

GTGAACACAA CGACGCCGAT CTCTGGGAAT CTCTTGAGAG GGCACACTTG AAAGATACTA    8880

TCCGCAGAAA TCCTCTTGGT CTTGATGCTG AGGTACTTAA TTAAATATTT CCATTTGGGA    8940

AAGTCTCATG TATTCAGTAA TAATAACTCA GTCTTTTTGG TCAGGTAACT GAGGCAGGAG    9000

AGAATTTCAG TGTTGGACAG AGACAGTTGT TGAGTCTTGC ACGTGCATTG TTACGAAGAT    9060

CTAAGATACT TGTTCTTGAT GAAGCAACTG CTGCAGTTGA CGTAAGAACT GATGTTCTCA    9120

TCCAAAAGAC CATCCGAGAA GAATTCAAGT CATGCACAAT GCTAATCATC GCTCATCGTC    9180

TCAATACTAT CATCGACTGT GACAAAGTTC TTGTCCTTGA TTCTGGAAAA GTACGTATAC    9240

AAAATATTCG ACCACTACTT GCATCAATTT AATCACTTTT GAGCTAACAT ATATTGAGAT    9300

TCCCAACACC TCAGGTTCAG GAATTCAGTT CACCGGAGAA TCTTCTTTCA AATGGAGAAA    9360

GTTCTTTCTC GAAGATGGTT CAAAGTACAG GAACTGCAAA CGCGGAGTAC TTACGTAGTA    9420

TAACACTAGA GAACAAACGT ACCAGAGAAG CTAACGGTGA TGATTCACAA CCTTTAGAAG    9480

GTCAAAGGAA ATGGCAAGCT TCTTCTCGTT GGGCTGCAGC TGCTCAATTT GCATTGGCTG    9540

TGAGCCTCAC TTCATCTCAC AACGACCTCC AAAGCCTTGA AATCGAAGAT GATAACAGTA    9600

TTTTGAAGAA AACAAAGGAC GCCGTCGTCA CTTTACGCAG TGTCCTTGAA GGGAAACATG    9660

ATAAAGAGAT TGAAGACTCT CTAAACCAAA GTGACATCTC TAGAGAGCGT TGGTGGCCAT    9720

CTCTTTACAA AATGGTCGAA GGTAACGTTA TTCTTAAGAT TTCTGATACG AGTATACGAC    9780

ATAAAGAATT GTTGAAGTTT CTTGATCTAA TAATTTGTGT ATATACTCTC AGGGCTTGCC    9840

GTGATGAGCA GATTGGCGAG GAACAGAATG CAACACCCGG ATTACAATTT AGAAGGGAAA    9900

TCGTTTGACT GGGACAATGT CGAGATGTAA ACGATGAAAG GCTTACACTA ATAGACCTAA    9960

AACTCCCATT TTGATGGAAC TTTTATTTGT ATTGCTTGGG ATACACGTAA CAAAATGCCC   10020

ATTAATCGTG GTGTAACTAT ATAGGCTATG CTTCTTTTGG GAAAAAGAGA GTTTGATTAC   10080

AGAGGATGTG ATGATAACAC AATTGGAATT CAAATTTGCA GCAAAATTTG GGAGAAAAAA   10140

AAAAGTCAAT GAGTGCAACA TGCCAACATG GTTTCAACTT CTGGACATGG ACAACCATTG   10200

GACATAATTT CTCTCACAGG ACCATGTTTT GTCATTGACA TTTTGCACAA AAATGTTCTA   10260

TTAAACATAT ATCTATAAAG AATTTGAACA ATTGTTAAAA AAACACTTAA AATATAAATT   10320

GCAATACAAA TTTCCTTTTT TT                                           10342
```

(2) INFORMATION FOR SEQ ID NO:6:

(i) SEQUENCE CHARACTERISTICS:
        (A) LENGTH: 1622 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Gly Phe Glu Pro Leu Asp Trp Tyr Cys Lys Pro Val Pro Asn Gly
 1               5                  10                  15

Val Trp Thr Lys Thr Val Asp Tyr Ala Phe Gly Ala Tyr Thr Pro Cys
                20                  25                  30

Ala Ile Asp Ser Phe Val Leu Gly Ile Ser His Leu Val Leu Leu Ile
            35                  40                  45

Leu Cys Leu Tyr Arg Leu Trp Leu Ile Thr Lys Asp His Lys Val Asp
        50                  55                  60
```

-continued

```
Lys Phe Cys Leu Arg Ser Lys Trp Phe Ser Tyr Phe Leu Ala Leu Leu
 65                  70                  75                  80

Ala Ala Tyr Ala Thr Ala Glu Pro Leu Phe Arg Leu Val Met Arg Ile
                 85                  90                  95

Ser Val Leu Asp Leu Asp Gly Ala Gly Phe Pro Pro Tyr Glu Ala Phe
                100                 105                 110

Met Leu Val Leu Glu Ala Phe Ala Trp Gly Ser Ala Leu Val Met Thr
                115                 120                 125

Val Val Glu Thr Lys Thr Tyr Ile His Glu Leu Arg Trp Tyr Val Arg
130                 135                 140

Phe Ala Val Ile Tyr Ala Leu Val Gly Asp Met Val Leu Leu Asn Leu
145                 150                 155                 160

Val Leu Ser Val Lys Glu Tyr Tyr Gly Ser Phe Lys Leu Tyr Leu Tyr
                165                 170                 175

Ile Ser Glu Val Ala Val Gln Val Ala Phe Gly Thr Leu Leu Phe Val
                180                 185                 190

Tyr Phe Pro Asn Leu Asp Pro Tyr Pro Gly Tyr Thr Pro Val Gly Thr
                195                 200                 205

Glu Asn Ser Glu Asp Tyr Glu Tyr Glu Glu Leu Pro Gly Gly Glu Asn
                210                 215                 220

Ile Cys Pro Glu Arg His Ala Asn Leu Phe Asp Ser Ile Phe Phe Ser
225                 230                 235                 240

Trp Leu Asn Pro Leu Met Thr Leu Gly Ser Lys Arg Pro Leu Thr Glu
                245                 250                 255

Lys Asp Val Trp His Leu Asp Thr Trp Asp Lys Thr Glu Thr Leu Met
                260                 265                 270

Arg Ser Phe Gln Lys Ser Trp Asp Lys Glu Leu Glu Lys Pro Lys Pro
                275                 280                 285

Trp Leu Leu Arg Ala Leu Asn Asn Ser Leu Gly Gly Arg Phe Trp Trp
                290                 295                 300

Gly Gly Phe Trp Lys Ile Gly Asn Asp Cys Ser Gln Phe Val Gly Pro
305                 310                 315                 320

Leu Leu Leu Asn Glu Leu Leu Lys Ser Met Gln Leu Asn Glu Pro Ala
                325                 330                 335

Trp Ile Gly Tyr Ile Tyr Ala Ile Ser Ile Phe Val Gly Val Val Leu
                340                 345                 350

Gly Val Leu Cys Glu Ala Gln Tyr Phe Gln Asn Val Met Arg Val Gly
                355                 360                 365

Tyr Arg Leu Arg Ser Ala Leu Ile Ala Ala Val Phe Arg Lys Ser Leu
                370                 375                 380

Arg Leu Thr Asn Glu Gly Arg Lys Lys Phe Gln Thr Gly Lys Ile Thr
385                 390                 395                 400

Asn Leu Met Thr Thr Asp Ala Glu Ser Leu Gln Gln Ile Cys Gln Ser
                405                 410                 415

Leu His Thr Met Trp Ser Ala Pro Phe Arg Ile Ile Val Ala Leu Val
                420                 425                 430

Leu Leu Tyr Gln Gln Leu Gly Val Ala Ser Ile Ile Gly Ala Leu Phe
                435                 440                 445

Leu Val Leu Met Phe Pro Ile Gln Thr Val Ile Ile Ser Lys Thr Gln
                450                 455                 460

Lys Leu Thr Lys Glu Gly Leu Gln Arg Thr Asp Lys Arg Ile Gly Leu
465                 470                 475                 480

Met Asn Glu Val Leu Ala Ala Met Asp Thr Val Lys Cys Tyr Ala Trp
```

-continued

```
                485                 490                 495
Glu Asn Ser Phe Gln Ser Lys Val Gln Thr Val Arg Asp Asp Glu Leu
                500                 505                 510
Ser Trp Phe Arg Lys Ala Gln Leu Leu Ser Ala Phe Asn Met Phe Ile
            515                 520                 525
Leu Asn Ser Ile Pro Val Leu Thr Val Val Ser Phe Gly Val Phe
            530                 535                 540
Ser Leu Leu Gly Gly Asp Leu Thr Pro Ala Arg Ala Phe Thr Ser Leu
545                 550                 555                 560
Ser Leu Phe Ser Val Leu Arg Phe Pro Leu Phe Met Leu Pro Asn Ile
                565                 570                 575
Ile Thr Gln Met Val Asn Ala Asn Val Ser Leu Asn Arg Leu Glu Glu
                580                 585                 590
Val Leu Ser Thr Glu Glu Arg Val Leu Leu Pro Asn Pro Ile Glu
            595                 600                 605
Pro Gly Gln Pro Ala Ile Ser Ile Arg Asn Gly Tyr Phe Ser Trp Asp
            610                 615                 620
Ser Lys Ala Asp Arg Pro Thr Leu Ser Asn Ile Asn Leu Asp Ile Pro
625                 630                 635                 640
Leu Gly Ser Leu Val Ala Val Val Gly Ser Thr Gly Glu Gly Lys Thr
                645                 650                 655
Ser Leu Ile Ser Ala Met Leu Gly Glu Leu Pro Ala Arg Ser Asp Ala
                660                 665                 670
Thr Val Thr Leu Arg Gly Ser Val Ala Tyr Val Pro Gln Val Ser Trp
                675                 680                 685
Ile Phe Asn Ala Thr Val Arg Asp Asn Ile Leu Phe Gly Ala Pro Phe
            690                 695                 700
Asp Gln Glu Lys Tyr Glu Arg Val Ile Asp Val Thr Ala Leu Gln His
705                 710                 715                 720
Asp Leu Glu Leu Leu Pro Gly Gly Asp Leu Thr Glu Ile Gly Glu Arg
                725                 730                 735
Gly Val Asn Ile Ser Gly Gly Gln Lys Gln Arg Val Ser Met Ala Arg
                740                 745                 750
Ala Val Tyr Ser Asn Ser Asp Val Cys Ile Leu Asp Glu Pro Leu Ser
            755                 760                 765
Ala Leu Asp Ala His Val Gly Gln Gln Val Phe Glu Lys Cys Ile Lys
            770                 775                 780
Arg Glu Leu Gly Gln Thr Thr Arg Val Leu Val Thr Asn Gln Leu His
785                 790                 795                 800
Phe Leu Ser Gln Val Asp Lys Ile Leu Leu Val His Glu Gly Thr Val
                805                 810                 815
Lys Glu Glu Gly Thr Tyr Glu Glu Leu Cys His Ser Gly Pro Leu Phe
                820                 825                 830
Pro Arg Leu Met Glu Asn Ala Gly Lys Val Glu Asp Tyr Ser Glu Glu
            835                 840                 845
Asn Gly Glu Ala Glu Val His Gln Thr Ser Val Lys Pro Val Glu Asn
            850                 855                 860
Gly Asn Ala Asn Asn Leu Gln Lys Asp Gly Ile Glu Thr Lys Asn Ser
865                 870                 875                 880
Lys Glu Gly Asn Ser Val Leu Val Lys Arg Glu Glu Arg Glu Thr Gly
                885                 890                 895
Val Val Ser Trp Lys Val Leu Glu Arg Tyr Gln Asn Ala Leu Gly Gly
                900                 905                 910
```

-continued

Ala Trp Val Val Met Met Leu Val Ile Cys Tyr Val Leu Thr Gln Val
        915                 920                 925

Phe Arg Val Ser Ser Ile Thr Trp Leu Ser Glu Trp Thr Asp Ser Gly
        930                 935                 940

Thr Pro Lys Thr His Gly Pro Leu Phe Tyr Asn Ile Val Tyr Ala Leu
945             950                 955                 960

Leu Ser Phe Gly Gln Val Ser Val Thr Leu Ile Asn Ser Tyr Trp Leu
            965                 970                 975

Ile Met Ser Ser Leu Tyr Ala Ala Lys Lys Met His Asp Ala Met Leu
        980                 985                 990

Gly Ser Ile Leu Arg Ala Pro Met Val Phe Phe Gln Thr Asn Pro Leu
        995                 1000                1005

Gly Arg Ile Ile Asn Arg Phe Ala Lys Asp Met Gly Asp Ile Asp Arg
        1010                1015                1020

Thr Val Ala Val Phe Val Asn Met Phe Met Gly Ser Ile Ala Gln Leu
1025                1030                1035                1040

Leu Ser Thr Val Ile Leu Ile Gly Ile Val Ser Thr Leu Ser Leu Trp
            1045                1050                1055

Ala Ile Met Pro Leu Leu Val Val Phe Tyr Gly Ala Tyr Leu Tyr Tyr
            1060                1065                1070

Gln Asn Thr Ser Arg Glu Ile Lys Arg Met Asp Ser Thr Thr Arg Ser
            1075                1080                1085

Pro Val Tyr Ala Gln Phe Gly Glu Ala Leu Asn Gly Leu Ser Ser Ile
            1090                1095                1100

Arg Ala Tyr Lys Ala Tyr Asp Arg Met Ala Glu Ile Asn Gly Arg Ser
1105                1110                1115                1120

Met Asp Asn Asn Ile Arg Phe Thr Leu Val Asn Met Ala Ala Asn Arg
            1125                1130                1135

Trp Leu Gly Ile Arg Leu Glu Val Leu Gly Gly Leu Met Val Trp Trp
            1140                1145                1150

Thr Ala Ser Leu Ala Val Met Gln Asn Gly Lys Ala Ala Asn Gln Gln
            1155                1160                1165

Ala Tyr Ala Ser Thr Met Gly Leu Leu Leu Ser Tyr Ala Leu Ser Ile
            1170                1175                1180

Thr Ser Ser Leu Thr Ala Val Leu Arg Leu Ala Ser Leu Ala Glu Asn
1185                1190                1195                1200

Ser Leu Asn Ser Val Glu Arg Val Gly Asn Tyr Ile Glu Ile Pro Ser
            1205                1210                1215

Glu Ala Pro Leu Val Ile Glu Asn Asn Arg Pro Pro Pro Gly Trp Pro
            1220                1225                1230

Ser Ser Gly Ser Ile Lys Phe Glu Asp Val Val Leu Arg Tyr Arg Pro
            1235                1240                1245

Glu Leu Pro Pro Val Leu His Gly Val Ser Phe Leu Ile Ser Pro Met
            1250                1255                1260

Asp Lys Val Gly Ile Val Gly Arg Thr Gly Ala Gly Lys Ser Ser Leu
1265                1270                1275                1280

Leu Asn Ala Leu Phe Arg Ile Val Glu Leu Glu Lys Gly Arg Ile Leu
            1285                1290                1295

Ile Asp Glu Cys Asp Ile Gly Arg Phe Gly Leu Met Asp Leu Arg Lys
            1300                1305                1310

Val Val Gly Ile Ile Pro Gln Ala Pro Val Leu Phe Ser Gly Thr Val
            1315                1320                1325

```
Arg Phe Asn Leu Asp Pro Phe Ser Glu His Asn Asp Ala Asp Leu Trp
    1330                1335                1340
Glu Ser Leu Glu Arg Ala His Leu Lys Asp Thr Ile Arg Arg Asn Pro
1345                1350                1355                1360
Leu Gly Leu Asp Ala Glu Val Thr Glu Ala Gly Glu Asn Phe Ser Val
                1365                1370                1375
Gly Gln Arg Gln Leu Leu Ser Leu Ala Arg Ala Leu Leu Arg Arg Ser
                1380                1385                1390
Lys Ile Leu Val Leu Asp Glu Ala Thr Ala Ala Val Asp Val Arg Thr
                1395                1400                1405
Asp Val Leu Ile Gln Lys Thr Ile Arg Glu Glu Phe Lys Ser Cys Thr
                1410                1415                1420
Met Leu Ile Ile Ala His Arg Leu Asn Thr Ile Ile Asp Cys Asp Lys
1425                1430                1435                1440
Val Leu Val Leu Asp Ser Gly Lys Val Gln Glu Phe Ser Ser Pro Glu
                1445                1450                1455
Asn Leu Leu Ser Asn Gly Glu Ser Ser Phe Ser Lys Met Val Gln Ser
                1460                1465                1470
Thr Gly Thr Ala Asn Ala Glu Tyr Leu Arg Ser Ile Thr Leu Glu Asn
                1475                1480                1485
Lys Arg Thr Arg Glu Ala Asn Gly Asp Asp Ser Gln Pro Leu Glu Gly
                1490                1495                1500
Gln Arg Lys Trp Gln Ala Ser Ser Arg Trp Ala Ala Ala Gln Phe
1505                1510                1515                1520
Ala Leu Ala Val Ser Leu Thr Ser Ser His Asn Asp Leu Gln Ser Leu
                1525                1530                1535
Glu Ile Glu Asp Asp Asn Ser Ile Leu Lys Lys Thr Lys Asp Ala Val
                1540                1545                1550
Val Thr Leu Arg Ser Val Leu Glu Gly Lys His Asp Lys Glu Ile Glu
                1555                1560                1565
Asp Ser Leu Asn Gln Ser Asp Ile Ser Arg Glu Arg Trp Trp Pro Ser
                1570                1575                1580
Leu Tyr Lys Met Val Glu Gly Leu Ala Val Met Ser Arg Leu Ala Arg
1585                1590                1595                1600
Asn Arg Met Gln His Pro Asp Tyr Asn Leu Glu Gly Lys Ser Phe Asp
                1605                1610                1615
Trp Asp Asn Val Glu Met
                1620

(2) INFORMATION FOR SEQ ID NO:7:

(i) SEQUENCE CHARACTERISTICS:
        (A) LENGTH: 1251 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

TTCACTTTTG TCCTTTTTTT CTTAACATCT ACTTTTGTCA TCAGCAAATT ATCTGTAAAT      60

AAGATAGGGT TTATGCTTAT TGCTACAATG AACCTAATCC TATGATGTGT ATTGCAATTT     120

GCAACCATGC GAGTTTAATT ATTTGTTTAC TGCTATAGTG ATCATTTTAT GATGTGTTTT     180

TATTAATTAC AAAACAGAGC ATCAAAAATC AAAAGAACAT ATCGCATAAT CGAACTATGC     240

TAATACCTCT CCTCAATCTT TGTTGTTGTT ATATTCAAGT AGCTTATTCT TTTGTTTTAT     300
```

```
TTTACGATTA GATTTCTCTA GAATTTAATT TATATTATTT AATCATACTT GATCAAGGTT      360

TGTAGCTTAA TCAATATCGT TATCGTGTCA TCCTGCAGAT TCAAATGATC AAGTCTAATA      420

ATCTACTTAT ATGTATTATA TATATTAGAT ACCACCAACG AAACAAAATC ATATTTCTAT      480

AACATTTGTT TGGTTAAATA TATTTAAAGA TTTGTAACAG TTGTTCGGGT TCAAAACTAT      540

CACTTTGTAG TTGTAGGATG AGGAAAAGTC GTGATATGAT CATCTACTAA AATCATGTGT      600

TTTTTAAAGA ACATGATTTT CATTGGATAG TTTAATAAAT GTTAAAAAAA TACTAAGTGT      660

CAAAGAAGAG ATTTGAACCA TATGTAGAAT ACTTGATTCG AATTTTTCCT GACGAATAAT      720

CTAATATCCT TTTCTCAAAA GAAAAAATG TTTGTTAACT TGGACACGAT ATTATTATCC       780

AACTTCCTTT CTAGATATTC ATTTTTAAAT TACCTATATA TTTTTATTTT CTCAAAATAT      840

ACTAAAAATT GGATAGAGCT ATTAAATAAA AAGATAGAA TTTAGAGAGA AATAGCAACA       900

TAATGAATTA TAATATAAAT ATTTTGTAAA GAAATAACAA ACTTTATAGT TAGTTTGCCT      960

AATATAGAAA AAAGATACAG TTATTTACCC ATTTGTTTGT GTGTAAAAAA AGGAGTAAAA     1020

TAAACAGAGA AAAGAGCTTC TTGTTTTTAC TTGTGAACGT TATTGACTTT TCGGCCTCTC     1080

TCTCTTCTCT ATACAAATAT ATGGATCTTC ATTTCTTCGT ATAGTGTAAG CAGTGACGCA     1140

TCCATTTATC ATCATCTCCT TATAAATCTC GAATCTGCCA CAGAGAGAGC GTGTGACAAA     1200

ATGAGTTCAT AAGATTCCGT TATCGTCTTC CTGATTCCTC CAAATCTCCG G              1251

(2) INFORMATION FOR SEQ ID NO:8:

(i) SEQUENCE CHARACTERISTICS:
            (A) LENGTH: 1368 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:8:

AAACAATTGG TGTATTTTGA ATTTTTCATG CAACGCACGT GAACAGCTTA ATTGCTTGAT       60

TGGAAACAAA CCTTTTTAGA ATTCATTAAT CAGTTTTAGG TGTTTTGGAA AATTAACGAA      120

CTATAGTGGA GATTAATTAA TTTTTATATTA GTCTTTTTTA GTACACAAAT CGAAGTTTCC    180

TAGATTTTTT CAAAGTTGAA ATAATATTG ATAATATTTA TCAACAATGA ATCTACAAAA      240

ACATAATTTT TTTGCCAAAC AAATAACACC GAAACAAGAT TCATTCACTA TTTTTGGTTT     300

AAAAAAAAAA ATCAAAATTA CACTATTATG AAGCCAATTT TTGTATGCAA AAAACCTGTA     360

TGTATCAATT TGTTTGTATT AAAAAGTAAG CATTTATGTC TTTTTTTTAT AAATAATAGA     420

AACACTTACT AGATGAATAG ATTTTTTGGT TTTAGAACAG AATACTATAA TTGTATTTAT     480

ATAGCTTTTT TATATTATTC GATATAGAAA AGTGTTATAA TAGGAAAAAT GTACCATATA     540

CTGTCAATAA CATATTTGAT TCTAAATATA AATAGAATTG TTTTAAAGAA ATATGATCGT     600

TTATAATTAA ATGGTTTTA ATGTCTTTTC TTGGGGCAAA AAACAAAGCT TGTCTTTCGT      660

CCATATATTT GCATCGTAAG GGGTGACGTA TCACTCTCTC TTTCTCTCAA ATATTATTCT     720

TCAATCTCTT TTTGGGGAAT CTTCGAGCAA ATTAGTGAGA GAACCCACCC ACTTTCTTTC     780

TCATATGAGT ACATAAGATC CCTTTTGAGT TTTCGTGTTT TGCCAAAATC TCCAGGTAAA     840

GCTTCTCCCT TTTTCTCTGT TTTCTCTGTT TTGTTATTCT CCCTTTTCTC CATTGTAGCT     900

TTTTCCTGTA AAGTGGGATT GATAGTTTTG TTTCATGGAT TTCAAATTTG TGTTATTTGA     960

CTCGATACCA TCTTAAATGC AGAGTCTTTT CGTGATAATA AAATTATGGA TTCGTTTCAA    1020
```

```
AGTTTTTTTT TTTTCGTATG GAAAACACTT GAGCTCTCTC AATCTTGTAG TCTTGACTCT    1080

TGATGATTCT TCTATGTTCT CGTTGTGATT GCTTGTCACT GTTCTATCTT TATATATGAT    1140

TAAATGCAAT TTTGCCCCTT TTTACGCGCG AATGTATTTA TTATCTTTCG CACTCTGGGT    1200

CCATTTCTTG TCACTTGAGC ACATAATGAT TGATTTATGA CTTTTTAAAG TTATGAAAAT    1260

TTATTATTTT TGTTGCTATG GTTTTTTGGA ATTAGAAGCT CATTTCAAAG TTGTTGATTT    1320

TCTTTGCAGG GTAGGGAATT GGTGTGGTAG CTTGTGATGC ACTGTGTT                 1368
```

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Ala Cys Asp Glu Phe Gly
1               5
```

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Ala Cys Asp His Ile Lys
1               5
```

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

```
GTGACAWWGC                                                              10
```

(2) INFORMATION FOR SEQ ID NO:12:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
GTTTCACAGT TTAAAGCGTA GTCTGGGACG TCGTATGGGT AATTTTCATT GACC            54
```

(2) INFORMATION FOR SEQ ID NO:13:

(i) SEQUENCE CHARACTERISTICS:

(A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AAACTGCAGA TGGCTGGTAA TCTTGTTTC                                          29

(2) INFORMATION FOR SEQ ID NO:14:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GCCTCTAGAT CAAGCGTAGT CTGGGACGTC GTATGGGTAA TTTTCATTGA                   50

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

AGATTAAGCC ATGCATGTCT                                                    20

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TGCTGGTACC AGACTTGCCC TCC                                                23

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GAAAGTGGAT GTGGGACGGG C                                                  21

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear

```
          (ii) MOLECULE TYPE: DNA (genomic)

(xi) SEQUENCE DESCRIPTION: SEQ ID NO:18:

TCCATATGTT TACTGGC                                                           17

(2) INFORMATION FOR SEQ ID NO:19:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:19:

AAACCGGTGC GGCCGCCATG GGGTTTGAGC CGT                                         33

(2) INFORMATION FOR SEQ ID NO:20:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:20:

AATTAACCCT CACTAAAGGG                                                        20
```

What is claimed is:

1. An isolated DNA encoding a plant GS-X pump, wherein the DNA comprises a nucleic acid sequence encoding AtMRP1 or AtMRP2.

2. A recombinant cell transformed with the isolated DNA of claim 1.

3. The recombinant cell of claim 2, wherein the cell is selected from the group consisting of a prokaryote cell and a eukaryote cell.

4. A vector comprising the isolated DNA of claim 1.

5. A transgenic plant or parts thereof, each transformed with an isolated DNA encoding a plant GS-X pump of claim 1, wherein the DNA comprises a nucleic acid sequence encoding AtMRP1 or AtMRP2.

6. A transgenic plant cell, transformed with an isolated DNA encoding a plant GS-X pump of claim 1, wherein the DNA comprises a nucleic acid sequence encoding AtMRP1 or AtMRP2.

7. A transgenic plant, stably transformed with an isolated DNA encoding a plant GS-X pump of claim 1, wherein the DNA comprises a nucleic acid sequence encoding AtMRP1 or AtMRP2.

8. An isolated DNA encoding a plant GS-X pump, wherein the DNA comprises a nucleic acid sequence encoding AtMRP1 or AtMRP2, and wherein the AtMRP1 or AtMRP2 each comprise an approximately 200 amino acid residue N-terminal extension domain, a first transmembrane spanning domain, a second transmembrane spanning domain, a first nucleotide binding fold domain, a second nucleotide binding fold domain, a putative CFTR-like regulatory domain rich in charged amino acid residues, and a C-terminal domain.

9. A recombinant cell transformed with the isolated DNA of claim 8.

10. The recombinant cell of claim 9, wherein the cell is selected from the group consisting of a prokaryote cell and a eukaryote cell.

11. A vector comprising the isolated DNA of claim 8.

12. A transgenic plant or parts thereof, each transformed with an isolated DNA encoding a plant GS-X pump of claim 8, wherein the DNA comprises a nucleic acid sequence encoding AtMRP1 or AtMRP2, and wherein the AtMRP1 or AtMRP2 each comprise DNA encoding an approximately 200 amino acid residue N-terminal extension domain, a first transmembrane spanning domain, a second transmembrane spanning domain, a first nucleotide binding fold domain, a second nucleotide binding fold domain, a putative CFTR-like regulatory domain rich in charged amino acid residues, and a C-terminal domain.

13. A transgenic plant cell, transformed with an isolated DNA encoding a plant GS-X pump of claim 8, wherein the DNA comprises a nucleic acid sequence encoding AtMRP1 or AtMRP2, and wherein the AtMRP1 or AtMRP2 each comprise an approximately 200 amino acid residue N-terminal extension domain, a first transmembrane spanning domain, a second transmembrane spanning domain, a first nucleotide binding fold domain, a second nucleotide binding fold domain, a putative CFTR-like regulatory domain rich in charged amino acid residues, and a C-terminal domain.

14. A transgenic plant, stably transformed with an isolated DNA encoding a plant GS-X pump of claim 8, wherein the DNA comprises a nucleic acid sequence encoding AtMRP1 or AtMRP2, and wherein the AtMRP1 or AtMRP2 each comprise an approximately 200 amino acid residue N-terminal extension domain, a first transmembrane spanning domain, a second transmembrane spanning domain, a first nucleotide binding fold domain, a second nucleotide binding fold domain, a putative CFTR-like regulatory domain rich in charged amino acid residues, and a C-terminal domain.

15. A transgenic plant, stably transformed with an isolated DNA encoding a plant GS-X pump, wherein the GS-X pump is AtMRP1 or AtMRP2.

16. An isolated DNA encoding a plant GS-X pump, wherein the DNA comprises a nucleic acid sequence sharing at least about 40% homology with AtMRP1 (SEQ ID NO: 4 or SEQ ID NO: 5) or AtMRP2 (SEQ ID NO: 1 or SEQ ID NO: 2).

17. A recombinant cell transformed with the isolated DNA of claim 16.

18. The recombinant cell of claim 17, wherein the cell is selected from the group consisting of a prokaryote cell and a eukaryote cell.

19. A vector comprising the isolated DNA of claim 16.

20. A transgenic plant or parts thereof, each transformed with an isolated DNA encoding a plant GS-X pump of claim 16, wherein the DNA comprises a nucleic acid sequence sharing at least about 40% homology with AtMRP1 (SEQ ID NO: 4 or SEQ ID NO: 5) or AtMRP2 (SEQ ID NO: 1 or SEQ ID NO: 2).

21. A transgenic plant cell, transformed with an isolated DNA encoding a plant GS-X pump of claim 16, wherein the DNA comprises a nucleic acid sequence sharing at least about 40% homology with AtMRP1 (SEQ ID NO: 4 or SEQ ID NO: 5) or AtMRP2 (SEQ ID NO: 1 or SEQ ID NO: 2).

22. A transgenic plant, stably transformed with an isolated DNA encoding a plant GS-X pump of claim 16, wherein the DNA comprises a nucleic acid sequence sharing at least about 40% homology with AMRP1 (SEQ ID NO: 4 or SEQ ID NO: 5) or AtMRP2 (SEQ ID NO: 1 or SEQ ID NO: 2).

23. An isolated DNA encoding a plant GS-X pump, wherein the DNA comprises a nucleic acid sequence comprising AtMRP1 (SEQ ID NO: 4 or SEQ ID NO: 5) or AtMRP2 (SEQ ID NO: 1 or SEQ ID NO: 2), and wherein the AtMRP1 or AtMRP2 each comprise DNA encoding an approximately 200 amino acid residue N-ter extension domain, a first transmembrane spanning domain, a second transmembrane spanning domain, a first nucleotide binding fold domain, a second nucleotide binding fold domain, a putative CFTR-like regulatory domain rich in charged amino acid residues, and a C-terminal domain, wherein each of said domains of the isolated DNA further shares at least about 40% homology with a same domain of SEQ ID NO: 4, or SEQ ID NO: 5, or SEQ ID NO: 1, or SEQ ID NO: 2.

24. A recombinant cell transformed with the isolated DNA of claim 23.

25. The recombinant cell of claim 24, wherein the cell is selected from the group consisting of a prokaryote cell and a eukaryote cell.

26. A vector comprising the isolated DNA of claim 23.

27. A transgenic plant or parts thereof, each transformed with an isolated DNA encoding a plant GS-X pump of claim 23, wherein each of said domains of the isolated DNA further shares at least about 40% homology with a same domain of SEQ ID NO: 4, or SEQ ID NO: 5, or SEQ ID NO: 1, or SEQ ID NO: 2.

28. A transgenic plant cell, transformed with an isolated DNA encoding a plant GS-X pump of claim 23, wherein the DNA comprises a nucleic acid sequence sharing at least about 40% homology with AtMRP1 (SEQ ID NO: 4 or SEQ ID NO: 5) or AtMRP2 (SEQ ID NO: 1 or SEQ ID NO: 2).

29. A transgenic plant, stably transformed with an isolated DNA encoding a plant GS-X pump of claim 23, wherein the DNA comprises a nucleic acid sequence sharing at least about 40% homology with AtMRP1 (SEQ ID NO: 4 or SEQ ID NO: 5) or AtMRP2 (SEQ ID NO: 1 or SEQ ID NO: 2).

* * * * *